(12) United States Patent
Helmerhorst et al.

(10) Patent No.: US 8,685,392 B2
(45) Date of Patent: Apr. 1, 2014

(54) ROTHIA SPECIES GLUTAMINE ENDOPEPTIDASES AND USE THEREOF

(75) Inventors: Eva J. Helmerhorst, Chestnut Hill, MA (US); Frank G. Oppenheim, Chestnut Hill, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 13/500,670

(22) PCT Filed: Oct. 7, 2010

(86) PCT No.: PCT/US2010/051828
§ 371 (c)(1),
(2), (4) Date: May 24, 2012

(87) PCT Pub. No.: WO2011/044365
PCT Pub. Date: Apr. 14, 2011

(65) Prior Publication Data
US 2012/0230976 A1 Sep. 13, 2012

Related U.S. Application Data

(60) Provisional application No. 61/249,343, filed on Oct. 7, 2009.

(51) Int. Cl.
*A61K 38/48* (2006.01)
*C12N 9/52* (2006.01)
*C12Q 1/37* (2006.01)

(52) U.S. Cl.
USPC ............................ 424/94.63; 435/220; 435/24

(58) Field of Classification Search
USPC ................................. 424/94.63; 435/220, 24
See application file for complete search history.

(56) References Cited

U.S. PATENT DOCUMENTS

| | | | |
|---|---|---|---|
| 7,303,871 B2 | 12/2007 | Hausch et al. | |
| 7,320,788 B2 | 1/2008 | Shan et al. | |
| 2005/0249719 A1 | 11/2005 | Shan et al. | |
| 2005/0281914 A1 | 12/2005 | Steele et al. | |
| 2006/0240475 A1 | 10/2006 | Khosla et al. | |
| 2008/0193436 A1 | 8/2008 | Shan et al. | |
| 2010/0092451 A1* | 4/2010 | Gass et al. | 424/94.63 |

FOREIGN PATENT DOCUMENTS

WO 2007/019411 2/2007

OTHER PUBLICATIONS

Dodson et al. Nucleotide and Predicted Amino Acid Sequence of *Rothia* ATCC 25296 Neprilysin Peptidase; integrated into UniprotKB/TrEMBL on Sep. 22, 2009. downloaded from http://www.uniprot.org/uniprot/C6R2W3.txt on Jun. 17, 2013.*
Bethune et al., J Pharmacol Exp Ther, 329(2):657-668 (2009). "Interferon-gamma released by gluten-stimulated celiac disease-specific intestinal T cells enhances the transepithelial flux of gluten peptides."
Cerf-Bensussan et al., Gut, 56(2):157-60 (2007). "A new approach to managing coeliac disease."
Gass et al., Gastroenterology, 133(2):472-80 (2007). "Combination enzyme therapy for gastric digestion of dietary gluten in patients with celiac sprue."
Gass et al., Cell Mol Life Sci, 64(3):345-55 (2007). "Prolyl endopeptidases."
Loponen et al., Academic Dissertation, University of Helsinki, Department of Food and Technology, 2006. "Prolamine degradation in sourdoughs."
Shan et al., Biochem J, 383(Pt 2):311-8 (2004). "Comparative biochemical analysis of three bacterial prolyl endopeptidases: implications for coeliac sprue."
Stepniak et al., Am J Physiol Gastrointest Liver Physiol, 291:G621-629 (2006). "Highly efficient gluten degradation with a newly identified prolyl endoprotease: implications for celiac disease."
Davy et al., Plant Physiol, 117:255-261 (1998). "Substrate specificity of barley cysteine endoproteases EP-A and EP-B."
Helmerhorst et al., The Journal of Biological Chemistry, 283(29):19957-19966 (2008). "Identification of Lys-Pro-Gln as a novel cleavage site specificity of saliva-associated proteases."
Helmerhorst et al., PLoS One, 5(10):e13264 (2010). "Discovery of a novel and rich source of gluten-degrading microbial enzymes in the oral cavity."
Tian et al., The Journal of Biological Chemistry, 281(10):6559-6572 (2006). "Determination of the substrate specificity of tripeptidyl-peptidase I using combinatorial peptide libraries and development of improved fluorogenic substrates."
Zamakhchari et al., PLoS ONE, 6(9):e24455 (2011). "Identification of *Rothia* bacteria as gluten-degrading natural colonizers of the upper gastro-intestinal tract."
Alvine Pharmaceuticals, Inc. website, "About Alvine" page. Accessed online on Jul. 7, 2010.
Alvine media release of Oct. 29, 2008, San Carlos, California. Available online at http://www.alvinepharma.com/press-october292008/.
Brown et al., The Australian Coeliac media release, (2008). "Clinical trials of ALV003—what it means for Australian coeliacs?"
De Palma et al., J. Leukoc. Biol., 87:765-778 (2010). "Pivotal Advance: Bifidobacteria and Gram-negative bacteria differentially influence immune responses in the proinflammatory milieu of celiac disease."
Helmerhorst, et al., AADR Annual Meeting, Mar. 3-6, 2010, Washington D.C. "988. The Oral Microflora Contains Gluten-Degrading Microorganisms," presented Mar. 5, 2010.
Lindfors et al., Clinical and Experimental Immunology, 152:552-558 (2008). "Live probiotic *Bifidobacterium lactis* bacteria inhibit the toxic effects induced by wheat gliadin in epithelial cell culture."
Mitea et al., Gut, 57:25-32 (2008). "Efficient degradation of gluten by a prolyl endoprotease in a gastrointestinal model: implications for coeliac disease."
Ou et al., Am J Gastroenterol, 104:3058-3067 (2009). Proximal Small Intestinal Microbiota and Identification of Rod-Shaped Bacteria Associated With Childhood Celiac Disease.

* cited by examiner

*Primary Examiner* — Jon P Weber
*Assistant Examiner* — Paul Martin
(74) *Attorney, Agent, or Firm* — Ronald I. Eisenstein; Nixon Peabody LLP

(57) ABSTRACT

The invention relates to glutamine endopeptidase enzymes from *Rothia* spp. bacteria that are naturally associated with the oral cavity, formulations comprising the glutamine endopeptidase enzymes and the use thereof for the treatment, prevention of allergic reaction and diagnosis of gluten allergy related diseases such as Celiac Sprue, gluten allergy and/or dermatitis herpetiformis.

15 Claims, 36 Drawing Sheets

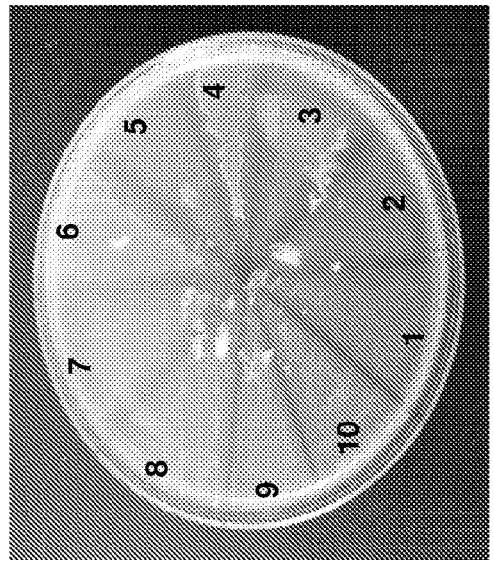

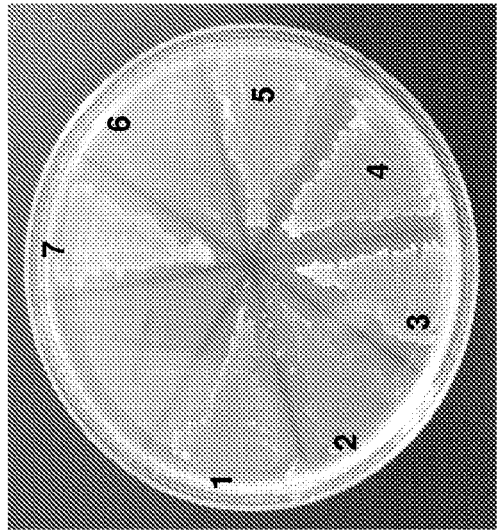

1=WSAN-14 = *Bifidobacterium longum* ATCC 15697
2=WSAN-16 = *Bifidobacterium longum* ATCC 15697
3=WSAN-24 = *Bifidobacterium longum* ATCC 15697
4=WSAN-25 = *Veilonella atypica* ot 524
5=PAN-0   = *Streptococcus pneumoniae* ot 734
6=PAN-5   = *Bifidobacterium dentium* ot 588
7=PAN-8   = *Bifidobacterium dentium* ot 588
8=PAN-18  = *Bifidobacterium dentium* ot 588
9=PAN-19  = *Bifidobacterium dentium* ot 588
10=PAN-23 = *Bifidobacterium dentium* ot 588

1=WSA-2B = *Rothia mucilaginosa* ot 681
2=WSA-7A = *Streptococcus mitis* ot 677
3=WSA-8  = *Rothia* sp. ot 188
4=WSA-10 = *Staphylococcus epidermis* ot 601
5=WSA-26 = *Rothia mucilaginosa* ot 681
6=WSA-27 = Unidentified
7=PA-10  = Unidentified

*FIG. 1*

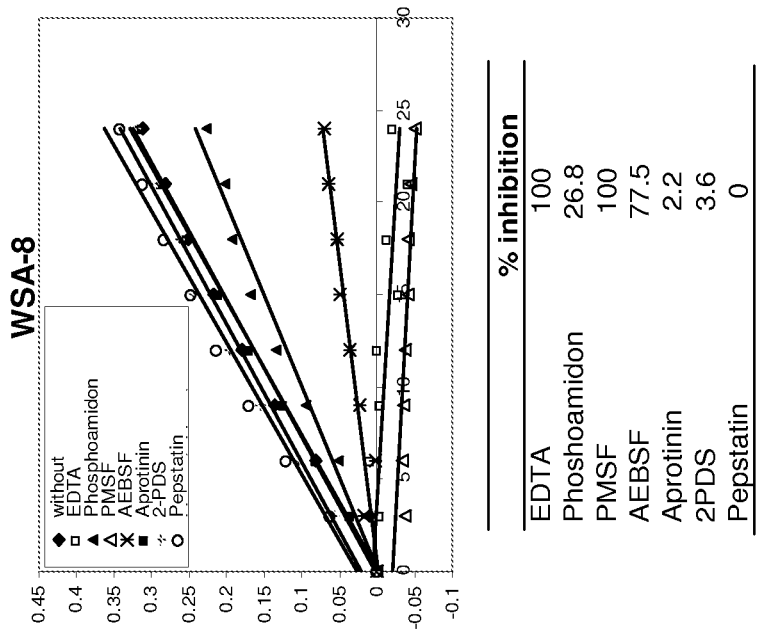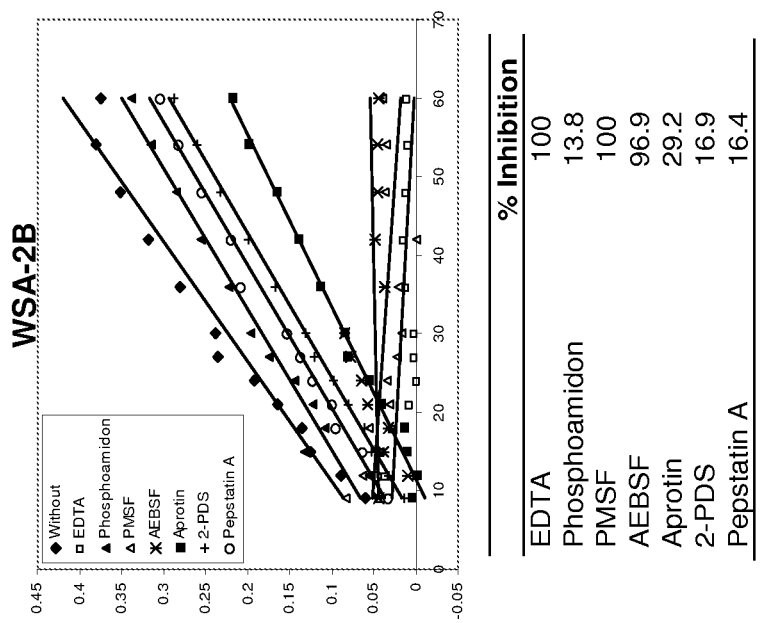
FIG. 7

| | L | Q | L | Q | P | F | P | Q | P | Q | L | P | Y | P | Q | P | Q | L | P | Y | P | Q | P | Q | L | P | Y | P | Q | P | Q | P | F |
|---|---|---|---|---|---|---|---|---|---|---|---|---|---|---|---|---|---|---|---|---|---|---|---|---|---|---|---|---|---|---|---|---|---|
| 33-mer | L | Q | L | Q | P | F | P | Q | P | Q | L | P | Y | P | Q | P | Q | L | P | Y | P | Q | P | Q | L | P | Y | P | Q | P | Q | P | F |
| P1 | | | | | | | | | | | L | P | Y | P | Q | P | Q | | | | | | | | | | | | | | | | |
| P2 | | | | | | | P | Q | P | Q | | | | | | | | | | | | | | | | | | | | | | | |
| P3 | | | | | | | | | | | | | | | | | | | | | | | | | | | | P | Q | P | Q | P | F |
| P4 | | | | | | | P | Q | P | Q | L | P | Y | | | | | | | | | | | | | | | | | | | | |
| P5 | | | | | | | | | | | | | | | | | | | P | Y | P | Q | P | Q | L | P | Y | | | | | | |
| P6 | L | Q | L | Q | P | F | P | Q | P | Q | L | P | Y | P | Q | P | Q | | | | | | | | | | | | | | | | |
| P7 | | | | | | | | | | | | | | | | | | L | P | Y | P | Q | P | Q | L | P | Y | | | | | | |
| P8 | | | | | | | Q | P | Q | L | P | Y | | | | | | | | | | | | | | | | | | | | | |
| P9 | | | | | | | | | | | | | | | | | | L | P | Y | P | Q | P | Q | L | P | Y | | | | | | |
| P10 | L | Q | L | Q | P | F | P | Q | P | Q | | | | | | | | | | | | | | | | | | | | | | | |
| P11 | L | Q | L | Q | P | F | P | Q | P | Q | L | P | Y | | | | | | | | | | | | | | | | | | | | |

| | F | L | Q | P | Q | Q | P | F | P | Q | Q | Q | Y | P | Q | Q | P | F | P | Q |
|---|---|---|---|---|---|---|---|---|---|---|---|---|---|---|---|---|---|---|---|---|
| 26-mer | F | L | Q | P | Q | Q | P | F | P | Q | Q | Q | Y | P | Q | Q | P | F | P | Q |
| P1 | | | Q | P | Q | Q | P | F | P | Q | Q | Q | Y | P | Q | Q | P | F | P | Q |
| P2 | | | | P | Q | Q | P | F | P | Q | Q | Q | Y | P | Q | | | | | |
| P3 | | | Q | P | | Q | P | | P | Q | Q | Q | Y | P | Q | | | | | |
| P4 | | | | | | | | | | Q | Q | Q | Y | P | Q | Q | P | F | P | Q |
| P5 | | | | | | | | | P | Q | Q | Q | Y | P | | | | | | |
| P6 | | | | | | | P | F | P | Q | Q | Q | Y | P | Q | | | | | |
| P7 | | | | | | | | | | Q | Q | Q | P | Y | P | Q | Q | P | F | P | Q |
| P8 | F | L | Q | P | Q | Q | P | F | P | Q | Q | Q | P | Y | P | Q | Q | P | F | P | Q |
| P9 | F | L | Q | P | Q | Q | P | F | P | Q | Q | Q | P | Y | P | Q | Q | P | F | P | Q |
| P10 | F | L | Q | P | Q | Q | P | F | | | | | | Y | P | Q | P | F | P | |

FIG. 15B

>gi|255326510|ref|ZP_05367591.1| neprilysin [*Rothia mucilaginosa* ATCC 25296] (SEQ. ID. NO: 1)

MTTNSGITKEWVDETVKPGDDFFRHVNGKWLATHEIPADRPKDGGLYTLRDNAEKHVRELVEKIAKEQPE

SRIGALYNSFMDVEKIEADGLEPLLKEIAPILNSATPSHLAVTLALLSRAGLPQLFAWYTSNDPKDPKNY

TFFLYQSGLGLPDESYYREEKHEAACAAYVEHIARMFQLTGLAEGFGLTPEQAAQLVFTHESELARLHWN

VVENRDAEATYNPYQATELDEKFPGFPFSQWLLALGADPETLGQVIVAQPSFFEGAAKLFTSIPLMSWKL

WAVWTVLRSRAPFMYDELVQESFNFYGKTLSGTQQIRERWKRGVGAVEKALGEEIGQEYVAVHFPPSHKE

KMLVLVGNLLEAYRESIESLDWMTEATRQKALEKLSKFVTKIGYPDKWRDFSALELVPGDLFENLRRTGA

FDADWLIARKGQPVDKAEWLMTPQTVNAYYMPPANEIVFPAAILQPPYFNPDADDAANYGNIGMIIGHEI

GHGFDDQGSRYDGDGKLESWWTEEDYAKFKERTAALVEQYNAYVPVGLDPKFHVNGELTLGENIGDLAGM

STALKAYRLALKKQGIESLADAPVIDGMTGIQRFFSNARGWCTKSRPQHAEVMISVDPHSPDEFRVNGV

VRNIDEFYEAFGVSEGDALYLAPEERVRIW

*FIG. 18*

| | | |
|---|---|---|
| ZP_05367591 | 1 | MT------------------------------------------T--N------------------SGI-TKEWVDETVKPGDFFRHVNGKWLA-HEIPADRPKDGGLY | 47 |
| YP_003363565 | 1 | MT------------------------------------------T--N------------------SGI-TKEWVDETVKPGDFFRHVNGKWLA-HEIPADRPKDGGLY | 47 |
| ZP_07073157 | 1 | MD-----------------------------------------NAKN------------------SGI-T-EWVDNAVKPGDFFRHVNGKWRLD-YEIPADRSKDGGLY | 49 |
| ZP_06905919 | 1 | MD-----------------------------------------NAKN------------------SGI-T-EWVDNAVKPGDFFRHVNGRWLD-YEIPADRSKDGGLY | 49 |
| YP_003315199 | 1 | MT-----------------------------TNEKNAAQEHDLRPGTTSGI-DVSALDHDVRPQDDLYRHVNGRWIASHVIPADRASDGGFR | 62 |
| YP_003325693 | 1 | MT-------------------------------------------IEALR---------------SGI-DLTALDPATRPQDDLYRHVNG-WIA-HEIPADRSMDGAFM | 50 |
| YP_003636471 | 1 | MT-------------------------------------------R-------------------SGV-PLDDLDPSVRPQDDLDFVNGRWAASYVIPPDRSMDGPFR | 46 |
| ZP_06830706 | 1 | ME------------------------------------------CMT-R----------------SGI-DLTHIDAGTRPQDDLFVHVNGKWLDEYEIPADRAVDGAFR | 49 |
| ZP_07359309 | 1 | MTDACATSP-PTGPASDSPAQHSQPASSSPAADAILAGVLE-AHTDTSVRPQDDLFRFVNGQWLT-AEIPADRPSSGAFT | 80 |
| | | |
| ZP_05367591 | 48 | TLRDNAEKHVRELVEKIAKE-----------------QPES---------RIGALYNSFMDVEKIEADGLEPLLKEIAPILNSATPSHLAVT | 113 |
| YP_003363565 | 48 | TLRDNAEKHVRELVEKIAKE-----------------QPES---------RIGALYNSFMDVEKIEADGLEPLLKEIAPILNSATPSHLAVT | 113 |
| ZP_07073157 | 50 | TLRDDAEKHVREIVERIAKE-----------------QPES---------RIGALYNSFMD-DKIESDGLEPLMREVAPILNAATSDQLAVT | 115 |
| ZP_06905919 | 50 | TLRDDAEKHVREIVERIAKE-----------------QPES---------RIGALYNSFMD-DKIESDGLEPLMREVAPILNAATSEQLAVT | 115 |
| YP_003315199 | 63 | RLHDEAEAHVRQI-EELGGR----------------DDIS-GEEA-QIGALYASFMD-ATVEAAGVDPLAQDLALVSSASTQAEL-GS | 132 |
| YP_003325693 | 51 | KLRDLSEERVRAI-TDLAGS----------------SDTEPGTTAGKIGDIYSSFMD-ARIAALGATPLAADLALIAGATSQAEL-GV | 122 |
| YP_003636471 | 47 | ALYDEAERQVLDI-TDAAQA----------------AGEGDGVEA-KIGALYASFMD-DAVRAAGVEPLREDLALVDAATTPAEL-VA | 117 |
| ZP_06830706 | 50 | TLYDKAEEDVKTL-QE-ASE------------SGAAHGTDAQKIGDLYSSFMDADAVEAAGLSPIAEELAAVANAADLSELAGI | 120 |
| ZP_07359309 | 81 | TLRDESEAACRQIVEELAEQFSSVAPEGAAEVLSTNRGRVGALYQAFMDEAHLEELGAEPLAEELAPVLGASSKEELARA | 160 |
| | | |
| ZP_05367591 | 114 | LAL-SRAGLPQLFAWYTSNDPKDPKNYTFFLYQSGLGLPDESYYREEKHEAACAAYVEHIARMF---------QI-GLAEG | 185 |
| YP_003363565 | 114 | LALLSRAGLPQIFAWYTSNDPKDPKNYTFFLYQSGLGLPDESYYREEKHEAACAAYVEHIARMF---------ELTG-AEG | 185 |
| ZP_07073157 | 116 | LALLSRAGLAQLLGWYTSIDQKDPEHYVFYL-QAGLGLPDEAYYREEKYEQVCAAYIEHIATMF---------ELIGFAES | 187 |
| ZP_06905919 | 116 | LALLSRAGLAQLLGWYTSIDQKDPEHYVFYLTQAGLGLPDEAYYREEKYEQVCAAY-EHIATMF---------ELTGLAES | 187 |
| YP_003315199 | 133 | LGALQRTGGAGAGFWVDNDAKDPEKYVVH-YQAGLGLPDESYYREDKYAETREAYVAHVARMLEISGTVAAEA--------- | 206 |
| YP_003325693 | 123 | LGALQRTGGGGAVGFYVDNDAADPEQYRVL-CQSGLGLPDESYYREEKYREDQYAPIREKYVPHVARMRLGG-----AAELLGV--- | 197 |
| YP_003636471 | 118 | VGR-QRTGALSAVDLYVDNDAKDPDSYVVHLVQGG-GLPDESYYREEQHAAVREKYLPHVARML-RL-----AAPVSGVVAA | 193 |
| ZP_06830706 | 121 | VGRIQRTGVGGGIGQYVDTDAKDSSRYIVHFTQSGIGLPDESYYREDNYAPIRDAYVEHIRKMF---------ELAGI--- | 189 |
| ZP_07359309 | 161 | -GEMTPVGFMGVVGADVEVDINDPERY-SWVGQSGLGLPDESYYREEAQAPLRQAYVEHVARMM---------ALAGITDS | 232 |

*FIG. 19*

```
ZP_05367591   186  FGLTPEQAAQLVFTHESELARLHWNVVENRDAEATYNPYQATELDEKFPGFPFSQWLLALGA------DPEILGQVIV  257
YP_003363565  186  FGLTPEQAAQLVFTHESELARLHWNVVENRDAEATYNPYQATELDEKFPGFPFSQWLLALGA------DPEILGQVIV  257
ZP_07073157   188  FNLTPMEAAQLIFSHETEIAAHHWDVVKNRDAEAKYNPVKATELDEKFPGFPLQQWLLALGA------DPEELGTVIV  259
YP_06905919   188  FNLTPMEAAQLIFSHETEIAAHHWDVVKNRDAEAKYNPVKAPELDEKFPGFPLQQWLLALGA------DPKELGTVIV  259
YP_003315199  207  ---SADAAARVLALETRLATHHWDVVRDRDSELTYNPTTLAALAETAPGFDWRAAWAVALGA------PEGALDDVVV  274
YP_003325693  198  -D--ADDAAARVVALESKLAGHHWDVVKDRDATLTYNPTT-AELAVTAPGFDWQAWAIALGA------PIGALDALVV  266
YP_003636471  194  GD--ADDLAARVVALESRIAAHHWDVVKDRDAELTYNALTLAELAARAPGFDWRAWAEEALGA------PAGALDRLVV  263
ZP_06830706   190  -E--YD--AQRVFDLETAIAGGHWDVVKRDAELGYNLVTLDDLRSQYGGFDWDAWISGLQA------TPEQLAEIVV  256
ZP_07359309   233  FGASGEDLAERVMAVETALAKGHWDRVTCRDVEKMNNPMSWQQIVDSAPDLPWDEWREG-RAAARSAGIEQTAFLEEAIV  312

ZP_05367591   258  AQPSFFEGAAKLFTSIPLMSWKLWAVTV-RSRAPFMYDELVQESFNFYGKTLSGTQQIRERWKRGVGAVEKALGEEIGQ  337
YP_003363565  258  AQPSFFEGAAKLFTSIPLMSWKLWAVTV-RSRAPFMYDELVQESFNFYGKTLSGTQQIRERWKRGVGAVEKALGEEIGQ  337
ZP_07073157   260  SQPSFLEGVANMWQSTPLMTWKLWALWCAIRSRAPYLPDAFVQENFNFYGRTLSGTEELRERWKRGVAAVENALDQELGK  339
YP_06905919   260  SQPSFLEGVASMWQSTPLMTWKLWALWCAIRSRAPYLPDAFVQENFNFYGRTLSGTEELRERWKRGVAAVENALDQELGK  339
YP_003315199  275  REPDEFTGFASLWTSEPLEDWKTWMVYHLVSARAPYLTDELVEANFDFYGRTLSGTQEVRERWKRGVSLVEGALGEAVGK  354
YP_003325693  267  REPSYAEGLAALWQSEPLEDWQVWAAYRLVTARAPYLTDE-VEANFDFYGRTLSGAQEVRERWKRGVALVEGALGEAVGE  346
YP_003636471  264  REPSFAEGLAALWTEVPVADWQAWATYHVVSSRAPYLTDELVEANFDFYGRTLSGAPELRDRWKRGVSLVQDLIGEAVGK  343
ZP_06830706   257  RQPGFVESFTELWTSRPLEDWKAWATWRV-HSRAAFLTEA-VAEDFAFFGTTLSGTQENRERWKRGVSLVESCLGEALGE  336
ZP_07359309   313  TQPDYLPHAAGVWQETDLED-KVWVAWHVVHGRASLLSGAFVEESFDFYGRTLQGTDELRPRWKRGVGLVESCLGEALGE  392

ZP_05367591   338  EYVAVHFPPSHKEKMLVLVGNLLEAYRESIESLDWMTEATRQKALEKLSKFVTK-GYPDKWRDFSALELVPGDLFENLRR  417
YP_003363565  338  EYVAVHFPPSHKEKMLVLVGNLLEAYRESIESLDWMTEATRQKALEKLSKFVTK-GYPDKWRDFSALELAPGDLFENLRR  417
ZP_07073157   340  EYVAVHFPPEHKEKMLKLVNNLLEAYRRSITNLDWMTEATREKALEKLSKFVTK-GYPDEWRDYSKLTLVPGDLFENLRR  419
YP_06905919   340  EYVAVHFPPEHKEKMLKLVNNLLEAYRRSITNLDWMTEATREKALEKLSKFVTK-GYPDEWRDYSKLTLVPGDLFENLRR  419
YP_003315199  355  VYVDRHFPPTHKSRMDVLVANLIEAYRQSITQLDWMGQETKTKALAKLSAFTPKVGYPVRWRDYSALVVDAGDLVGNVRR  434
YP_003325693  347  QYVARHFPPAHKARMDELVANLVAAYRESIEGLDWMTDETKAKALAKLEKFTPK-GYPVKWRDYSALVIDADDLVGNVRR  426
YP_003636471  344  VYVERHFPPSHKERMDELVANLVEAYRRSITELEWMGEETRQRALEKLARFTPK-GYPARWRDYSALEVRADDLVGNVRR  423
ZP_06830706   337  LYVERHFPPESKARMQELVANLQEAYRRNISDLEWMSPATRQAALAKLDKFTPK-GYPDKWRDYSAVEIDPADLVGNYRS  416
ZP_07359309   393  IYVERHFPPSHKSAMEALVGRLIEAYHQSISSLEWMSPATRERALEKLALFTPK-GYPVRWRDYSAVEVVPGDVLASVRS  472
```

*FIG. 19 continued*

```
ZP_05367591    418 TGAFDADWLIARKGQPVDKAEWLMTPQTVNAYYMPPANEIVFPAAILQPPYFNPDADDAANYGNIGMIIGHEIGHGFDDQ 497
YP_003363565   418 TGAFDADWLIARKGQPVDKSEWLMTPQTVNAYYMPPANEIVFPAAILQPPYFNPDADDAANYGNIGMIIGHEIGHGFDDQ 497
ZP_07073157    420 TAAFNSDFMIDRAGDPVDKNEWLMSPQTVNAYYMPPANEIVFPAAILRPPFFDPEADDAANYGGIGMVIGHEIGHGFDDK 499
ZP_06905919    420 AAAFNSDFMIDRAGDPVDKNEWLMSPQTVNAYYMPPANEIVFPAAILRPPFFDPEADDAANYGGIGMVIGHEIGHGFDDK 499
YP_003315199   435 SNSVDLDRELAKIGQPIDRDEWFMTPQTVNAYYNPSMNEIVFPAAILQPPFFDPEAEDAANYGGIGAVIGHEIGHGFDDQ 514
YP_003325693   427 SNAFDLDHELGKVGKPLDRDEWFMTPQTVNAYYNPGMNEIVFPAAILQPPFFDPEADDAVNYGGIGGVIGHEIGHGFDDQ 506
YP_003636471   424 SNAFDLDRELGKIGRPIDRDEWFMTPQTVNAYYNPGMNEIVFPAAILQPPFFDPEAEDAANYGGIGAVIGHEIGHGFDDQ 503
ZP_06830706    417 GFAAEHDRDIAKLGGPVDRDEWFMTPQTVNAYYNPGMNEIVFPAAILQPPFFDPEADDAANYGGIGAVIGHEIGHGFDDQ 496
ZP_07359309    473 VERADMAYSLNKL-KPVDRDEWHMTPQTVNAYYNPTMNEIVFPAAILQPPFFDPQADDAVNYAGIGAVIGHEIGHGFDDQ 552

ZP_05367591    498 GSRYDGDGKLESWWTEEDYAKFKERTAALVEQYNAYVP--------VGLDP-KFH-VNGELTLGEN-GDLAGMSIALKA 566
YP_003363565   498 GSRYDGDGKLESWWTEEDYAKFKERTSALVEQYNAYVP--------VGLDP-KFH-VNGELTLGEN-GDLAGMSIALKA 566
ZP_07073157    500 GAIYDGDGALNNWWTEEDFAEFTKRTSALVQQYNAYTP--------ANLDPQKFQ-VNGELTLGEN-GDLSGLSIAIRA 569
ZP_06905919    500 GAIYDGDGALNNWWTEEDFAEFTKRTSALVQQYNAYTP--------ANLDPQKFR-VNGELTLGEN-GDLSGLSIAIRA 569
YP_003315199   515 GSKYDGAGRLEDWTGSDRAEFEKRTAALIEQYDAFHP---------AQLDADRT--VNGALTIGEN-GDLGGLSIAIKA 583
YP_003325693   507 GSKYDGDGRLQDWTAEDRAEFEKRTGALIAQYDAFVP---------EQLGADGAH-VNGSLTIGEN-GDLGGLSIAIRA 576
YP_003636471   504 GSKYDGDGRLVDWWTAEDRAEFERRTKSLVDQYAQYSP---------RQLG--GSHRVNGELTIGEN-GDLGGLSIAVRA 572
ZP_06830706    497 GAKYDGDGNMVDWWTDDRTEFGKRTKALIEQYNDFEP---------KDL--PGHH-VNGEFTIGEN-GDLGGLSIALEA 564
ZP_07359309    553 GSTFDGTGKVSDWWTQEDREAFTERTSALISQYDAYTPKVVVAKHREAGTAQEEIPHVNGALTIGEN-GDLGGLGIALKA 632

ZP_05367591    567 YRIA---KKQGIESLADAPVIDGMTGIQRFFFSNARGWCTKSRPQHAEVMISVDPHSPDEFRVNGVVRN-DEFYEAFGVS 644
YP_003363565   567 YCIA---KKQGIESLADAPVIDGMTGIQRFFFSNARGWCTKSRPQHAEVMISVDPHSPDEFRVNGVVRN-DEFYEAFGVS 644
ZP_07073157    570 YEIA---AEQGITSLEDAPVIDDMTAAQRLFWS-AQGWRTKSRPQHAEMMISVDPHSPDEFRVNGVVRN-DEFYDAFDVP 647
ZP_06905919    570 YEIA---AEQGITSLEDAPVIDGMTAAQRLFWS-AQGWRTKSRPQHAEMMISVDPHSPDEFRVNGVVRN-DEFYDAFDVP 647
YP_003315199   584 YEIS------G-TDLSAAPSVDGLSGTERVFLSWAQVWQTTMRDEAMVQRLATDPHSPAEFRCNGVVSNLDEFHTTYNVQ 657
YP_003325693   577 YRIA_AAAREG-ATLDDAPVIDGLTGLERVFLGWAQVWQSKGRDEEVIRRLATDPHSPNEFRCNGIVRNVDEFHDAYGVR 655
YP_003636471   573 YEIA------G-HPLDEAPVLDGYTGLQRLFMGWAHSWRTKGRDEEVIRRLATDPHSPPEFRCNGVIRNLDSFHDAFDVQ 646
ZP_06830706    565 YRI----ATEG-T----EAPVLDELDGLQRVFFGWAQVWRTKARKEEALRRLAVDPHSPPEFRCNGVIRNLDSFHDAFDVQ 636
ZP_07359309    633 YSIA---ADAGIPSVDEAPVIDGLTGLQRFFYSWARIWRSKSRPDYAELLLTVDPHSPAEFRCNGIVRNVDAFYKAFAVD 710
```

*FIG. 19 continued*

| | | | |
|---|---|---|---|
| ZP_05367591 | 645 | EGDALYLAPEERVRIW | 660 |
| YP_003363565 | 645 | EGDALYLAPEERMRIW | 660 |
| ZP_07073157 | 648 | EGSKLYLAPEDRVRIW | 663 |
| ZP_06905919 | 648 | EGSKLYLAPEDRVRIW | 663 |
| YP_003315199 | 658 | PGDALYLAPEDRVRIW | 673 |
| YP_003325693 | 656 | EGDALWLAPEDRVRIW | 671 |
| YP_003636471 | 647 | PDDALWLDPEQRVRIW | 662 |
| ZP_06830706 | 637 | PGDALYLEPEKRVKIW | 652 |
| ZP_07359309 | 711 | SDDALWLPPNERVSIW | 726 |

FIG. 19 continued

```
ZP_05367591   1    M--------- ---------- ---------- ----TTNSGI TKEWVDETVK
YP_003363565  1    M--------- ---------- ---------- ----TTNSGI TKEWVDETVK
YP_003325693  1    MTI------- ---------- ---------- ---EALRSGI DLTALDPATR
YP_003636471  1    m--------- ---------- ---------- -----TRSGV PLDDLDPSVR
ZP_07359309.  1    mtdacatspt ptgpasdspa qhsqpaSSSP AADAILAGVL ETAHTDTSVR
YP_003275516  1    mtasdtTL-- ---------- ---------- -NSSSRNSGL DLEWVDDSVR
YP_001131754  1    M-TVEA---- ---------- ---------- TSDTSAKSGI DLRYVDADAR
YP_003379113  1    ---------- ---------- ---------- -----MTAGI DITGLSTTVR
 YP_951040.1  1    M-TVEA---- ---------- ---------- --TRNLKSGI DLRYVDTDAR
YP_002882628  1    mtTTEA---- ---------- ---------- --APSPAADD PTAAADPAVR
ZP_04382847.  1    ---------- ---------- ---------- -MTAHRSGI DLTHLDGDTR
 YP_705057.1  1    M-----ER-- ---------- ---------- -MTAQRSGI DLTHLDNDTR
YP_003199539  1    m--------- ---------- ------TASP AADVI----- -------VPR
ZP_06184089.  1    MTK------- ---------- ---------- ---NPLLGAL DPNEFDNNIR
YP_003645328  1    M--------- ---------- ---------- ----TSEPAL DLSFVDPDIR
ZP_03393889.  1    m--------- ---------- ---------- TNSTDTETQS ATSQFSTTPR
YP_002322079  1    M-----TN-- ---------- ---------- -ETETLTSGI DPASFSSVIK ZP_05367591   18   PGDDFFRHVN GKWLATHEIP ADRPKDGGLY TLRDNAEKHV RELVEKIAK-
YP_003363565  18   PGDDFFRHVN GKWLATHEIP ADRPKDGGLY TLRDNAEKHV RELVEKIAK-
YP_003325693  21   PQDDLYRHVN GTWIATHEIP ADRSMDGAFM KLRDLSEERV RAIITDLAG-
YP_003636471  17   PQDDLDLFVN GRWAASYVIP PDRSMDGPFR ALYDEAERQV LDIITDAAQ-
ZP_07359309.  51   PQDDLFRFVN GQWLTTAEIP ADRPSSGAFT TLRDESEAAC RQIVEELAE-
YP_003275516  28   VQDDLFAHVN GKWLERHVIP EDRAIDGAFH VLRDRAEENV RDIITECAE-
YP_001131754  26   PQDDLFGHVN GRWLAEYQIP GDRATDGAFR TLYDRAEEQI RDLITEAAS-
YP_003379113  16   PQDDLYRHAN GRWLDEHEIP ADKAIYGAFH ALGDTAELNV RSIVERTLD-
 YP_951040.1  24   PQDDLFGHVN GRWLAEYQIP ADRATDGAFR TLHDRAEEQI RDLITEVAG-
YP_002882628  25   PQDDLYRHVN GTWLRTHEIP ADRARDGVVF DLRDQAELDV RAIVEESGAg
ZP_04382847.  20   AQDDLFVHVN GKWLAEYEIP ADRAVDGAFR TLYDKAEEDV QTIITEAAE-
 YP_705057.1  23   AQDDLFVHVN GKWIDDYEIP ADRAIDGAFR TLYDKAEVDV QTIIEEAAD-
YP_003199539  14   PQDDLFRHVN GPWLATAEIP ADRSADGAFY QLRDEAEKDS RAIIEDAAA-
ZP_06184089.  21   PQDDLYRFVN GKWIEACQIP ADKSADGSFY VLTENSEKQV RAIIEDCVE-
YP_003645328  18   VQDDLFGHVN GKWLDGHEIP ADRSSDGAFY ALRDAAELHV KEIVEEAAA-
ZP_03393889.  22   PQDDLYLAIN GEWISNHVIP ADRPIDGAFY KLRDEAEENV RELITTAAD-
YP_002322079  23   PTNDLFRYVN GPWIDTYRLP DDRSRYGSFD KLAEDAENQV RDILDa----

ZP_05367591   67   E--QPES--- ---------R ---------I GALYNSFMDV EKIEADGLEP
YP_003363565  67   E--QPES--- ---------R ---------I GALYNSFMDV EKIEADGLEP
YP_003325693  70   SSD-TEP--- ----GTTAGK ---------I GDLYSSFMDT ARIAALGATP
YP_003636471  66   A--AGEG--- ----DGVE-- -------AKI GALYASFMDT DAVRAAGVEP
ZP_07359309.  100  Qfssvapega aevlSTNRGR ---------V GALYQAFMDE AHLEELGAEP
YP_003275516  77   S--SPPS--- ----GSDALK ---------I GDLFASFMDT DHIDALGIGP
YP_001131754  75   A--HAAE--- ----GTDQQR ---------I GDLYASFMDE QTVRDRGLAP
YP_003379113  65   A--GHPE--- ----GSEARK ---------I ADLYRSFLDE DTVERLGADP
 YP_951040.1  73   S--GAAR--- ----GTDEQR ssgsidaSRI GDLYASFMDE DTVRARGLTP
YP_002882628  75   TLD-APD--- ----ADEARK ---------I AALYRSFMDT EAIEAAGVAP
ZP_04382847.  69   S--NSAA--- ----GTDAQR ---------I GDLYSSFMDA DAVEAAGLGP
 YP_705057.1  72   S--GAAP--- ----GTDAQR ---------I GDLYGSFMDA DVVEAAGLAP
YP_003199539  63   AADGAEP--- ----GSPVQL ---------I GDLYRSFMDV EAVERQGLAP
ZP_06184089.  70   G--KIAG--- ----E-LAGK ---------V AALYGSFMDE AQVEADSAPS
YP_003645328  67   D--AAAT--- ----G-DAAK ---------I GDLYSSFMDT AAIEAAGVAP
ZP_03393889.  71   A--DPNS--- ---------R ---------V ARLYNSFMDE AAINDAGAAP
YP_002322079  69   ------D--- ----DCPATK ---------S QALYHSFLNT DAIEAAGLDP
```

*FIG. 20*

```
ZP_05367591    94  LLKEIAPILN SATPSHLAVT LA-LLSRAGL PQLFAWYTSN DPKDPKNYTF
YP_003363565   94  LLKEIAPILN SATPSHLAVT LA-LLSRAGL PQLFAWYTSN DPKDPKNYTF
YP_003325693  103  LAADLALIAG ATSQAELTGV LG-ALQRTGG GGAVGFYVDN DAADPEQYRV
YP_003636471   98  LREDLALVDA ATTPAELTVA VG-RLQRTGA LSAVDLYVDN DAKDPDSYVV
ZP_07359309   141  LAEELAPVLG ASSKEELARA LG-EMTPVGF MGVVGADVEV DINDPERYTS
YP_003275516  109  IRGELDKIAG IDSTIALARR MG-RLTRHGV GGLFGFYVDT DARQSDRYLV
YP_001131754  107  LLDELGAIDA AGSPDALAEV LG-SLQRTGI GGATGLYVDT DSKNSTRYLL
YP_003379113   97  IADQLALAGS IEDRDALVAA LG-TLELQGV GGIFHYWVDV DEKKSDQYVV
 YP_951040.1  114  LRDELAAVDA ADTPEALARV LG-ALQRVGV GGGTGLYVDT DSKNSSRYLL
YP_002882628  108  LAPDLALIEN ATDRSALARA MG-TLQRTGV GGALGMWVDT DADDPTAYRA
ZP_04382847.  101  IDDELDAVAD APDRSSLATV IG-RHQRVGV GGAISHYVDT DAKNSERYLI
 YP_705057.1  104  IAGELADVAS AADLSALAAV IG-RQQRTGV GGAVGHYVDT DAKNSERYLV
YP_003199539   97  IAARLTEVEG VDSPAALMRT LG-RLRRSGV GGAFAIDVDT DPGDPDRYVL
ZP_06184089.  101  LERLFGPLRT AKTKGDlrdl wakTWKMGTY DGFFSMGIDI DLNNPDCYIN
YP_003645328   98  VADELAEIRW ADSAIDLATV LG-RLQRTGV GGLLGYYVDT DAKRSDRYLV
ZP_03393889.   98  LAQDLEMIAS AENAHELALA LG-RLDRLGV GGALGYWVEK DSG-SDLDAL
YP_002322079   97  IRDELDLIDS AIDKAALTRV LG-TINPAGG PDLFGLAVYG DPGDPDRNIA ZP_05367591   143  FLYQSGLGLP DESYYREEK- ----HEAACA AYVEHIARMF QLT-----GL
YP_003363565  143  FLYQSGLGLP DESYYREEK- ----HEAACA AYVEHIARMF ELT-----GL
YP_003325693  152  YLCQSGLGLP DEAYYREDQ- ----YAPIRE KYVPHVARML RLG-------
YP_003636471  147  HLVQGGLGLP DEAYYREEQ- ----HAAVRE KYLPHVARML RLA-----AP
ZP_07359309.  190  WVGQSGLGLP DESYYREEA- ----QAPLRQ AYVEHVARMM ALA-------
YP_003275516  158  HIVQSGLGLP DESYYHPDAd gndiHAETRA AYAAHVERMF ALA-------
YP_001131754  156  HLTQSGIGLP DESYFREEQ- ----HAEILA AYPGHIAAMF GLV-------
YP_003379113  146  YLTQGGLSLP DESYYRDDA- ----FQEQRT AYVAHVARML GLA-------
 YP_951040.1  163  HLSQSGIGLP DESYFREER- ----HAEILA AYPGHIAAMF GLV-------
YP_002882628  157  YLYQSGLGLP DESYYRSEE- ----QATTRE AYVAHVARML RLA-------
ZP_04382847.  150  HFSQSGISLP DESYYREDN- ----YAEIRE KYVAHIDKMF ILA-------
 YP_705057.1  153  HFSQSGIGLP DESYYRQDD- ----HAEIRA AYVKHIAKMF ALA-------
YP_003199539  146  NLYQGGIGLP DESYYSDAA- ----HADVLS AYAAFLPSIL ELA-------
ZP_06184089.  151  YFSQDGIGLP ERAYFLEEK- ----HREVLQ AYREHVGRMF SLS-------
YP_003645328  147  QVTQSGISLP DEAYYRDEQ- ----YAPLRA KFTAHVADTF RLAtrlapAL
ZP_03393889.  146  YLLQSGLGLP DEAYYRESG- ----HADTLA AYEQHVAAML KLL-------
YP_002322079  146  HLEQAGLCLP DEAYYREDH- ----YVPVRE AYVAMVATQL VNA-------

ZP_05367591   183  AEG----FGL ---------- ----IPE--- ---------- ----------
YP_003363565  183  AEG----FGL ---------- ----IPE--- ---------- ----------
YP_003325693  190  --GAAELLGV ---------- ----DAD--- ---------- ----------
YP_003636471  187  VSGVV-A-AG ---------- ----DAD--- ---------- ----------
ZP_07359309.  228  --GLIDSFGA ---------- ----SGE--- ---------- ----------
YP_003275516  201  --G-----FD ---------- ----APA--- ---------- ----------
YP_001131754  194  --LGG-D-PG ---------- ----EHA--- ---------- ----------
YP_003379113  184  --G-----LA ---------- ----DAE--- ---------- ----------
 YP_951040.1  201  --YGG-D-PD ---------- ----DHA--- ---------- ----------
YP_002882628  195  --GVA-A-DA ---------- ----EAD--- ---------- ----------
ZP_04382847.  188  --G-----VG ---------- ----YD---- ---------- ----------
 YP_705057.1  191  --G-----VD ---------- ----YD---- ---------- ----------
YP_003199539  184  --G-----IP ---------- ----ESA--- ---------- ----------
ZP_06184089.  189  --GFMSS-ES ---------- ----QSQ--- ---------- ----------
YP_003645328  192  LEGIV-T-AG ---------- ----EED--- ---------- ----------
ZP_03393889.  184  --SSH-D-DG agdlstalaa felvDPA--- ---------- ----------
YP_002322079  184  --GYA-P-AA ---------- ----ESNggd elpantgdde snapttvpse
```

*FIG. 20 continued*

```
ZP_05367591  192  ---QAAQLVF THESELARLH WNVVENRDAE ATYNPYQATE LDEKFPGFP-
YP_003363565 192  ---QAAQLVF THESELARLH WNVVENRDAE ATYNPYQATE LDEKFPGFP-
YP_003325693 201  ---DAAARVV ALESKLAGHH WDVVKDRDAT LTYNPTTIAE LAVTAPGFD-
YP_003636471 198  ---DLAARVV ALESRIAAHH WDVVKDRDAE LTYNALTLAE LAARAPGFD-
ZP_07359309. 239  ---DLAERVM AVETALAKGH WDRVTCRDVE KMNNPMSWQQ IVDSAPDLP-
YP_003275516 207  ---DRAATVL DLETAIAEHH WDVVARRDAE RTYNLMSLAE FESAAAGFD-
YP_001131754 203  ---ATAQRIV ALETKLAAAH WDVVKRRDAD LTYNLRTFAE LTDESPGFD-
YP_003379113 190  ---GAAERIL ALETRLAAGH WDVVKNRDVT ATYNKFDRAR LDALMPGFD-
 YP_951040.1 210  ---ATADRIV ALETKIAAAH WDVVKRRDAD LTYNLRTFAE VTDQAPGFD-
YP_002882628 204  ---AVAGRIM DLETRLAAAH WDRVRDRDAV ATHNPTAWAE LADVARGFD-
ZP_04382847. 193  -----AQRVF ELEKKIAAGH WDVVKRRDAD LSYNLVGFEE LTEQNPGLD-
 YP_705057.1 196  -----AQRVF DLETKIAAGH WDVVKRRDAE LSYNLLTLDQ LPA---GLD-
YP_003199539 190  ---GAGAAVV ELETAVAAGH WDRVRSRDSS QTYNPKDRAG LDALLPGPL-
ZP_06184089. 199  ---AAGNTVV DFETEIARLH WDNVKTRDTD ATNNPMTWAE LAAKLPVFD-
YP_003645328 203  ---AAAASVL DLETAIAAGH WNVVDRRDAD KSYNLRTFAD LGTEAPALQl
ZP_03393889. 207  ---AAAARIV AFEKRIAAGH WNVVDTRDAL KTYNKTAIAD LPTGFPVAE-
YP_002322079 216  aalDMARHFL AVETKIAANH WDNVATRDSV KTYNPTDYAD LAATLKNFD- ZP_05367591  238  --FSQWLLAL G-ADPET--- ---------- -L-------- GQVIVAQPSF
YP_003363565 238  --FSQWLLAL G-ADPET--- ---------- -L-------- GQVIVAQPSF
YP_003325693 247  --WQAWAIAL G-APTGA--- ---------- -L-------- DALVVREPSY
YP_003636471 244  --WRAWAEAL G-APAGA--- ---------- -L-------- DRLVVREPSF
ZP_07359309. 285  --WDEWREGI R-AAARS--- ---------- -Agieqtafl EEAIVTQPDY
YP_003275516 253  --LGEWFGGL GtVGDAT--- ---------- -F-------- AEVVVGQPSF
YP_001131754 249  --WTRWLGGL G-ADRDK--- ---------- -A-------- ADVVVRQPDY
YP_003379113 236  --WSRWLPNA G-VPESA--- ---------- -F-------- EQVVVRQPDY
 YP_951040.1 256  --WPGWLAGL G-GTAEQ--- ---------- -A-------- AEVVVRQPDY
YP_002882628 250  --ADAWAEGL R-VPADA--- ---------- -F-------- DVVVLREPSF
ZP_04382847. 237  --WAAWLSGL G-ADSEK--- ---------- -F-------- AEIVVRQPDF
 YP_705057.1 237  --WSSWIGAL G-GTSEQ--- ---------- -F-------- AEIVVRQPDF
YP_003199539 236  --WDAWLDGL G-ADPSV--- ---------- -L-------- DQVVVRQPDY
ZP_06184089. 245  --LDAWRAAS R-LPEKM--- ---------- -F-------- TQVNVGMPDF
YP_003645328 250  raWTAALTAA E-AFAEV--- ---------- -F-------- AEVNVRQPSF
ZP_03393889. 253  --WLAATGVN E-TNQTA--- ---------- -I-------- DTIVVMMPSY
YP_002322079 265  --LASWIDAW Q-TAYDAtea akaqsidfks vF-------- ARIIVHEPSF ZP_05367591  263  FEGAAKLFTS IPLMSWKLWA VWTVLRSRAP FMYDELVQES FNFYGKTLSG
YP_003363565 263  FEGAAKLFTS IPLMSWKLWA VWTVLRSRAP FMYDELVQES FNFYGKTLSG
YP_003325693 272  AEGLAALWQS EPLEDWQVWA AYRLVTARAP YLTDEIVEAN FDFYGRTLSG
YP_003636471 269  AEGLAALWTE VPVADWQAWA TYHVVSSRAP YLTDELVEAN FDFYGRTLSG
ZP_07359309. 318  LPHAAGVWQE TDLEDLKVVV AWHVVHGRAS LLSGAFVEES FDFYGRTLQG
YP_003275516 279  VSGAAGLIAS RPLDDWKTWL AWRLLRSAAP YLSSEFVEEN FDFYGRTLSG
YP_001131754 274  LTAFASLWSG SSLEDWKDWL RWRVIHGRAF LLTDELIAED FSFYGKRLSG
YP_003379113 261  FTSAAEALQE LELDHWKEWL SWRIVHSAAP LLSSAFVAEN FEFYGRTLTG
 YP_951040.1 281  LTAFAGLWAD ESLEDWKNWL RWRVIHARAF LLTDELIAED FSFYGRRLSG
YP_002882628 275  FAALGEAWTD VPLEQWREWL TWRVVRSRAP YLTDEIVTAN FDFYGRTLTG
ZP_04382847. 262  LRTFTALWAS ESLDDWKAWA AWKVLHARSP YLHSALVDET FAFYGTTLSG
 YP_705057.1 262  LTTLTELWTS EDIDDWKAWA TWNVIRSRAP YLTQALVDEN FAFYGKTLTG
YP_003199539 261  FTALAALLTP DHLPAWRAWL SWQIVRSLAP LGPAELVEKN FDFYGRTLSG
ZP_06184089. 270  FAGMDQLWAE TDFETLRLWM TWQALNGQVS LLSNALVQAN FEFYGKRLAG
YP_003645328 277  VTHAAALLSD RPLAQWRTWL AWRVLRARSP YLSDELVAAN FAFYGTALTG
ZP_03393889. 278  FEHLSKLWQD TDLADLRLWA LWRVLHQRAA YLSDDFSAES FNFYGRTLQG
YP_002322079 304  LTGLDAFWAE ADLADLKLWA RVHMILGFAS SLSRDFDTTN FDFYGKVLSG
```

FIG. 20 continued

```
ZP_05367591  313  TQQIRERWKR GVGAVEKALG EEIGQEYVAV HFPPSHKEKM LVLVGNLLEA
YP_003363565 313  TQQIRERWKR GVGAVEKALG EEIGQEYVAV HFPPSHKEKM LVLVGNLLEA
YP_003325693 322  AQEVRERWKR GVALVEGALG EAVGEQYVAR HFPPAHKARM DELVANLVAA
YP_003636471 319  APELRDRWKR GVSLVQGALG EAVGKVYVER HFPPSHKERM DELVANLVEA
ZP_07359309. 368  TDELRPRWKR GVGLVESCLG EALGEIYVER HFPPSHKSAM EALVGRLIEA
YP_003275516 329  AQTNRDRWKR GVSFVEGAMG FAVGKLYVDK HFPPEAKARM DELIANLVAA
YP_001131754 324  TEEIRDRWKR GVSVVEALMG EALGKLYVER HFPPQAKARM DELVANLREA
YP_003379113 311  APELRERWKR GLGVVGSALG EAVGQLYVAE FFPPVAKARM VELVGNLVEA
 YP_951040.1 331  TEEIRERWKR GVSVVESLMG EALGRLYVER HFPPHAKARM DELVDNLREA
YP_002882628 325  AQELRERWKR GVALVEGALG EAVGRIYVQR HFPPTHKARM DTLVANLVEA
ZP_04382847. 312  TEENRERWKR GVSLVQDLLG EAVGKLYVDR HFPAEAKTRM LELVANLQEA
 YP_705057.1 312  AEEIRERWKR GVSLVQDLLG EAVGKLYVER HFPADAKARM QELVANLQEA
YP_003199539 311  TPELRERWKR GVGFVEMAAN EAVGRLYVER HFPPESKRRM DELVANLLAA
ZP_06184089. 320  REVIRDRWKR GVSLASSVMG EALGQLYVAR HFPPDSKEKM SRLVDNLIAA
YP_003645328 327  ATENRERWKR GVGLVEEHLG FAVGELYTAR HFPADSKARM QALVADLVEA
ZP_03393889. 328  STEQRARWKR GVAFADGAVG HDVGKLYVEK HFPPEYKEQV LELVDYLLAA
YP_002322079 354  AKKQRDRWKR AVSLVNGVCG EDVGREYARL HFPESSKRRM EELVANLIDA

ZP_05367591  363  YRESIESLDW MTEATRQKAL EKLSKFVTKI GYPDKWRDFS ALELVPGDLF
YP_003363565 363  YRESIESLDW MTEATRQKAL EKLSKFVTKI GYPDKWRDFS ALELAPGDLF
YP_003325693 372  YRESIEGLDW MTDETKAKAL AKLEKFTPKI GYPVKWRDYS ALVIDADDLV
YP_003636471 369  YRRSITELEW MGEETRQRAL EKLARFTPKI GYPARWRDYS ALEVRADDLV
ZP_07359309. 418  YHQSISSLEW MSPATRERAL EKLALFTPKI GYPVRWRDYS AVEVVPGDVL
YP_003275516 379  YRRNITDLEW MTPETRTKAL AKLDKFTPKI GYPATWRDYG ALIVDRGDLI
YP_001131754 374  YRVSINTLDW MTPQTREKAL VKLDKFTPKI GYPNTWRDYS ALVIERDDLY
YP_003379113 361  YRQRIEALDW MSPETRQRAL DKLGRFTPKI GYPDKWRDYS ALEVAPDDLV
 YP_951040.1 381  YRVSINSLDW MTPQTREKAL VKLDKFTPKI GYPNKWRDYS ALVIARDDLY
YP_002882628 375  YRRSITSLDW MGPDTRERAL AKLAAFTPKI GYPVRWRDYS SLELVPGDVV
ZP_04382847. 362  YRRNISDLEW MSPQTREAAL AKLEKFTPKI GYPDKWRDYA GLEISATDLV
 YP_705057.1 362  YRRNISDLDW MSPETRQAAL RKLEKFTPKI GYPDKWRDYS AVTISRDDLV
YP_003199539 361  YRTEIGKLPW MGEQTRARAL EKLDAFTPKI GYPARWRDYT ALTVAADDLI
ZP_06184089. 370  YRESISSLEW MGSETRAKAL EKLSLFTPKI GYPDKWRNYE KLDVSAPTLV
YP_003645328 377  YRRRIVELPW MTPATRERAL EKLGKFTPKI GYPDAARDYS SLQIQRDDLL
ZP_03393889. 378  YRERISQLPW MTKATQERAL EKLSLFKAKI GYPERWRDYS AMELg-GSLM
YP_002322079 404  YRVSIANSDW LGEDTKAKAL EKISKFTPKI GYTNHWRDYS ALSVSADALP

ZP_05367591  413  ENLRRTG-AF DADWLIARKG QPVDKAEWLM TPQTVNAYYM PPANEIVFPA
YP_003363565 413  ENLRRTG-AF DADWLIARKG QPVDKSEWLM TPQTVNAYYM PPANEIVFPA
YP_003325693 422  GNVRRSN-AF DLDHELGKVG KPLDRDEWFM TPQTVNAYYN PGMNEIVFPA
YP_003636471 419  GNVRRSN-AF DLDRELGKIG RPIDRDEWFM TPQTVNAYYN PGMNEIVFPA
ZP_07359309. 468  ASVRSVE-RA DMAYSLNKLT KPVDRDEWHM TPQTVNAYYN PTMNEIVFPA
YP_003275516 429  GNVARAS-SF EQEREFAKIG APVDRDEWFM TPQTVNAYYN PGMNEIVFPA
YP_001131754 424  GNYRRGY-AL EYDRDLAKLG GPVDRDEWFM TPQTVNAYYN PGMNEIVFPA
YP_003379113 411  GNVRRSV-AV ETARELAKLG GPVDRTEWQM TPQTVNAYYN PAMNEIVFPA
 YP_951040.1 431  GNYQRGY-AL EYDRDLAKLG GPVDRDEWFM TPQTVNAYYN PGMNEIVFPA
YP_002882628 425  ANVRAAS-TY ELDRDLAKIG RPVDRDEWFM PPQTVNAYYN PGMNEVVFPA
ZP_04382847. 412  GNYRRGY-AA EYDRDLAKLG GPVDRDEWFM TPQTVNAYYN PGMNEIVFPA
 YP_705057.1 412  GNYRSGY-AA EYDRDLAKLG GPVDRDEWFM TPQTVNAYYN PGMNEIVFPA
YP_003199539 411  GNAARAA-AF ELDRELGKLG GPVDRDEWFM SPQTVNAYYN PGMNEIVFPA
ZP_06184089. 420  EKVASAS-QF GTDFWIDKLG GPVDHTIWHM TPQTVNAYYN PTDNEIVFPA
YP_003645328 427  GNVRRGN-AA EHDREFAKIG APVDRDEWFM TPQTVNAYYN PGMNEIVFPA
ZP_03393889. 427  DNARAAS-AF AHDYEVAKLG TPANRDEWHG TPQTVNAFYN PVVNDITFPA
YP_002322079 454  AENAKAAnLY ETGYQLAKVG KAVDKDEWLM NPQTVNAYYE PSMNVIVFPA
```

FIG. 20 continued

```
ZP_05367591  462  AILQPPYFNP DADDAANYGN IGMIIGHEIG HGFDDQGSRY DGDGKLESWW
YP_003363565 462  AILQPPYFNP DADDAANYGN IGMIIGHEIG HGFDDQGSRY DGDGKLESWW
YP_003325693 471  AILQPPFFDP EADDAVNYGG IGGVIGHEIG HGFDDQGSKY DGDGRLQDWW
YP_003636471 468  AILQPPFFDA EADDAANYGG IGAVIGHEIG HGFDDQGSKY DGDGRLVDWW
ZP_07359309. 517  AILQPPFFDP QADDAVNYAG IGAVIGHEIG HGFDDQGSTF DGTGKVSDWW
YP_003275516 478  AILQPPFFDP DADDAANYGG IGAVIGHEIG HGFDDQGAKY DGDGNLVNWW
YP_001131754 473  AILQPPFFDA DADDAANYGG IGAVIGHEIG HGFDDQGAKY DGDGNLVDWW
YP_003379113 460  AILQPPFFAL DADDALNYGA IGAVIGHEIG HGFDDQGSRY DGDGNISDWW
 YP_951040.1 480  AILQPPFFDA DADDAANYGG IGAVIGHEIG HGFDDQGAKY DGDGNLVNWW
YP_002882628 474  AILQPPFFDP DAADAANYGS IGAVIGHEIG HGFDDQGSRY DGDGRLADWW
ZP_04382847. 461  AILQPPFFDA AADDAANYGG IGAVIGHEIG HGFDDQGAKY DGDGNMVDWW
 YP_705057.1 461  AILQPPFFDA AADDAANYGG IGAVIGHEIG HGFDDQGAKY DGDGNMVDWW
YP_003199539 460  AILQPPFFDP EADDAVNYGV IGAVIGHEIG HGFDDQGSKY DGRGALQDWW
ZP_06184089. 469  GILQPPFFDP QADDAVNYGS IGAVIGHEIG HGFDDQGAKF DGHGKVENWW
YP_003645328 476  AILQPPFFAP TADDAVNFGG IGAVIGHEIG HGFDDQGAKY DGDGNLEDWW
ZP_03393889. 476  AILQPPFFSP DASPAENFGG IGAVIGHEIG HGFDDQGSQY DGHGNLHQWW
YP_002322079 504  AILQPPFFDP KAEDAANYGG IGAVIGHEIG HGFDDQGSQY DGDGKLNNWW

ZP_05367591  512  TEEDYAKFKE RTAALVEQYN AYVPVGLD-- PK-------- FH--------
YP_003363565 512  TEEDYAKFKE RTSALVEQYN AYVPVGLD-- PK-------- FH--------
YP_003325693 521  TAEDRAEFEK RTGALIAQYD AFVPEQLGAD G--------- AH--------
YP_003636471 518  TAEDRAEFER RTKSLVDQYA QYSPRQLG-- GS-------- HR--------
ZP_07359309. 567  TQEDREAFTE RTSALISQYD AYTPKVVV-- AK-------- HReagtaqeE
YP_003275516 528  SDADREEFSS RTAKLIEQYG EFTPEGLD-- PK-------- YK--------
YP_001131754 523  TDEDRAEFGK RTTALIEQYE QFTPRGLE-- PS-------- HH--------
YP_003379113 510  TDEDRAAFEV RANRLVEQYD ALEPAEAP-- G--------- QH--------
 YP_951040.1 530  TDQDRDEFGL RTKALIEQYE ELVPRGLE-- PS-------- HH--------
YP_002882628 524  TPEDRAEFET RTAALVAQYD AFSPAQLD-- GS-------- RH--------
ZP_04382847. 511  TDEDRSEFGK RTKALIEQYN EFPKELP-- G--------- HH--------
 YP_705057.1 511  TDDDRTEFGK RTKALIEQYN EFPKALP-- G--------- HN--------
YP_003199539 510  TPADRAAFEQ LTGRLIDQYS ALEPKNTP-- G--------- HH--------
ZP_06184089. 519  TETDLKEFEK RTRALIAQYD QYVPRGLP-- EE-------- FH--------
YP_003645328 526  TDTDREEFGK RTRALIEQYD ELTPRELGAD SE-------- HH--------
ZP_03393889. 526  TDEDRAAFEK LTSALVDQYE GLVPQALR-- EQaeega--- ---------D
YP_002322079 554  TDEDRKNFEA RTGALIAQYN SFVPLQLA-- EKyadesdka PH--------

ZP_05367591  544  ---VNGELTL GENIGDLAGM SIALKAYRLA L-----KKQG IE--------
YP_003363565 544  ---VNGELTL GENIGDLAGM SIALKAYCLA L-----KKQG IE--------
YP_003325693 554  ---VNGSLTI GENIGDLGGL SIAIRAYRIA LAAAREG--- ----------
YP_003636471 550  ---VNGELTI GENIGDLGGL SIAVRAYEIA L-----G--- ----------
ZP_07359309. 607  IPHVNGALTI GENIGDLGGL GIALKAYSLA LADA-----G IP--------
YP_003275516 560  ---VNGGFTI GENIGDLGGL SIALVAYQLA T-----EG-- ----------
YP_001131754 555  ---VNGAFTV GENIGDLGGL SIALLAYRLS L-----KG-- ----------
YP_003379113 541  ---VNGALTL GENIGDLGGL SIAYTAYEIS L-----AG-- ----------
 YP_951040.1 562  ---VNGAFTV GENIGDLGGL SIALLAYRLS L-----KG-- ----------
YP_002882628 556  ---VSGGLTV GENIGDLGGL AIAVDAYEIA L-----GR-- ----------
ZP_04382847. 542  ---VNGEFTI GENIGDLGGL SIAIAAYKIA T-----EG-- ----------
 YP_705057.1 542  ---VNGEFTI GENIGDLGGL SIAIAAYRIA T-----EG-- ----------
YP_003199539 541  ---VNGALTI GENIGDVGGL GIAYQAWRIS L-----GD-- ----------
ZP_06184089. 551  ---VNGALTI GENIGDLGGL DIAWKAYLLA L-----KDQG IN--------
YP_003645328 560  ---VNGGFTV GENIGDLGGL GIALVAYGIA R-----ERAG gtvd------
ZP_03393889. 562  LPGVNGRFTL GENIGDLGGL GIAVAFRRF LAARGKE--- ----------
YP_002322079 594  ---VNGALTI GENIGDLGGV NIALKAYAFA LGKAagkpda eedgspaaik
```

*FIG. 20 continued*

```
ZP_05367591  578    -SLADAPVID GMTGIQRFFF SNARGWCTKS RPQHAEVMIS VDPHSPDEFR
YP_003363565 578    -SLADAPVID GMTGIQRFFF SNARGWCTKS RPQHAEVMIS VDPHSPDEFR
YP_003325693 588    ATLDDAPVID GLTGLERVFL GWAQVWQSKG RDEEVLRRLA TDPHSPNEFR
YP_003636471 579    HPLDEAPVLD GYTGLQRLFM GWAHSWRTKG RDEEVIRRLA TDPHSPDEFR
ZP_07359309. 644    -SVDEAPVID GLTGLQRFFY SWARIWRSKS RPDYAELLLT VDPHSPAEFR
YP_003275516 590    ---TTPPVID GLTGVQRVFY SWAEIWRTKT REAEAIKRLS IDPHSPPEFR
YP_001131754 585    ---EPAPVID GLTGVQRVFY GWAQVWRTKS REAEAIRRLA VDPHSPPEFR
YP_003379113 571    ---AEAPVID GLTGAERFFL AWANAWSTKT RPAEVVRRLA IDPHSPPEFR
 YP_951040.1 592    ---EPAPVID GLTGEQRVFF GWAQVWRTKS REAEAIRRLA VDPHSPPEFR
YP_002882628 586    ---RPdrae- ----LRELFA SWAVSWREKG HDAEVIRLLT IDPHSPPEFR
ZP_04382847. 572    ---TEPPVID GLTGLQRVFF GWAQVWRTKA REAEALRRLA VDPHSPPEFR
 YP_705057.1 572    ---SEPEVLD GLTGIQRVFF GWAQVWRTKA RDAEALRRLA VDPHSPPEFR
YP_003199539 571    ---QSAPVID GLTGAQRFFR SWATVWRLKM REAEQVRMLS IDPHSPAEFR
ZP_06184089. 585    -DPADAPVIE GYTGAQRFFY SWALSWQNKT RVEAAKQLIA IDPHSPAEFR
YP_003645328 596    ---DPSTEAD GLTGLQRVFY SWGQIWRGKS RPEEAIRRLA IDPHSPPEFR
ZP_03393889. 599    LGLEDAP--- --ETYRDLFK QWALVWRSKI RPEFARQLLA IDPHSPAEFR
YP_002322079 641    ALLDTAPEMD GFTGLQRFFL SYASIWRTKN RDELAEQYLQ IDPHSPAEFR ZP_05367591  627    VNGVVRNIDE FYEAFGVSEG DALYLAPEER VRIW-
YP_003363565 627    VNGVVRNIDE FYEAFGVSEG DALYLAPEER MRIW-
YP_003325693 638    CNGIVRNVDE FHDAYGVREG DALWLAPEDR VRIW-
YP_003636471 629    CNGVVRNIDE FYTAFDVQPD DALWLDPEQR VRIW-
ZP_07359309. 693    CNGIVRNVDA FYKAFAVDSD DALWLPPNER VSIW-
YP_003275516 637    CNGVVRNIDV FYDAFDVKPG DTLYLDEADR VRIW-
YP_001131754 632    CNGVIRNMDA FYDAFDVDPE DALYLEPQRR VHIWN
YP_003379113 618    CNAVVRNIDA FHEAFGVGPD DAMWLAPEQR VRIW-
 YP_951040.1 639    CNAVVRNMDA FYDAFEVDED DELYLEPQRR VHIWN
YP_002882628 628    CNGVVANLDA FAEAFDVQPG DGLWIDPQDR VRIW-
ZP_04382847. 619    CNGVVRNLDT FHEEFDVKPG DALYLEPEKR VKIW-
 YP_705057.1 619    CNGVVRNLDT FHDAFDVKPG DALYLDQEER VKIW-
YP_003199539 618    CNQVVRNIAE FHEAFDTRPT DGLWLDEQDR VRIW-
ZP_06184089. 634    CNGVVANLDL FAKTFGLKPG DDLWIEPENR VRIW-
YP_003645328 643    CNAIASNLDE FYSAFGVTEG DTLFLAPERR VSIW-
ZP_03393889. 644    CNVIASNIDE FHEAFGTSAG DGMWREPNER VNIW-
YP_002322079 691    TNGIASNVDL FYDAFGVTEG DAMWLAPKDR VSIW-
```

FIG. 20 continued

ROTHIA SPECIES GLUTAMINE ENDOPEPTIDASES AND USE THEREOF

CROSS REFERENCE TO RELATED APPLICATION

This application is a 35 U.S.C. §371 National Phase Entry Application of International Application No. PCT/US2010/051828, filed Oct. 7, 2010, which designates the United States, and which claims benefit under 35 U.S.C. §119(e) of the U.S. Provisional Application No. 61/249,343 filed Oct. 7, 2009, the contents of which are incorporated herein by reference in its entirety.

GOVERNMENT SUPPORT

This invention was made with Government support under contract No. DE18132 and AI087803 awarded by the National Institutes of Health. The Government has certain rights in the invention.

REFERENCE TO SEQUENCE LISTING

This application contains a Sequence Listing which has been submitted in ASCII format via EFS-Web and is hereby incorporated by reference in its entirety. The ASCII copy, created on Apr. 5, 2012, is named 20120406_SequenceListing_TextFile_701586_066292_US.txt and is 180 kilobytes in size.

BACKGROUND OF INVENTION

Celiac disease, also called celiac sprue or gluten-sensitive enteropathy, is a disease which develops in susceptible individuals in response to the intake of dietary gluten. The disease is caused by an immune reaction to gluten, most noticeably, to gliadin-derived peptides. These peptides elicit an immune response damaging microvilli which are tiny protrusions that line the small intestine. Their destruction causes malabsorption of nutrients leading to a variety of generalized gastrointestinal disease symptoms such as diarrhea and abdominal pain. Additional and secondary symptoms include weight loss, fatigue, anemia, osteopenia and skin and tooth enamel defects.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of these patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Gluten allergy and gluten intolerance are related ailments which result from an overreaction of a subject's immune system to gluten and gliadin that are normally considered harmless. The symptoms are very similar to celiac sprue or gluten-sensitive enteropathy but without the enteropathy. Afflicted subjects have an abundance of IgG and IgA antibodies against α/β-gliadin. Typical symptoms are abdominal pain, gas, bloating and diarrhea; there is a general feeling of sickness and fatigue after grain-based products are consumed. Severe allergy can led to Gluten-sensitive idiopathic neuropathy where the typical symptoms are ataxia and peripheral neuropathies because the primary tissue targeted are the central nervous system and peripheral nerves.

There is currently no good marketed treatment for celiac disease or the various gluten and gliadin allergy related diseases. In most cases, the symptoms are reversible and can be avoided if the patients refrain from the intake of gluten. Complete elimination of gluten from the diet is not easy to achieve and maintain. Glutens are abundantly contained in dietary products made of wheat, barley and rye. Moreover, gluten is also widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

The gluten-free diet advice is to be followed for a lifetime, and intake of gluten, even in small amounts, can cause an immediate immunological response. In view of the serious and widespread nature of Celiac Sprue, the development of a non-dietary therapy would allow patients to lead a more normal life and find a broad application in the gluten-sensitive patient population. The present invention addresses such needs.

Current approaches geared towards the development of treatment options for celiac disease and allergic gluten sensitivity focus on enzyme preparations that are able to digest the immunogenic gluten/gliadin oligopeptides into smaller fragments that do not elicit an immune response. Gluten proteins are remarkably resistant to digestive enzymes operating in the gastro-intestinal tract due to the low content of lysine/arginine and the high proline content. Enzymes capable of gluten digestion are considered an attractive therapeutic option.

SUMMARY OF THE INVENTION

Embodiments of the invention are based on the discovery of specific enzymatic activities in human whole saliva and dental plaques. The specific enzymatic activities are from glutamine endopeptidase enzyme(s) found in Rothia species bacteria living in the human mouth and dental plaque therein. The glutamine endopeptidase enzyme can cleave the peptide bond after the Gln within the Xaa-Pro-Gln (-XPQ- motif), where Xaa is any amino acid, Pro is proline and Gln is glutamine. This tripeptide motif is also particularly abundant in known celiac T-cell gluten epitopes. The inventors showed that the saliva-associated glutamine endopeptidase enzymes can degrade gluten/gliadins in vitro. Glutens and gliadins are proline and glutamine rich proteins that are the cause of the immune response in Celiac Sprue, gluten allergy and dermatitis herpetiformis. The discovery of this enzyme provides the use of the enzyme for non-dietary therapies of Celiac Sprue, gluten allergy and dermatitis herpetiformis.

Embodiments of the invention provide an isolated glutamine endopeptidase enzyme having enzymatic activity to break down glutens into small peptide fragments. In some embodiments, the enzyme has an apparent molecular weight of about 70-75 lcDa as determined by gliadin zymograms or sodium dodecyl sulfate polyacrylamide gel electrophoresis, has a functional pH range of 3-10 as determined by detectable Z-YPQ-pNA cleaving activity within a 24 hour digestion period, complete digestion is achieved at 72 hours under the described assay conditions, has a functional pH range of 7-10 as determined by substantially complete Z-YPQ-pNA cleavage within a 1 hour digestion period, cleaves the peptide bond after XPY and XPQ motifs in glutens, is 100% inhibited by 1 mM of EDTA or PMSF, is a metal-ion dependent protease, is precipitated by 25-45% ammonium sulphate, and is negatively charged at pH>5.0. In one embodiment, the enzyme is derived from a *Rothia* species bacterium.

In one embodiment, provided herein is a formulation for use in treatment of Celiac Sprue, gluten allergy and/or dermatitis herpetiformis, the formulation comprises an effective dose of an extract from a *Rothia* species bacteria or an isolated glutamine endopeptidase enzyme and a pharmaceutically acceptable excipient, wherein the extract from the *Rothia* species bacteria contains a glutamine endopeptidase enzyme.

Embodiments of the invention also provide a method of treating Celiac Sprue, gluten allergy and/or dermatitis herpetiformis in a subject in need thereof, the method comprises administering to a subject when consuming a gluten-containing foodstuff an effective dose of an extract from a *Rothia* species bacteria, an isolated glutamine endopeptidase enzyme, or a formulation comprising an isolated glutamine endopeptidase enzyme; wherein the extract from the *Rothia* species bacteria contains a glutamine endopeptidase enzyme that attenuates gluten toxicity in the subject.

In one embodiment, provided herein is a method of detoxifying gluten, the method comprises contacting gluten-containing foodstuff with an effective dose of an extract from a *Rothia* species bacterium, an isolated glutamine endopeptidase enzyme, or a formulation comprising an isolated glutamine endopeptidase enzyme, wherein the extract from the *Rothia* species bacteria contains a glutamine endopeptidase enzyme. In one embodiment, the extract is a purified sample of the enzyme.

In one embodiment, the subject has been diagnosed with Celiac Sprue, gluten allergy and/or dermatitis herpetiformis.

In one embodiment, provided herein is a method of predicting/diagnosing Celiac Sprue, gluten allergy and/or dermatitis herpetiformis in a subject in need thereof, the method comprises (a) contacting a biological sample from the subject with a fixed amount of gliadin or synthetic gliadin-derived enzyme substrate for a 24 hour period; (b) measuring the amount of gliadin degradation; and (c) comparing the amount of gliadin degradation for the biological sample with that obtained for a control assay, wherein the control assay is a mixture of a same fixed amount of gliadin with an isolated glutamine endopeptidase enzyme or a formulation that contains a glutamine endopeptidase enzyme for a 24 hour period, wherein the extent of gliadin degradation of less than 50% of that of the control assay indicates the subject likely have Celiac Sprue, gluten allergy and/or dermatitis herpetiformis. The biological sample can be whole saliva or dental plaque derived from the subject. The fixed amount of gliadin used in the assay is such that when an equivalent corresponding sample from a healthy subject, e.g. saliva or dental plaque, is mixed with the fixed amount of gliadin, 100% of the gliadin is digested within 24 hours under the same assay conditions. A healthy subject is one who does not have, diagnosed with or have symptoms associated with Celiac Sprue, gluten allergy, gluten intolerance and/or dermatitis herpetiformis as determined by the various methods known in the art and also described herein. For the control assay, the amount of an isolated glutamine endopeptidase enzyme or a formulation that contains a glutamine endopeptidase enzyme used is that which will digest 100% of the fixed amount of gliadin within a 24 hour period. In one embodiment, the diagnostic assay and the control assay are conducted in parallel under the same conditions.

In one embodiment, the glutamine endopeptidase enzyme is derived from the *Rothia* species described herein appears in the 70-75 kDa region in a gliadin zymogram, is active in a saliva sample, is a metal-ion dependent protease, and attenuates gluten toxicity by cleaving the peptide bond after glutamine at -XPQ- and XPY motifs in gluten-containing foodstuff, wherein X=any amino acids, P=proline, Q=glutamine and Y=tyrosine.

In another embodiment, the glutamine endopeptidase enzyme from the *Rothia* species described herein appears in the 70-75 kDa region in a gliadin zymogram and is active in a sample of dental plaque.

In another embodiment, the glutamine endopeptidase enzyme from the *Rothia* species described herein appears in the 70-75 kDa region in a gliadin zymogram and is heat labile. Boiling at 100° C. for 5 minutes abolishes the endopeptidase activity.

In one embodiment, the glutamine endopeptidase enzyme from the *Rothia* species has a pH optimum range between 7-10 for its enzymatic activity, i.e., digestion of proteins with -XPQ- and -XPY- motifs results in smaller protein fragments.

In one embodiment, the glutamine endopeptidase enzyme comprises at least 45% amino acid sequence identity to SEQ. ID. NO: 1. In another embodiment, the glutamine endopeptidase enzyme comprises SEQ. ID. NO: 1. The enzyme can be conjugated with other molecules to increase stability, e.g., to PEG. In another embodiment, the glutamine endopeptidase enzyme consists essentially of SEQ. ID. NO: 1. In yet another embodiment, the glutamine endopeptidase enzyme consists of SEQ. ID. NO: 1.

In one embodiment, the glutamine endopeptidase enzyme is a recombinantly synthesized glutamine endopeptidase enzyme. In some embodiments, the recombinantly synthesized glutamine endopeptidase enzyme comprising at least 45% amino acid sequence identity or similarity to SEQ. ID. NO: 1 is used. In some embodiments of the methods described, the recombinant enzyme has modifications that increase the enzyme stability, enzyme activity and potency such that a smaller amount of enzyme is necessary to achieve the desired gluten digestion. Modifications can include but are not limited to changes in amino acid changes, amino acid modifications (e.g., acetylation, PEGylation), and fusion protein.

In some embodiments, the *Rothia* species bacteria is *Rothia mucilaginosa* ot 681 (strain WSA-2B), *Rothia* species ot 188 (strain WSA-8) *Rothia mucilaginosa* ATCC 25296 and *Rothia dentocariosa* ATCC 17931. These *Rothia* species bacteria can grow on gluten-limited media. Extracts from these bacteria exhibit glutamine endopeptidase activity.

In some embodiments, the extract from *Rothia* species bacteria is selected from a group consisting a clarified lysate of a *Rothia* species bacteria, a 25-45% ammonium sulphate precipitate of the lysate of a *Rothia* species bacteria where the precipitate has been resuspended in buffer and desalted, the supernatant fluid of a suspension of a *Rothia* species bacteria, and a suspension of a *Rothia* species bacteria.

In one embodiment, the extract from *Rothia* species bacteria, the glutamine endopeptidase enzyme or formulation containing the glutamine endopeptidase enzyme is administered just before, during, or just after consumption of gluten-containing foodstuff.

In one embodiment, the extract from the *Rothia* species bacteria, the glutamine endopeptidase enzyme enzyme or formulation containing the glutamine endopeptidase enzyme enzyme is administered orally.

In one embodiment, the extract from the *Rothia* species bacteria, the glutamine endopeptidase enzyme enzyme or formulation containing the glutamine endopeptidase enzyme enzyme is admixed to the gluten-containing foodstuff.

In one embodiment, the extract from the *Rothia* species bacteria, the glutamine endopeptidase enzyme enzyme or formulation containing the glutamine endopeptidase enzyme enzyme comprises an enteric coating.

In one embodiment, the extract from the *Rothia* species bacteria, the glutamine endopeptidase enzyme enzyme or formulation containing the glutamine endopeptidase enzyme enzyme is a lyophilized preparation.

In one embodiment, the extract from the *Rothia* species bacteria, the glutamine endopeptidase enzyme enzyme or formulation containing the glutamine endopeptidase enzyme enzyme is formulated for oral administration.

In one embodiment, the effective dose of the extract from the *Rothia* species bacteria, the glutamine endopeptidase enzyme enzyme or formulation containing the glutamine endopeptidase enzyme enzyme ranges from 0.01 mg to 500 mg/kg body weight.

BRIEF DESCRIPTION OF TILE DRAWINGS

FIG. 1 demonstrates the identification of seven aerobic and ten anaerobic strains that grew well on gluten-limited agar where gluten is the only nitrogen source. None of the strains grew on agar containing the same ingredients without gluten (not shown). Note: predominant aerobic species: *Rothia*; predominant anaerobic species: *Bifidobacterium*.

FIG. 2 shows the degradation of gliadins by the mixture of bacteria in dental plaque (FIG. 2A) or strain WSA-8 (FIG. 2B) suspended in saliva ion buffer. Both cell suspensions had an $OD_{620}$ of 1.0. Gliadin was added to a final concentration of 250 µg/ml (SIGMA-ALDRICH® Cat. No. G3375). After various incubation time points, 100 µl aliquots were removed, boiled and subjected to SDS PAGE. Lane 1: molecular weight standard; lanes 2-7, cell/gliadin mixtures incubated for 0, 2, 4, 6, 24 and 48 h, respectively. Arrow points to the major constituent in the gliadin mixture. Note that gliadins are faster degraded by strain WSA-8 (FIG. 2B) than by the mixture of micoorganisms present in dental plaque (FIG. 2A).

FIG. 3 shows the degradation of gliadins by strains WSA-2B (FIG. 3A) and WSA-8 (FIG. 3B). Cells were grown on gluten limited agar and suspended in saliva ion buffer to an $OD_{620}$=1.0. Lane 1: molecular weight standard, lanes 2-7: Cell/gliadin mixture incubated for 0, 5, 15, 30, 60 and 120 min, respectively; Lanes 8 and 9: gliadins incubated for 0 and 120 min in boiled cell suspensions; lanes 10 and 11: cell suspensions without added gliadins; Lanes 12 and 13: gliadins incubated for 0 and 2 hr in saliva ion buffer. Arrow points to the major constituent in the gliadin mixture. Note: both strains rapidly degraded gliadins, WSA-8 a little faster than WSA-2B.

FIG. 4A-4D shows the relationship between cell density and proteolytic activity. WSA-2B or WSA-8 cells were suspended in saliva ion buffer to a final concentration of $OD_{620}$=0.15, 0.3, 0.6, and 1.2. Z-KPQ-pNA or Z-YPQ-pNA was added as enzymatic substrates to final concentrations of 200 µM. Note that the rate of substrate hydrolysis increased with increasing cell density. The fact that both KPQ and YPQ were cleaved signifies that the amino acid at position p3 has little influence on enzyme recognition. As expected, boiled cell suspensions ($OD_{620}$=1.2) were devoid of enzymatic activities.

FIG. 5 shows the gliadin zymography (8%) of WSA-2B and WSA-8. Strains were cultured on *Brucella* agar (BA) or gluten-limited agar (GA), and suspended in saliva ion buffer. In each lane cells from 150 µl suspension ($OD_{620}$=5.0) were loaded. Lane 1: molecular weight standard; lane 2: WSA-2B grown on BA; lane 3: WSA-2B grown on GA; lane 4: WSA-8 grown on BA; lane 5: WSA-8 grown on GA. Clear bands indicate the presence of an enzyme with gliadin-degrading activity. Note that the molecular weight of the enzymes is approximately 70 kDa.

FIG. 6 shows the total ion chromatogram of an in-gel tryptic digest of the WSA-8 glutamine endopeptidase enzyme. The chromatogram shows multiple peptide fragments.

FIG. 7 shows the hydrolysis of Z-YPQ-pNA (200 µM) by a cell suspension of WSA-2B (FIG. 7A) or WSA-8 (FIG. 7B) in saliva ion buffer in the absence and presence of various protease inhibitors. Saliva ion buffer contains 50 mM KCl, 1 mM $K_2HPO4$, 1 mM $CaCl_2$ and 0.1 mM $MgCl_2$ (pH 6.5). Cells were preincubated with the inhibitors for 15 min at room temperature prior to the addition of substrate. Z-YPQ-pNA hydrolysis was followed at 405 nm. Initial velocities of the enzymatic reaction are plotted. Note that PMSF and EDTA completely inhibited YPQ-cleavage activities.

FIG. 8 shows the gliadin zymography of WSA-8 cells with and without PMSF. A cell suspension of WSA-8 ($OD_{620nm}$=5.0) was incubated for 15 min at room temperature with and without added PMSF, a serine protease inhibitor (final concentration 1 mM). Following incubation, cells (150 µl) were harvested and subjected to gliadin zymography. Lane 1, Molecular weight standard; lane 2: WSA-8 without PMSF; lane 3, WSA-8 with PMSF. Note: pre-incubation with PMSF abolishes all activity.

FIG. 9 shows the gliadin substrate hydrolysis by three commercially obtained strains: *Kocuria* varians ATCC 15306; *R. mucilaginosa* ATCC 25296; and *R. dentocariosa* ATCC 17931. Strain WSA-8 was included for comparison. Note that *R. dentocariosa* but not the phylogenetically closely related species *Kocuria* varians cleaves Z-YPQ-pN. None of the strains exhibited noticeable activity towards the QQP, PFP or PPF substrates.

FIG. 10 shows the gliadin zymography (6%) of *Rothia* strains developed at low and neutral pH (pH 7.0). Per lane 150 µl cells ($OD_{620}$=5.0) were loaded after cell disruption. Lane 1, MW standard, lanes 2 and 6, strain WSA-2B (*R. mucilaginosa*); lanes 3 and 7: strain WSA-8 (*Rothia* spp. of 188), lanes 4 and 8: strain WSA-26 (*R. mucilaginosa*); lanes 5 and 9: *R. mucilaginosa* (ATCC 25296). After electrophoresis, the gel was cut in the middle and one half was renatured and developed at pH=3 (left panel) and the other half at pH=7 (right panel). Note that at pH=3, the protease produced by WSA-8 had retained some of its activity.

FIG. 11 shows the effects of pH on WSA-8 glutamine endopeptidase enzyme activity. WSA-8 cells grown on *Brucella* agar were suspended to a final $OD_{620}$ of 1.2 in 20 mM Tris buffers ranging in pH from 2.0 to 10.0. The synthetic substrate Z-YPQ-pNA was added to a final concentration of 200 µM. Substrate hydrolysis was assessed at 405 nm hourly for the first 6 hours followed by a reading at 24 h and 72 h.

FIGS. 12A and 12B show the gliadin 33-mer fragmentation by WSA-8. Cells grown on agar were harvested and suspended in saliva ion buffer to a final $OD_{620}$ of 1.2 and incubated with gliadin 33-mer (final concentration 250 µg/ml). After 0 h, 2 h and 5 h, aliquots were removed, boiled, filtered and analyzed by RP-HPLC. Peaks 1 to 11, as indicated by arrows, were collected for structural analysis by LC-ESI-MS/MS (FIG. 12A). Sequences of the peptides of peak 1 to 11 are shown in FIG. 12B; larger arrows indicate QPQ cleavage sites, and narrow arrows indicate LPY, QPF and PFP cleavage sites on the 33-mer.

FIGS. 13A and 13B show the gliadin 26-mer fragmentation by WSA-8. Cells grown on agar were harvested and suspended in saliva ion buffer to a final $OD_{620}$ of 1.2 and incubated with gliadin 26-mer (final concentration 250 μg/ml). After 0 h, 2 h and 5 h, aliquots were removed, boiled, filtered and analyzed by RP-HPLC. Peaks 1 to 10, as indicated by arrows, were collected for structural analysis by LC-ESI-MS/MS (FIG. 13A). Sequences of the peptides of peak 1 to 10 are shown in FIG. 13B; larger arrows indicate QPQ cleavage sites, and narrow arrows indicate LPY, QPF and PFP cleavage sites on the 33-mer.

FIGS. 14A and 14B show the gliadin 33-mer fragmentation by R. mucilaginosa ATCC 25296. Cells grown on agar were harvested and suspended in saliva ion buffer to a final $OD_{620}$ of 1.2 and incubated with gliadin 33-mer (final concentration 250 μg/ml). After 0 h, 2 h and 5 h, aliquots were removed, boiled, filtered and analyzed by RP-HPLC. Peaks 1 to 11, as indicated by arrows, were collected for structural analysis by LC-ESI-MS/MS (FIG. 14A). Sequences of the peptides of peak 1 to 11 are shown in FIG. 14B; larger arrows indicate QPQ cleavage sites, and narrow arrows indicate LPY, QPF and PFP cleavage sites on the 33-mer.

FIGS. 15A and 15B show the gliadin 26-mer fragmentation by R. mucilaginosa ATCC 25296. Cells grown on agar were harvested and suspended in saliva ion buffer to a final $OD_{620}$ of 1.2 and incubated with gliadin 26-mer (final concentration 250 μg/ml). After 0 h, 2 h and 5 h, aliquots were removed boiled, filtered and analyzed by RP-HPLC. Peaks 1 to 7, as indicated by arrows, were collected for structural analysis by LC-ESI-MS/MS (FIG. 15A). Sequences of the peptides of peak 1 to 7 are shown in FIG. 15B; larger arrows indicate QPQ cleavage sites, and narrow arrows indicate LPY, QPF and PFP cleavage sites on the 33-mer.

FIG. 16 shows the DEAE chromatogram of R. mucilaginosa ATCC 25296 sonicated cell supernatant fractions enriched for enzyme activity using ammonium sulfate fractionation. A total amount of 670 mg protein was loaded onto the column. Dotted trace: total protein (A214 nm); solid trace: Z-YPQ-pNA hydrolysis activity.

FIG. 17A shows the SDS PAGE of partially purified R. mucilaginosa enzyme(s). R. mucilaginosa cell extract (20 μg protein/lane): Lane 1: protein standard (5 ul, Bio-Rad all blue); lane 2: empty; lane 3: P-0a; lane 4: P-0b; lane 5: P-0c, lane 6: P-1; lane 7: P-2: lane 8: R. mucilaginosa extract before DEAE fractionation; lane 10 (zymogram): R. mucilaginosa cells ($OD_{620}$=5.0, 300 μl).

FIG. 17B shows the gliadin zymography of DEAE fractions of partially purified R. mucilaginosa enzyme(s). R. mucilaginosa cell extract (20 μg protein/lane): Lane 1: protein standard (5 ul, Bio-Rad all blue); lane 2: empty; lane 3: P-0a; lane 4: P-0b; lane 5: P-0c, lane 6: P-1; lane 7: P-2: lane lane 9: R. mucilaginosa extract before DEAE fractionation; lane 10 (zymogram). R. mucilaginosa cells ($OD_{620}$=5.0, 300 μl).

Figure 17:
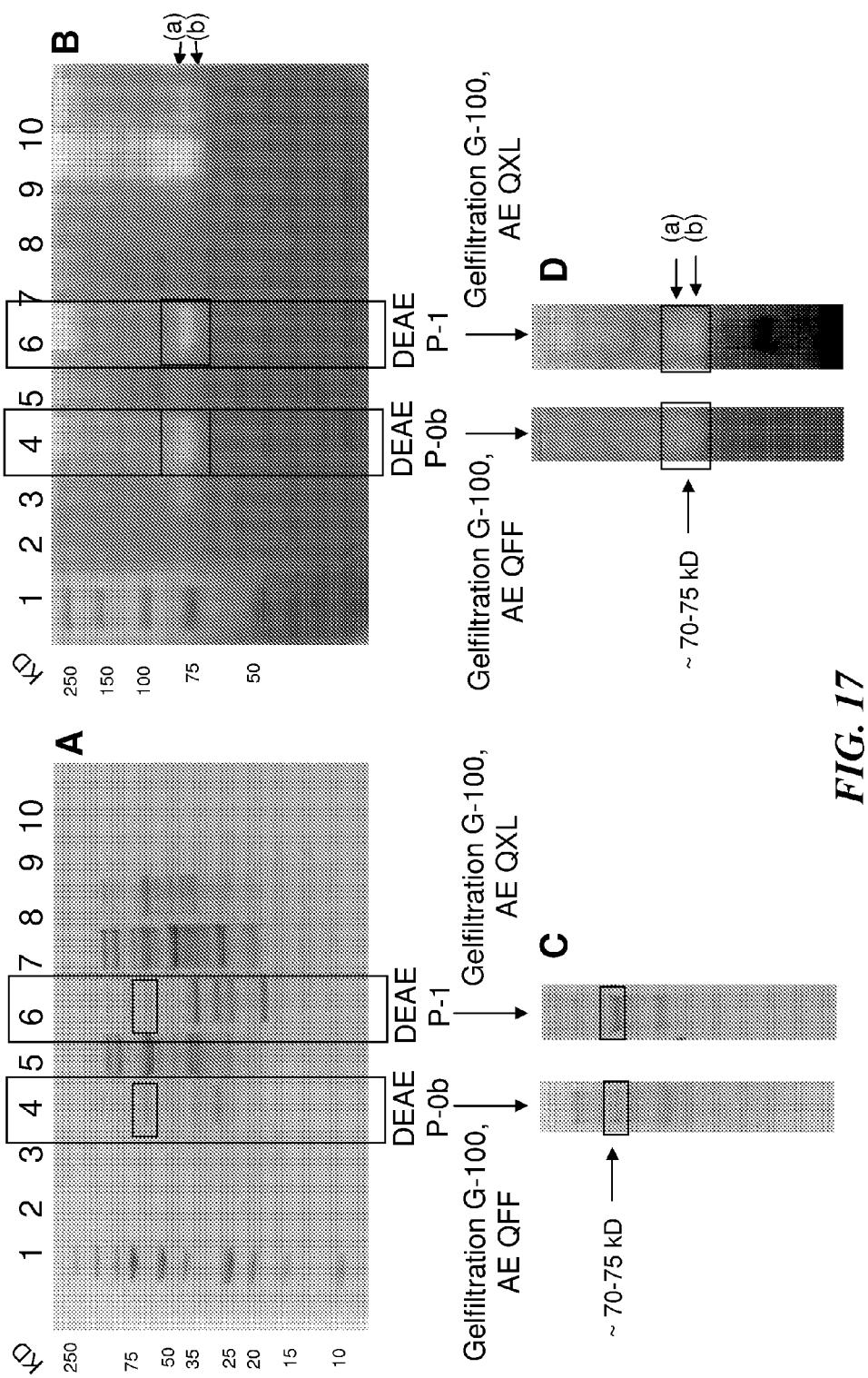
FIG. 17C shows the SDS PAGE of P-0b and P-1 fractions following further purification by gelfiltration and anion exchange (AE) chromatography (see Materials and Methods for experimental details). Arrows (a and b) point to two active protease bands exhibiting apparent molecular weights of 75 and 70 kD, respectively.
FIG. 17D shows the zymography of the same samples loaded in FIG. 17C, confirming gliadin-degrading activity in the enriched fractions.
Figure 17E:
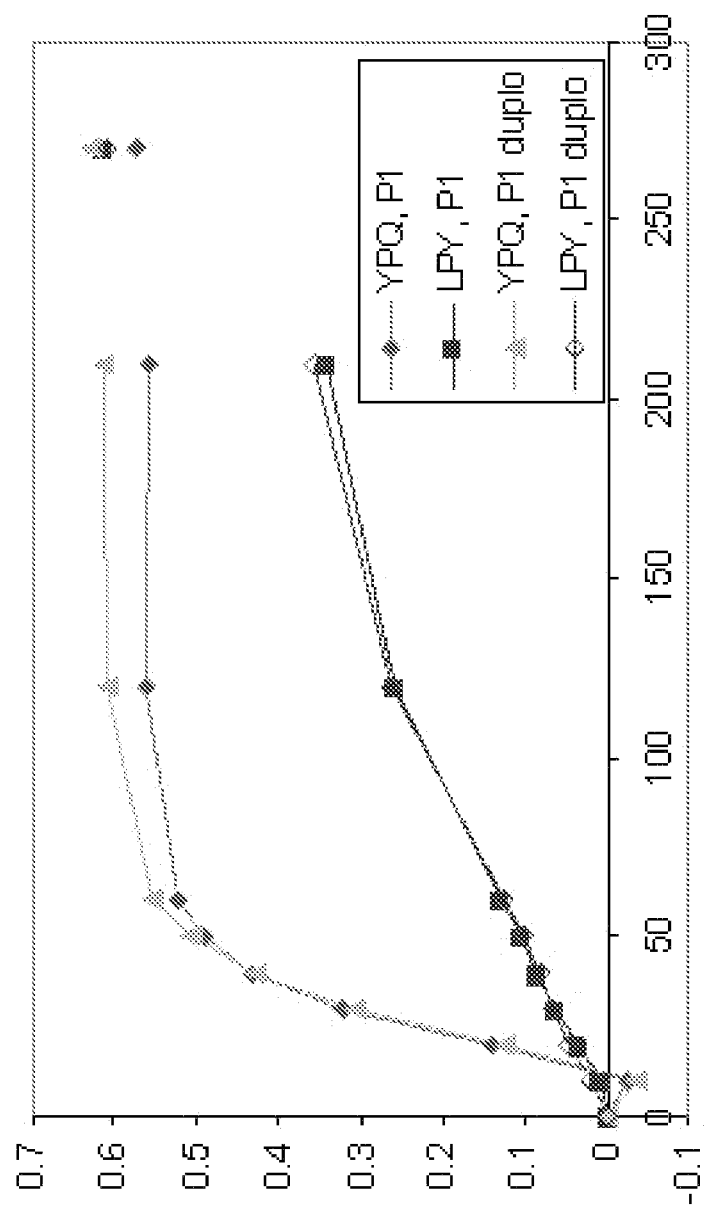

FIG. 17E shows the evaluation of cleavage specificity of the semi-pure enzyme preparation (DEAF P1 purified by gel filtration and HiTrap AE QXL, FIGS. 17 C and D right lanes). Final enzyme concentration: 122 ug/ml. Note that both Z-YPQ-pNA and Z-LPY-pNA are hydrolysed. No hydrolysis occurred in the absence of enzyme (not shown). Enzymatic kinetic rates were higher towards Z-YPQ-pNA than towards Z-LPY-pNA. Both substrates were completely hydrolyzed after 16 h (last measurement).

FIG. 18 shows the amino acid sequence of R. mucilaginosa neprilysin (SED. ID. NO: 1) and the conserved regions that are important for the glutamine endopeptidase enzyme activity (in bold).

FIG. 19 shows the amino acid sequence alignment of closely related sequences in Table 6. The sequences are ZP_05367591 (SEQ. ID. NO: 1), YP_003363565 (SEQ. ID. NO: 23), ZP_07073157 (SEQ. ID. NO: 24), ZP_06905919 (SEQ. ID. NO: 25), YP_003315199 (SEQ. ID. NO: 26), YP_003325693 (SEQ. ID. NO: 27), YP_003636471 (SEQ. ID. NO: 28), ZP_06830706 (SEQ. ID. NO: 29) and ZP_07359309 (SEQ. ID. NO: 30) in the order of appearance.

FIG. 20 shows the amino acid sequence alignment of closely related sequences of bacteria neprilysins ZP_05367591 (SEQ. ID. NO: 1), YP_003363565 (SEQ. ID. NO: 48), YP_003325693 (SEQ. ID. NO: 49), YP_003636471 (SEQ. ID. NO: 50), ZP_07359309. (SEQ. ID. NO: 51), YP_003275516 (SEQ. ID. NO: 52), YP_001131754 (SEQ. ID. NO: 53), YP_003379113 (SEQ. ID. NO: 54), YP_951040.1 (SEQ. ID. NO: 55), YP_002882628 (SEQ. ID. NO: 56), ZP_04382847 (SEQ. ID. NO: 57), YP_705057.1 (SEQ. ID. NO: 58), YP_003199539 (SEQ. ID. NO: 59), ZP_06184089 (SEQ. ID. NO: 60), YP_003645328 (SEQ. ID. NO: 61), ZP_03393889 (SEQ. ID. NO: 62), and YP_002322079 (SEQ. ID. NO: 63) in the order of appearance respectively.

Figure 21:
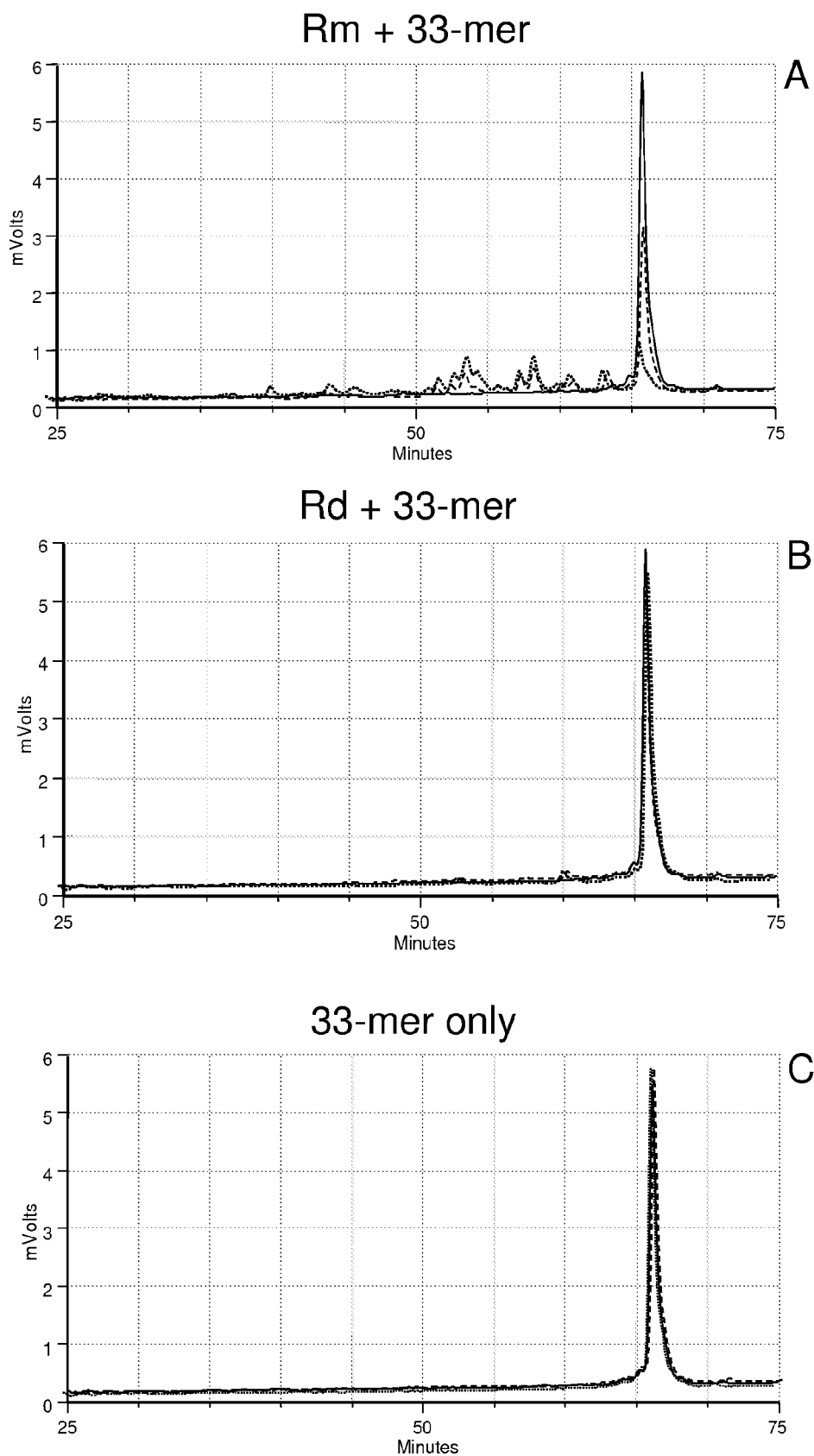

FIG. 21A-21C show the comparison of 33-mer degradation by R. mucilaginosa ATCC 25296 (Rm) and R. dentocariosa ATCC 17931 (Rd). Cells were suspended in saliva ion buffer to an OD620 of 1.2 and 33-mer was added to a final concentration of 250 μg/ml. At 0 h (solid line), 2 h (dashed line) and 5 h (dotted line) 100 μl sample aliquots were analyzed by RP-HPLC. Note that Rd (middle panel) is unable to cleave the 33-mer.

Figure 22:
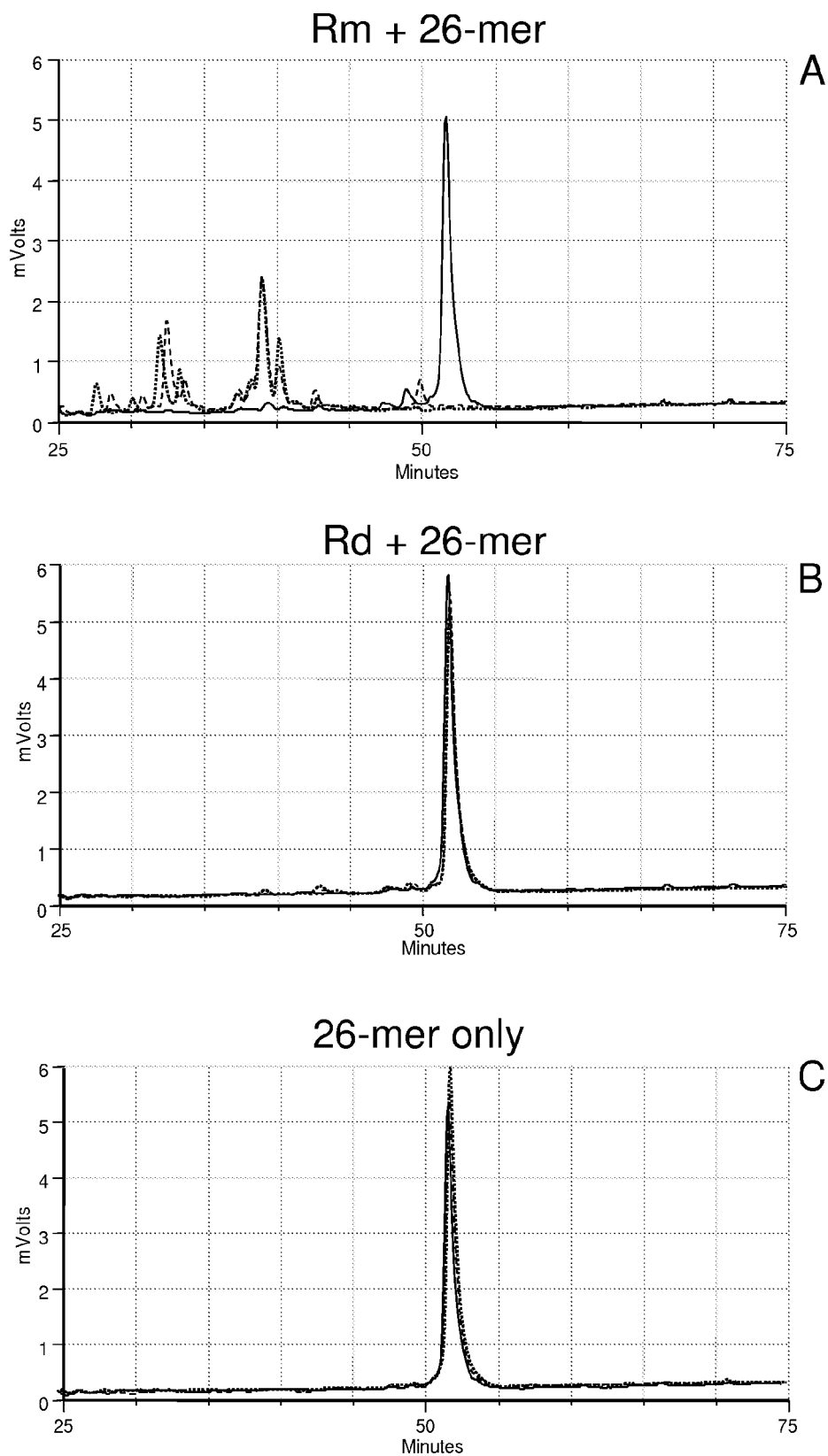

FIG. 22A-22C show the comparison of 26-mer degradation by R. mucilaginosa ATCC 25296 (Rm) and R. dentocariosa ATCC 17931 (Rd). Cells were suspended in saliva ion buffer to an OD of 1.2 and 26-mer was added to a final concentration of 250 ug/ml. At 0 h (solid line), 2 h (dashed line) and 5 h (dotted line) 100 ul sample aliquots were analyzed by RP-HPLC. Note that Rd (middle panel) is unable to cleave the 26-mer.

Figure 23:
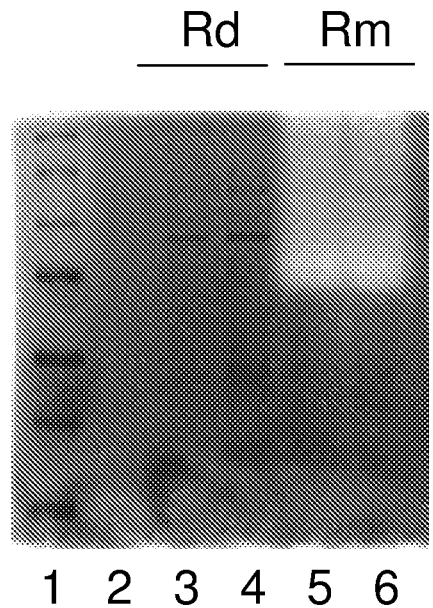

FIG. 23 shows the gliadin zymogram of R. dentocariosa (Rd) and R. mucolaginosa (Rm). Lane 1, MW standard; lane 2, empty; lane 3: Rd cells harvested from 150 μl OD=5.0; lane 3, Rd cells from 300 μl OD=5.0, lane 4, Rm cells from 150 μl 013=5.0; lane 5, Rm cells from 300 μl OD=5.0. Note: no gliadin-degrading enzymes noticeable in Rd cell suspensions.

Figure 24:
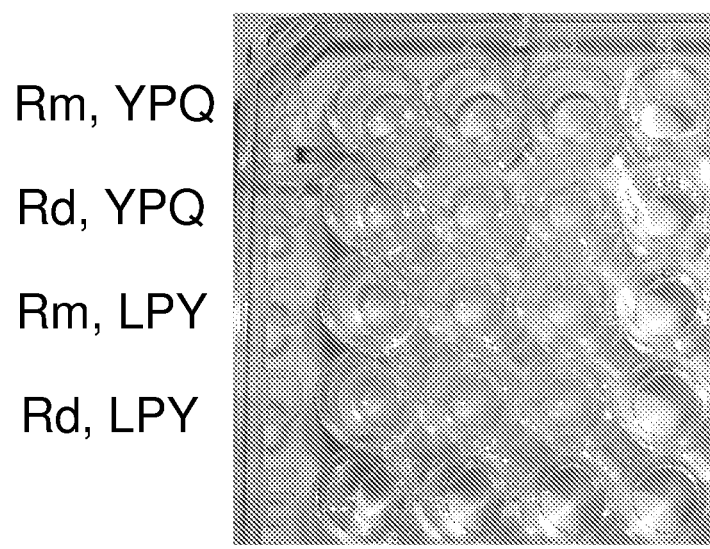

FIG. 24 shows Z-YPQ-pNA and Z-LPY-pNA hydrolysis by R. mucilaginosa (Rm) and R. dentocariosa (Rd). Note: R. dentocariosa is unable to cleave Z-LPY-pNA (picture taken after 72 h).

DETAILED DESCRIPTION OF THE INVENTION

The inventors have discovered that human whole saliva (WS) and dental plaque contain enzymatic activities that cleaves the Xaa-Pro-Gln (-XPQ-) bond after Gln, where Xaa is any amino acid, Pro is proline and Gln is glutamine. This tripeptide is also particularly abundant in known celiac T-cell gluten epitopes. The inventors showed that the saliva-associated glutamine endopeptidase enzyme(s) can degrade gluten/gliadins in vitro. Gluten/gliadins are proline and glutamine rich proteins that are the cause of the adverse immune response in Celiac Sprue, gluten allergy and dermatitis herpetiformis. The discovery of this enzyme provides the use of the enzyme(s) for non-dietary therapies of Celiac Sprue, gluten allergy and dermatitis herpetiformis.

In order to isolate and identify the glutamine endopeptidase enzyme(s), the inventors started with isolating and identifying the gliadin-degrading bacteria from human WS and also dental plague. These gliadin-degrading bacteria are *Rothia* species bacteria (FIG. 1). The inventors further isolated, purified and functionally characterized the glutamine endopeptidase enzyme from *Rothia mucilaginosa* ATCC 25296 that was naturally associated with the oral cavity (FIGS. 16 and 17A-E). The functional enzyme characterizations included the approximate molecular weight of the enzyme as determined by gliadin zymograms and by SDS-PAGE, cleavage specificity of this protease, capacity to degrade toxic gliadin epitopes, pH activity and inhibitor sensitivity profiles. Enzymes were obtained by chromatography and zymography and structurally characterized by LC-ESI-MS/MS. The inventors have identified the enzyme neprilysin as a gluten/gliadin-degrading glutamine endopeptidase enzyme protease from *R. mucilaginosa*.

Accordingly, embodiments of the invention provide an isolated glutamine endopeptidase enzyme. In one embodiment, the isolated glutamine endopeptidase enzyme is purified from a *Rothia* species bacterium. In one embodiment, the isolated glutamine endopeptidase enzyme is a recombinantly synthesized glutamine endopeptidase enzyme. In one embodiment, the enzyme is a protein.

In some embodiments, the enzyme has an apparent molecular weight of about 70-75 kDa as determined by gliadin zymograms. It also has an apparent molecular weight of about 70-75 kDa as determined by SDS-PAGE. In some embodiments, the apparent molecular weight of the enzyme is determined by gel filtration chromatography, which is a technique known to one skilled in the art.

In some embodiments, the enzyme has a functional pH range of 3-10. Within this range of pHs, there is detectable Z-YPQ-pNA and gliadin peptides cleaving activities within a 24 hour digestion period. Complete digestion is achieved at 72 hours under the described assay conditions. At a pH range of 7-10, there is substantially complete Z-YPQ-pNA cleavage within a 1 hour digestion period. Detectable Z-YPQ-pNA and gliadin peptides cleaving activities refers to at least 10% of the substrate used in the assay, i.e., Z-YPQ-pNA, 33-mer or 26-mer, is digested to smaller peptide fragments. Z-YPQ-pNA and the 26 mer and 33 mer gliadin peptides can be used as the substrates for assaying glutamine endopeptidase enzyme activity. Enzyme activity assay is assessed by measuring proteolytic activities towards a) gliadin-derived paranitroanilide(pNA)-linked synthetic enzyme substrates b) a mixture of natural gliadins and c) synthetic, highly immunogenic, gliadin peptides (33-mer of α2-gliadin and 26-mer of γ-gliadin) as described. Detectable Z-YPQ-pNA and gliadin peptides cleaving activities refers to at least 10% of the substrate used in the assay, i.e., Z-YPQ-pNA, 33-mer or 26-mer, is digested to smaller peptide fragments. Methods of detecting smaller peptide fragments are well known to one skilled in the art, e.g., by RP-HPLC and mass spectrometery as described herein. In some embodiments, the enzyme is active at pH 7.0, 7.2, 7.5, 7.7, 8.0, 8.2, 8.5, 8.7, 9.0, 9.2, 9.5, 9.7 and 10, including all the intermediate pHs between 7.0 to 10.0, wherein 100% of the substrate is cleaved within a 1 hour digestion period.

In one embodiment, the enzyme cleaves the peptide bond after a -XPY- or -XPQ- motif in glutens. In another embodiment, the enzyme cleaves the peptide bond immediately after a -XPQ- motif and proline is the amino acid at the P1' position after the motif.

In some embodiments, the enzyme does not cleave the peptide bonds after the QPF, PFP, QQP, and PPF motifs in glutens.

In one embodiment, the enzyme is inhibited by an agent selected from the group consisting of EDTA, PMSF, AEBSF, omapatrilat, opiorphin, RB-101, and UK-414,495. The concentration of the inhibiting agent ranges from about 0.01 µM to about 1.0 mM and the percent inhibition ranges from about 10% to 100% depending on the concentration of inhibition agent used. In some embodiments, the inhibiting agent ranges from about 0.01 µM to about 0.1 mM, from about 0.01 µM to about 0.05 mM, from about 0.01 µM to about 0.5 mM, from about 0.1 µM to about 0.5 mM, from about 0.1 µM to about 1 mM, from about 1 µM to about 0.1 mM, from about 1 µM to about 0.05 mM, from about 1 µM to about 0.5 mM, from about 1 µM to about 1 mM, from about 5 µM to about 0.1 mM, from about 5 µM to about 0.05 mM, from about 5 µM to about 0.5 mM, from about 5 µM to about 1 mM, from about 10 µM to about 0.1 mM, from about 10 µM to about 0.05 mM, from about 10 µM to about 0.5 mM, from about 10 µM to about 1 mM, from about 0.1 mM to about 0.5 mM, from about 0.1 mM to about 1 mM, and from about 0.5 µM to about 1.0 mM. In some embodiments, the percent inhibition is about 15%, 20%, 25%, 30%, 35%, 40%, 45%, 50%, 55%, 60%, 65%, 70%, 75%, 80%, 85%, 90%, 95% and 99%. In one embodiment, the enzyme is 100% inhibited by 1 mM EDTA or PMSF.

In some embodiments, the enzyme is a metal-ion dependent protease. In one embodiment, the enzyme is a zinc-dependent protease. In one embodiment, there is one zinc molecule per molecule of enzyme.

In one embodiment, the enzyme is a metal-ion dependent serine protease.

In some embodiments, the enzyme is precipitated by 25-45% ammonium sulphate in a lysate containing the enzyme. The enzyme is negatively charged at pH P>5.0. Examples of a lysate containing the enzyme include but are not limited to a *R. mucilaginosa* bacterial lysate and the yeast lysate where yeast is the protein expression host for the recombinantly synthesized enzyme In some embodiments, the isolated glutamine endopeptidase enzyme is isolated and purified from a *Rothia* species bacterium, such as *R. mucilaginosa* ATCC 25296, WSA-8, *R. mucilaginosa* of 681, *R. mucilaginosa* DY-18, *R. dentocariosa* M567 and *R. dentocariosa* ATCC 17931.

In another embodiment, the isolated glutamine endopeptidase enzyme is isolated from a bacterium selected from the group consisting of *R. mucilaginosa* ATCC 25296, WSA-8, *R. mucilaginosa* of 681, *R. mucilaginosa* DY-18, *R. dentocariosa* M567, *R. dentocariosa* ATCC 17931, *R. mucilaginosa* DY-18, *Xylanimonas cellulosilytica* DSM 15894, *Cellulomonas flavigena* DSM 20109, *Actinomyces viscosus* C505, *Gordonia bronchialis* DSM 43247, *Mycobacterium gilvum* PYR-GCK, *Kribbella flavida* DSM 17836, *Mycobacterium vanbaalenii* PYR-1, *Beutenbergia cavernae* DSM 12333, *Rhodococcus jostii* RHA 1, *Nakamurella multipartita* DSM 44233, *Mobiluncus mulieris* 28-1, *Tsukamurella paurometabola* DSM 20162, *Corynebacterium amycolatum* SK46, *Bifidobacterium longum* subsp. *infantis* ATCC 15697, *Sanguibacter keddieii* ATCC 51767 and *Cellulomonas flavigena* ATCC 482.

Figure 9:
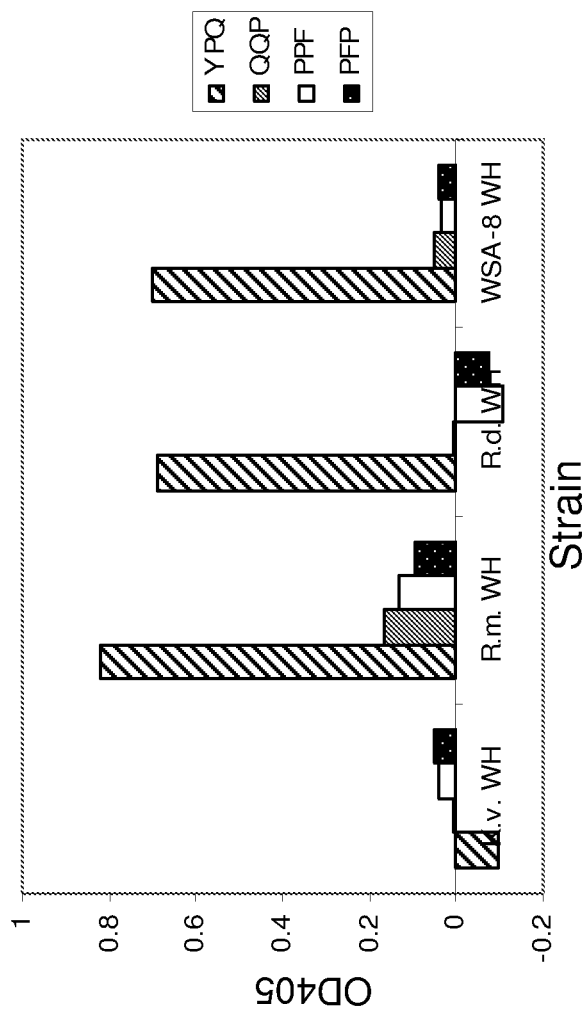

The inventors showed that cell suspensions from the commercial strain of R. dentocariosa ATCC 17931 exhibited glutamine endopeptidase enzyme activity in FIG. 9 using synthetic peptides such as Z-YPQ-pNA as the enzyme substrate. However, in separate experiments, the inventors also showed that cell suspensions of R. dentocariosa ATCC 17931 did not exhibit any detectable glutamine endopeptidase enzyme activity when using the oligopeptides 33-mer or the 26-mer as enzyme substrates (see FIG. 21-24). The observed differences could be due to the different assay methods used and the fact that cell suspensions were used. The smaller synthetic peptides may have fitted better into the enzyme active site than the oligopeptides. These smaller synthetic peptides and the 33-mer asd 26-mer oligopeptides do not accurately reflex the natural substrate of the enzyme. The glutamine endopeptidase enzyme in R. dentocariosa ATCC 17931 had only 76% identity to SEQ. ID. NO: 1 and is classified as a metalloendopeptidase PepO rather than a neprilysin. A metalloendopeptidase PepO may have different substrate specificity compared to a neprilysin and this can also account for the negative results obtained for the cell suspension of R. dentocariosa ATCC 17931 with the 33-mer and the 26-mer as shown in FIGS. 21-24.

Many proteins exist in an active (mature state) and in an inactive (pro-protein state). It is also a known fact that an enzyme's activity is regulated by its environment. The presence of inhibitory factors of the glutamine endopeptidase enzyme in the cell suspension in FIG. 22-24 could produce the negative results obtained.

In some embodiments, the enzyme comprises at least 60% amino acid sequence identity or similarity to NEIVFPAAILQPP (SEQ. ID. NO: 31), FDDQGSRYDGDG (SEQ. ID. NO: 32), DPHSPDEF (SEQ. ID. NO: 33), NGVVRNIDEFY (SEQ. ID. NO: 34), and RVRIW (SEQ. ID. NO: 35), and has a "bHEbbHbc" motif, wherein H=histidine, E=glutamate, 'b' is an uncharged amino acid residue, and 'c' a hydrophobic amino acid residue, wherein "bHEbbHbc" motif forms part of the metal-binding site, wherein the enzyme cleaves Z-YPQ-pNA or gliadin peptides substrates within a 24 hour digestion period at a pH range from 3-10.

In some embodiments, the enzyme consists essentially of at least 60% amino acid sequence identity or similarity to NEIVFPAAILQPP (SEQ. ID. NO: 31), FDDQGSRYDGDG (SEQ. ID. NO: 32), DPHSPDEF (SEQ. ID. NO: 33), NGVVRNIDEFY (SEQ. ID. NO: 34), and RVRIW (SEQ. ID. NO: 35), and has a "bHEbbHbc" motif, wherein H=histidine, E=glutamate, 'b' is an uncharged residue, and 'c' a hydrophobic residue, the "bHEbbHbc" motif forms part of the metal-binding site.

In other embodiments, the enzyme has at least 70% identity, at least 80% identity, at least 90% identity, at least 95% identity or at least 99% identity to NEIVFPAAILQPP (SEQ. ID. NO: 31), FDDQGSRYDGDG (SEQ. ID. NO: 32), DPHSPDEF (SEQ. ID. NO: 33), NGVVRNIDEFY (SEQ. ID. NO: 34), and RVRIW (SEQ. ID. NO: 35). More preferably, the enzyme has at least 70% similarity, at least 80% similarity, at least 90% similarity, at least 95% similarity or at least 99% similarity to NEIVFPAAILQPP (SEQ. ID. NO: 31), FDDQGSRYDGDG (SEQ. ID. NO: 32), DPHSPDEF (SEQ. ID. NO: 33), NGVVRNIDEFY (SEQ. ID. NO: 34), and RVRIW (SEQ. ID. NO: 35).

In some embodiments, the "bHEbbHbc" motif is IGHEIGHGF (SEQ. ID. NO: 47).

In some embodiments, the sequences NEIVFPAAILQPP (SEQ. ID. NO: 31), FDDQGSRYDGDG (SEQ. ID. NO: 32), DPHSPDEF (SEQ. ID. NO: 33), NGVVRNIDEFY (SEQ. ID. NO: 34), and RVRIW (SEQ. ID. NO: 35) form part of the enzyme active site, for example, in binding the oligopeptide substrate, co-ordinating the metal ion and the nucleophile exchange.

In another embodiment, the enzyme further comprises at least 60% amino acid sequence identity or similarity to VNGKWL (SEQ. ID. NO: 36), EIPADRP (SEQ. ID. NO: 37), RIGALY (SEQ. ID. NO: 38), EIAPIL (SEQ. ID. NO: 39), and QSGLGLPDESYYREE (SEQ. ID. NO: 40).

In another embodiment, the enzyme further consists essentially of at least 60% amino acid sequence identity or similarity to VNGKWL (SEQ. ID. NO: 36), EIPADRP (SEQ. ID. NO: 37), RIGALY (SEQ. ID. NO: 38), EIAPIL (SEQ. ID. NO: 39), and QSGLGLPDESYYREE (SEQ. ID. NO: 40).

In other embodiments, the enzyme has at least 70% identity, at least 80% identity, at least 90% identity, at least 95% identity or at least 99% identity to VNGKWL (SEQ. ID. NO: 36), EIPADRP (SEQ. ID. NO: 37), RIGALY (SEQ. ID. NO: 38), EIAPIL (SEQ. ID. NO: 39), and QSGLGLPDESYYREE (SEQ. ID. NO: 40). More preferably, the enzyme has at least 70% similarity, at least 80% similarity, at least 90% similarity, at least 95% similarity or at least 99% similarity to VNGKWL (SEQ. ID. NO: 36), EIPADRP (SEQ. ID. NO: 37), RIGALY (SEQ. ID. NO: 38), EIAPIL (SEQ. ID. NO: 39), and QSGLGLPDESYYREE (SEQ. ID. NO: 40).

In some embodiments, the sequences VNGKWL (SEQ. ID. NO: 36), EIPADRP (SEQ. ID. NO: 37), RIGALY (SEQ. ID. NO: 38), EIAPIL (SEQ. ID. NO: 39) and QSGLGLPDESYYREE (SEQ. ID. NO: 40) are important for co-ordinating the protein to fold its three dimentional shape for the endopeptidase enzyme activity.

In some embodiments, the enzyme further comprises at least 60% amino acid sequence identity or similarity to FYGKTLSGTQQIRE (SEQ. ID. NO: 41), RWKRGV (SEQ. ID. NO: 42), LDWMT (SEQ. ID. NO: 43), WRDFSAL (SEQ. ID. NO: 44), MTPQTVNAYY (SEQ. ID. NO: 45) and NEIVFPAAILQPP (SEQ. ID. NO: 31).

In some embodiments, the enzyme further consists essentially of at least 60% amino acid sequence identity or similarity to FYGKTLSGTQQIRE (SEQ. ID. NO: 41), RWKRGV (SEQ. ID. NO: 42), LDWMT (SEQ. ID. NO: 43), WRDFSAL (SEQ. ID. NO: 44), MTPQTVNAYY (SEQ. ID. NO: 45) and NEIVFPAAILQPP (SEQ. ID. NO: 31).

In other embodiments, the enzyme has at least 70% identity, at least 80% identity, at least 90% identity, at least 95% identity or at least 99% identity to FYGKTLSGTQQIRE (SEQ. ID. NO: 41), RWKRGV (SEQ. ID. NO: 42), LDWMT (SEQ. ID. NO: 43), WRDFSAL (SEQ. ID. NO: 44), MTPQTVNAYY (SEQ. ID. NO: 45) and NEIVFPAAILQPP (SEQ. ID. NO: 31). More preferably, the enzyme has at least 70% similarity, at least 80% similarity, at least 90% similarity, at least 95% similarity or at least 99% similarity to FYGKTLSGTQQIRE (SEQ. ID. NO: 41), RWKRGV (SEQ. ID. NO: 42), LDWMT (SEQ. ID. NO: 43), WRDFSAL (SEQ. ID. NO: 44), MTPQTVNAYY (SEQ. ID. NO: 45) and NEIVFPAAILQPP (SEQ. ID. NO: 31).

In some embodiments, the sequences FYGKTLSGTQQIRE (SEQ. ID. NO: 41), RWKRGV (SEQ. ID. NO: 42), LDWMT (SEQ. ID. NO: 43), WRDFSAL (SEQ. ID. NO: 44), MTPQTVNAYY (SEQ. ID. NO: 45) and NEIVFPAAILQPP (SEQ. ID. NO: 31) are important for co-ordinating the protein to fold its three dimentional shape for the endopeptidase enzyme activity.

In some embodiments, the enzyme is a protein comprising at least 45% amino acid sequence identity or similarity to SEQ. ID. NO: 1. In other embodiments, the enzyme is a protein consisting of at least 45% amino acid sequence identity or similarity to SEQ. ID. NO: 1. In other embodiments, the enzyme is a protein consisting essentially of at least 45% amino acid sequence identity or similarity to SEQ. ID. NO: 1.

In other embodiments, the enzyme has at least 50% identity, at least 55% identity, at least 60% identity, at least 65% identity, at least 70% identity, at least 75% identity, at least 80% identity, at least 85% identity, at least 90% identity, at least 95% identity or at least 99% identity to SEQ. ID. NO: 1. More preferably, the enzyme has at least 50% similarity, at least 55% similarity, at least 60% similarity, at least 65% similarity, at least 70% similarity, at least 75% similarity, at least 80% similarity, at least 85% similarity, at least 90% similarity, at least 95% similarity or at least 99% similarity to SEQ. ID. NO: 1.

In some embodiments, the enzyme comprises a functional fragment of a whole intact protein, wherein the functional fragment cleaves the peptide bond after a -XPY- or -XPQ- motif in glutens. In one embodiment, the whole intact protein is SEQ. ID. NO: 1. In one embodiment, the functional fragment cleaves the peptide bond immediately after a -XPQ- motif and proline is the amino acid at the P1' position after the motif.

In another embodiment, the functional fragment comprises at least 20 contiguous amino acid residues. In other embodiments, the functional fragment comprises at least 40, at least 60, at least 80, at least 100, at least 120, at least 140, at least 160, at least 180, at least 200, at least 220, at least 240, at least 260, at least 280, at least 300, at least 320, at least 340, at least 360, at least 380, at least 400, at least 420, at least 440, at least 460, at least 480, at least 500, at least 520, at least 540, at least 560, at least 580, at least 600, at least 620, at least 640, or at least 660 contiguous amino acid residues.

The functional fragment can be assayed for the peptide bond cleavage using any methods known in the art, including but not limited to those described herein where Z-YPQ-pNA, Z-LPY-pNA, 26 mer and 33 mer gliadin peptides are used as substrates. In one embodiment, the functional fragment has at least 20% activity compared to the whole intact protein using the same assay method and substrate. In other embodiments, the functional fragment has at least 30% activity, at least 40% activity, at least 50% activity, at least 60% activity, at least 70% activity, at least 80% activity, at least 90% activity, at least 95% activity, at least 99% activity compared to the whole intact protein using the same assay method and substrate.

In one embodiment, the enzyme is neprilysin.

In another embodiment, the enzyme is neprilysin isolated from a bacterium selected from the group consisting of *R. mucilaginosa* ATCC 25296, WSA-8, *R. mucilaginosa* of 681, *R. mucilaginosa* DY-18, *R. dentocariosa* M567, *R. dentocariosa* ATCC 17931, *R. mucilaginosa* DY-18, *Xylanimonas cellulosilytica* DSM 15894, *Cellulomonas flavigena* DSM 20109, *Actinomyces viscosus* C505, *Gordonia bronchialis* DSM 43247, *Mycobacterium gilvum* PYR-GCK, *Kribbella flavida* DSM 17836, *Mycobacterium vanbaalenii* PYR-1, *Beutenbergia cavernae* DSM 12333, *Rhodococcus jostii* RHA1, *Nakamurella multipartita* DSM 44233, *Mobiluncus mulieris* 28-1, *Tsukamurella paurometabola* DSM 20162, *Corynebacterium amycolatum* SK46, *Bifidobacterium longum* subsp. *infantis* ATCC 15697, *Sanguibacter keddieii* ATCC 51767 and *Cellulomonas flavigena* ATCC 482.

Neprilysin belongs to the peptidase M13 superprotein family (pfam01431: Peptidase_M13). Members of this family are typically type-II membrane anchored enzymes which are known, or believed to activate or inactivate oligopeptide (pro)-hormones such as opioid peptides, or in the bacteria, the protein member is believed to be involved with milk protein cleavage. Other members of this superfamily include endothelin-converting enzyme, metalloendopeptidase, metalloendopeptidase PepO, and zinc metalloprotease.

The neprilysin (NEP) family of zinc metallopeptidases includes neprilysin, endothelin-converting enzyme-2 (ECE-2), PEX, damage induced neuronal endopeptidase (DINE), Kell and several neprilysin-like proteins. The best characterised of this family is neprilysin. Neprilysin (EC=3.4.24.11) is also known as membrane metallo-endopeptidase, neutral endopeptidase (NEP), CD10, and common acute lymphoblastic leukemia antigen (CALLA). Neprilysin is expressed at the cell surface of a variety of cell types.

Enzymatically, neprilysin functions both as an endopeptidase with a thermolysin-like specificity and as a dipeptidyl-carboxypeptidase. Neprilysin are oligopeptidases, the enzyme digests oligo- and polypeptides, but not proteins. It is a zinc-dependent metalloprotease enzyme and binds one zinc ion per protein molecule.

Structurally, neprilysin consists of a short cytoplasmic domain, a membrane-spanning region and a large extracellular domain. The cytoplasmic domain contains a conformationally-restrained octapeptide, which is thought to act as a stop transfer sequence that prevents proteolysis and secretion. The protein fold of the peptidase domain for neprilysin resembles that of thermolysin, also an enzyme member of the Peptidase_M13 super family. The active site residues for members of the NEP family and thermolysin typically occurs in the motif HEXXH. In crystallographic studies, the HEXXH motif forms parts of the metal-binding site. The HEXXH motif is relatively common, but can be more stringently defined for metalloproteases as 'abXHEbbHbc', where 'a' is most often valine or threonine and forms part of the S1' subsite in thermolysin and neprilysin, 'b' is an uncharged residue, and 'c' a hydrophobic residue. Proline is never found in this site, possibly because it would break the helical structure adopted by this motif in metalloproteases (Rawlings N D and Barrett A J., 1995, Meth. Enzymol. 248 183-228). Catalysis of the hydrolysis of internal, alpha-peptide bonds in a polypeptide chain occur by a mechanism in which water acts as a nucleophile, one or two metal ions hold the water molecule in place, and charged amino acid side chains are ligands for the metal ions.

In one embodiment, the isolated glutamine endopeptidase enzyme is not thermolysin.

Proteins having at least 50% sequence identity or similarity to SEQ. ID. NO: 1 are shown in Table 6, in FIG. 19 and FIG. 20. Sequence alignment of SEQ. ID. NO: 1, a neprilysin isolated from *R. mucilaginosa* ATCC 25296 using the BLASTP algorithm produced over 100 similar sequences in the public bacteria databases alone; the similar sequences had at least 45% similarity to SEQ. ID. NO: 1.

SEQ. ID. NO: 1 is the amino acid sequence of neprilysin predicted in *R. mucilaginosa* ATCC 25296 contig00029, whole genome shotgun sequence (RefSeq: ZP_05367591).

```
  1 MTTNSGITKE WVDETVKPGD DFFRHVNGKW LATHEIPADR PKDGGLYTLR DNAEKHVREL

61 VEKIAKEQPE SRIGALYNSF MDVEKIEADG LEPLLKEIAP ILNSATPSHL AVTLALLSRA

121 GLPQLFAWYT SNDPKDPKNY TFFLYQSGLG LPDESYYREE KHEAACAAYV EHIARMFQLT

181 GLAEGFGLTP EQAAQLVFTH ESELARLHWN VVENRDAEAT YNPYQATELD EKFPGFPFSQ

241 WLLALGADPE TLGQVIVAQP SFFEGAAKLF TSIPLMSWKL WAVWTVLRSR APFMYDELVQ
```

```
301 ESFNFYGKTL SGTQQIRERW KRGVGAVEKA LGEEIGQEYV AVHFPPSHKE KMLVLVGNLL

361 EAYRESIESL DWMTEATRQK ALEKLSKFVT KIGYPDKWRD FSALELVPGD LFENLRRTGA

421 FDADWLIARK GQPVDKAEWL MTPQTVNAYY MPPANEIVFP AAILQPPYFN PDADDAANYG

481 NIGMIIGHEI GHGFDDQGSR YDGDGKLESW WTEEDYAKFK ERTAALVEQY NAYVPVGLDP

541 KFHVNGELTL GENIGDLAGM SIALKAYRLA LKKQGIESLA DAPVIDGMTG IQRFFFSNAR

601 GWCTKSRPQH AEVMISVDPH SPDEFRVNGV VRNIDEFYEA FGVSEGDALY LAPEERVRIW
```

The coding sequence of neprilysin within the *R. mucilaginosa* ATCC 25296 contig00029 is found at region 5574 to 7556 of the contig00029 RefSeq: NZ_ACV001000010.1. (SEQ ID NO 22)

```
   1 atgactacta actctggaat cactaaagaa tgggtggatg aaaccgtcaa gccgggcgac
  61 gatttcttcc gccacgtcaa cggcaagtgg cttgctaccc acgaaatccc ggcggaccgc
 121 cccaaggacg gcggcctgta caccctccgc gataacgcag agaagcacgt gcgtgagctg
 181 gtggagaaga tcgcgaagga gcagccggag tcccgcatcg gcgcgctgta caactccttc
 241 atggatgttg agaagattga ggcggacggc ctggaacctc tgctgaagga aatcgccccg
 301 attctgaact cggcaacccc ctcccacctg gctgtgacct tggcgctgct gtctcgtgcg
 361 ggtctgccgc agctgttcgc ctggtacacc agcaacgacc cgaaggaccc gaagaattac
 421 acgttcttcc tgtaccagtc gggcctgggt ctgccggatg aatcctacta ccgtgaagag
 481 aagcacgagg ctgcatgcgc ggcgtatgtt gagcatattg cccgcatgtt ccagctgacc
 541 ggtctggctg agggcttcgg tctcaccccg gagcaggcgg ctcagctggt gttcacccac
 601 gagtctgagc tggctcgtct gcactggaac gtcgtggaga accgcgacgc tgaggcgacc
 661 tacaacccgt accaggcgac cgagctggac gagaagttcc ccggcttccc gttctcgcag
 721 tggctgctgg ctctgggtgc tgacccggag accctgggtc aggttattgt ggctcagccg
 781 tccttctttg agggtgcggc gaagctgttc acctccatcc cgctgatgag ctggaagctg
 841 tgggctgtgt ggactgttct gcgttcgcgt gcgccgttca tgtacgacga gctggttcag
 901 gagagcttca acttctacgg caagaccctt tccggtactc agcagattcg tgagcgttgg
 961 aagcgcggcg tgggcgctgt cgagaaggct ctgggtgagg agattggcca ggagtacgta
1021 gctgtgcact tcccgccctc gcacaaggag aagatgctgg ttctggtcgg caacctcctt
1081 gaggcgtacc gcgagtctat tgagtcgctg gactggatga ctgaggcaac ccgtcagaag
1141 gcgctggaga agctgtcgaa gttcgtcacc aagatcggtt accccgataa gtggcgtgac
1201 ttctccgcgc tggagctcgt tcccggtgac ctgttcgaga acctgcgccc caccggtgcg
1261 ttcgatgctg actggctgat tgcccgtaag ggtcagccgg tggataaggc ggagtggctg
1321 atgactccgc agaccgtgaa cgcgtactac atgccgccgg cgaatgagat tgtgttcccg
1381 gcagcgattc tgcagccgcc gtacttcaac ccggatgctg acgatgcggc gaactacggc
1441 aatatcggca tgattattgg ccacgagatt ggtcacggtt ttgacgatca gggttcccgc
1501 tatgacggtg acggcaagct ggagagctgg tggactgagg aggattacgc gaagttcaag
1561 gagcgtaccg cagccctggt ggagcagtac aacgcgtacg ttccggtggg tctggacccg
1621 aagttccacg tgaacggtga gctgactctg ggcgagaaca ttggcgacct ggctggcatg
1681 tcgattgcgt tgaaggcgta ccgtctggct ttgaagaagc agggcattga gtcgctggct
1741 gacgcgccgg tgattgacgg catgaccggt attcagcgtt tcttcttctc gaatgctcgc
1801 ggctggtgca cgaagtcccg cccgcagcat gctgaggtga tgatttcggt ggatccgcat
```

```
-continued
1861 tcgccggatg agttccgtgt gaacggtgtg gtgcgcaata ttgatgagtt ctatgaggcg 1921 tttggcgtct ctgagggcga tgcactgtac ctggctccgg aggagcgcgt gcgcatctgg 1981 tag
```

In one embodiment, provided herein is a recombinantly synthesized glutamine endopeptidase enzyme that comprises at least 45% amino acid sequence identity or similarity to SEQ. ID. NO: 1 is used. In another embodiment, provided herein is a recombinantly synthesized glutamine endopeptidase enzyme that consist of at least 45% amino acid sequence identity or similarity to SEQ. ID. NO: 1. In yet another embodiment, provided herein is a recombinantly synthesized glutamine endopeptidase enzyme is SEQ. ID. NO: 1. In yet another embodiment, provided herein is a recombinantly synthesized glutamine endopeptidase enzyme that consists essentially of at least 45% amino acid sequence identity or similarity to SEQ. ID. NO: 1.

In other embodiments, the recombinantly synthesized glutamine endopeptidase enzyme has at least 50% identity, at least 55% identity, at least 60% identity, at least 65% identity, at least 70% identity, at least 75% identity, at least 80% identity, at least 85% identity, at least 90% identity, at least 95% identity or at least 99% identity to SEQ. ID. NO: 1. More preferably, the enzyme has at least 50% similarity, at least 55% similarity, at least 60% similarity, at least 65% similarity, at least 70% similarity, at least 75% similarity, at least 80% similarity, at least 85% similarity, at least 90% similarity, at least 95% similarity or at least 99% similarity to SEQ. ID. NO: 1.

One skilled in the art would be able to use standard recombination molecular techniques to synthesize recombinantly neprilysin. For example, design PCR primers based on SEQ. ID. NO: 1 for PCR cloning the coding sequence from the genomic DNA sequence of a *Rothia* species bacterium. One skilled in the art would also know to include modifications to the coding sequence for efficient protein synthesis and purification in non-bacteria systems such as yeast and mammalian cell lines. Modifications to the coding sequence can include but are not limited to removal of signal peptide, addition or change of signal peptide, change to the preferred codon usage of protein synthesis host and fusion protein formation.

In some embodiments, one skilled in the art would also know to include modifications to the coding sequence for increasing the enzyme stability, enzyme activity and enzyme potency such that a smaller amount of enzyme is necessary to achieve the desired gluten digestion. Modifications can include but are not limited to changes in amino acid changes, amino acid modifications (e, g., acetylation, PEGylation), and fusion protein formation.

The isolated glutamine endopeptidase enzyme that is purified from a *Rothia* species bacteria or is a recombinantly synthesized enzyme is useful in non-dietary based methods related to the treatment, prevention of additional immune reaction and diagnosis of Celiac sprue, gluten allergy and/or dermatitis herpetiformis as well as the detoxifying gluten-containing foodstuff.

The present invention provides methods for treating the symptoms of Celiac sprue, gluten allergy and/or dermatitis herpetiformis by decreasing the levels of toxic gluten oligopeptides in foodstuffs, either prior to or after ingestion by a subject. The gluten oligopeptides are "toxic" to these subjects, causing an autoimmune response by the body's immune system to synthesize antibodies to against itself, resulting in loss of nutrient-absorbing villi in the small intestines. A well studied gluten oligopeptide is the 33-mer gliadin oligopeptide, LQLQPFPQPQLPYPQPQLPYPQPQLPYPQPQPF (SEQ. ID. NO: 2) (Lu Shan, et al., 2002, Science, 297:2275-2279; Frits Koning, et al., 2003, Science 299:513). Proline/glutamine-rich proteins are digested by trypsin, chymotrypsin, elastase and carboxypeptidase in the gut and smaller oligopeptides are produced which are resistant to further digestion by endogenous trypsin, chymotrypsin, elastase and carboxypeptidase in the gut. These digestion-resistant gluten oligopeptides are presumably toxic because they bind to HLA-DQ2 and stimulate T cell infiltration in the small intestines. By digestion with an extract from a *Rothia* species bacteria, these toxic oligopeptides are cleaved into fragments, thereby preventing or relieving their toxic effects in Celiac Sprue, gluten allergy or dermatitis herpetiformis subjects. Digestion of the toxic gluten oligopeptides to small not-toxic fragments can also be achieved with contacting the gluten oligopeptides with a *Rothia* species bacterium or with an isolated glutamine endopeptidase that is derived a *Rothia* species bacterium. The glutamine endopeptidase derived from a *Rothia* species bacterium has been shown to cleave an internal peptide bond after glutamine at a Xaa-Pro-Gln (XPQ) type motif in a peptide, e.g. gluten oligopeptides: Z-KPQ-pNA (benzyloxycarbonyl-lysine-proline-glutamine-paranitroanilide) and Z-YPQ-Pna (benzyloxycarbonyl-tyrosine-proline-glutamine-paranitroanilide). Gluten oligopeptides tend to be rich in proline and glutamine. In the 33-mer gliadin oligopeptide, LQLQPF-PQPQLPYPQPQLPYPQPQLPYPQPQPF (SEQ. ID. NO: 2), there are eight glutamine endopeptidase cleavage sites of the Xaa-Pro-Gln (XPQ) type, namely 1 FPQ, 4 QPQ and 3 YPQ sites. X or Xaa=any amino acids, P or Pro=proline, Q or Gln=glutamine, Y=lysine, F=phenylalanine, Z=benzyloxycarbonyl group and pNA is para-nitroanilide. Furthermore, there are three sequences of the Xaa-Pro-Tyr (XPY) type where Y=Tyr (tyrosine).

In the human body microorganisms outnumber human eukaryotic cells by an order of magnitude. The preponderance of these microorganisms can be found in the gastrointestinal (GI) tract, where they live for the most part in symbiosis with the host. Due to its rich colonization, the GI tract has been considered a "super organ" with functions provided not only by host—but by bacteria-derived proteins as well. The mutually beneficial relationship between the host and its colonizers is most evident in the biology of digestion. Many complex carbohydrates cannot be degraded by the arsenal of human digestive enzymes but can be hydrolyzed by bacterial glycosidases yielding catabolic compounds that can subsequently be utilized by the host. This represents a symbiotic relationship where the moist and nutrient-rich environment of the GI tract offers an ideal habitat for microbial colonization and at the same time the host benefits from optimal energy recovery from ingested food stuff (Camp et al., 2009, Gastroenterology 136(6):1989-2002).

Dietary gluten comprises a family of proteins that is subdivided into gliadins and glutenins, nutrients that are abundantly present in the Western diet. Gluten is fairly difficult to digest because of its unusual amino acid content and sequence. The predominant amino acids in the gluten sequences are proline and glutamine, which are not recognized by the typical proteolytic enzymes secreted by the stomach and the pancreas. In ~0.5 and 2% of the human population the undigestable gluten fragments cause an immunologic response leading to celiac disease. Most of those diagnosed with celiac disease require a strict life long adherence to a gluten free diet. This is extremely difficult to maintain since even minor gluten contamination are present in many foods not overtly known for gluten content. One of the therapeutic strategies to counteract or prevent the deleterious effect of these minor amounts of dietary gluten focuses on proteolytic enzymes to aid in their degradation, thus preventing their antigenic presentation to and activation of intestinal T cells. We discovered that potent gluten digestive enzymes are naturally associated with the upper GI tract, i.e., with microorganisms colonizing the oral cavity (Helmerhorst et al., 2010, PLoS One, in press). Such microorganisms may actually play a role in gluten digestion which and this role has so far not been recognized. In addition, such enzymes should be explored to investigate their potential clinical usefulness in the protection against celiac disease in subjects at risk. Host resident gluten-degrading microorganisms are apparently a viable source of novel enzyme(s) of tremendous interest. These enzymes offer the additional advantage to be potentially exploited as probiotic agents to generate more long lasting changes in the GI gluten digestive capacity of celiac patients.

Accordingly, the present invention provides a method of treating Celiac Sprue, gluten allergy and/or dermatitis herpetiformis to a subject in need thereof, the method comprises administering to the subject an effective dose of an extract from a *Rothia* species bacterium; wherein the extract from the *Rothia* species bacteria contains a glutamine endopeptidase enzyme that attenuates gluten toxicity in the subject.

In some embodiments, the extract from *Rothia* species bacteria is selected from a group consisting of an isolated glutamine endopeptidase enzyme, a clarified lysate of a *Rothia* species bacteria, a 25-45% ammonium sulphate precipitate of the lysate of a *Rothia* species bacteria where the precipitate has been resuspended in buffer and desalted, the supernatant fluid of a suspension of a *Rothia* species bacteria, and a suspension of a *Rothia* species bacteria. In one embodiment, the isolated glutamine endopeptidase enzyme is purified from a *Rothia* species bacterium. In another embodiment, the isolated glutamine endopeptidase enzyme is a recombinantly synthesized glutamine endopeptidase enzyme. In another embodiment, the isolated glutamine endopeptidase enzyme is neprilysin. In another embodiment, the isolated glutamine endopeptidase enzyme is selected from the proteins in Table 6. In yet another embodiment, the isolated glutamine endopeptidase enzyme is SEQ. ID. NO: 1.

In one embodiment, the extract comprises the purified enzyme and a pharmaceutically acceptable carrier. For example, the enzyme can be at least 20% pure, at least 35% pure, at least 45% pure, at least 55% pure, at least 65% pure, at least 75% pure, at least 85% pure, at least 95% pure, at least 95% pure, at least 99% pure, wherein all the percentages between 20 and 99 are explicitly included. The extraction can be further purified, for example, from the 70-75 kDa extraction using standard purification schemes known in the art, e.g. size exclusion chromatography to isolate the 70-75 kDa fractions from a clarified crude extract of a *Rothia* species bacteria cell lysate. The bacteria can be lysed by standard methods known in the art, e.g. with lysozymes and treatment in a par bomb. The lysate can then be clarified by ultracentrifugation at 100,000×G force for 1 hour at 4° C. The clarified lysate can then be concentrated and then fractioned with commercially available gel filtration matrix such as SEPHACRYL® (S-100/200/300/400/500) from GE Healthcare Life Sciences. Fractions with glutamine endopeptidase activity can be determined by methods known in the art and those described herein. One skilled in the art will be able to make minor modification for the enzyme being studied.

In one embodiment, the glutamine endopeptidase enzyme is purified in the following method: *R. mucilaginosa* ATCC cells were cultured from *Brucella* agar plates (Hardy Diagnostics, Santa Maria, Calif.) in 4 liter BHI for 24 h at 37° C. while shaking. Cells were harvested and suspended in 50 mM TrisHCl and 50 mM NaCl (pH 8.0) and concentrated to a final O.D. of 67 at 620 nm. Cells were sonicated for 20 times at a power setting of 7 using the Branson cell lysis sonifier the degree of lysis was monitored spectrophotometrically and sonication was terminated when the turbidity was reduced by 90%. The sonicate was centrifuged at 31,000×g for 20 min. The supernatant was collected and precipitated with 25-45% saturated ammonium sulfate. The precipitate was collected by centrifugation at 10,000×g for 20 min, and the pellet was dissolved, concentrated and desalted using centrifuge tubes with a 50 kD MW cut-off (MILLIPORE®). An aliquot of 670 mg protein was obtained. This protein was applied to a DEAE SEPHAROSE® Fast Flow column (GE Healthcare) of 2.6 cm×82.5 cm connected to an FPLC system (Pharmcia Biotech). Chromatographic separation of proteins was achieved at a flow rate of 0.7 ml/min and applying a gradient of 0-10% buffer B (containing 50 mM Tris HCl and 1M NaCl (pH 8.0) from 0 to 70 min; 10-35% buffer B from 70-2070 min, and 35-100% buffer B from 2070 to 2427 min. Fractions containing 24 ml were collected and protease activities were measured by mixing 200 µl of each fraction with 3 µl Z-YPQ-pNA (final concentration 150 mM). Active fractions were desalted, concentrated and 6.5 mg of protein was loaded onto a G-100 gel filtration column (SEPHADEX® G-100, Pharmacia fine Chemical Piscataway, N.J.) of 2.6 cm×82.5 cm. Samples were eluted at a flow rate of 0.5 ml/min. Collected fractions with activity were concentrated as described above and subjected either to a 1-ml column of HITRAP QFF anion-exchange chromatography (GE Healthcare, City, State) or to a 1-ml column of HITRAP QXL anion-exchange chromatography (GE Healthcare) Samples were eluted with a linear gradient of buffer B (formulation as described above). Fractions were again evaluated for activity, concentrated and analyzed for protein composition by SDS PAGE.

In one embodiment, the method is practiced when the subject is consuming any gluten-containing foodstuff. In another embodiment, the method is practiced prior to the consumption of gluten-containing foodstuff, wherein the subject is about to have some gluten-containing food or the subject suspects that there might be gluten or wheat-derived ingredients in the food that the subject is about to be consumed. In another embodiment, the method is practiced whenever food is consumed or three times a day with the three major meals of a day: breakfast, lunch and dinner.

Accordingly, in some embodiments, the extract from *Rothia* species bacteria is administered just before, during, or just after consumption of gluten-containing foodstuff.

In one embodiment, the extract from *Rothia* species bacteria is administered prior to consumption of gluten-containing foodstuff.

In one embodiment, the extract from *Rothia* species bacteria is administered in a gluten-containing foodstuff, e.g., incorporated into the gluten-containing foodstuff.

In one embodiment, the extract from *Rothia* species bacteria is administered from 1 hour prior to 1 hour after the subject has consumed a gluten-containing foodstuff.

In one embodiment, the extract from *Rothia* species bacteria is administered just before, during, or just after consumption of gluten-containing foodstuff.

Accordingly, the present invention also provides a method of detoxifying gluten-containing foodstuff, the method comprising contacting gluten-containing foodstuff with an effective dose of an extract from a *Rothia* species bacterium, wherein the extract from the *Rothia* species bacteria contains a glutamine endopeptidase enzyme. Detoxifying gluten-containing foodstuff has the same meaning as attenuating gluten toxicity. The goal is to reduce the amount of proline and glutamine rich oligopeptides that elicit immune responses characteristics of Celiac Sprue, gluten allergy and/or dermatitis herpetiformis.

In some aspects, the methods described herein comprise administering to a subject an effective dose of a *Rothia* species bacterium, an extract from a *Rothia* species bacteria or an isolated glutamine endopeptidase.

In other aspects, the methods described herein comprise contacting the gluten-containing foodstuff with an effective dose of a *Rothia* species bacterium, an extract from *Rothia* species bacteria or an isolated glutamine endopeptidase. In one embodiment, the contacting is performed in vitro prior to consumption of the gluten-containing food stuff. In another embodiment, the contacting is performed in vivo prior to, concurrent with or after consumption of the gluten-containing foodstuff. For example, the effective dose of a *Rothia* species bacterium, an extract from *Rothia* species bacteria or an isolated glutamine endopeptidase can be in the form of a lyophilized powder that is sprinkled upon the gluten-containing foodstuff, similar to putting grated cheese on pasta.

In another embodiment, the *Rothia* species bacteria is *R. mucilaginosa* ot 681 (strain WSA-2B, aka WSB 26), *Rothia* species ot 188 (strain WSA-8), *R. mucilaginosa* ATCC 25296 and *R. dentocariosa* ATCC 17931. These *Rothia* species bacteria can grow on gluten-limited media (FIG. 1). Extracts from these bacteria exhibit glutamine endopeptidase activities. Gluten-limited agar formulation contains per liter: Gluten: 23 g, Sodium chloride: 5.0 g, soluble starch: 1.0 g, Agar No. 2: 12.0 g, Sodium bicarbonate: 0.4 g, Glucose: 1.0 g, Sodium pyruvate: 1.0 g, Cysteine HCl monohydrate: 0.5 g, L-Arginine: 1.0 g, Soluble pyrophosphate: 0.25 g, Sodium succinate: 0.5 g, Haemin: 0.01 g, Vit K: 0.001 g.

Figure 5:
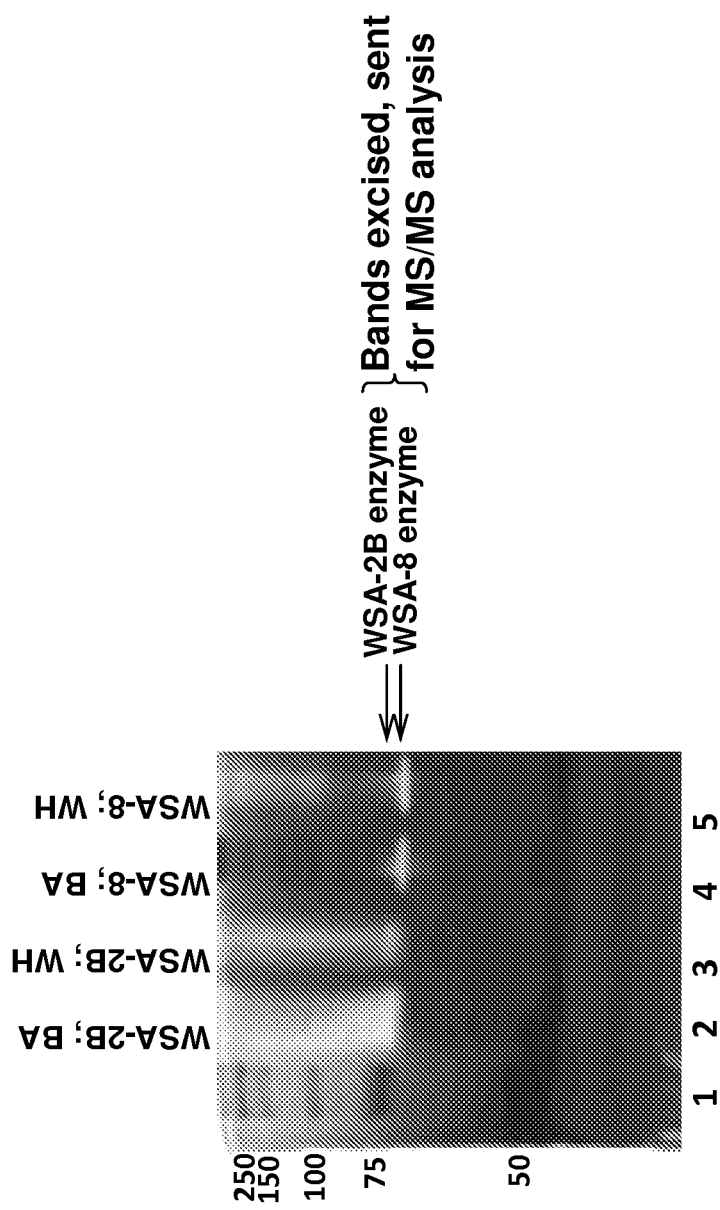
Figure 6:
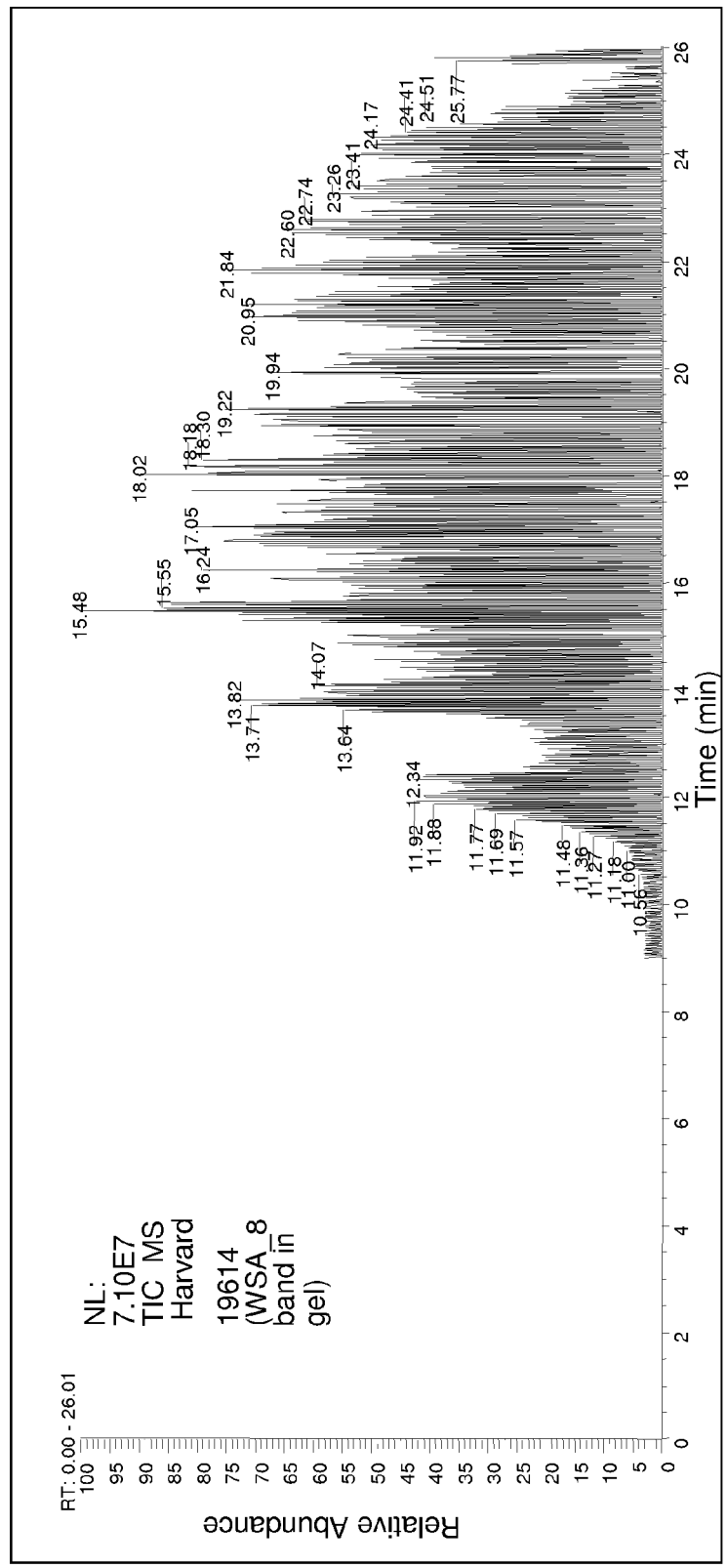

In one embodiment, the glutamine endopeptidase enzyme appears in the region of 70-75 kDa in a 6% gliadin zymogram (see FIG. 5). Therefore, in one embodiment, the apparent molecular size of the glutamine endopeptidase enzyme present in the extract, derived or isolated from a *Rothia* species bacterium is 70-75 kDa. Zymography is an electrophoretic technique, based on SDS-PAGE that includes a substrate copolymerized with the polyacrylamide gel, for the detection of enzyme activity. Samples are prepared in the standard SDS-PAGE treatment buffer but without boiling, and without a reducing agent. Following electrophoresis, the SDS is removed from the gel (or zymogram) by incubation in unbuffered Triton X-100, followed by incubation in an appropriate digestion buffer, e.g., 20 mM Tris, pH=8.0, for an optimized length of time at 37° C. or other optimum temperature for the enzyme. The zymogram is subsequently stained (commonly with Amido Black or Coomassie Brilliant Blue), and areas of digestion appear as clear bands against a darkly stained background where the substrate has been degraded by the enzyme. Zymography is an established method in the filed of Enzymology, e.g., in Lantz M S, Ciborowski P (1994) Methods Enzymol. 235: 563-594; and Snoek-van Beurden P A, Von den Hoff J W (2005) Biotechniques 38: 73-83. These references are hereby incorporated by reference in their entirety. One skilled in the art will be able to make minor modification for the enzyme being studied.

In one embodiment, the glutamine endopeptidase enzyme is active in a saliva sample. The normal pH range of human saliva is between 5 and 8. Accordingly, the glutamine endopeptidase enzyme present in the extract, derived or isolated from a *Rothia* species bacterium is active in a pH range of between about 5 and about 8. In one embodiment, the glutamine endopeptidase enzyme has a functional pH range of 3-10 within which there is detectable Z-YPQ-pNA cleaving activity within a 24 hour digestion period according to the assay method described herein. In another embodiment, the glutamine endopeptidase enzyme has a functional pH range of 7-10 within which there is substantially complete Z-YPQ-pNA cleavage within a 1 hour digestion period according to the assay method described herein.

In another embodiment, the glutamine endopeptidase enzyme is a metal-ion dependent protease (see FIG. 7). Addition of a divalent cation metal chelator, ethylenediaminetetraacetic acid (EDTA) completely inhibited YPQ cleavage activity. This indicates that the enzyme is a metal-ion dependent enzyme. In one embodiment, the glutamine endopeptidase enzyme present in the extract, derived or isolated from a *Rothia* species bacteria is inhibited by 1 mM 1-10 Phenanthroline. In one embodiment, the glutamine endopeptidase enzyme present in the extract, derived or isolated from a *Rothia* species bacterium is inhibited by 1 mM EDTA. Addition of the serine protease inhibitor, phenylmethanesulphonylfluoride or phenylmethylsulphonyl fluoride (PMSF) completely inhibited YPQ cleavage activity. In one embodiment, the glutamine endopeptidase enzyme present in the extract, derived or isolated from a *Rothia* species bacterium is inhibited by 0.1-1 mM PMSF. In one embodiment, the glutamine endopeptidase enzyme present in the extract, derived or isolated from a *Rothia* species bacterium is inhibited by 0.1-1 mM 4-(2-Aminoethyl) benzenesulfonyl fluoride hydrochloride (AEBSF).

In one embodiment, the glutamine endopeptidase enzyme attenuates gluten toxicity by cleaving the peptide bond after glutamine at -XPQ- motifs in gluten-containing foodstuff, wherein X=any amino acids, P=proline, and Q=glutamine, or at XPY where Y=tyrosine.

Accordingly, in some embodiments, the glutamine endopeptidase of a *Rothia* species described herein is capable of cleaving of any of the following peptides, including known T cell epitopes in gluten, under optimal conditions: QLQPF-PQPQLPY (SEQ. ID. NO: 3) or PFPQPQLPY (SEQ. ID. NO: 4), PQPQLPYPQPQLPY (SEQ. M. NO: 5) or PQPQLPYPQ (SEQ. ID. NO: 6), QPQQSFPQQQ (SEQ. ID. NO: 7) or PQQSFPQQQ (SEQ. ID. NO: 8), QLQPF-PQPELPY (SEQ. ID. NO: 9), PQPELPYPQPELPY (SEQ. ID. NO: 10), QPQQSFPEQQ (SEQ. ID. NO: 11); IQPQQ-PAQL (SEQ. ID. NO: 12); QQPQQPYPQ (SEQ. ID. NO: 13); SQPQQQFPQ (SEQ. ID. NO: 14); QQPFPQQPQ (SEQ. ID. NO: 15); or PFSQQQQPV (SEQ. ID. NO: 16), including 33-mer from alpha-gliadin, LQLQPF(PQPQLPY)$_3$PQPQPF (SEQ. ID. NO: 2), and the 26-mer from gamma-gliadin, FLQPQQPFPQQPQQPYPQQPQQPFPQ (SEQ. ID. NO: 17). In some embodiments, the glutamine endopeptidase of a *Rothia* species described herein have a kcat/Km of at least about 2.5 s$^{-1}$ M$^{-1}$, usually at least about 250 s$^{-1}$ M$^{-1}$ and preferably at least about 25000 s$^{-1}$ M$^{-1}$ for cleaving of any of the peptides described herein. A glutamine endopeptidase of a *Rothia* species described herein have a specificity kcat/Km>2 mM$^{-1}$ s$^{-1}$ for the quenched fluorogenic substrate Abz-QPQQP-Tyr(NO$_2$)-D. Methods of assaying such enzymatic activities are known to those skilled in the art, e.g., by HPLC or fluorescence spectroscopy and as described in U.S. Pat. No. 7,534,426, the reference is hereby incorporated by reference in its entirety. For the fluorescence spectroscopy-based assays, suitable fluorophores can be attached to the amino- and carboxy-termini of the peptides.

In one embodiment, the effective dose of the extract from the *Rothia* species bacterium is administered orally. In other embodiments, the effective dose of the *Rothia* species bacteria or the glutamine endopeptidase enzyme derived or isolated from a *Rothia* species bacterium is administered orally.

In one embodiment, the extract from the *Rothia* species bacteria is admixed to the gluten-containing foodstuff. In other embodiments, the *Rothia* species bacteria or the glutamine endopeptidase enzyme derived or isolated from a *Rothia* species bacterium is admixed to the gluten-containing foodstuff. For example, the extract, the bacteria or enzyme is mixed with the gluten-containing foodstuff prior to ingesting.

In one embodiment, the extract from the *Rothia* species bacteria is formulated with a pharmaceutically acceptable excipient or carrier. In other embodiments, the *Rothia* species bacteria or the glutamine endopeptidase enzyme derived or isolated from a *Rothia* species bacterium is formulated with a pharmaceutically acceptable excipient or carrier.

In one embodiment, the extract from the *Rothia* species bacteria is contained in a formulation that comprises an enteric coating. In other embodiments, the *Rothia* species bacteria or the glutamine endopeptidase enzyme derived or isolated from a *Rothia* species bacterium is contained in a formulation that comprises an enteric coating.

In one embodiment, the extract from the *Rothia* species bacteria is a lyophilized preparation. In other embodiments, the *Rothia* species bacteria, the glutamine endopeptidase enzyme derived or isolated from a *Rothia* species bacterium, recombinant enzyme, or various supernatants of the *Rothia* spp. lysate is lyophilized. Lyophilization or freeze-drying is a means of drying, achieved by freezing the wet substance and causing the ice to sublime directly to vapor by exposing it to a low partial pressure of water vapor. In practice, the substance may not be completely frozen, especially if non-aqueous solutions are present, and most lyophilization processes are completed by a period of desorption drying. The purpose of freeze-drying is to increase the shelf life, or preserve a specimen, be it food, microbial organisms, or, in some circumstances to decrease the size of the product. For various purposes, such as stable storage, the extract, bacteria or isolated enzyme can be lyophilized. Lyophilization is preferably performed on an initially concentrated preparation, e.g. of at least about 1 mg/ml for extract or isolated enzyme preparation and 1000 bacteria/ml. PEG can be added to improve the enzyme stability. In some embodiments, lyophilized extract, bacteria or isolated enzyme is without loss of specific activity. The lyophilized extract, bacteria or isolated enzyme and excipients is useful in the production of enteric-coated capsules or tablets, e.g., a single capsule or tablet can contain at least about 1 mg usually at least about 10 mg of *Rothia* species bacterial extract or isolated glutamine endopeptidase enzyme, and may contain at least 100 mg glutamine endopeptidase, at least about 200 mg, at least about 300 mg, at least about 400 mg, at least about 500 mg, up to about 1000 mg protein, including all the numbers between 1-1000 mg. Wherein lyophilized bacteria comprises the enteric-coated capsules or tablets, a single capsule or tablet can contain at least about 1000, at least about 10,000, at least about 100,000, at least about 1 billion *Rothia* species bacteria, including all the numbers between 1-1 billion. As described in detail here, enteric coatings can be applied, where a substantial fraction of the activity is retained, and is stable for at least about 1 month at 4° C. The method of lyophilizing bacteria is known to one skilled in the art, e.g. U.S. Pat. Nos. 4,205,132, 4,444,760, 5,192,743, 5,529,915, 6,750,330, and 7,572,893, all of which are incorporated by reference inn their entirety.

In one embodiment, the extract from the *Rothia* species bacteria is formulated for oral administration. In other embodiments, the *Rothia* species bacteria or the glutamine endopeptidase enzyme derived or isolated from a *Rothia* species bacterium is formulated for oral administration. For example, as capsules of a lyophilized preparation described. One or two capsule is taken with gluten-containing foodstuff.

In one embodiment, the effective dose of the extract from the *Rothia* species bacteria from ranges 0.01 mg to 500 mg/kg body weight. In another embodiment, wherein the *Rothia* species bacteria are used, the effective dose of the *Rothia* species bacteria ranges from 1000 to 1 billion *Rothia* species bacteria. In another embodiment, wherein the glutamine endopeptidase enzyme derived or isolated from a *Rothia* species bacterium is used, the effective dose of the enzyme is from 0.01 mg to 500 mg/kg body weight.

In one embodiment, the subject has been diagnosed with Celiac Sprue, gluten allergy/gluten intolerance and/or dermatitis herpetiformis. In another embodiment, the subject is a mammal, preferably a human. Current diagnosis methods for Celiac sprue include but are not limited to one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet.

In one embodiment of the methods described herein further comprises administering an effective dose of prolyl endopeptidase ranging from 0.01 mg to 500 mg/kg body weight. Prolyl endopeptidase (PREP or PEP) or prolyl oligopeptidase (EC 3.4.21.26), (sometimes also known as post-proline cleaving enzyme) is a large cytosolic enzyme that belongs to a distinct class of serine peptidases. The enzyme cleaves peptide bonds at the C-terminal side of proline residues. Its activity is confined to action on oligopeptides of less than 10 kDa and it has an absolute requirement for the trans-configuration of the peptide bond preceding proline. Some types of prolyl endopeptidase have been used in studies to decrease the propensity of gluten-containing wheat products to aggravate coeliac disease (Stepniak D, et al., 2006, Am J Physiol Gastrointest Liver Physiol 291 (4): G621-9), e.g. PEP derived or isolated from *Flavobacterium meningosepticum, Sphingomonas capsulate, Penicillium citrinum, Lactobacillus helveticus* and *Myxococcus Xanthus* in U.S. Patent Application No: 20060002917 and 20080193436, and in U.S. Pat. Nos. 7,563,864, 7,303,871, and 7320788. These references are hereby incorporated by reference in their entirety.

In one embodiment, the glutamine endopeptidase enzyme is isolated from a *Rothia* species bacterium by conventional protein purification methods known to those skilled in the art, e.g. as described in the Current Protocols in Molecular Biology and the Current Protocols in Protein Sciences. The protein fraction of an extract from a *Rothia* species bacterium can be concentrated by ammonium sulphate precipitation, and then purified by ion exchange chromatography on DEAE SEPHAROSE® CL-6B and gel filtration on SEPHADEX® G-100. Sample fractions are taken at each step and assayed for -XPQ- cleavage activity in order to follow the location of the enzyme. Such -XPQ- cleavage activity assays are well known in the art and are also described here.

In one embodiment, the present invention provides a pharmaceutical formulation for use in treatment of Celiac Sprue, gluten allergy and/or dermatitis herpetiformis comprising an effective dose of an extract from a *Rothia* species bacteria and a pharmaceutically acceptable excipient, wherein the extract from the *Rothia* species bacteria contains a glutamine endopeptidase enzyme that attenuates gluten toxicity in the subject.

In another embodiment, the pharmaceutical formulation comprising an effective dose of a *Rothia* species bacteria and a pharmaceutically acceptable excipient, wherein the *Rothia* species bacteria contains a glutamine endopeptidase enzyme that attenuates gluten toxicity in the subject.

In another embodiment, the pharmaceutical formulation comprising an effective dose of an isolated glutamine endopeptidase enzyme and a pharmaceutically acceptable excipient, wherein the glutamine endopeptidase enzyme that attenuates gluten toxicity in the subject. In one embodiment, the isolated glutamine endopeptidase enzyme is derived or isolated from a *Rothia* species bacterium. In one embodiment, the isolated glutamine endopeptidase enzyme is a recombinant protein. In one embodiment, the isolated glutamine endopeptidase enzyme is neprilysin.

In some embodiments of the pharmaceutical formulations described herein, the glutamine endopeptidase enzyme appears in the region of 70-75 kDa in a gliadin zymogram, is active in a saliva sample, is a metal-ion dependent protease, is stable to acid conditions, and detoxifies gluten by cleaving the peptide bond after glutamine at -XPQ- motifs in gluten-containing foodstuff, wherein X=any amino acids, P=proline, and Q=glutamine. In one embodiment, glutamine endopeptidase enzyme is active in a buffer that mimics the ion composition of saliva, e.g. saliva ion buffer described herein.

In some embodiments of the pharmaceutical formulations described herein, the *Rothia* species bacteria is *R. mucilaginosa* ot 681 (strain WSA-2B) *Rothia* species ot 188 (strain WSA-8), *R. mucilaginosa* ATCC 25296 and/or *R. dentocariosa* ATCC 17931. In some embodiments, the pharmaceutical formulations comprises more than one *Rothia* species bacteria or glutamine endopeptidase isolated from more than one type of bacteria described herein.

In some embodiments of the pharmaceutical formulations described herein, the extract, *Rothia* species bacteria or the isolated glutamine endopeptidase enzyme is lyophilized.

In some embodiments of the pharmaceutical formulations described herein, the effective dose of the extract ranges from 0.01 mg to 500 mg/kg body weight when the formulation comprises the extract and/or isolated glutamine endopeptidase enzyme, and 1000 to 1 billion bacteria when the formulation comprises the *Rothia* species bacteria.

In some embodiments of the pharmaceutical formulations described herein, the formulation is suitable for oral administration, e.g., an emulsion, a suspension, a tablet or a capsule.

In some embodiments of the pharmaceutical formulations described herein, the formulation comprises an enteric coating.

In some embodiments of the pharmaceutical formulations described herein, the formulation further comprises an effective dose of prolyl endopeptidase ranging from 0.01 mg to 500 mg/kg body weight. The prolyl endopeptidase can be isolated from *F. meningosepticum, S. capsulate, P. citrinum, L.s helveticus* and *M. Xanthus*. In other embodiments, the pharmaceutical formulations can comprise more that one prolyl endopeptidases, wherein the prolyl endopeptidases are from several origins or sources, e.g. from a formulation comprising prolyl endopeptidases isolated from *F. meningosepticum* and *S. capsulate*.

In one embodiment, the present invention provides a method of predicting/diagnosing Celiac Sprue, gluten allergy and/or dermatitis herpetiformis in a subject in need thereof, the method comprises determining the extent of digestion of a fixed amount of gliadin within 24 hour period by a biological sample obtained from a subject, for example, unstimulated whole saliva, stimulated whole saliva or dental plaque wherein when less than 50% of the fixed amount of gliadin digested indicates the subject likely have Celiac Sprue, gluten allergy/intolerance and/or dermatitis herpetiformis.

In one embodiment, the subject expresses the HLA-DQ2, DQ2.5, DQ2.2/DQ7.5 or DQ8 allele and/or has the HLA-DQ2, DQ2.5, DQ2.2/DQ7 or DQ8 antigen. Such subjects would be considered at risk of developing Celiac Sprue, gluten allergy/intolerance and/or dermatitis herpetiformis.

In another embodiment, the subject exhibits at least one symptom that is known to be associated Celiac Sprue, gluten allergy and/or dermatitis herpetiformis, e.g. itchy skin with no obvious rash or insect bites or those described herein. Such subjects would be considered at risk of developing Celiac Sprue, gluten allergy/intolerance and/or dermatitis herpetiformis.

In one embodiment, the subject is related to another subject who is diagnosed with Celiac Sprue and/or dermatitis herpetiformis. The relationship can be immediate and direct, e.g. as in father, mother, siblings; or indirect, e.g. as in cousins, aunt, uncle, grandparents. Such subjects would be considered at risk of developing Celiac Sprue, gluten allergy/intolerance and/or dermatitis herpetiformis.

For the diagnostic method, the fixed amount of gliadin is 250 µg/ml. The gliadin used can be commercially available gliadin extract from wheat (SIGMA-ALDRICH® Cat. No. G3375). The gliadin extract is a mixture of gliadins with the most prominent constituent being about 37 kDa in size (as evidenced from the gel electrophoresis). Methods of gliadin extract use are will known in the art and are also described in experiments in FIGS. 2, 3, 5, and 8 of the Example 1 section.

In one embodiment, a biological sample obtained from a subject is a sample of whole saliva or dental plaques. In one embodiment, the sample of whole saliva is unstimulated whole saliva. Unstimulated whole saliva is saliva that had naturally accumulated in the oral cavity between swallowings and it is collected by expectoration in graduated cylindrical tubes places on ice.

In another embodiment, the sample of whole saliva is stimulated whole saliva. Stimulated whole saliva is collected when donors are chewing on a 1 g bolus of tasteless paraffin wax (parafilm). The masticatory stimulated saliva is collected in graduated cylindrical tubes places on ice.

In one embodiment, the dental plaques are supragingival plaque samples. These are collected from interproximal dental spaces with an explorer 24 hr after refraining from oral hygiene and are suspended in saliva ion buffer to an $OD_{620nm}$ of ~1.0 prior to mixing with the gliadin.

In one embodiment, the saliva or dental plaque is suspended in saliva ion buffer and mixed with a gliadin-derived enzymatic substrate, such as A-Xaa-Pro-Gln-B where A is an N-terminal protective group, e.g. benzyloxycarbonyl and B is the reporter group, e.g. paranitroanilide, and Xaa is an amino acid present in zero, 1 or more copies. Saliva or plaque suspended in saliva ion buffer is then incubated with this substrate to allow cleavage of the peptide bond after glutamine. This cleavage is indicative of glutamine endopeptidase activity, and is monitored spectrophotometrically, luminometrically or fluorimetrically by asy methods known to one skilled in the art. Subjects showing statistically significant differences ($P<0.05$) from values obtained from a healthy pool of subjects will be considered at risk for displaying or developing Celiac Sprue and/or dermatitis herpetiformis and/or gluten allergy.

In another embodiment, gliadin-degrading protease(s) in the saliva and/or plaque samples from patients suffering from Celiac Sprue and/or dermatitis herpetiformis and/or gluten allergy or of those at risk of developing the disease is visualized and quantitated by gliadin zymography. Gliadin zymography is a technique similar to gelatin zymography, except that gliadin is incorporated in the gel as the enzymatic substrate instead of gelatin. Aliquots of 100 ul of saliva or suspended plaque sample will be dried and suspended in sample buffer containing 0.125 M Tris-HCl, 20% (v/v) glycerol, 4% sodium dodecyl sulfate, and 0.005% (w/w) bromophenol blue. Gel electrophoresis will be carried out at 4° C. at a constant voltage of 100 V, followed by renaturing of the gel in 2.5% (v/v) triton X-100 and developing of enzyme activity for 24 h at 37 C. in 20 mM Tris buffer (pH=7.5). Protease band intensities are quantitated by densitometric analysis. The absence of one or more protease bands in the overall gliadin zymogram protease pattern will be considered a diagnostic marker for displaying or developing Celiac Sprue and/or dermatitis herpetiformis and/or gluten allergy.

In another embodiment, the amount of *Rothia* species will be quantitated in saliva or dental plaque samples using strain-specific complimentary $^{32}$P-labeled DNA or RNA probes against unique 16S DNA domains or by generating oligolabeled DNA fragments (Feinberg et al., Anal. Biochem 132: 6-13 (1983). A 200 µl aliquot of whole saliva or suspended dental plaque samples will be mixed with 150 µl 10 mM Tris and 1 mM EDTA. From this mixture, 200 µl will be mixed with 100 µl 0.5M NaOH. *Rothia*-specific DNA and RNA levels will be quantitated following Nothern and Southern blot analysis known to those skilled in the art. Measures of quantitation will be based on the pixel intensities of the read-out system. DNA/RNA will also be quantitated using TAQ-MAN®-derivatized probes instead of radiolabeled probes. In this case, DNA/RNA is isolated from *Rothia* species, followed by quantative PCR and read-out of a fluorescent signal the intensity of which is related to the numbers of *Rothia* DNA/RNA present in the sample. *Rothia* levels will be expressed relative to total bacterial DNA in the saliva or plaque sample, which will be quantitated using a probe complimentary to a highly conserved DNA domain. Subjects showing statistically significant differences in *Rothia* levels (P<0.05) from values obtained from a healthy pool of subjects will be considered at risk for displaying or developing Celiac Sprue and/or dermatitis herpetiformis and/or gluten allergy.

The method of assessing the degree and mode of digestion can be determined by protein gel electrophoresis or mass spectrometry respectively that are known in the art and are described herein.

In one embodiment, the invention provides a kit for predicting/diagnosing Celiac Sprue, gluten allergy/intolerance and/or dermatitis herpetiformis in a subject in need thereof, comprising: an amount of gliadin substrate and reagents to assay for the endopeptidase activity by determining the amount of undigested gliadin.

In a further embodiment, the kit provides materials, reagents and instructions such as containers and buffers for performing the assay, and a chart for comparing the results and making a decision based on the results. For example, the kit can have a measured quantity of saliva ion buffer, e.g. 5 ml in a screw-cap container, measured amount of a gliadin solution, a measured amount of reagents to assay for undigested gliadin and instruction and a chart of possible color results. In using this exemplary kit, this entire volume of 5 ml is emptied into the buccal cavity of a subject and the subject swishes the buffer vigorously for 1 minute and spits buffer back into the original container. Next, the measured amount of a gliadin solution is added. The container is capped tightly, the contents mixed by repeated inverting the container for 1 minute and left at room temperature for 24 hours. At the end of that period, the measured amount of reagents to assay for undigested gliadin is added and mixed. In one embodiment, the reagents to assay for undigested gliadin produces a color read out. The color read out of the container is observed and compared to a chart that is provided with the kit. As another example, the kit can have a measured quantity of saliva ion buffer, a graduated container for collecting saliva, measured amount of a gliadin solution, a measured amount of reagents to assay for undigested gliadin and instruction and a chart of possible color results. In using this exemplary kit, the subject collects the required amount of saliva in the graduated container for collecting saliva, and then the saliva is diluted with the measured quantity of saliva ion buffer and mixed with the measured amount of a gliadin solution and left at room temperature for 24 hours before assaying for the amount of undigested gliadin.

DEFINITIONS OF TERMS

As used herein, the term "treat", "treating" or "treatment" means to stabilize or improve the clinical symptoms of the subject. "Treat", "treating" or "treatment" also means to relieve or alleviate at least one symptom associated with such condition, or to slow or reverse the progression or anticipated progression of such condition, at bringing about ameliorations of the symptoms of the pathology. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the likes. In one embodiment, the symptom of Celiac Sprue, gluten allergy and/or dermatitis herpetiformis is alleviated by at least 20%, at least 30%, at least 40%, or at least 50%. In one embodiment, the symptom of Celiac Sprue, gluten allergy and/or dermatitis herpetiformis is alleviated by more that 50%. In one embodiment, the symptom of Celiac Sprue, gluten allergy and/or dermatitis herpetiformis is alleviated by 80%, 90%, or greater.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of elements that do not materially affect the basic and novel or functional characteristic(s) of that embodiment of the invention.

The term "consisting of" in reference to the isolated enzyme, methods, and respective components thereof as described herein, which are exclusive of any element not recited in that description of the embodiment As used herein, the term "effective dose" refers to an amount of a biologically active molecule or conjugate thereof sufficient to exhibit a detectable therapeutic effect, e.g. reduction in the symptoms associated with Celiac sprue, gluten allergy and/or dermatitis herpetiformis, e.g. fatigue, chronic diarrhea, malabsorption of nutrients, weight loss, abdominal distension, anemia, the presence of antibodies specific for tissue transglutaminase, the presence of pro-inflammatory T cells and cytokines, and damage to the villus structure of the small intestines. The specific amount that is therapeutically effective can be readily determined by an ordinary medical practitioner, and can vary depending on factors known in the art, such as, for example, the subject's history and age, the stage of pathological processes, and the administration of other agents or therapeutics that inhibit pathological processes in Celiac sprue, gluten allergy and/or dermatitis herpetiformis.

As used herein, in one embodiment, the term "an extract from a *Rothia* species" refers to a clarified aqueous solution that formerly comprised a *Rothia* species for example, a suspension of *Rothia* species in phosphate buffered saline (PBS) that was agitated for 1 hour at room temperature and then centrifuged at 1000×G for 10 minutes to sediment the bacteria. The supernatant PBS fluid is "an extract from a *Rothia* species". Similarly, a clarified saliva sample is "an extract from a *Rothia* species".

In another embodiment, "an extract from a *Rothia* species" can also mean a clarified periplasmic extraction of a *Rothia* species, for example, a suspension of *Rothia* species in phosphate buffered saline (PBS) with 20% or 500 mM sucrose and is then agitated for 1 hour at 4° C. and then centrifuged at 1000×G for 10 minutes to sediment the bacteria. In the presence of high sucrose concentration, the bacteria undergo osmotic shock. Such methods of making periplasm extracts are well known to those skilled in the art, e.g. as described in U.S. Pat. No. 5,856,142, this reference is hereby incorporated by reference in its entirety.

In another embodiment, "an extract from a *Rothia* species" can also mean a clarified cell lysate of a *Rothia* species, wherein the bacteria are lysed in a suitable buffer and the lysate is centrifuged at 20,000×G for 30 minutes to sediment the cell debris. In other embodiments, ultracentrifugation clarified cell lysate of a *Rothia* species and a chromatography fraction containing a 70-75 kDa protein with a glutamine endopeptidase activity as assayed by gliadin zymography and other methods described herein are also considered "extracts from a *Rothia* species".

As used herein, the term "a glutamine endopeptidase" refers to a proteolytic peptidase that breaks peptide bonds of non-terminal amino acids (i.e. within the molecule) at the -XPQ- or -Xaa-Pro-Gln- triplet sequence and the breakage occurs immediately after the glutamine residue. X or Xaa=any amino acids, P or Pro=proline, and Q or Gln=glutamine.

As used herein, the term "attenuates gluten toxicity" in the context of a glutamine endopeptidase refers to the endopeptidase enzyme reduces, weakens or lessen in the amount, degree, and/or the density of toxic gluten oligopeptides production from gluten-containing foodstuff before or after the normal digestion of gluten-containing foodstuff by endogenous trypsin, chymotrypsin, elastase and carboxypeptidase in the gut. This is achieved by digesting the toxic gluten oligopeptides to smaller peptide fragments that are lacking the T cell epitopes in glutens. The activity of a glutamine endopeptidase from *Rothia* species described herein, before and/or after the digestion of gluten oligopeptides produced by endogenous trypsin, chymotrypsin, elastase and carboxypeptidase would result in less than 10% of the post-digestion products being longer than PQPQLPYPQ (SEQ. ID. NO: 6) which has nine amino acid residues. This can be assessed by the longer retention times on a C18 reverse phase HPLC column monitored at $A_{215}$ and such methods of well known to one skilled in the art.

The assessment of "attenuation of gluten toxicity" can be determined by measuring the ability of the extract of *Rothia* species or isolated glutamine endopeptidase from *Rothia* species described herein to increase the concentration of free $NH_2$-termini in a reaction mixture containing 1 mg/ml of undigested or trypsin/chymotrypsin/elastase/carboxypeptidase pre-digested gluten substrate and 10 μg/ml of the extract or glutamine endopeptidase from a *Rothia* species, incubated at 37° C. for 1 hour. An attenuation of gluten toxicity activity useful in the practice of the present invention will increase the concentration of the free amino termini under such conditions, usually by at least about 25%, more usually by at least about 50%, and preferably by at least about 100%. Additionally, there would be a reduction in the residual molar concentration of oligopeptides greater than about 1000 Da in a 1 mg/ml trypsin/chymotrypsin/elastase/carboxypeptidase pre-digested gluten substrate after a 1 hour incubation with 10 μg/ml of the extract or enzyme by at least about 2-fold, usually by at least about 5-fold, and preferably by at least about 10-fold. The concentration of such oligopeptides can be estimated by methods known in the art, for example size exclusion chromatography and the like.

In another embodiment, "attenuates gluten toxicity" also refers to reducing the ability of a gluten oligopeptide to bind to HLA-DQ. The ability of a substrate to bind to HLA-DQ is indicative of its toxicity; fragments smaller than about 8 amino acids are generally not stably bound to Class II MHC. The detoxification of whole gluten can be monitored by polyclonal T cell lines derived from intestinal biopsies of celiac or gluten allergic patients, by LC-MS-MS and by ELISA assays using monoclonal antibodies capable of recognizing sequences specific to gliadin.

For example, an extract of a *Rothia* species or the isolated glutamine endopeptidase from *Rothia* species described herein can reduce the potency by which a trypsin/chymotrypsin/elastase/carboxypeptidase pre-digested gluten substrate can antagonize binding of PQPELPYPQPQLP (SEQ. ID. NO: 18) to HLA-DQ2. Treatment with an extract of *Rothia* species bacteria or the isolated glutamine endopeptidase from *Rothia* bacteria described herein that digests toxic oligopeptides, by reducing the concentration of the toxic oligopeptides, prevents a mixture containing them from competing with a test peptide for MHC binding. Such a competition assay can be performed by incubating 1 mg/ml trypsin/chymotrypsin/elastase/carboxypeptidase pre-digested gluten substrate with 10 μg/ml of the extract or enzyme, and the ability of the resulting solution to displace radioactive PQPELPYPQPQLP (SEQ. ID. NO: 19) pre-bound to HLA-DQ2 molecules can then be quantified, with a reduction of displacement, relative to a non-treated control, indicative of utility in the methods of the present invention.

In yet another embodiment, "attenuates gluten toxicity" also refers to reducing the anti-tTG antibody and/or anti-gliadin antibodies response to a "gluten challenge diet" in a Celiac sprue or gluten allergic/gluten intolerance patient by at least about 2-fold, more usually by at least about 5-fold, and preferably by at least about 10-fold. A "gluten challenge diet" is defined as the intake of 100 g bread per day for 3 days by an adult Celiac Sprue or gluten allergic patient previously on a gluten-free diet. The anti-tTG antibody (ATA) and anti-gliadin antibodies (AGA) response can be measured in peripheral blood using standard clinical diagnostic procedures, as known in the art.

As used herein, the term "admix" in the context of gluten-containing foodstuff refers to mixing or blending with gluten-containing foodstuff.

As used herein, the term "glutens" refers to a mixture of proteins, including gliadins and glutelins, found in wheat grains and other grain, which are not soluble in water and which give wheat dough its elastic texture. "Glutens" also refer to the prolamins that are found in rye, barley, and oats.

As used herein, the term "glutelin" refers to prolamin-like proteins that are found in grass seeds, e.g. wheat, and they are soluble in dilute acids or bases, detergents, chaotropic or reducing agents. "Glutelin" tend to be rich in prolines and glutamine.

As used herein, the term "prolamins" refers to a group of plant storage proteins having high proline content and is found in the seeds of cereal grains such as wheat (gliadin), barley (hordein), rye (secalin), corn (zein) and as a minor protein, avenin in oats. They are characterized by a high glutamine and proline content and are generally soluble only in strong alcohol solutions. Some prolamins, notably gliadin from wheat, and similar proteins found in the grass seed of the *Triticeae* species can induce coeliac disease in genetically predisposed individuals.

As used herein, the term "gliadin" refers to the alcohol-soluble, glutamine and proline-rich prolamin glycoprotein found in wheat. This is one of the proteins that induce coeliac disease in genetically predisposed individuals. In other embodiments, gliadins also encompass proline-rich prolamin glycoproteins from other sources. Examples of gliadin sequences include but are not limited to wheat alpha gliadin sequences, for example as provided in GENBANK accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

As used herein, the term "gluten-containing foodstuff" refers to food and/or ingredients of food that has gluten and other proteins found in wheat, barley, rye, and oats. "Gluten-containing foodstuff" also to refer to food and/or ingredients of foods that are made of wheat, barley, rye, and oats.

As used herein, the term "consuming gluten-containing foodstuff" refers to ingesting food made of wheat, rye, barley, and oats, e.g. pizza, cake, etc. as well as ingesting food made with ingredients that are made with wheat, rye, barley, and oats, e.g. soy sauce and chocolate cookie dough ice cream.

As used herein, the term "diagnosed of Celiac sprue, gluten allergy/gluten intolerance and/or dermatitis herpetiformis" refers to having the symptoms associated with Celiac sprue, gluten allergy and/or dermatitis herpetiformis, e.g. fatigue, chronic diarrhea, malabsorption of nutrients, weight loss, abdominal distension, anemia, the presence of antibodies specific for tissue transglutaminase (ATA), antibodies specific for α/β,γ-gliadin (AGA), the presence of pro-inflammatory T cells and cytokines, and damage to the villus structure of the small intestines.

As used herein, the term "toxic gluten oligopeptides" refers are peptides derived during normal human digestion of gliadins and related storage proteins from dietary cereals, e.g. wheat, rye, barley, and the like. Such oligopeptides are believed to act as antigens for T cells in Celiac Sprue. For binding to Class H MHC proteins, immunogenic peptides are usually from about 8 to 20 amino acids in length, more usually from about 10 to 18 amino acids. Such peptides may include XPQ and XPY motifs, such as the motif PQPQLPYPQ (SEQ. ID. NO: 6). Determination of whether an oligopeptide is immunogenic for a particular patient is readily determined by standard T cell activation and other assays known to those of skill in the art. Other examples of immunogenic gliadin oligopeptides are described in Wieser (1995) Baillieres Clin Gastroenterol 9(2):191-207, incorporated herein by reference. "Toxic gluten oligopeptides" also refers are peptides that comprise known T cell epitopes in gluten, e.g. QLQPFPQPQLPY (SEQ. ID. NO: 3) or PFPQPQLPY (SEQ. ID. NO: 4), PQPQLPYPQPQLPY (SEQ. ID. NO: 5) or PQPQLPYPQ (SEQ. ID. NO: 6), QPQQSFPQQQ (SEQ. ID. NO: 7) or PQQSFPQQQ (SEQ. ID. NO: 8), QLQPFPQPELPY (SEQ. ID. NO: 9), PQPELPYPQPELPY (SEQ. ID. NO: 10), QPQQSFPEQQ (SEQ. ID. NO: 11); IQPQQPAQL (SEQ. ID. NO: 12); QQPQQPYPQ (SEQ. ID. NO: 13); SQPQQQFPQ (SEQ. ID. NO: 14); QQPFPQQPQ (SEQ. ID. NO: 15); or PFSQQQQPV (SEQ. ID. NO: 16), including 33-mer from alpha-gliadin, LQLQPF(PQPQLPY)₃PQPQPF (SEQ. ID. NO: 2), and the 26-mer from gamma-gliadin, FLQPQQPF-PQQPQQPYPQQPQQPFPQ (SEQ. ID. NO: 17).

The term "isolated" refers to the enzyme protein which is substantially or essentially free from bacterial components which normally accompany or interact with the enzyme as found in the bacteria.

As used herein, the term "inhibited" or "inhibition" when used in the context with the glutamine endopeptidase activity means the reduction of the cleavage of -XPQ-containing peptides by at least about 50%, about 60%, about 70%, about 80%, about 90%, about 100% by any assay described herein or known in the art, wherein X is any amino acid, P is proline and Q is glutamine.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

As used herein, "identity" means the percentage of identical amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ea., Oxford University Press, New York, 1988; Biocomputing: Informatics and—14 Genome Projects, Smith, D. W., ea., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988)). Methods to determine identity are designed to give the largest match between the sequences tested. Moreover, methods to determine identity are codified in publicly available computer programs such as BLASTP.

The terms "identical" or percent "identity", in the context of two or more polypeptide sequences, refers to two or more sequences or subsequences that are the same or have a specified percentage of amino acid residues are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., amino acid sequence of the enzyme described herein), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2: 482, 1981, by the homology alignment algorithm of Needleman & Wunsch, J. Mol. Biol. 48: 443, 1970, by the search for similarity method of Pearson & Lipman, Proc. Nat'l. Acad. Sci. USA 85: 2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, Ausubel et al., eds. 1995 supplement).

Programs for searching for alignments are well known in the art, e.g., BLAST and the like. For example, if the target species is human, a source of such amino acid sequences or gene sequences (germline or rearranged antibody sequences) can be found in any suitable reference database such as GENBANK, the NCBI protein databank, VBASE, a database of human antibody genes, and the Kabat database of immunoglobulins or translated products thereof. If the alignments are done based on the nucleotide sequences, then the selected genes should be analyzed to determine which genes of that subset have the closest amino acid homology to the originating species antibody. It is contemplated that amino acid sequences or gene sequences which approach a higher degree homology as compared to other sequences in the database can be utilized and manipulated in accordance with the procedures described herein. Moreover, amino acid sequences or genes which have lesser homology can be utilized when they encode products which, when manipulated and selected in accordance with the procedures described herein, exhibit specificity for the predetermined target antigen. In certain embodiments, an acceptable range of homology is greater than about 50%. It should be understood that target species can be other than human.

A preferred example of algorithm that is suitable for determining percent sequence identity and sequence similarity are the BLAST and BLAST 2.0 algorithms, which are described in Altschul et al., Nuc. Acids Res. 25: 3389-3402, 1977 and Altschul et al., J. Mol. Biol. 215: 403-410, 1990, respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89: 10915, 1989) alignments (B) of 50, expectation (E) of 10, M=5, N=−4, and a comparison of both strands.

The terms "similar" or percent "similar", in the context of two or more polypeptide sequences, refers to two or more sequences or subsequences that are similar or have a specified percentage of amino acid residues are similar (i.e., about 60% similarity, preferably 65%, 70%, 75%, 80%, 85%, 90%, 91%, 92%, 93%, 94%, 95%, 96%, 97%, 98%, 99%, or higher similarity over a specified region (e.g., amino acid sequence of the enzyme described herein), when compared and aligned for maximum correspondence over a comparison window or designated region) as measured using a BLAST or BLAST 2.0 sequence comparison algorithms with default parameters described below, or by manual alignment and visual inspection. Similarity occurs when the amino acids are not the same but are "conservative amino acid substitution of those in the reference protein, e.g., the neprilysin sequence from *R. mucilaginosa*. The term also includes sequences that have deletions and/or additions, as well as those that have substitutions.

As described below, the preferred algorithms can account for gaps and the like. Preferably, similarity exists over a region that is at least about 25 amino acids or nucleotides in length.

As used herein, the term "conservative amino acid substitution" is one in which the amino acid residue is replaced with an amino acid residue having a side chain with a similar charge and size. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, the term "substantially complete" in reference to Z-YPQ-pNA cleavage means "the same as complete, total or very close to complete", such as 99%, 99.3%, 99.5%, 99.99%, and 100% Z-YPQ-pNA cleavage.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid, and the like.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

The term "functional fragment" in reference to the enzyme refers to functional portion of the enzyme and not the whole intact enzyme. The functional fragment has an amino acid residue sequence that is shorter than that of a whole intact enzyme described herein. For example, if the enzyme is neprilysin, the whole intact enzyme is 660-amino acid long, while a functional fragment is only a portion of the 660 amino acid polypeptide, such as, only 100-amino acid long. "Functional fragments" have peptide bond cleavage activities; they cleave the peptide bond after a -XPY- or -XPQ- motif in glutens.

As used herein, the term "active" when used with the enzyme refers to the enzyme cleaving activity. Therefore when an enzyme is "active", it means that the enzyme exhibit detectable cleaving activity, preferably cleaving the peptide bond after a -XPY- or -XPQ- motif in glutens.

Celiac Sprue, Gluten Allergy and/or Dermatitis Herpetiformis

Celiac sprue, also known as celiac disease, gluten-sensitive enteropathy, and gluten-induced enteropathy, is a chronic disease of the digestive tract that interferes with the digestion and absorption of nutrients from food. People with celiac sprue cannot tolerate gluten. Celiac disease is an inherited, autoimmune disease in which the lining of the small intestine is damaged from eating gluten and other proteins found in wheat, barley, rye, and possibly oats. There is a propensity of Celiac disease in individuals who possess the HLA-DQ8 class II antigen receptor gene. The exact cause of celiac disease is unknown although it is believed that intestinal damage is caused by interactions between specific gliadin oligopeptides and the HLA-DQ2, DQ2.5, DQ2.2/DQ7 or DQ8 antigen, which in turn induce proliferation of T lymphocytes in the sub-epithelial layers. T helper 1 cells and cytokines apparently play a major role in a local inflammatory process leading to villus atrophy of the small intestine. The intestines contain projections, called villi that absorb nutrients. The lining villi become damaged due to the body's immune reaction. In undiagnosed or untreated celiac disease, these villi become flattened. Because the lining of the intestine contains essential enzymes for digestion and absorption, its destruction leads to malabsorption, a difficulty in absorption of food and essential nutrients. As result, Celiac sprue is often considered a malabsorption disorder. This affects the ability to absorb nutrients properly. The disease can develop at any point in life, from infancy to late adulthood. Those with a family member with celiac disease are at greater risk for developing the disease. The disorder is most common in Caucasians and those of European ancestry. Women are affected more commonly than men.

The symptoms of celiac disease can vary significantly from person to person. This is part of the reason the diagnosis is frequently delayed. For example, one person may have constipation, a second may have diarrhea, and a third may have no irregularity in stools.

A non-limiting list of gastrointestinal symptoms include abdominal pain, abdominal distention, bloating, gas, indigestion, constipation, decreased appetite that may also be increased or unchanged, diarrhea, chronic or occasional lactose intolerance which is common upon diagnosis, but usually goes away following treatment, nausea and vomiting, stools that float, are foul smelling, bloody, or "fatty", and unexplained weight loss although people can be overweight or of normal weight upon diagnosis.

A non-limiting list of nonintestinal symptoms include anemia (low blood count), bone and joint pain, bone disease such as osteoporosis, kyphoscoliosis, and fracture, breathlessness due to anemia, bruising easily, dental enamel defects and discoloration, depression, fatigue, growth delay in children, hair loss, hypoglycemia due to low blood sugar, irritability and behavioral changes, malnutrition, mouth ulcers, muscle cramps, nosebleeds, seizures, short stature, unexplained skin disorders (dermatitis herpetiformis), swelling which can be general or abdominal, and vitamin or mineral deficiency which can include single or multiple nutrient (for example, iron, folate, vitamin K).

There is currently no treatment for celiac disease except the advice to follow a lifelong gluten-free diet. This allows the intestinal villi to heal. Patients are advised to eliminate foods, beverages, and medications that contain wheat, barley, rye, and possibly oats. The health care provider may prescribe vitamin and mineral supplements to correct nutritional deficiencies. Occasionally, corticosteroids (such as prednisone) may also be prescribed for short-term use or in patients suffering from refractory sprue. Following a well-balanced, gluten-free diet is generally the only treatment needed to stay well.

The current diagnosis method includes a complete blood count (CBC) to detect signs of anemia, testing for an increase in alkaline phosphatase level which may indicate bone loss, testing for low cholesterol and albumin levels which may be signs of malabsorption and malnutrition, testing for an increase in liver enzymes and abnormal blood clotting, and detection of specific antibodies to tissue transglutaminase and gliadin. The health care provider will order these antibody test if Celiac sprue is suspected. If the tests are positive, upper endoscopy is usually performed to sample a piece of tissue (biopsy) from the first part of the small intestine (duodenum). An endoscopy with enteroscopy, particularly of the lower sections of the intestine most commonly affected, will show a flattening of the villi. A follow-up biopsy or blood work may be ordered several months after the diagnosis and treatment. These confirm the disease. Normal results mean that the patient has responded have responded to treatment, thereby confirming the diagnosis.

Formulation of Pharmaceutical Compositions and Applications Thereof

The extract from the *Rothia* species bacteria, *Rothia* species bacteria or the glutamine endopeptidase enzyme derived or isolated from a *Rothia* species bacterium can be incorporated into a variety of formulations for therapeutic administration in accordance with the present invention. For example, a simple formulation can incorporate an extract, *Rothia* species bacteria, or enzyme described herein with an excipient combined in solution, then frozen and lyophilized. The resulting powder can be formulated in a capsule, sachet, pill, and the like, and may further be formulated to comprise an enteric coating.

In one embodiment, the extract, *Rothia* species bacteria, or enzyme described herein are formulated into pharmaceutical compositions by combination with appropriate, pharmaceutically acceptable carriers or diluents, and are formulated into preparations in solid, semi-solid, or liquid forms, such as tablets, capsules, powders, granules, solutions, gels, and microspheres. As such, administration of the extract, *Rothia* species bacteria, or the enzyme described herein can be achieved by oral administration.

In pharmaceutical dosage forms, the extract, *Rothia* species bacteria, or enzyme described herein can be administered alone or in appropriate association, as well as in combination, with other pharmaceutically active compounds to provide a cocktail of activities. The following methods and excipients are exemplary and are not to be construed as limiting the invention. The currently pharmaceutically active compounds used in the treatment and alleviation of symptoms of Celiac Sprue includes the following: an inhibitor of tissue transglutaminase (see U.S. Pat. No. 7,579,313), an anti-inflammatory agent, an anti-ulcer agent, a mast cell-stabilizing agent, and/or and anti-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

In one embodiment, the formulation or administration protocol combines an extract, *Rothia* species bacteria, and/or glutamine endopeptidase enzyme described herein with an inhibitor of transglutaminase 2 (TG2) (see U.S. Pat. No. 7,579,313). Such formulations can provide additional protection from gluten mediated enteropathy, as TG2 has been shown to have a significant pro-inflammatory effect on gluten peptides in the celiac gut. In particular, TG2 inhibitors containing halo-dihydroisoxazole, diazomethylketone or dioxoindole moieties are useful for this purpose.

In one embodiment, the formulation or administration protocol combines an extract, *Rothia* species bacteria, and/or glutamine endopeptidase enzyme described herein with an anti-inflammatory agent, e.g. a statin; p38 MAP kinase inhibitor; anti-TNFalpha agent; etc.

In another embodiment, the formulation comprises a cocktail of an extract, *Rothia* species bacteria, and/or glutamine endopeptidase enzyme described herein and a selection of several proteases such as the prolyl endopeptidases from *Flavobacterium meningosepticum, Sphingomonas capsulate, Penicillium citrinum, Lactobacillus helveticus* and *Myxococcus Xanthus* described in U.S. Patent Application Nos: 20060002917 and 20080193436, and in U.S. Pat. Nos. 7,563, 864, 7,303,871, and 7320788. These references are hereby incorporated by reference in its entirety.

In one embodiment, the formulation comprises an extract from a *Rothia* species bacterium, the glutamine endopeptidase enzyme described herein or a Pegylated form thereof. PEGylation is the process of covalent attachment of poly (ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) increase the hydrodynamic size (size in solution) of the agent which prolongs its circulatory time by reducing renal clearance. PEGylation can also provide water solubility to hydrophobic drugs and proteins.

Methods of PEGylating proteins are known to one of ordinary skill in the art, e.g. U.S. Pat. No. 7,585,837 and also described herein. The reference is hereby incorporated by reference in its entirety. The first step of the PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc made available for conjugation. Preferred end groups for heterobifunctional PEGs are maleimide, vinyl sulfones, pyridyl disulfide, amine, carboxylic acids and NHS esters.

Pharmaceutical formulations can be administered by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation.

For oral preparations, the extract, *Rothia* species bacteria, or enzyme described herein can be used alone or in combination with appropriate additives to make tablets, powders, granules or capsules, for example, with conventional additives, such as lactose, mannitol, corn starch or potato starch; with binders, such as microcrystalline cellulose, cellulose derivatives, acacia, corn starch or gelatins; with disintegrants, such as corn starch, potato starch or croscarmellose sodium; with lubricants, such as talc or magnesium stearate; and if desired, with diluents, buffering agents, moistening agents, preservatives, colorants, and flavoring agents.

For enteral administration, a composition can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet can be made by compression or molding, optionally with one or more accessory ingredients. Compressed tablets can be prepared by compressing in a suitable machine the active compound in a free-flowing form, e.g., a powder or granules, optionally mixed with accessory ingredients, e.g., binders, lubricants, inert diluents, surface active or dispersing agents. Molded tablets can be made by molding in a suitable machine, a mixture of the powdered active compound with any suitable carrier.

A syrup or suspension can be made by adding the extract, *Rothia* species bacteria, or enzyme described herein to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration can be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropylt-dimethylammonio-1-propanesulfonate), Big-CHAPS(N,N-bis(3-D-gluconamidopropylt-cholamide), chlorobutanol, octoxynol-9, benzyl alcohol, phenols, cresols, and alkyl alcohols. An especially preferred oral absorption enhancer for the present invention is sodium lauryl sulfate.

In one embodiment of the invention, the formulations comprising an extract, a *Rothia* species bacteria, or an enzyme described herein and the oral formulations comprise enteric coatings, so that the extract, *Rothia* species bacteria, or enzyme described herein is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

As regards formulations for administering the extract, a *Rothia* species bacterium, or an enzyme described herein, one particularly useful embodiment is a tablet formulation comprising the extract, the *Rothia* species bacteria, or the enzyme described herein with an enteric polymer casing. An example of such a preparation can be found in WO2005/021002. The active material in the core can be present in a micronized or solubilized form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The extract, the *Rothia* species bacteria, or the enzyme described herein preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg as free base of the active ingredient. Particularly preferably, the core contains 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1,2-,3,4-diepoxybutane. The casing can also include starch and/or dextrin.

Preferred enteric coating materials are the commercially available EUDRAGIT® enteric polymers such as EUDRAGIT® L, EUDRAGIT® S and EUDRAGIT® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or CITROFLEX® or CITROFLEX® A2. Non-aqueous plasticisers include these, and also diethyl and dibutyl phthalate and dibutyl sebacate. A preferred plasticiser is triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876.

In an example, lactose monohydrate, microcrystalline cellulose, the active ingredient—e.g. the extract form Rothia species, the hydroxypropyl methyl cellulose and half of the croscarmellose sodium are screened into a 10 Liter Fielder high-shear blender (any suitable high shear blender could be used) and blended for 5 minutes at 300 rpm with the chopper off. The mixture is then granulated by the addition of about 750 ml water whilst continuing to blend. The granules are dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate is screened into the blender and the mixing process continued for a further 1 minute at 10 rpm. The lubricated mix is compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18. Other enteric-coated preparations of this sort can be prepared by one skilled in the art, using these materials or their equivalents.

The compositions can be formulated as a sustained release composition. For example, sustained-release means or delivery devices are known in the art and include, but are not limited to, sustained-release matrices such as biodegradable matrices or semi-permeable polymer matrices in the form of shaped articles, e.g., films, or microcapsules that comprise the extract, Rothia species bacteria, or enzyme described herein A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly (2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(–)-3-hydroxybutyric acid (EP 133,988). Sustained-release compositions also include liposomally entrapped an extract, Rothia species bacteria, or enzyme described herein. Such liposomes can be prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) anilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446). For examples of sustained release compositions, see U.S. Pat. No. 3,773, 919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

Methods for preparing liposomes and microspheres for administration to a patient are known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, and Jein, TIPS19:155-157 (1998), the contents of which are hereby incorporated by reference.

Preferred micro particles are those prepared from biodegradable polymers, such as polyglycolide, polylactide and copolymers thereof. Those of skill in the art can readily determine an appropriate carrier system depending on various factors, including the desired rate of drug release and the desired dosage.

Formulations are typically provided in a unit dosage form, where the term "unit dosage form," refers to physically discrete units suitable as unitary dosages for the subjects, each unit containing a predetermined quantity of the extract, Rothia species bacteria, or enzyme described herein in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents that are inherently nontoxic and nontherapeutic, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2 dimethylaminoethanol, 2 diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA, and sugar alcohols such as mannitol or sorbitol.

In one embodiment, the pharmaceutical formulation to be used for therapeutic administration must be sterile. Sterility is readily accomplished by filtration through sterile filtration membranes (e.g., 0.2 micron membranes).

Depending on the subject and condition being treated and on the administration route, an extract, Rothia species bacteria, or enzyme described herein can be administered in dosages of 0.01 mg to 500 mg/kg body weight per day, e.g. about 20, 100, 250, 500 or more mg/day or about 0.5, 1, 1.5, or more g/day for an average person for the extract or the enzyme and 1000 to 1 million bacteria per dose per day for the Rothia species bacteria. A typical dose of the extract or enzyme described herein in subjects will be in at least about 1 mg/adult subject, more usually at least about 10 mg/adult subject; and usually at least about 50, 150, 250, 500 or more mg/adult subject; usually not more than about 5 g, not more than about 1 g, or not more than about 500 mg/adult subject. Efficient proteolysis of gluten in vivo for an adult can, depending on diet and other factors, require at least about 500 units of a therapeutically efficacious glutamine endopeptidase from Rothia species bacteria described herein. In some embodiments, low dose of glutamine endopeptidase, such as 1000 units, can be used. In other embodiments, such as for the rapid detoxification of 5-10 g ingested gluten, as much as 20,000-50,000 units, or as much as 1,000,000 Units can be provided in unit dose form. One unit is defined as the amount of enzyme required to hydrolyze 1 μmol of Z-KPQ-pNA or Z-YPQ-pNA per min under specified conditions. Most glutamine endopeptidases have specific activities in the range of 5-50 units/mg protein. For barley EP-B2 (whose specific activity of a PEP is in the 1000 Units/mg range, as measured with Cbz-Phe-Arg-pNA), low dose glutenase may consist of 10,000-100,000 Units, whereas high-dose PEPs contains as much as 1,000,000 Units. It will be understood by those of skill in the art that the dose can be raised, but that additional benefits may not be obtained by exceeding the useful dosage. Dosages will be appropriately adjusted for pediatric formulation. In children the effective dose may be lower, for example at least about 0.1, 0.5, 1, 10, 20, 100, 150, 250 or more mg.

The skilled artisan will appreciate that certain factors may influence the dosage and timing required to effectively treat a subject, including but not limited to the severity of the disease or disorder, previous treatments, the general health and/or age of the subject, and other diseases present. The dose levels can also depend on whether the extract, Rothia species bacteria, or enzyme is use, the severity of the symptoms and the susceptibility of the subject to side effects. The isolated enzyme can be more potent than the extract or the bacteria. Moreover, treatment of a subject with a therapeutically effective dose can include a single treatment or a series of treatments. Estimates of effective dosages and in vivo half-lives for the extract, *Rothia* species bacteria, or enzyme encompassed by the invention can be made using conventional methodologies or on the basis of in vivo testing using an appropriate animal model, as known in the art, or as described herein. Preferred dosages for a given enzyme are readily determinable by those of skill in the art by a variety of means.

The therapeutic effect can be measured in terms of clinical outcome or can be determined by immunological or biochemical tests. For example, in the treatment of Celiac sprue, suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease, e.g. as set forth in Pyle et al, Clin. Gastroenterol. Hepatol. 3:679-686, 2005.

Various methods for administration may be employed, it being appreciated that the formulations of the extract, *Rothia* species bacteria, or enzyme described herein provided by the present invention provide improved formulations for oral administration. For example, in the treatment of Celiac Sprue with an extract, *Rothia* species bacteria, or enzyme described herein, the present invention provides unit dose forms of the extract, *Rothia* species bacteria, or enzyme described herein suitable for administration with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

The methods of the invention are used to treat foods to be consumed or that are consumed by individuals having from Celiac Sprue and/or dermatitis herpetiformis by delivering an effective dose of an extract, *Rothia* species bacteria, or enzyme described herein. If the extract, *Rothia* species bacteria, or enzyme described herein is administered directly to a human subject, then the active agent(s) are contained in a pharmaceutical formulation. Alternatively, the desired effects can be obtained by incorporating the extract, *Rothia* species bacteria, or enzyme described herein into food products. Diagnosis of suitable subjects can utilize a variety of criteria known to those of skill in the art. A quantitative increase in antibodies specific for gliadin, and/or tissue transglutaminase is indicative of the disease. Family histories and the presence of the HLA alleles HLA-DQ2 and/or HLA-DQ8 are indicative of a susceptibility to the disease (Fernando Fernández-Bañares, 2006, Eur. J. Gastoent. Hepatology, 17:1333-8).

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art, e.g. is US Patent Application 20080299108. Alternatively, one can look for a reduction in symptoms of a disease.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

Unless otherwise explained, all technical and scientific terms used herein have the same meaning as commonly understood by one of ordinary skill in the art to which this disclosure belongs. Definitions of common terms in celiac sprue, gluten allergy, celiac disease, immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); Current Protocols in Immunology (CPI) (John E. Coligan, et. al., ed. John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); Animal Cell Culture Methods (Methods in Cell Biology, Vol.

57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following alphabetized paragraphs:

[A] An isolated glutamine endopeptidase enzyme that cleaves a peptide bond after XPQ and XPY motifs in glutens.

[B] The isolated enzyme of paragraph [A], wherein the enzyme has an apparent molecular weight of about 70-75 kDa as determined by gliadin zymograms or by SDS-PAGE.

[C] The isolated enzyme of paragraph [A] or [B], wherein the enzyme has a functional pH range of 3-10 as determined by detectable Z-YPQ-pNA cleaving activity within a 24 hour digestion period and a functional pH range of 7-10 as determined by substantially complete Z-YPQ-pNA cleavage within a 1 hour digestion period.

[D] The isolated enzyme of any one of paragraphs [A]-[C], wherein the enzyme is 100% inhibited by 1 mM of EDTA or PMSF.

[E] The isolated enzyme of any one of paragraphs [A]-[D], wherein the enzyme is derived from a *Rothia* species bacteria., wherein the *Rothia* species bacteria is selected from the group consisting of *R. mucilaginosa* ot 681 (strain WSA-2B), *R. mucilaginosa* ATCC 25296 and *Rothia* species ot 188 (strain WSA-8).

[F] The isolated enzyme of any one of paragraphs [A]-[E], wherein the enzyme is a recombinantly synthesized enzyme.

[G] The isolated enzyme of any one of paragraphs [A]-[F], wherein the enzyme has an amino acid sequence that show at least 45% identity or at least 60% similarity to SEQ. ID. NO: 1.

[H] The isolated enzyme of any one of paragraphs [A]-[F], wherein the enzyme comprises SEQ. ID. NO: 1.

[I] The isolated enzyme of any one of paragraphs [A]-[F], wherein the enzyme consists essentially of SEQ. ID. NO: 1.

[J] The isolated enzyme of any one of paragraphs [A]-[F], wherein the enzyme is SEQ. ID. NO: 1.

[K] A formulation for use in the treatment of Celiac Sprue, gluten allergy and/or dermatitis herpetiformis, the formulation comprising an effective dose of an isolated enzyme of any one of paragraphs [A]-[J] and a pharmaceutically acceptable carrier.

[L] A formulation for use in treatment of Celiac Sprue, gluten allergy and/or dermatitis herpetiformis, comprising: an effective dose of an extract from a *Rothia* species bacteria and a pharmaceutically acceptable excipient, wherein the extract from the *Rothia* species bacteria contains a glutamine endopeptidase enzyme.

[M] The formulation of paragraph [K] or [L], wherein the enzyme is stable in acid conditions.

[N] The formulation of paragraph [L] or [M], wherein the formulation is suitable for oral administration.

[O] The formulation of any one of paragraphs [L]-[N], wherein the formulation comprises an enteric coating.

[P] The formulation of any one of paragraphs [L]-[O] further comprises an effective dose of prolyl endopeptidase ranging from 0.01 mg to 500 mg/kg body weight.

[Q] The use of the formulation of any one of paragraphs [L]-[P] for digesting gluten-containing food stuff.

[R] The use of the formulation of paragraph [Q], wherein the formulation is administered within one hour of eating.

[S] A method of detoxifying gluten, the method comprising contacting gluten-containing foodstuff with an effective dose of an isolated enzyme of any one of claims [A]-[J] or a formulation of any one of paragraphs [L]-[P].

[T] The method paragraph [S], wherein the contacting is performed in vitro prior to consumption of the gluten-containing food stuff.

[U] The method of paragraph [S], wherein the contacting is performed in vivo by administration of the effective dose prior to, concurrent with or after consumption of the gluten-containing food stuff.

[V] A method of treating Celiac Sprue, gluten allergy and/or dermatitis herpetiformis in a subject in need thereof, the method comprising administering to the subject an effective dose of an isolated enzyme of any one of paragraphs [A]-[J] or a formulation of any one of paragraphs [L]-[P], wherein gluten toxicity is attenuated in the subject.

[W] The method of paragraph [V], wherein the effective dose is administered prior to consumption of gluten-containing foodstuff.

[X] The method of paragraph [V], wherein the effective dose is administered in a gluten-containing foodstuff.

[Y] The method of paragraph [V], wherein the effective dose is administered from 1 hour prior to 1 hour after the subject has consumed a gluten-containing foodstuff.

[Z] The method of paragraph [V], wherein the effective dose is administered just before, during, or just after consumption of gluten-containing foodstuff.

[AA] The method of any one of paragraphs [V], [W], [Y]-[Z], wherein the effective dose is administered orally.

[BB] The method of paragraph [X], wherein the effective dose is admixed to the gluten-containing foodstuff.

[CC] The method of any one of paragraphs [V]-[BB], wherein one determines that the subject has been diagnosed with Celiac Sprue, gluten allergy and/or dermatitis herpetiformis.

[DD] An assay for diagnosing Celiac Sprue, gluten allergy and/or dermatitis herpetiformis in a subject comprising
a) contacting a biological sample from the subject with a fixed amount of gliadin for a 24 hour period;
b) measuring the amount of gliadin degradation; and
c) comparing the amount of gliadin degradation for the biological sample with that obtained for a control assay, wherein the control assay is a mixture of a same fixed amount of gliadin with an isolated enzyme of paragraphs [A]-[J] or a formulation of paragraphs [L]-[P] for a 24 hour period, wherein the extent of gliadin degradation of less than 50% of that of the control assay indicates the subject likely have Celiac Sprue, gluten allergy and/or dermatitis herpetiformis.

[EE] The method of paragraph [DD], wherein the subject is at risk of developing Celiac Sprue, gluten allergy and/or dermatitis herpetiformis.

[FF] The method of paragraph [DD] or [EE], wherein the fixed amount of gliadin is 250 μg/ml.

[GG] The method of any one of paragraphs [DD]-[FF], wherein the determining is performed by protein gel electrolysis.

[HH] The method of any one of paragraphs [DD]-[FF], wherein the determining is performed by mass spectrometry.

[II] The method of any one of paragraphs [DD]-[HH], wherein the biological sample is whole saliva.

[JJ] The method of paragraph [II], wherein the saliva is unstimulated saliva.

[KK] The method of paragraph [II], wherein the saliva is stimulated saliva.

[LL] The method of any one of paragraphs [DD]-[HH], wherein the biological sample is dental plaque, wherein the dental plaque is suspended in saliva ion buffer to an $OD_{620}$ of ~1.0 prior to mixing with the gliadin.

[MM] A kit for predicting/diagnosing Celiac Sprue, gluten allergy and/or dermatitis herpetiformis in a subject in need thereof, comprising a gliadin and a reagent for assaying undigested gliadin containing a vial containing an isolated enzyme of paragraphs [A]-[J] or a formulation of paragraphs [L]-[P].

This invention is further illustrated by the following example which should not be construed as limiting. The contents of all references cited throughout this application, as well as the figures and table are incorporated herein by reference.

EXAMPLES

Materials and Methods

Collection of dental plaque and whole saliva samples—Prior to sample collection informed consent was obtained from the participating subject according to protocols approved by the Institutional Review Board at Boston University. The subject presented with good oral health without overt signs of gingival inflammation or other oral or systemic conditions. Supragingival plaque was collected from interproximal dental spaces with an explorer 24 h after refraining from oral hygiene. The plaque material was suspended in 500 μl saliva ion buffer, the composition of which is 50 mM KCl, 1.5 mM potassium phosphate, 1 mM $CaCl_2$ and 0.1 mM $MgCl_2$, pH 7.0. Masticatory stimulated whole saliva (WS) (5 ml) was obtained by expectoration as described previously (Campese et al., 2009, Arch. Oral. Biol. 54:345-53).

Plating of oral microorganisms on *Brucella*-limited agar and gluten-limited agar—An aliquot of 50 μl of 1:1000 diluted dental plaque or WS suspensions were plated on gluten-limited agar (GA), the formula for each liter is: 23 g wheat gluten (Sigma), 5 g sodium chloride, 1 g soluble starch, 12 g Agar No. 2, 0.4 g sodium bicarbonate, 1 g glucose, 1 g sodium pyruvate, 0.5 g cysteine hydrochloride monohydrate, 0.01 g haemin, 0.001 g vitamin K, 1 g L-arginine, 0.25 g soluble pyrophosphate and 0.5 g socium succinate. Incubations were carried out at 37° C. under aerobic conditions or in a sealed pot that was rendered anaerobic using GASPAK® pouches (Beckton-Dickinson, Franklin Lakes, Md.). Individual colonies were transferred to GA plates, and after 48 h incubation were subcultured on *Brucella* agar (Hardy Diagnostics, Santa Maria, Calif.). Subculturing on *Brucella* agar plates was continued until cultures that were macroscopically and microscopically pure were obtained. The strains were then plated once more on GA to confirm growth on this selective agar formulation. For long term storage, bacteria were kept at −80° C. in a glycerol/BHI broth mixture (20/80% v/v). To the stocks of anaerobic microorganisms DMSO was added to a final concentration of 5%.

Microbial speciation and identification by 16S rRNA—Microbial colonies with gliadin-degrading activity were identified by 16S rRNA analysis. DNA extraction was performed using the ULTRACLEANT™ Microbial DNA Isolation Kit (Mo Bio Laboratories, Carlsbad, Calif.) following the manufacturer's instructions for the isolation of genomic DNA from Gram-positive bacteria. Purified DNA was sequenced using an ABI prism cycle-sequencing kit (BIGDYE® Terminator Cycle Sequencing kit) on an ABI 3100 Genetic Analyser (Applied Biosystems, Foster City, Calif.). Reactions used a quarter-dye chemistry as previously described (Paster et al. 2001, J. Bacteriol. 183:3770-83; Aas et al., 2005, J Clin. Microbiol. 43:5721-32). Partial sequences were identified by BLASTN analysis against the Human Oral Microbiome Database containing sequencing of over 35,000 clones and isolates. Sequences were assembled from the ABI electropherogram files using Sequencher 4.9 (Gene Codes Corporation, Ann Arbor, Mich.).

Degradation of paranitroanilide-derived substrates—Four gliadin-derived substrates, Z-YPQ-pNA, Z-QQP-pNA, Z-PPF-pNA and Z-PFP-pNA, were chemically synthesized (Anaspec, Fremont, Calif.) and dissolved in 50-75% dimethyl sulfoxide to 20 mM. The dental plaque suspension was diluted in saliva ion buffer to an $OD_{620}$ of 1.2. Bacterial strains were grown on *Brucella* agar for 24 or 48 h, harvested with a cotton swab and suspended in saliva ion buffer to an $OD_{620}$ of 1.2. An aliquot of 200 μl of dental plaque or bacterial suspensions was added to 2 μl of the paranitroanilide-derivatized substrates in a 96-well microliter plate (final concentration of substrates is 200 nM). Z-YPQ-pNA, Z-PPF-pNA and Z-PFP-pNA showed mild precipitation upon mixing with the plaque suspension in saliva ion buffer which did not interfere with efficient substrate hydrolysis. Enzyme activity was monitored spectrophotometrically at 405 nm. For some experiments, measurements were carried out in the kinetic mode. All values were corrected for the lowest absorbance values measured after addition of the enzyme source to the substrate.

Degradation of gliadins in-solution—A mixture of gliadins was purchased from SIGMA (Cat. No. G3375, St. Louis, Mo.) and dissolved to 5 mg/ml in 60% (v/v) ethanol Gliadins were added to suspensions of dental plaque and bacterial strains WSA-2B and WSA-8 ($OD_{620}$=~1.0). Experimental incubation time points were 0, 2, 4, 6, 24 and 72 hr, or 0, 5, 15, 30, 60 and 120 min. After the indicated incubation time intervals, 100 µl aliquots were removed and boiled to inactivate enzyme activity. EDTA was added to a final concentration of 2.5 mM, samples were dried using a speed-vac (Savant, Thermo Electron, Waltham, Mass.) and analyzed on pre-cast 12% gels (NOVEX, INVITROGEN, Carlsbad, Calif.). Electrophoresis, gel straining and destaining were carried out as described (Helmerhorst et al., 2010, PLoS One, in press).

Degradation of gliadins in-gel (gliadin zymography)—Bacteria were suspended in saliva ion buffer to a final $OD_{620}$ of 5.0. A 150 µl aliquot was centrifuged. The bacterial pellet was suspended in 20 µl zymogram buffer and analyzed by gliadin zymography as described (Helmerhorst et al., 2010, PLoS One, in press). In some experiments the zymogram gel contained 6% instead of 8% acrylamide. With the lower percentage of acrylamide, a better separation of the enzymes in the 70 kD region was achieved. After electrophoresis was completed, the zymogram gel was further processed by incubation in renaturing and developing buffers (INVITROGEN, Carlsbad, Calif.). Enzymatic activities were revealed by staining with 0.1% (w/v) Coomassie Brilliant Blue R-250 in 10% (v/v) acetic acid and 40% (v/v) methanol and destaining in the same solution not containing the dye.

Degradation of 33-mer and 26-mer gliadin domains and RP-HPLC analysis—Synthetic highly immunogenic peptides derived from α-gliadin (LQLQPF-PQPQLPYPQPQLPYPQPQLPYPQPQPF; a 33-mer, SEQ. ID. NO: 2; Shan et al., 2002, Science 297(5590):2275-9) or γ-gliadin (FLQPQQPFPQQPQQPYPQQPQQPFPQ; 26-mer, SEQ. ID. NO: 17; Shan et al., 2005, J Proteome Res. 4:1732-41) were synthesized at a purity of 95% (21st Century Biochemicals, Marlboro, Mass.). Both peptides were dissolved in milliQ water at 10 mg/ml, the concentration was verified by measurement of the OD at 215 nm (ε=20). The 33-mer or the 26-mer was added to a suspension of strains WSA-8 or Rothia mucilaginosa ATCC 25296 in saliva ion buffer ($OD_{620}$ 1.2). After t=0 h, 2 h and 5 h incubation, 100 µl aliquots were removed and boiled to inactivate enzyme activity. The 100 µl aliquots were mixed with 900 µl buffer A containing 0.1% (v/v) trifluoroacetic acid (TFA), filtered over a 0.22 µm filter (Pall Cooperation, Ann Arbor, Mich.). RP-HPLC was carried out using a HPLC Model 715 (Gilson, Middleton, Wis.) and a C-18 column (TSK-GEL 5 µm, ODS-120T, 4.6×250 mm, TOSOHaas, Montgomeryville, Pa.). Peptides were eluted sing a linear gradient from 0% to 55% buffer B containing 80% (v/v) acetonitrile and 0.1% (v/v) TFA over a 75 min time interval at a flow rate of 1.0 ml/min (Helmerhorst et al., 2010, PLoS One, in press). The eluate was monitored at 219 and 230 nm and eluting fractions were collected using peak width and peak sensitivity settings of 1.2 and 5, respectively (Unipoint version 3.3, Gilson).

Mass Spectrometric Characterization of 33-mer/26-mer fragments using Liquid Chromatography Electrospray Ionization Tandem Mass Spectrometry (LC-ESI-MS/MS)—Mass spectrometry was conducted using a capillary nanoflow liquid chromatography and electrospray ionization tandem mass spectrometer (LC-ESI-MS/MS) as previously described (Sun et al., 2009, Faseb J 23:2691-701). In brief, HPLC fractions containing individual gliadin degradation peptides were concentrated under vacuum and suspended in 5% acetonitrile in 0.1% formic acid. 1-3 µl samples were injected using an autosampler (Micro AS, Thermo Finnigan, San Jose, Calif.). Separation/elution of peptides was achieved using an in-line capillary C-18 column (Magic C-18, Micron Bioresource) applying a gradient from 5 to 95% acetonitrile in 0.1% formic acid over a 35 min time interval at a flow rate of 250 nl/min.

The raw MS/MS data of the mixture of gliadins were searched against an in-house generated database containing the sequences of just these two peptides using SEQUEST software (Bioworks Browser 3.3.1, Thermo-Finnigan). X-corr values applied were 1.5, 2.2 and 3.5 for Z=1, 2, and 3, resp. DCn and peptide probabilities were set at >0.1 and <0.05, respectively. The suitability of the selected settings to avoid false positive identifications has been reported (Helmerhorst et al., 2010, PLoS One, in press).

Chromatographic separation of R. mucilaginosa enzymes—R. mucilaginosa ATCC 25296 cells were cultured from Brucella agar plates (Hardy Diagnostics, Santa Maria, Calif.) in 4 liter BHI for 24 h at 37° C. while shaking. Cells were harvested and suspended in 50 mM Tris-HCl and 50 mM NaCl (pH 8.0) and concentrated to a final O.D. of 67 at 620 nm. Cells were sonicated for 20 times at a power setting of 7 using the Branson cell lysis sonifier the degree of lysis was monitored spectrophotometrically and sonication was terminated when the turbidity was reduced by 90%. The sonicate was centrifuged at 31,000×g for 20 min. The supernatant was removed and subjected to ammonium sulfate precipitation. The active fraction was found to be enriched in the precipitate obtained using 25-45% saturated ammonium sulfate. This precipitate was collected by centrifugation at 10,000×g for 20 min. The precipitate was dissolved, concentrated and desalted using centrifuge tubes with a 50 kD MW cut-off (MILLIPORE®). An aliquot of 670 mg protein was applied to a DEAE SEPHAROSE® Fast Flow column (GE Healthcare) of 2.6 cm×82.5 cm connected to an FPLC system (Pharmacia Biotech). Chromatographic separation of proteins was achieved at a flow rate of 0.7 ml/min and applying a gradient of 0-10% buffer B (50 mM Tris-HCl and 1M NaCl (pH 8.0) from 0 to 70 min; 10-35% buffer B from 70-2070 min, and 35-100% buffer B from 2070 to 2427 min. Fractions of 24 ml were collected and protease activities were measured by mixing 200 µl of each fraction with 3 µl Z-YPQ-pNA (final concentration 150 mM). Active fractions were desalted, concentrated and 6.5 mg of protein was loaded onto a G-100 gel filtration column (SEPHADEX® G-100, Pharmacia fine Chemical Piscataway, N.J.) of 2.6 cm×82.5 cm. Samples were eluted at a flow rate of 0.5 ml/min. Collected fractions with activity were concentrated as described above and subjected either to a 1-ml column of HITRAP QFF anion-exchange chromatography (GE Healthcare, City, State) or to a 1-ml column of HITRAP QXL anion-exchange chromatography (GE Healthcare). Fractions were again evaluated for activity, concentrated and analyzed for protein composition by SDS PAGE.

Gliadin zymography, in-gel digestion and LC-ESI-MS/MS characterization of enzymes—Active chromatographic fractions that showed a reduction in protein complexity compared to the starting material were subjected to gliadin zymography for activity analysis and to achieve further separation of proteins by electrophoresis. Active bands were excised with a scalpel on a clean glass plates and transferred to individual EPPENDORF tubes labeled (a) for the upper band and (b) for the lower band. From several repeat experiments, six upper and six lower band gel slices were separately processed. Proteins in the gel slices were digested in-gel with trypsin and analyzed by LC-ESI-MS/MS (Taplin Mass Spectrometry facility, Harvard Medical School, Boston, Mass.). Data were searched against a R. mucilaginosa database which was downloaded from NCBI using BIOWORKS software version 3.1. Peptide filter criteria applied were delta CN>0.1, peptide probability <0.5 and Xcorr values 2.2 and 3.5 for Z=2+ and Z=3+ for fully tryptic peptides and 2.4 and 3.75 for Z=2+ and Z=3+ for partially tryptic peptides.

Example 1

Some types of prolyl glutamine endopeptidase isolated from wheat, designate EP-B2 have been used in studies to decrease the propensity of gluten-containing wheat products to aggravate coeliac disease (Vora et al., Biotechnol Bioeng. 2007 Sep. 1; 98(1):177-85 and Gass et al., Gastroenterology. 2007 August; 133(2):472-80). The inventors have discovered that human whole saliva and dental plaque contain enzymatic activities that can cleave the Xaa-Pro-Gln (-XPQ-) bond after Gln, where Xaa is any amino acid, Pro is proline and Gln is glutamine (Helmerhorst et al., J. Biol. Chem. 29:19957-66, 2008). This tripeptide is also particularly abundant in known celiac T-cell gluten epitopes. Based on this, the inventors tested to determine whether the saliva-associated enzymes can degrade gluten/gliadins. This was confirmed experimentally by showing that plaque bacterial suspensions cleave gliadin. To isolate the microorganisms producing the gliadin-degrading enzymes, dental plaque was cultured on selective agar media containing only gluten as the protein source. Strains that can grow in this type of agar were further tested for their capacity to cleave gliadin-derived enzymatic substrates and gliadin in solution and in gel. Two microorganisms showing by far the highest gliadin-degrading activities were *R. mucilaginosa* ot 681 (WSA-2B=WSA-26) and *Rothia* species ot 188 (strain WSA-8) (see FIGS. 1, 2 and 3). Plaque consists of >600 different species (at the World Wide Web site of "homd" organization). The identification of *Rothia* species is significant, considering that these species are fairly uncommon in oral specimens as they rank approximately at #200 in order of abundance. *Rothia* showed preferential cleavage after the -XPQ- sequence (FIG. 4). The highly immunogenic 33-mer gliadin oligopeptide, LQLQPF-PQPQLPYPQPQLPYPQPQLPYPQPQPF (SEQ. ID. NO: 2), contains eight potential cleavage sites of the Xaa-Pro-Gln (XPQ) type, namely one FPQ, four QPQ and three YPQ sites. Gliadin zymography was conducted to gain insight into the approximate molecular weight of the glutamine endopeptidase enzymes from WSA-2B and WSA-8. The enzymes produced by WSA-2B and WSA-8 differ slightly in molecular weight, but both appeared in the 70-75 kDa region (8% zymogram results presented in FIG. 5; 6% zymogram results presented in FIG. 10). A series of protease inhibitors were used to determine the class of the gliadin degrading enzymes. Complete inhibition of activity of the glutamine endopeptidase activity was achieved with PMSF and EDTA (FIG. 7) indicating that the enzymes are metal-ion dependent proteases.

The enzyme responsible for cleaving gliadin-derived enzymatic substrate can be extracted from whole unlysed bacteria. Clarified supernatant fluid of a suspension of whole bacteria exhibited the cleaving property. Increase cleaving activity can be obtained by lysing the bacteria, e.g., through sonication. These indicate that the enzyme is secreted into the periplasmic space and exterior as well as located in the interior of the bacterium cell or be membrane associated and released upon membrane disruption.

In addition, two commercially available *Rothia* species were tested for their capacity to cleave gliadin-derived enzymatic substrates. Both *R. mucilaginosa* ATCC 25296, *Rothia dentocariosa* ATCC 17931 were exhibited the cleaving property towards Z-YPQ-pNA (FIG. 9).

Given the efficient growth of *Rothia* species on gluten-limited agar, and their capacity to efficiently degrade gliadin, the exploitation of *Rothia* species and the enzymes produced by these microorganisms for therapeutic and diagnostic applications in celiac disease as well as gluten allergy in envisioned.

Example 2

Selection and 16S RNA speciation of gluten-degrading oral bacteria—Gluten is a collection of glutenins and gliadins of varying lengths and compositions. All gluten proteins are rich in glutamine and proline residues (Wieser, 2007, Food Microbial. 24:115-9). Experiments were conducted to explore if gluten-limited agar (GA) is suitable to select for oral microorganismsms capable of metabolizing gluten. Bacteria from dental plaque and whole saliva were plated on GA and subcultured on *Brucella* agar to purity. A total of 7 aerobic strains and 10 anaerobic strains were harvested applying the selective plating strategy (FIG. 1). The strains did not grow on control agar formulations that contained all the ingredients of the GA agar except wheat gluten (data not shown). The strains harvested from the oral specimens were unique in terms of their capacity to utilize gluten as a substrate. The 17 strains were identified by 16S rRNA analysis. The RNA typing results revealed that some of the strains were actually the same species. For instance, strains WSA-2B and WSA-26 were both typed as *R. mucilaginosa* of 681; strains WSAN-14, -16, and -24 were identified as *Bifidobacterium longum*; and strains PAN-5, -8, -18, and -19 were typed as *Bifidobacterium dentium*. Strain WSA-27 contained two species (contaminated) and strain PA-10 was a non-oral microorganism (contaminant). Both strains were excluded from further analysis.

Hydrolysis of paranitroanilide-derivatized substrates—In earlier work the inventors have demonstrated that human dental plaque bacteria cleave the synthetic substrates Z-YPQ-pNA, Z-QQP-pNA, Z-PPF-pNA and Z-PFP-pNA (Helmerhorst et al., 2010, PLoS One, in press). The time span needed for the complete hydrolysis of all four substrates was 24 h. Cleavage of these four substrates by the 15 oral species as well as by mixed dental plaque were assessed (Table 4). Interestingly, none of the anaerobic strains cleaved any of the four substrates. On the other hand, in the aerobic category, *R. mucilaginosa* and *Rothia* ot188, but not the *Streptococcus* or *Staphylococcus* were particularly efficient in cleaving Z-YPQ-pNA. In contrast to Z-YPQ-pNA, the substrates Z-QQP-pNA, Z-PPF-pNA and Z-PFP-pNA were not cleaved, not even upon prolonged incubation times. For two of the strains, WSA-2B (*R. mucilaginosa*) and WSA-8 (Rothia ot188) the precise time course of Z-YPQ-pNA cleavage was investigated and compared to the cleavage of another substrate of the XPQ type, namely Z-KPQ-pNA. Both substrates were hydrolyzed in a cell-density and time-dependent fashion (FIG. 4). At the highest cell densities evaluated ($OD_{620}$ 1.2) WSA-2B completely hydrolysed Z-YPQ-pNA and Z-KPQ-pNA after 6 h, whereas strain WSA-8 cleavage of these substrates was completed after 3 h and 1 h, respectively.

Figure 2:
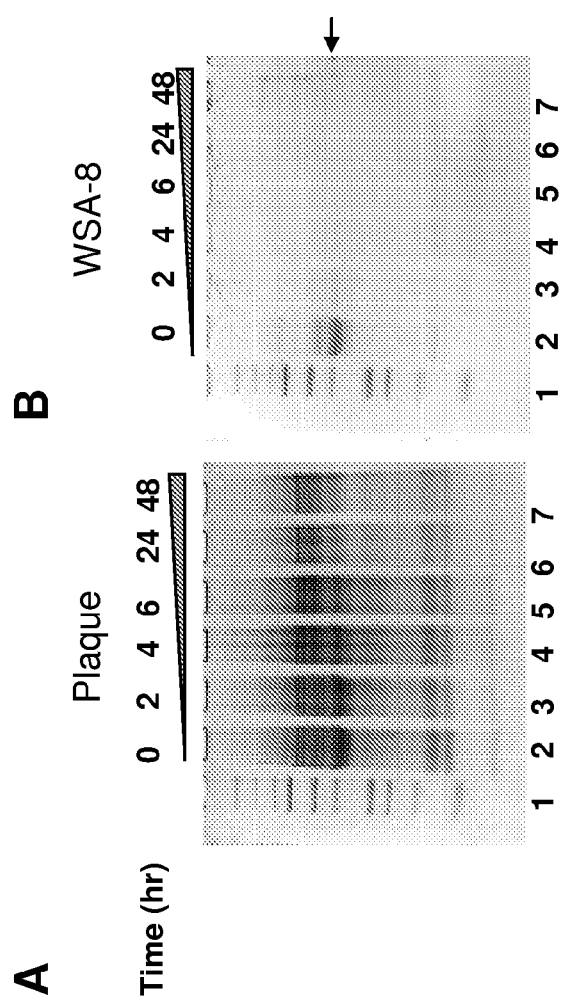
Figure 3:
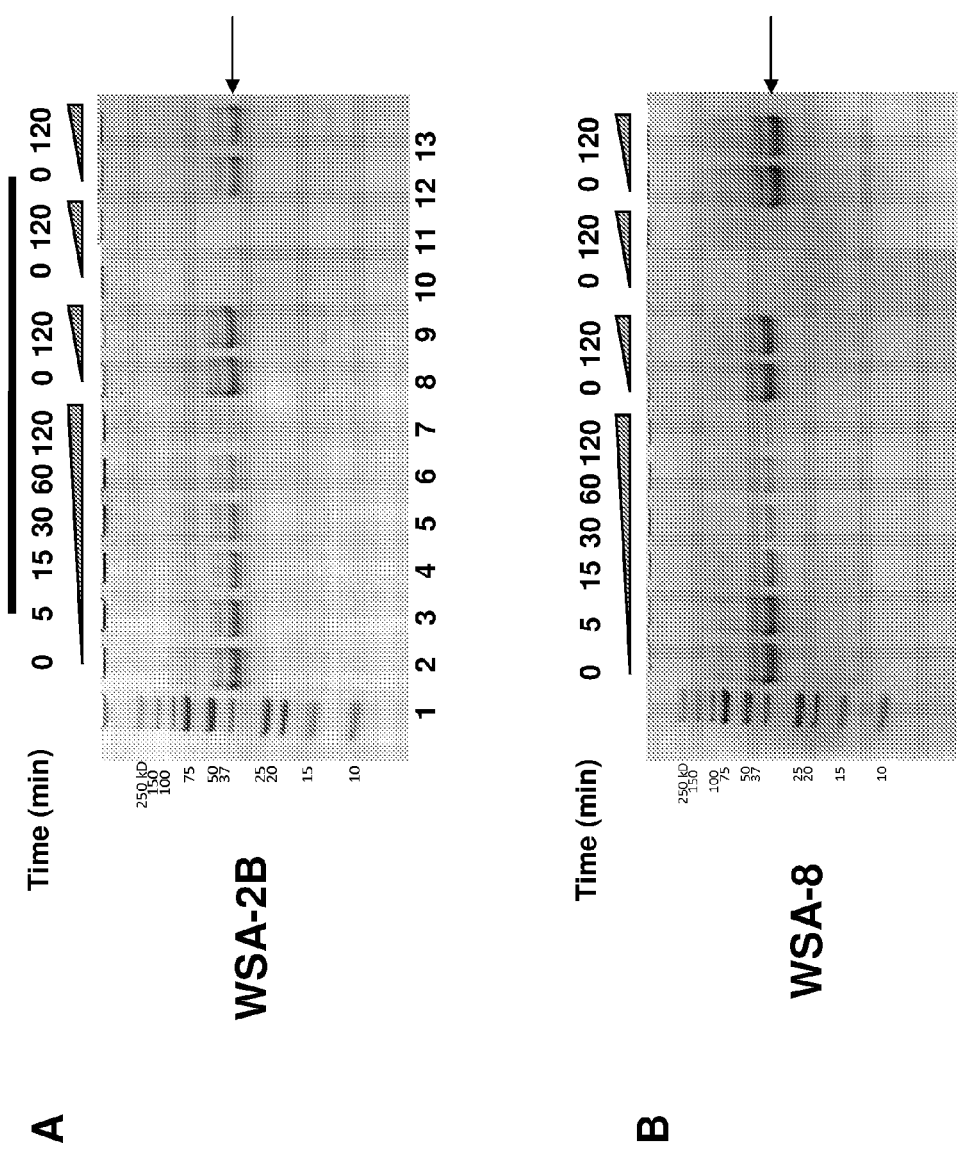
Figure 4:
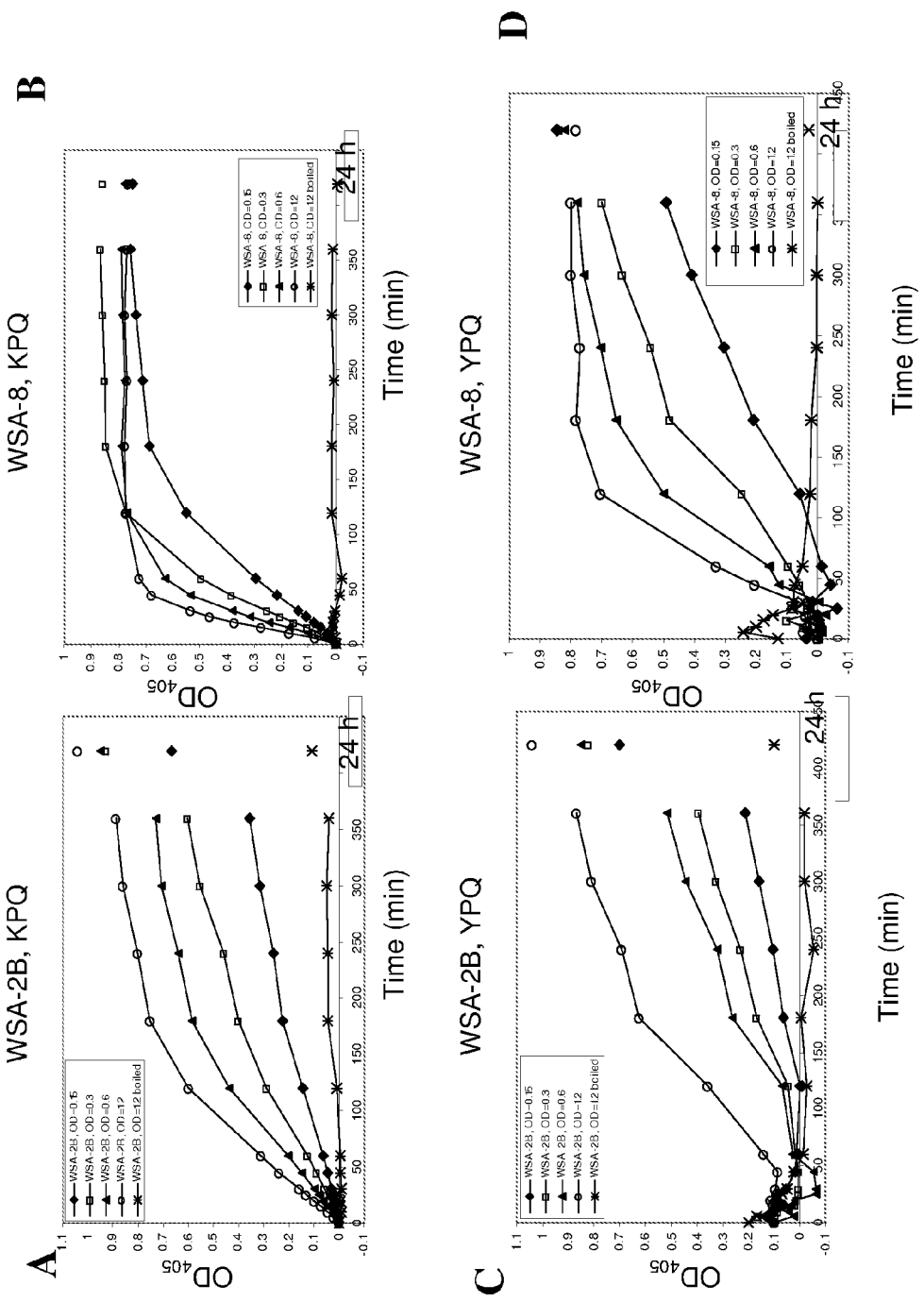

Gliadin degradation in solution—The inventors compared gliadin degradation by plaque bacteria and by strain WSA-8 (FIGS. 2 and 3). For a proper comparison, whole plaque and WSA-8 bacteria were suspended in saliva ion buffer to the same optical density ($OD_{620}$ 1.2). A mixture of gliadins (SIGMA) was added to the suspension to a final concentration of 250 µg/ml. After incubation for various time intervals at 37° C., 100 µl aliquots were removed from the incubation mixture and boiled to inactivate the enzyme. SDS-PAGE analysis shows that the major protein in the gliadin preparation, exhibiting a molecular weight of approximately 37 kD, was susceptible to degradation, albeit at a fairly low rate, in mixed dental plaque (FIGS. 2 and 3). Gliadins were however highly susceptible to the proteases produced by strain WSA-8, as evidenced from the fact that within 2 h of incubation the added amount of gliadin (250 µg/ml) was completely degraded. The precise time course for gliadin degradation by WSA-8 was established by sampling at shorter time intervals within the 2 h incubation time period (FIG. 4B). Data indicated that 50% of the added gliadin amount was degraded by WSA-8 in about 30 minutes. Similar results were obtained with gliadins incubated with strain WSA-2B (data not shown). These results demonstrate that *Rothia* species do not only cleave synthetic gliadin tripeptide substrates but are also highly effective in degrading gluten. Furthermore, their activities far exceed the activities present in mixed dental plaque.

Figure 10:
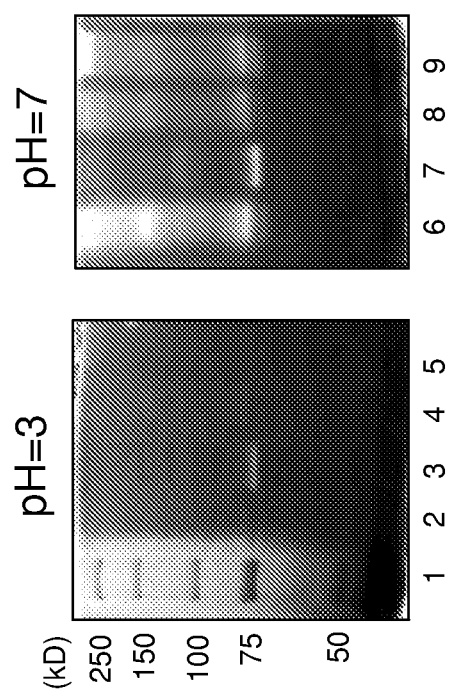

Determination of enzyme molecular weight by gliadin zymography—The next series of experiments were designed to gain more insight into enzyme characteristics of the *Rothia* organisms. First, *R. mucilaginosa* strain 25296 was obtained from the American Type Culture Collection (ATCC) for comparison to the strains that were isolated from the oral cavity. Strains WSA-2B, -8-26 and the ATCC strain were subjected to gliadin zymography. In this study, a zymogram with 6% instead of 8% acrylamide was employed in the separating gel. With the lower percent acrylamide a better resolution of proteins in the 70 kD region was achieved. The zymogram that was developed at neutral pH showed that all strains express gliadin-degrading enzymes appearing as clear bands in the zymogram. As expected, the protease patterns of strains WSA-2B, WSA-26 and the *R. mucilaginosa* ATCC strain were quite similar, showing a major double band in the 70-75 kD region in addition to some activity in the higher molecular weight regions (FIG. 5 and FIG. 10). Strain WSA-8 displayed a single prominent protease band with an electrophoretic mobility around 70 kD (FIG. 5 and FIG. 10).

Figure 8:
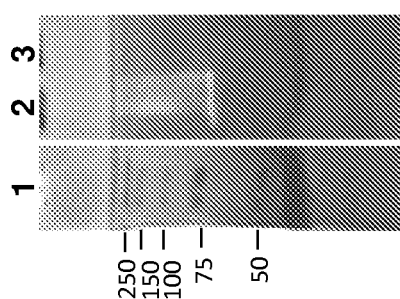
Figure 11:
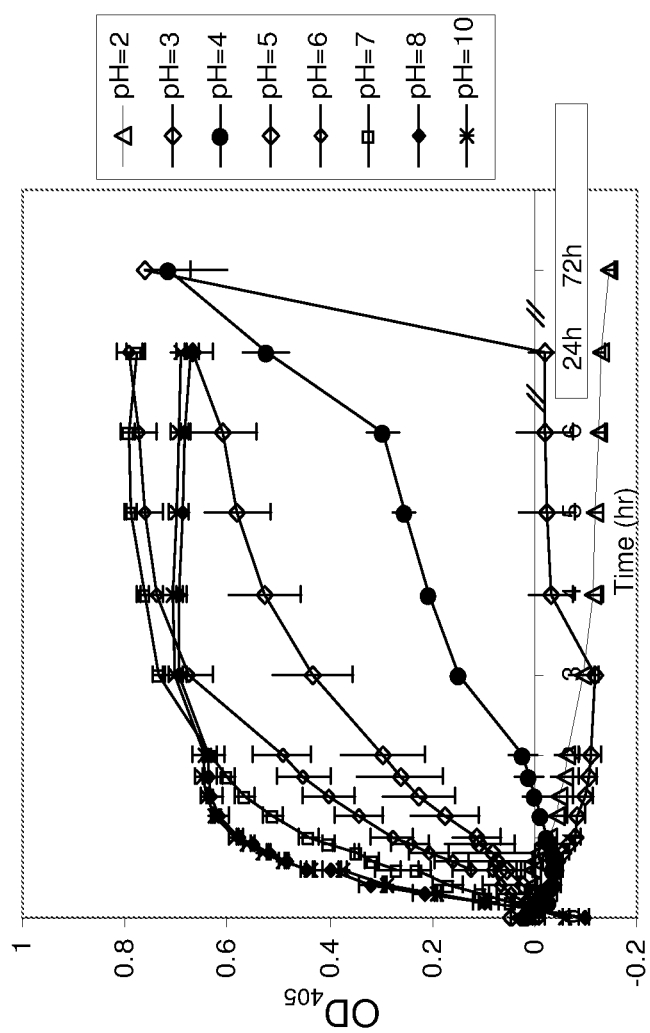

Inhibitor sensitivity of the gliadin-degrading enzymes— Strains WSA-2B and WSA-8 were chosen to investigate the sensitivity of the enzymes to a series of protease inhibitors. The inhibitors tested were EDTA and phophoamidon inhibiting metallo proteases, PMSF and AEBSF inhibiting serine proteases, aprotinin, an inhibitor of trypsin-like enzymes, 2-PDS being an inhibitor of cysteine proteases and pepstatin A inhibiting aspartyl proteases. Inhibitory effects were monitored toward the capacity to hydrolyze Z-YPQ-pNA. The initial rate of substrate proteolysis (Vi) was determined during the first 30 minute incubation time interval. From the slopes obtained in the absence and presence of inhibitors, it could be established that EDTA and PMSF were the most effective inhibitors, abolishing enzyme activity in both strains completely. AEBSF, a PMSF analog, was also effective yielding 97% inhibition in WSA-2B and 78% inhibition in WSA-8. The other inhibitors yielded <30% inhibition (FIG. 7). The inhibitory effect of PMSF toward gliadin degradation was confirmed in a gliadin zymogram, showing that the protease band is not detectable in cells that were pre-incubated with PMSF (FIG. 8). The inhibitory effect of EDTA signifies a strong metal ion requirement for the enzymes in question and the inhibition by PMSF and AEBSF classifies the gliadin-degrading enzymes as proteases.

pH activity analysis. To further investigate the pH range over which strain WSA-8 was active, we studied Z-YPQ-pNA substrate hydrolysis by WSA-8 cells suspended in 20 mM Tris ranging in pH from 2.0 to 10.0. The WSA-8 enzymes showed optimal activities at pH values >7.0, similar to the observations made with mixed dental plaques suspensions (Helmerhorst et al., 2010, PLoS One, in press). Substrate hydrolysis rates showed reductions at pH 6, 5 and 4 parallel with decreasing pH values. At pH 3.0 reactions proceeded at a very slow pace, but after 72 h, complete substrate hydrolysis was observed (FIG. 11). At pH 2.0, no activity was observed over the 72 h time span examined (FIG. 11).

Figure 12A:
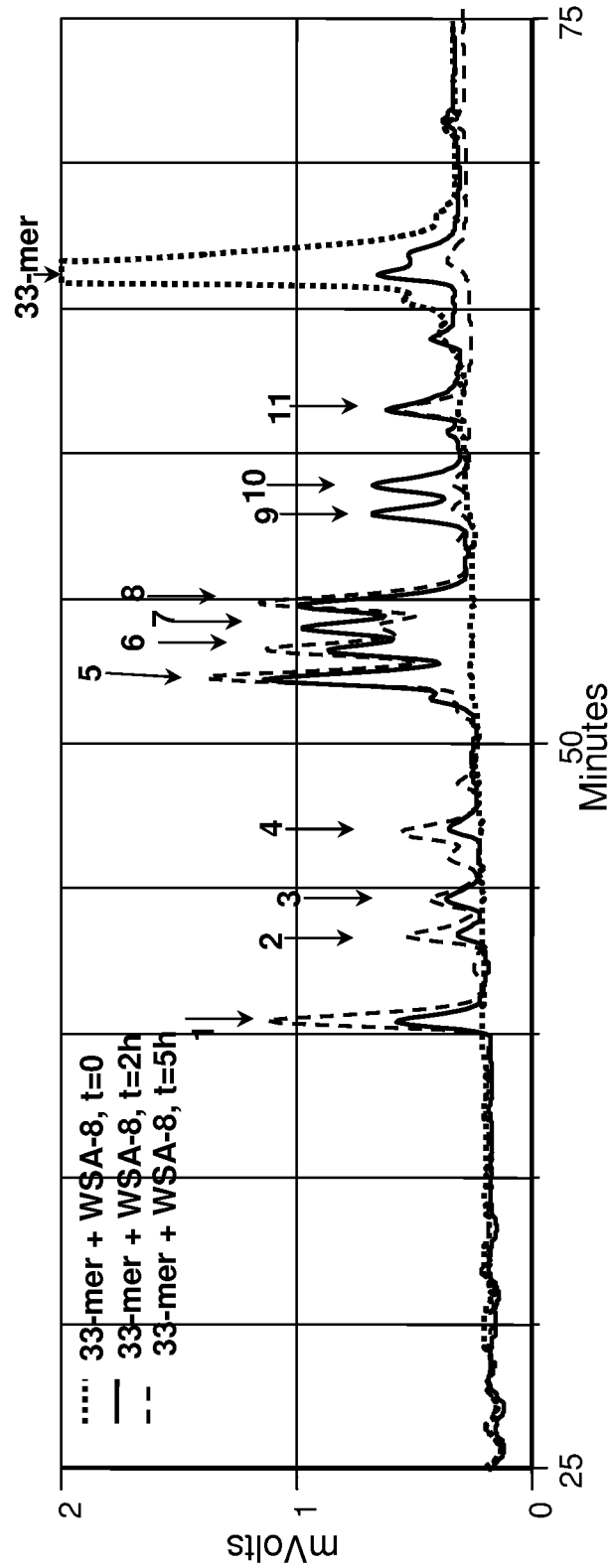

Degradation of the 33-mer and 26-mer—Within the gliadin sequences, certain peptide regions are particularly immunogenic and resistant to degradation by human-derived digestive enzymes. These are a 33-mer peptide (also denoted as "superantigen"; Schuppan et al., 2009, Gastroenterology 137:1912-33; (Hausch et al., 2002, Am J Physiol Gastrointest Liver Physiol 283(4):G996-G1003) present in alpha-gliadins, and a 26-mer peptide from gamma gliadins (Shan et al., 2002, Science 297(5590):2275-9). Both peptides are rich in the XPQ sequences which are the prospective primary enzymatic targets. The 33-mer and the 26-mer were incubated (final concentrations 250 µg/ml) with suspensions of WSA-8 and *R. mucilaginosa* (ATCC 25296). After 0, 2 h, and 5 h incubation, 100 µl aliquots were removed, boiled and analyzed by RP-HPLC. The intact 33-mer peptide eluted after 66 min (FIG. 12A, peak off scale). In the presence of WSA-8 cells the 33-mer was proteolytically cleaved, as evidenced by disappearance of the peak at 66 min and appearance of degradation fragments. Complete degradation was observed between 2 h-5 h incubation. The degradation fragments were collected and structurally characterized by LC-ESI-MS/MS analysis. From the N- and C-termini of these superantigen peptides, the enzymatic cleavage site specificities could be derived. Consistent with our initial hypothesis, prominent cleavage was observed after QPQ↓ (three sites, indicated with the larger arrows, FIG. 12B). Interestingly, cleavage at XPQ↓P did not occur indicating that a proline residue in the p1' position prevents enzyme recognition and/or effective cleavage activity by WSA-8 (FIG. 12B). A novel, recurring cleavage site specificity was noted after LPY↓ and this specific activity was confirmed with the enzymatic substrate Z-LPY-pNA (data not shown). Cleavage was furthermore observed after QPF↓ and after PFP↓ which was somewhat unexpected based on the inactivity of WSA-8 towards the synthetic enzyme substrates Z-PPF-pNA and Z-PFP-pNA (Table 4). It was noted that extension of the incubation time from 2 to 5 h led to the cleavage of fragments originally eluting in peaks 9 and 10 to smaller peptides eluting now in peaks 1 to 4 demonstrating extensive degradation of the 33-mer peptide by WSA-8.

Figure 13A:
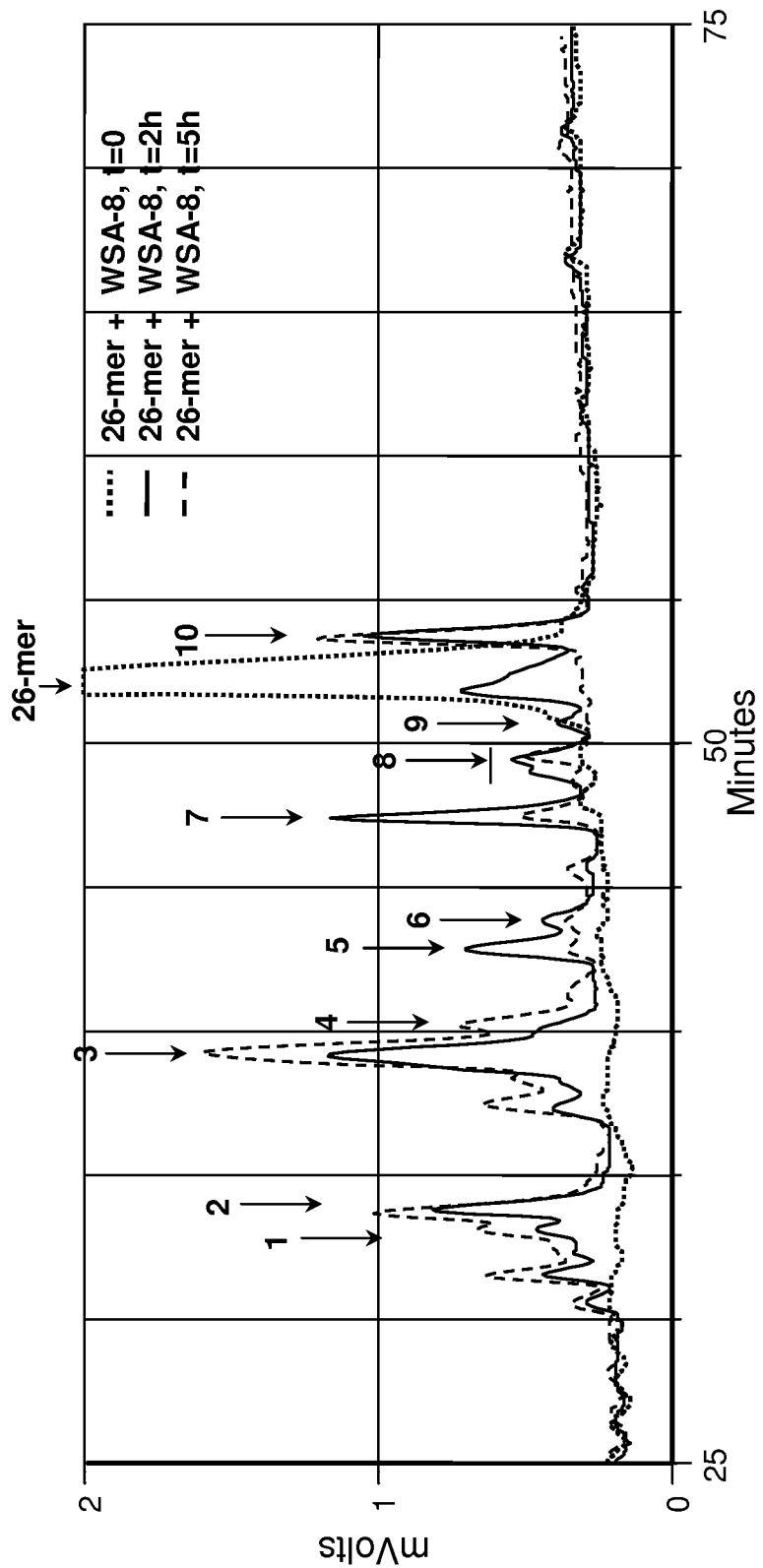

Proteolytic fragmentation analysis of the 26-mer (FIG. 13) revealed cleavage activities after XPQ (the larger arrows, FIG. 13B) with only one of such tripeptide not cleaved in the N-terminal domain after Q5. QPY was cleaved possibly by the same enzyme(s) which recognizes LPY in the 33-mer. Seven additional cleavage sites were observed with varying cleavage site specificities (FIG. 13B).

Figure 14A:
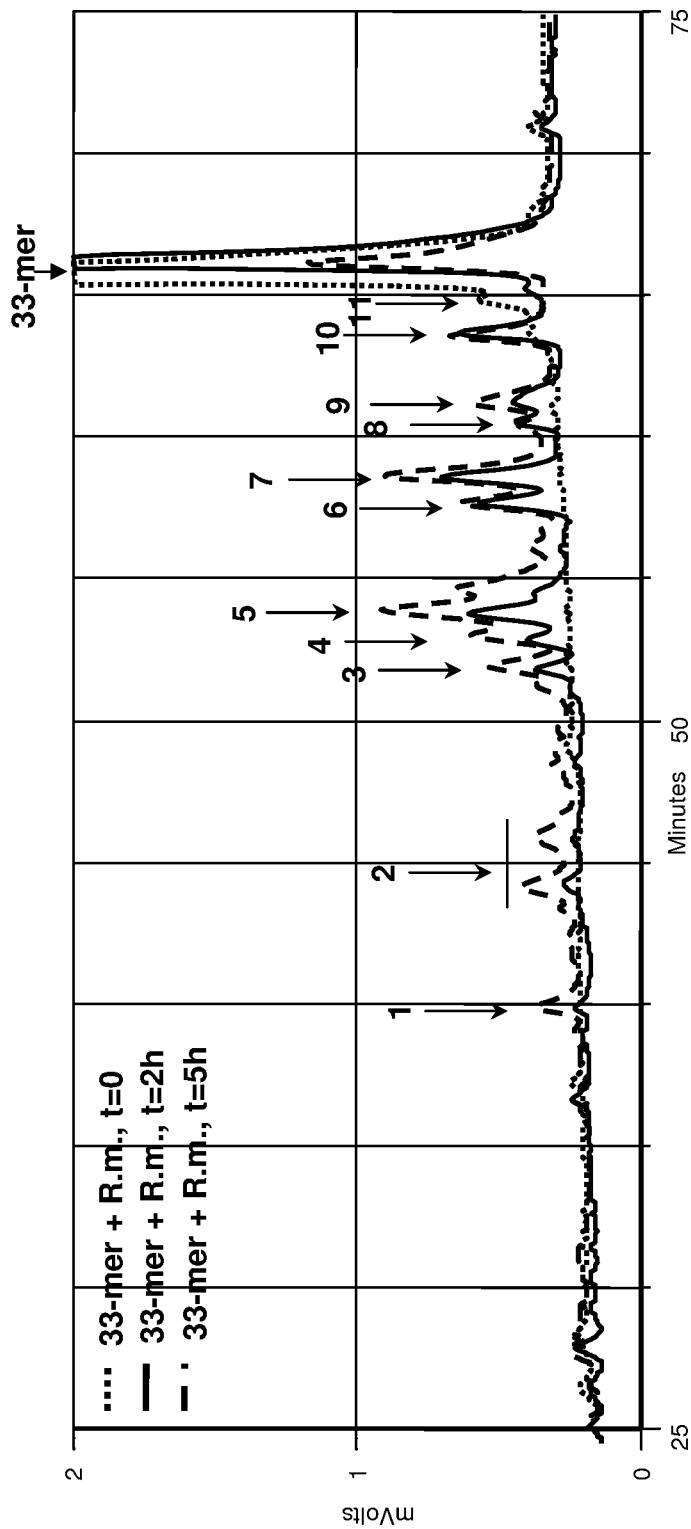
Figure 14B:
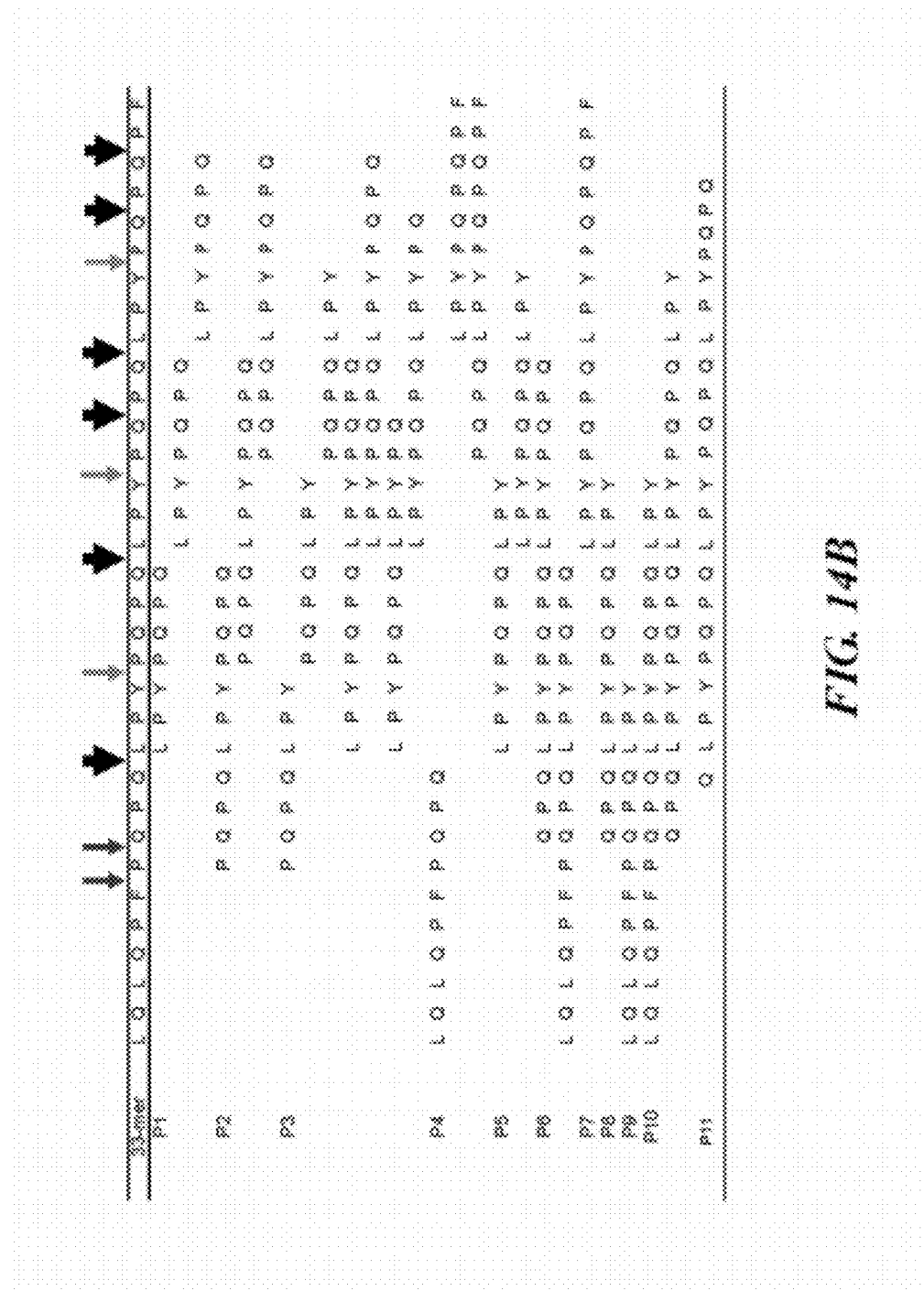
Figure 15A:
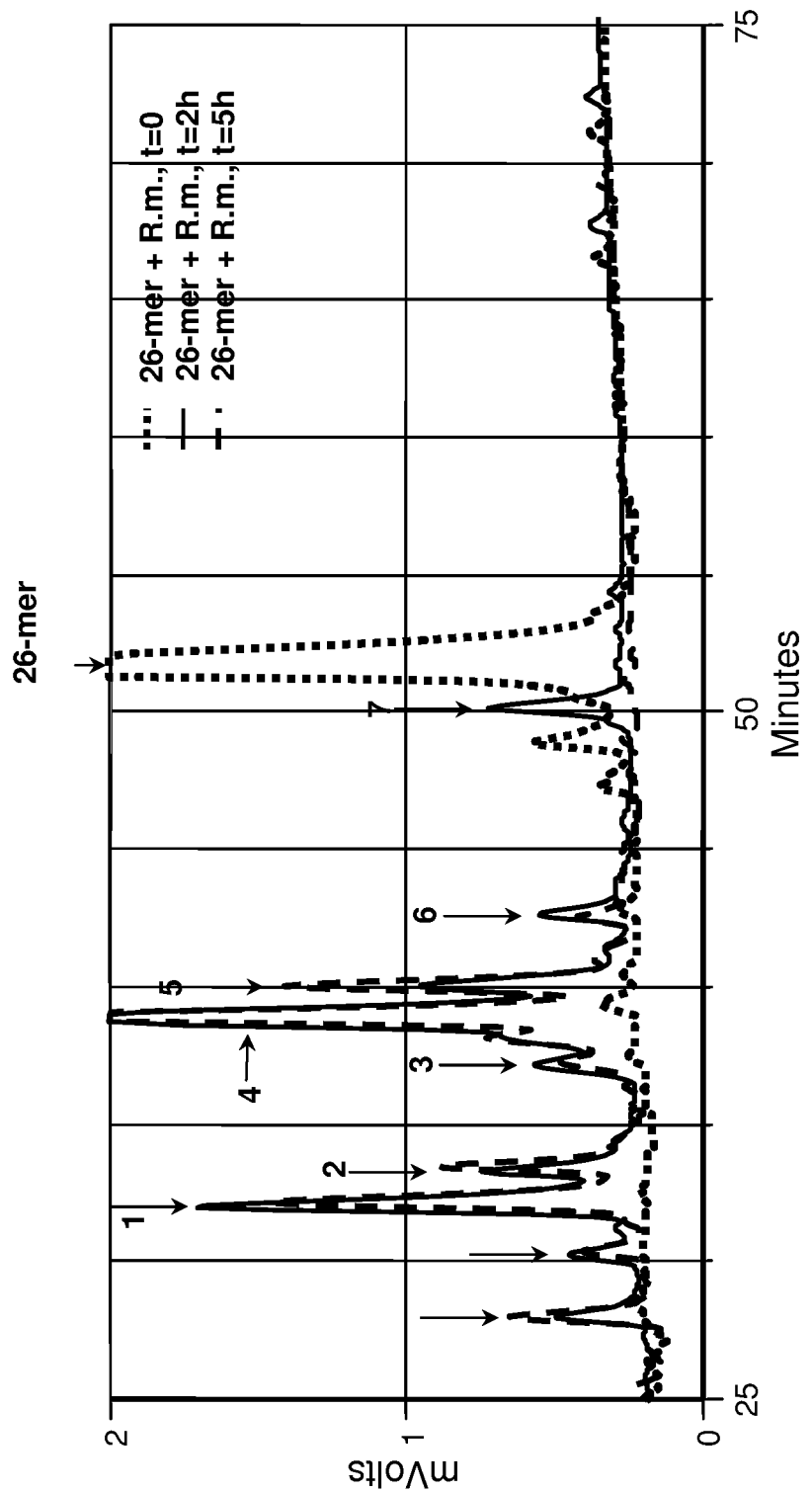
Figure 15B:
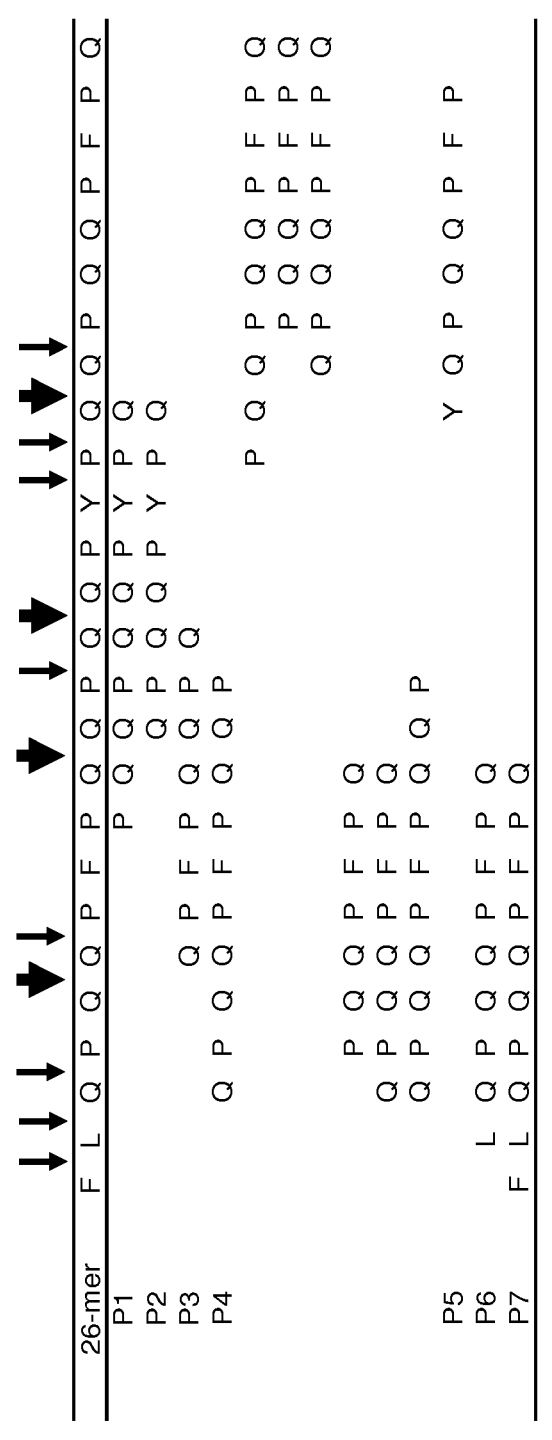

Results of the proteolysis of the 33-mer and 26-mer by *R. mucilaginosa* ATCC 25296 are shown in FIGS. 14 and 15, respectively. As for WSA-8, XPQ and LPY were again identified as prominent protease target sites (FIGS. 14B and 15B). Interestingly, while WSA-8 was unable to cleave XPQ when proline occupied the P1' position, *R. mucilaginosa* was able to target XPQ↓P as evidenced from three peptides resulting from this cleavage eluting in peak 3. Cleavage at these sites is significant since it is well known that proline in the p1' position frequently interferes with efficient degradation by proteolytic enzymes. This indicated that the enzymes produced by *R. mucilaginosa* exhibit unusually efficient cleavage capacities towards these gluten domains.

Figure 16:
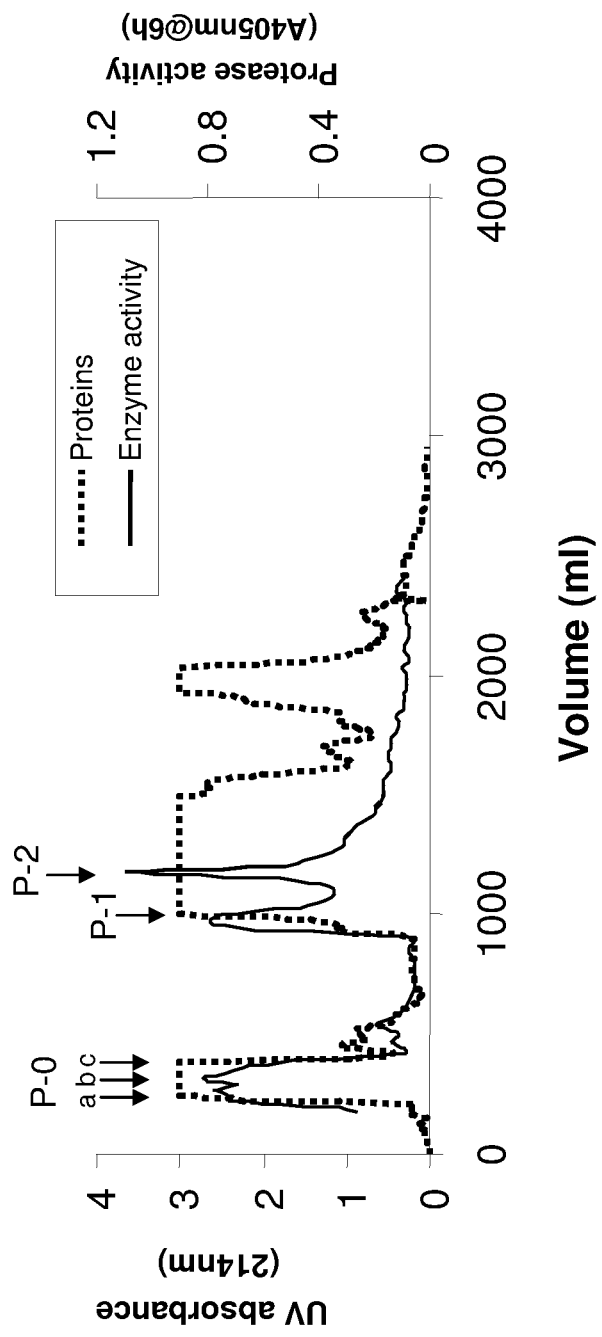

Isolation of the enzyme from *R. mucilaginosa* ATCC 25296—*R. mucilaginous* cells were sonicated and proteins of interest were partially isolated by step-wise salt precipitation with ammonium sulfate. FIG. 16 shows the DEAE chromatogram of the enzyme fraction partially enriched by ammonium sulfate precipitation and the protease activity in the DEAE eluate. The total protein pattern (dotted trace, measured at 214 nm) of the eluate is complex as expected and most of the peaks were off-scale. The proteolytic cleavage of z-YPQ-pNA was assessed in all fractions collected and indicated that enzymatic activity was present in peaks P-0, P-1 and P-2. The P-0 peak eluting in the void volume before the gradient with buffer B contained proteins not binding to the DEAE resin. Activity analysis indicated that three different sub-peaks were present in P-0 which were separately collected and designated P-0a, P-0b and P-0c. The peaks were turbid in solution, suggesting the presence of hydrophobic components or lipoproteins. This is not unexpected since the proteins originated from a cell sonicate. Peaks P1 and P2 eluted from the DEAE column within the gradient and should be considered anionic proteins. FIG. 17A shows the SDS PAGE and FIG. 17B shows the gliadin zymography of the collected DEAE peaks. Strong gliadin-degrading activity was associated with P-0b and P1 in the 70-75 kD region of the zymogram and bands with similar electrophoretic mobility were also present in the SDS gel (boxed). Interestingly, P2 did not show activity in the zymogram (repeatedly observed) and was not considered for further purification.

Fractions P-0b and P1 were concentrated and subjected to G-100 gel filtration chromatography. Unfortunately this step yielded only minimal further purification of individual proteins (data not shown). To improve purification the P-0b and P-1 fractions were then further subjected to HiTrap QQF and HiTrap QXL chromatographic resins which both represent strong anion-exchange resins. The NaCl concentration in buffer A was reduced to 25 mM to facilitate protease binding to the anion exchange column since no binding was observed to cation-exchange resins. Fractions collected from both columns were evaluated for Z-YPQ-pNA hydrolysis activity. Selected peaks were subsequently analyzed by SDS-PAGE (FIG. 17C) and gliadin zymography (FIG. 17D). The results show that this anion exchange separation yielded partially pure and enzyme enriched preparations. The specific activity in these fractions was >50 fold increased compared to the starting material applied to the DEAE column. The clear bands observed in the zymogram gel confirmed proteolytic activity towards gliadin. Various repeats of these experiments resulted in 6 experimental samples all showing a double band in the zymograms at 70 and 75 kD with proteolytic activity. The upper 75 kD band was designated (a) and the lower 70 kD band (b). Six upper and six lower bands were excised, digested in-gel with trypsin and analyzed by LC-ESI-MS/MS.

Identification of Neprilysin—Table 5 summarizes proteins that were identified by >2 peptides and exhibited molecular weight values between 50 and 80 kD. Indicated are the protein names, whether or not the protein is an enzyme (based on functional assignments listed at NCBI), the NCBI accession number, the calculated molecular weight based on the cumulative mass of the amino acid residues in the protein sequence, and the number of times the proteins was found in the six gel slices. When the sequences were carefully analyzed it was noted that oligopeptide-binding protein was highly homologous with extracellular solute-binding proteins. While repeatedly identified, these proteins belong to a superfamily of proteins that are functionally involved in oligopeptide transport. Most other proteins identified were likewise involved in cell metabolic processes unrelated to proteolytic activity. In fact, only one of the proteins identified, neprilysin, is a peptidase and hence a proteolytic enzyme. It exhibits a calculated molecular weight of 74 kD exactly matching the 70-75 kD weight range noted in the gels. The primary amino acid sequence of *R. mucilaginosa* neprilysin is shown in FIG. 18. It was identified both in band (a) and in band (b). Its appearances in both bands indicate different isoforms of the enzyme. In band (a) it was found only in 1 of the 6 gel samples, but by a very high number of peptides (9). In band (b) it was present in 2 of the 6 gel slices and identified by the presence of multiple peptides (7 peptides).

Neprilysin belongs to the peptidase M13 super family. M13 peptidases are well-studied metallo-proteases found in a wide range of organisms including mammals and bacteria. The metal ion dependency of this enzyme is consistent with the current observation that proteolytic activity towards gliadins is completely inhibited in the presence of EDTA (FIG. 7). In mammals M13 proteases participate in processes such as cardiovascular development, blood-pressure regulation, nervous control of respiration, and regulation of the function of neuropeptides in the central nervous system. In bacteria they may be used for digestion of milk. The present report provides evidence that neprilysin can play an additional role in the digestion of dietary gluten. This finding opens new avenues for the clinical exploitation of this enzyme in the treatment of celiac disease.

CONCLUSION

Gluten proteins are primarily found in barley and wheat and they cause celiac disease in genetically predisposed subjects. Gluten, by virtue of being rich in glutamine and proline residues, is notoriously difficult to digest by human digestive enzymes. Glutamine endoproteases and gliadin degrading activity were reported in human dental plaque. The present study was initiated to isolate the responsible microorganisms and to functionally and structurally characterize the gliadin degrading enzymes. The ultimate goal is to explore the therapeutic usefulness of such enzymes in the treatment of celiac disease.

Oral specimens containing a mixture of microorganisms were cultured and sub-cultured on *Brucella* agar and gluten-limited agar to identify and isolate gluten-degrading strains. Enzyme activities in pure bacterial suspensions was assessed by measuring proteolytic activities towards a) gliadin-derived paranitroanilide(pNA)-linked synthetic enzyme substrates b) a mixture of natural gliadins and c) synthetic, highly immunogenic, gliadin peptides (33-mer of α2-gliadin and 26-mer of γ-gliadin). Gliadin zymography was utilized to obtain the approximate molecular weights of the enzyme(s), their pH activity range and inhibitor profiles. Bacteria of interest were speciated by 16S RNA analysis. Enzymes were purified from sonicated cell culture supernatants by DEAE anion-exchange chromatography, G-100 gel filtration chromatography and HiTrap anion-exchange chromatography. Enzyme activity in collected fractions was monitored using the synthetic peptide Z-YPQ-pNA and the overall protein profile was assessed by SDS-PAGE. Samples enriched in microbial enzymes were subjected to gliadin zymography, active bands were excised, trypsinized and analyzed by LC-ESI-MS/MS. Principal findings: Bacteria with strong gliadin degrading activities were identified as *R. mucilaginosa* and *Rothia* spp of 188. Cell suspensions degraded Z-YPQ-pNA but not Z-QQP-pNA, Z-PPF-pNA or Z-PFP-pNA. Importantly, *Rothia* cells cleaved the 33-mer and the 26-mer gliadin immunogenic domains which are otherwise indigestible by gastro-intestinal enzymes of mammalian origin. Analysis of the sites cleaved using peptide isolation by RP-HPLC and structural characterization by LC-ESI-MS/MS confirmed the recognition of the XPQ↓ sequence by both *Rothia* species. The sequence of XPX↓P was recognized by *R. mucilaginosa* only. Another identified prominent cleavage site was after LPY↓. Gliadin zymography yielded evidence for the presence of two major enzyme bands of ~70 and ~75 kD in *R. mucilaginosa* and one such band of ~70 kD in *Rothia* ot188. The enzymes were active over a broad pH range (pH 3-10) as assessed by Z-YPQ-pNA hydrolysis, and optimal activities were observed at pH>7.0. The most efficient inhibitors of enzyme activity were EDTA and PMSF (100% inhibition). DEAE chromatographic separation of sonicated Rothia cell supernatant yielded peaks with enzyme activity in the void (P0) as well as in early-eluting peaks (P1 and P2). LC-ESI-MS/MS analysis of protease enriched fractions following excision from the zymogram yielded the identification of the enzyme neprilysin in both zymogram bands. The theoretical mass of neprilysin (74 kD) closely matches the experimental MW of the enzyme in the SDS and zymogram gels.

TABLE 1

Comparison of amino acid sequences of salivary basic proline-rich protein 2 (PRB2) from human saliva and wheat omega-5 gliadin protein from *Triticum aestivum*\* (SEQ. ID. NO: 20 and 21 respectively in the order of appearance)

>sp|P02812|PRB2_HUMAN Basic salivary proline-rich protein 2 OS = Homo sapiens GN = PRB2 PE = 1 SV = 3

MLLILLSVALLALSSAQNLNEDVSQEESPSLIAGNPQGAPPQGGNKPQGPPSPPGKPQGP

PPQGGNQPQGPPPPPGKPQGPPPQGGNKPQGPPPPGKPQGPPPQGDKSRSPRSPPGKPQG

PPPQGGNQPQGPPPPPGKPQGPPPQGGNKPQGPPPPGKPQGPPPQGDNKSRSSRSPPGKP

QGPPPQGGNQPQGPPPPPGKPQGPPPQGGNKPQGPPPPGKPQGPPPQGDNKSQSARSPPG

KPQGPPPQGGNQPQGPPPPPGKPQGPPPQGGNKSQGPPPPGKPQGPPPQGGSKSRSSRSP

PGKPQGPPPQGGNQPQGPPPPPGKPQGPPPQGGNKPQGPPPPGKPQGPPPQGGSKSRSAR

SPPGKPQGPPQQEGNNPQGPPPPAGGNPQQPQAPPAGQPQGPPRPPQGGRPSRPPQ

>tr|Q402I5|Q402I5_WHEAT Omega-5 gliadin OS = Triticum aestivum PE = 4 SV = 1

MKTFIIFVLLAMAMNIASASRLLSPRGKELHTPQEQFPQQQQFPQPQQFPQQQIPQQHQI

PQQPQQFPQQQQFLQQQQIPQQQIPQQHQIPQQPQQFPQQQQFPQQHQSPQQQFPQQQFP

QQKLPQQEFPQQQISQQPQQLPQQQQIPQQPQQFLQQQQFPQQQPPQQHQFPQQQLPQQQ

QIPQQQQIPQQPQQIPQQQQIPQQPQQFPQQQFPQQQFPQQQFPQQEFPQQQQFPQQQIA

RQPQQLPQQQQIPQQPQQFPQQQQFPQQSPQQQQFPQQQFPQQQQLPQKQFPQPQQIPQ

QQQIPQQPQQFPQQQFPQQQQFPQQEFPQQQFPQQQFHQQQLPQQQFPQQQFPQQQFPQ

QQQFPQQQQLTQQQFPRPQQSPEQQQFPQQQFPQQPQQFPQQQFPIPYPPQQSEEPSPY

QQYPQQQPSGSDVISISGL

\*XPQ sequences are highlighted in red and underlined.

TABLE 2

Characteristics of gliadins from *Triticum aestivum* and human salivary basic proline-rich proteins[1]

| Protein | # a.a. | % Q | % P | %(Q + P) | #XPQ |
|---|---|---|---|---|---|
| α/β-gliadins | 293 | 34 | 15 | 49 | 16-23 |
| γ-gliadins | 290 | 31 | 16 | 47 | 2-39 |
| ω5-gliadins | 439 | 51 | 19 | 70 | 72 |
| ω-gliadins | 306 | 24 | 19 | 43 | 8-38 |
| PRB1 | 393 | 16 | 37 | 53 | 47-48 |
| PRB2 | 416 | 15 | 37 | 52 | 50 |
| PRB3 | 309 | 14 | 35 | 49 | 20 |
| PRB4 | 310 | 14 | 34 | 48 | 21 |

[1] Excluding fragments and clones, there were total of 11 sequences for alpha/beta-gliadin, 154 sequences for gamma-gliadins, 1 sequence for omega-5-gliadin and 3 sequences for omega-gliadins.

TABLE 3

Cleavage specificities of trypsin and of enzymes associated with dental plaque bacteria towards gliadins.

| Enzyme source | Total # gliadin peptides observed[a] | Cleavage sites (% of total)[b] | | | | | |
|---|---|---|---|---|---|---|---|
| | | XXR/K | XPQ | XQP | XFP | XPF | Other |
| Pure Trypsin | 71 | 40 | 2 | 0 | 1 | 3 | 25 |
| Plaque bacteria enzyme mixture | 94 | 0 | 32 | 26 | 12 | 7 | 17 |

[a] By LC-ESI-MS/MS, based on Xcorr values of 2.2 and 3.5 for doubly and triply charged peptides, resp.
[b] Only C-terminal cleavages were considered.

Note:
prominent cleavage activity against XPQ and XQP in the gliadin sample incubated with plaque supernatant enzymes.

TABLE 4

Enzymatic characteristics of the selected aerobic and anaerobic strains growing on gluten agar.

| Aer/Anaer | Strain ID/type[a] | Growth on gluten agar | Oral Species | Hydrolysis of gluten-based substrates[b] | | | |
|---|---|---|---|---|---|---|---|
| | | | | YPQ | QQP | PPF | PFP |
| Aerobic | WSA-2B = *Rothia mucilaginosa* ot 681 | Y | Y | +++ | — | — | — |
| | WSA-7A = *Streptococcus mitis* ot 677 | Y | Y | — | — | — | — |
| | WSA-8 = *Rothia* sp. ot 188 | Y | Y | +++ | — | — | — |
| | WSA-10 = *Staphylococcus epidermis* ot 601 | Y | Y | — | — | — | — |
| | WSA-26 = *Rothia mucilaginosa* ot 681 | Y | Y | +++ | — | — | — |
| Anaerobic | WSAN-14 = *Bifidobacterium longum* ATCC 15697 | Y | Y | — | — | — | — |
| | WSAN-16 = *Bifidobacterium longum* ATCC 15697 | Y | Y | — | — | — | — |
| | WSAN-24 = *Bifidobacterium longum* ATCC 15697 | Y | Y | — | — | — | — |
| | WSAN-25 = *Veilonella atypica* ot 524 | Y | Y | — | — | — | — |
| | PAN-0 = *Streptococcus pneumoniae* ot 734 | Y | Y | — | — | — | — |
| | PAN-5 = *Bifidobacterium dentium* ot 588 | Y | Y | — | — | — | — |
| | PAN-8 = *Bifidobacterium dentium* ot 588 | Y | Y | — | — | — | — |
| | PAN-18 = *Bifidobacterium dentium* ot 588 | Y | Y | — | — | — | — |
| | PAN-19 = *Bifidobacterium dentium* ot 588 | Y | Y | — | — | — | — |
| | PAN-23 = *Bifidobacterium dentium* ot 588 | Y | Y | — | — | — | — |
| | Whole Plaque mixture | Y | Y | +++ | +++ | +++ | +++ |

Note:
WSA-2B = WSA-26 = *Rothia mucilaginosa*. For subsequent experiments strains WSA-2B (*Rothia mucilaginosa* ot 681) and WSA-8 (*Rothia* sp. ot 188) were selected.
[a]Speciation carried out by 16S RNA analysis
[b]Final concentration of substrate: 200 μM. Bacteria added in saliva ion buffer, OD = 1.2. Hydrolysis measured at 405 nm after 24 h incubation.

TABLE 5

Proteins with MW between 50 and 80 kD identified by ≥2 peptides in band (a) and band (b) by LC-ESI-MS/MS

| Band | Protein | Enzyme | ID/Acc# | (kD) MW | Max # peptides found | Times identified in 6 samples |
|---|---|---|---|---|---|---|
| (a)~75 kD | oligopeptide-binding protein [*Rothia mucilaginosa* ATCC 25296] * | N | ZP_05368706 | 62 | 7 | 3 *** |
| | L-lactate permease [*Rothia mucilaginosa* ATCC 25296] | N | ZP_05367274 | 56 | 2 | 1 |
| | PTS system, glucose subfamily, IIBCA component [*Rothia mucilaginosa* ATCC 25296] | N | ZP_05368708 | 72 | 2 | 1 |
| | cytochrome D ubiquinol oxidase subunit 1 [*Rothia mucilaginosa* ATCC 25296] | N | ZP_05367386 | 58 | 2 | 2 *** |
| | serine/threonine-protein kinase PknB [*Rothia mucilaginosa* ATCC 25296] | N | ZP_05367629 | 75 | 2 | 1 |
| | 2-oxoglutarate dehydrogenase, E2 component, dihydrolipoamide succinyltransferase [*Rothia mucilaginosa* ATCC 25296] | N | ZP_05368146 | 55 | 5 | 4 *** |
| | neprilysin [*Rothia mucilaginosa* ATCC 25296] ** | Y | ZP_05367591 | 74 | 9 | 1 |
| | extracellular solute-binding protein, family 5 [*Rothia mucilaginosa* ATCC 25296] * | N | ZP_05368703 | 62.0538 | 2 | 1 |
| | extracellular solute-binding protein, family 5 [*Rothia mucilaginosa* ATCC 25296] * | N | ZP_05368704 | 61.911 | 2 | 1 |
| | penicillin-binding protein [*Rothia mucilaginosa* ATCC 25296] | N | ZP_05367785 | 76 | 5 | 1 |
| | putative ABC transporter substrate-binding protein [*Rothia mucilaginosa* ATCC 25296] | N | ZP_05368162 | 75 | 2 | 1 |
| | sodium/proline symporter [*Rothia mucilaginosa* ATCC 25296] | N | ZP_05367828 | 52 | 2 | 1 |
| (b)~70 kD | ABC transporter, ATP-binding protein [*Rothia mucilaginosa* ATCC 25296] | N | ZP_05368390 | 67 | 3 | 1 |
| | penicillin-binding protein [*Rothia mucilaginosa* ATCC 25296] | N | ZP_05367785 | 77 | 11 | 3 *** |
| | PTS system, glucose subfamily, IIBCA component [*Rothia mucilaginosa* ATCC 25296] | N | ZP_05368708 | 72 | 3 | 1 |
| | iiabc fructose/xylitol-pts [*Rothia mucilaginosa* ATCC 25296] | N | ZP_05367712 | 68 | 10 | 2 *** |
| | putative ABC transporter transmembrane protein [*Rothia mucilaginosa* ATCC 25296] | N | ZP_05368162 | 69 | 5 | 1 |
| | cytochrome D ubiquinol oxidase subunit 1 [*Rothia mucilaginosa* ATCC 25296] | N | ZP_05367386 | 58 | 3 | 3 *** |
| | oligopeptide-binding protein [*Rothia mucilaginosa* ATCC 25296] * | N | ZP_05368706 | 62 | 8 | 3 *** |
| | 2-oxoglutarate dehydrogenase, E2 component, dihydrolipoamide succinyltransferase [*Rothia mucilaginosa* ATCC 25296] | N | ZP_05368146 | 55 | 3 | 5 *** |
| | ABC transporter, ATP-binding protein [*Rothia mucilaginosa* ATCC 25296] | N | ZP_05368611 | 62 | 2 | 1 |
| | oxidoreductase, molybdopterin binding [*Rothia mucilaginosa* ATCC 25296] | N | ZP_05367779 | 59 | 2 | 1 |
| | neprilysin [*Rothia mucilaginosa* ATCC 25296] ** | Y | ZP_05367591 | 74 | 7 | 2 *** |
| | sodium/proline symporter [*Rothia mucilaginosa* ATCC 25296] | N | ZP_05367828 | 52 | 2 | 1 |
| | extracellular solute-binding protein, family 5 [*Rothia mucilaginosa* ATCC 25296] * | N | ZP_05368703 | 62.053 | 9 | 1 |
| | extracellular solute-binding protein, family 5 [*Rothia mucilaginosa* ATCC 25296] * | N | ZP_05368704 | 61.911 | 10 | 3 *** |

TABLE 5-continued

Proteins with MW between 50 and 80 kD identified by ≥2 peptides in band (a) and band (b) by LC-ESI-MS/MS

| Band | Protein | Enzyme | ID/Acc# | (kD) MW | Max # peptides found | Times identified in 6 samples |
|---|---|---|---|---|---|---|
| | putative ABC transporter substrate-binding protein [*Rothia mucilaginosa* ATCC 25296] | N | ZP_05368612 | 75 | 4 | 1 |
| | extracellular solute-binding protein, family 5 [*Rothia mucilaginosa* ATCC 25296] * | N | ZP_05368701 | 61.766 | 9 | 1 |
| | extracellular solute-binding protein, family 5 [*Rothia mucilaginosa* ATCC 25296] * | N | ZP_05368702 | 62.938 | 3 | 2 *** |
| | extracellular solute-binding protein, family 5 [*Rothia mucilaginosa* ATCC 25296] * | N | ZP_05368705 | 62.0708 | 5 | 1 |

* structurally related proteins
** peptidases
*** proteins identified in more than 1 sample
Note:
Multiple proteins were identified in bands (a) and (b), likely because of the close proximity of both bands in the zymogram. The only enzyme identified was neprilysin.

TABLE 6

Protein searched: Neprilysin from *Rothia mucilaginosa*, ZP_05367591

| Accession number | Species | Protein name | (exact same aa) Percent identical | (same and alike aa) Percent positives |
|---|---|---|---|---|
| ZP_05367591 | *Rothia mucilaginosa* | neprilysin predicted | 100 | 100 |
| YP_003363565 | *Rothia mucilaginosa* | metalloendopeptidase | 99 | 99 |
| ZP_07073157 | *Rothia dentocariosa* | metalloendopeptidase PepO | 76 | 87 |
| ZP_06905919 | *Rothia dentocariosa* | metalloendopeptidase PepO | 76 | 87 |
| YP_003315199 | *Sanguibacter keddieii* | endothelin-converting enzyme | 53 | 69 |
| YP_003325693 | *Xylanimonas cellulosilytica* | neprilysin | 53 | 70 |
| YP_003636471 | *Cellulomonas flavigena* | neprilysin | 52 | 67 |
| ZP_06830706 | *Rhodococcus equi* | metalloendopeptidase PepO | 52 | 66 |
| ZP07359309 | *Actinomyces viscosus* | neprilysin | 50 | 64 |

TABLE 7

Updated characteristics of gliadins from *Triticum aestivum* and human salivary basic proline-rich proteins[1]

| Protein | # a.a[a] | % Q | % P | %(Q + P) | #XPQ |
|---|---|---|---|---|---|
| α/β-gliadins | 288[b] | 34 | 15 | 49 | 7-22 |
| γ-gliadins | 276[c] | 31 | 16 | 47 | 2-38 |
| ω-gliadins | 356[d] | 24 | 19 | 43 | 8-72 |
| PRB1 | 392 | 16 | 37 | 53 | 47 |
| PRB2 | 416 | 15 | 37 | 52 | 50 |
| PRB3 | 309 | 14 | 35 | 49 | 20 |
| PRB4 | 310 | 14 | 34 | 48 | 21 |

[a]Including signal peptides
[b,c,d]Average number of amino acids in α/β-gliadins (58 entries), γ-gliadins (110 entries), ω-gliadins (8 entries)

What is claimed is:

1. A gluten-containing foodstuff comprising a formulation comprising an isolated glutamine endopeptidase enzyme that cleaves a peptide bond after a QPF and a PFP motif in glutens.

2. The formulation of claim 1, wherein the isolated enzyme has an apparent molecular weight of about 70-75 kDa as determined by gliadin zymograms or by sodium dodecyl sulfate polyacrylamide gel electrophoresis.

3. The formulation of claim 2, wherein the isolated enzyme has a functional pH range of 3-10 as determined by detectable Z-YPQ-pNA cleaving activity within a 72 hour digestion period and a functional pH range of 7-10 as determined by substantially complete Z-YPQ-pNA cleavage within a 1 hour digestion period.

4. The formulation of claim 3, wherein the isolated enzyme is 100% inhibited by 1 mM of PMSF.

5. The formulation of claim 4, wherein the isolated enzyme is derived from a *Rothia* species bacteria, wherein the *Rothia* species bacteria is selected from the group consisting of *Rothia mucilaginosa* ot 681 (strain WSA-2B), *Rothia mucilaginosa* ATCC 25296 and *Rothia* species ot 188 (strain WSA-8).

6. The formulation of claim 5, wherein the isolated enzyme is stable in acid conditions.

7. The formulation of claim 6, wherein the isolated enzyme is lyophilized.

8. The formulation of claim 7, wherein the isolated enzyme has an amino acid sequence that show at least 60% similarity to SEQ. ID. NO: 1.

9. The formulation of claim 7, wherein the isolated enzyme comprises SEQ. ID. NO: 1.

10. The formulation of claim 7, wherein the isolated enzyme consists essentially of SEQ. ID. NO: 1.

11. The formulation of claim 7, wherein the isolated enzyme is SEQ. ID. NO: 1.

12. The formulation of claim 11 further comprising a prolyl endopeptidase.

13. A method of digesting gluten, the method comprising contacting a gluten-containing foodstuff with an effective dose of a formulation comprising an isolated glutamine endopeptidase enzyme that cleaves a peptide bond after a QPF and a PFP motif in glutens.

14. The method of claim 13, wherein the contacting is performed in vitro prior to consumption of the gluten-containing food stuff.

15. The method of claim 13, wherein the contacting is performed in vivo concurrent with or after consumption of the gluten-containing food stuff.

* * * * *

SEQUENCE LISTING

<160> NUMBER OF SEQ ID NOS: 136

<210> SEQ ID NO 1
<211> LENGTH: 660
<212> TYPE: PRT
<213> ORGANISM: Rothia mucilaginosa

<400> SEQUENCE: 1

Met Thr Thr Asn Ser Gly Ile Thr Lys Glu Trp Val Asp Glu Thr Val
1               5                   10                  15

Lys Pro Gly Asp Asp Phe Phe Arg His Val Asn Gly Lys Trp Leu Ala
            20                  25                  30

Thr His Glu Ile Pro Ala Asp Arg Pro Lys Asp Gly Gly Leu Tyr Thr

-continued

```
                35                  40                  45
Leu Arg Asp Asn Ala Glu Lys His Val Arg Glu Leu Val Glu Lys Ile
 50                  55                  60

Ala Lys Glu Gln Pro Glu Ser Arg Ile Gly Ala Leu Tyr Asn Ser Phe
 65                  70                  75                  80

Met Asp Val Glu Lys Ile Glu Ala Asp Gly Leu Glu Pro Leu Leu Lys
                 85                  90                  95

Glu Ile Ala Pro Ile Leu Asn Ser Ala Thr Pro Ser His Leu Ala Val
                100                 105                 110

Thr Leu Ala Leu Leu Ser Arg Ala Gly Leu Pro Gln Leu Phe Ala Trp
                115                 120                 125

Tyr Thr Ser Asn Asp Pro Lys Asp Pro Lys Asn Tyr Thr Phe Phe Leu
                130                 135                 140

Tyr Gln Ser Gly Leu Gly Leu Pro Asp Glu Ser Tyr Tyr Arg Glu Glu
145                 150                 155                 160

Lys His Glu Ala Ala Cys Ala Ala Tyr Val Glu His Ile Ala Arg Met
                165                 170                 175

Phe Gln Leu Thr Gly Leu Ala Glu Gly Phe Gly Leu Thr Pro Glu Gln
                180                 185                 190

Ala Ala Gln Leu Val Phe Thr His Glu Ser Glu Leu Ala Arg Leu His
                195                 200                 205

Trp Asn Val Val Glu Asn Arg Asp Ala Glu Ala Thr Tyr Asn Pro Tyr
                210                 215                 220

Gln Ala Thr Glu Leu Asp Glu Lys Phe Pro Gly Phe Pro Phe Ser Gln
225                 230                 235                 240

Trp Leu Leu Ala Leu Gly Ala Asp Pro Glu Thr Leu Gly Gln Val Ile
                245                 250                 255

Val Ala Gln Pro Ser Phe Phe Glu Gly Ala Ala Lys Leu Phe Thr Ser
                260                 265                 270

Ile Pro Leu Met Ser Trp Lys Leu Trp Ala Val Trp Thr Val Leu Arg
                275                 280                 285

Ser Arg Ala Pro Phe Met Tyr Asp Glu Leu Val Gln Glu Ser Phe Asn
                290                 295                 300

Phe Tyr Gly Lys Thr Leu Ser Gly Thr Gln Gln Ile Arg Glu Arg Trp
305                 310                 315                 320

Lys Arg Gly Val Gly Ala Val Glu Lys Ala Leu Gly Glu Ile Gly
                325                 330                 335

Gln Glu Tyr Val Ala Val His Phe Pro Pro Ser His Lys Glu Lys Met
                340                 345                 350

Leu Val Leu Val Gly Asn Leu Leu Glu Ala Tyr Arg Glu Ser Ile Glu
                355                 360                 365

Ser Leu Asp Trp Met Thr Glu Ala Thr Arg Gln Lys Ala Leu Glu Lys
370                 375                 380

Leu Ser Lys Phe Val Thr Lys Ile Gly Tyr Pro Asp Lys Trp Arg Asp
385                 390                 395                 400

Phe Ser Ala Leu Glu Leu Val Pro Gly Asp Leu Phe Glu Asn Leu Arg
                405                 410                 415

Arg Thr Gly Ala Phe Asp Ala Asp Trp Leu Ile Ala Arg Lys Gly Gln
                420                 425                 430

Pro Val Asp Lys Ala Glu Trp Leu Met Thr Pro Gln Thr Val Asn Ala
                435                 440                 445

Tyr Tyr Met Pro Pro Ala Asn Glu Ile Val Phe Pro Ala Ala Ile Leu
450                 455                 460
```

```
Gln Pro Pro Tyr Phe Asn Pro Asp Ala Asp Ala Ala Asn Tyr Gly
465                 470                 475                 480

Asn Ile Gly Met Ile Ile Gly His Glu Ile Gly His Gly Phe Asp Asp
            485                 490                 495

Gln Gly Ser Arg Tyr Asp Gly Asp Gly Lys Leu Glu Ser Trp Trp Thr
        500                 505                 510

Glu Glu Asp Tyr Ala Lys Phe Lys Glu Arg Thr Ala Ala Leu Val Glu
            515                 520                 525

Gln Tyr Asn Ala Tyr Val Pro Val Gly Leu Asp Pro Lys Phe His Val
530                 535                 540

Asn Gly Glu Leu Thr Leu Gly Glu Asn Ile Gly Asp Leu Ala Gly Met
545                 550                 555                 560

Ser Ile Ala Leu Lys Ala Tyr Arg Leu Ala Leu Lys Lys Gln Gly Ile
                565                 570                 575

Glu Ser Leu Ala Asp Ala Pro Val Ile Asp Gly Met Thr Gly Ile Gln
            580                 585                 590

Arg Phe Phe Phe Ser Asn Ala Arg Gly Trp Cys Thr Lys Ser Arg Pro
        595                 600                 605

Gln His Ala Glu Val Met Ile Ser Val Asp Pro His Ser Pro Asp Glu
    610                 615                 620

Phe Arg Val Asn Gly Val Val Arg Asn Ile Asp Glu Phe Tyr Glu Ala
625                 630                 635                 640

Phe Gly Val Ser Glu Gly Asp Ala Leu Tyr Leu Ala Pro Glu Glu Arg
                645                 650                 655

Val Arg Ile Trp
            660

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Leu Gln Pro Phe Pro Gln Pro Gln Leu Pro Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 4

Pro Phe Pro Gln Pro Gln Leu Pro Tyr
1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Gln Pro Gln Leu Pro Tyr Pro Gln Pro Gln Leu Pro Tyr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Gln Pro Gln Leu Pro Tyr Pro Gln
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Pro Gln Gln Ser Phe Pro Gln Gln Gln
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Gln Gln Ser Phe Pro Gln Gln Gln
1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Leu Gln Pro Phe Pro Gln Pro Glu Leu Pro Tyr
1               5                   10

<210> SEQ ID NO 10
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Pro Gln Pro Glu Leu Pro Tyr Pro Gln Pro Glu Leu Pro Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Pro Gln Gln Ser Phe Pro Glu Gln Gln
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Gln Pro Gln Gln Pro Ala Gln Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Pro Gln Gln Pro Tyr Pro Gln
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gln Pro Gln Gln Gln Phe Pro Gln
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Pro Phe Pro Gln Gln Pro Gln
1               5
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Phe Ser Gln Gln Gln Gln Pro Val
1               5

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Gln Pro Glu Leu Pro Tyr Pro Gln Pro Gln Leu Pro
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Gln Pro Glu Leu Pro Tyr Pro Gln Pro Gln Pro Leu Pro
1               5                   10

<210> SEQ ID NO 20
<211> LENGTH: 416
<212> TYPE: PRT
<213> ORGANISM: Homo sapiens

<400> SEQUENCE: 20

Met Leu Leu Ile Leu Leu Ser Val Ala Leu Leu Ala Leu Ser Ser Ala
1               5                   10                  15

Gln Asn Leu Asn Glu Asp Val Ser Gln Glu Glu Ser Pro Ser Leu Ile
            20                  25                  30

Ala Gly Asn Pro Gln Gly Ala Pro Pro Gln Gly Gly Asn Lys Pro Gln
        35                  40                  45

Gly Pro Pro Ser Pro Pro Gly Lys Pro Gln Gly Pro Pro Gln Gly
    50                  55                  60

Gly Asn Gln Pro Gln Gly Pro Pro Pro Pro Gly Lys Pro Gln Gly

```
                65                  70                  75                  80
Pro Pro Pro Gln Gly Gly Asn Lys Pro Gln Gly Pro Pro Pro Gly
                    85                  90                  95
Lys Pro Gln Gly Pro Pro Gln Gly Asp Lys Ser Arg Ser Pro Arg
                   100                 105                 110
Ser Pro Pro Gly Lys Pro Gln Gly Pro Pro Gln Gly Gly Asn Gln
                   115                 120                 125
Pro Gln Gly Pro Pro Pro Pro Gly Lys Pro Gln Gly Pro Pro Pro
                   130                 135                 140
Gln Gly Gly Asn Lys Pro Gln Gly Pro Pro Pro Gly Lys Pro Gln
145                 150                 155                 160
Gly Pro Pro Pro Gln Gly Asp Asn Lys Ser Arg Ser Arg Ser Pro
                   165                 170                 175
Pro Gly Lys Pro Gln Gly Pro Pro Gln Gly Gly Asn Gln Pro Gln
                   180                 185                 190
Gly Pro Pro Pro Pro Gly Lys Pro Gln Gly Pro Pro Pro Gln Gly
                   195                 200                 205
Gly Asn Lys Pro Gln Gly Pro Pro Pro Gly Lys Pro Gln Gly Pro
                   210                 215                 220
Pro Pro Gln Gly Asp Asn Lys Ser Gln Ser Ala Arg Ser Pro Gly
225                 230                 235                 240
Lys Pro Gln Gly Pro Pro Gln Gly Gly Asn Gln Pro Gln Gly Pro
                   245                 250                 255
Pro Pro Pro Gly Lys Pro Gln Gly Pro Pro Gln Gly Gly Asn
                   260                 265                 270
Lys Ser Gln Gly Pro Pro Pro Gly Lys Pro Gln Gly Pro Pro Pro
                   275                 280                 285
Gln Gly Gly Ser Lys Ser Arg Ser Ser Arg Ser Pro Gly Lys Pro
                   290                 295                 300
Gln Gly Pro Pro Gln Gly Gly Asn Gln Pro Gln Gly Pro Pro Pro
305                 310                 315                 320
Pro Pro Gly Lys Pro Gln Gly Pro Pro Gln Gly Gly Asn Lys Pro
                   325                 330                 335
Gln Gly Pro Pro Pro Gly Lys Pro Gln Gly Pro Pro Gln Gly
                   340                 345                 350
Gly Ser Lys Ser Arg Ser Ala Arg Ser Pro Gly Lys Pro Gln Gly
                   355                 360                 365
Pro Pro Gln Gln Glu Asn Asn Pro Gln Gly Pro Pro Pro Ala
370                 375                 380
Gly Gly Asn Pro Gln Gln Pro Gln Ala Pro Ala Gly Gln Pro Gln
385                 390                 395                 400
Gly Pro Pro Arg Pro Pro Gln Gly Gly Arg Pro Ser Arg Pro Pro Gln
                   405                 410                 415

<210> SEQ ID NO 21
<211> LENGTH: 439
<212> TYPE: PRT
<213> ORGANISM: Triticum aestivum

<400> SEQUENCE: 21

Met Lys Thr Phe Ile Ile Phe Val Leu Leu Ala Met Ala Met Asn Ile
1               5                   10                  15

Ala Ser Ala Ser Arg Leu Leu Ser Pro Arg Gly Lys Glu Leu His Thr
                20                  25                  30

Pro Gln Glu Gln Phe Pro Gln Gln Gln Phe Pro Gln Pro Gln Gln
```

```
                  35                  40                  45
Phe Pro Gln Gln Gln Ile Pro Gln Gln His Gln Ile Pro Gln Gln Pro
 50                  55                  60
Gln Gln Phe Pro Gln Gln Gln Phe Leu Gln Gln Gln Gln Gln Gln Ile Pro
 65              70                  75                  80
Gln Gln Gln Ile Pro Gln Gln His Gln Ile Pro Gln Gln Pro Gln Gln
             85                  90                  95
Phe Pro Gln Gln Gln Phe Pro Gln Gln His Gln Ser Pro Gln Gln
                100                 105                 110
Gln Phe Pro Gln Gln Gln Phe Pro Gln Gln Lys Leu Pro Gln Gln Glu
        115                 120                 125
Phe Pro Gln Gln Gln Ile Ser Gln Gln Pro Gln Gln Leu Pro Gln Gln
130                 135                 140
Gln Gln Ile Pro Gln Gln Pro Gln Gln Phe Leu Gln Gln Gln Gln Phe
145                 150                 155                 160
Pro Gln Gln Gln Pro Gln Gln His Gln Phe Pro Gln Gln Gln Leu
                165                 170                 175
Pro Gln Gln Gln Ile Pro Gln Gln Gln Ile Pro Gln Gln Pro
                180                 185                 190
Gln Gln Ile Pro Gln Gln Gln Ile Pro Gln Gln Pro Gln Gln Phe
            195                 200                 205
Pro Gln Gln Gln Phe Pro Gln Gln Phe Pro Gln Gln Phe Pro
                210                 215                 220
Gln Gln Glu Phe Pro Gln Gln Gln Phe Pro Gln Gln Gln Ile Ala
225                 230                 235                 240
Arg Gln Pro Gln Gln Leu Pro Gln Gln Gln Ile Pro Gln Gln Pro
                245                 250                 255
Gln Gln Phe Pro Gln Gln Gln Phe Pro Gln Gln Gln Ser Pro Gln
                260                 265                 270
Gln Gln Gln Phe Pro Gln Gln Gln Phe Pro Gln Gln Gln Leu Pro
                275                 280                 285
Gln Lys Gln Phe Pro Gln Pro Gln Gln Ile Pro Gln Gln Gln Gln Ile
        290                 295                 300
Pro Gln Gln Pro Gln Gln Phe Pro Gln Gln Gln Phe Pro Gln Gln
305                 310                 315                 320
Gln Phe Pro Gln Gln Gln Glu Phe Pro Gln Gln Gln Phe Pro Gln Gln
                325                 330                 335
Gln Phe His Gln Gln Gln Leu Pro Gln Gln Gln Phe Pro Gln Gln Gln
                340                 345                 350
Phe Pro Gln Gln Gln Phe Pro Gln Gln Gln Phe Pro Gln Gln Gln
                355                 360                 365
Gln Leu Thr Gln Gln Gln Phe Pro Arg Pro Gln Gln Ser Pro Glu Gln
        370                 375                 380
Gln Gln Phe Pro Gln Gln Gln Phe Pro Gln Gln Pro Gln Gln Phe
385                 390                 395                 400
Pro Gln Gln Gln Phe Pro Ile Pro Tyr Pro Pro Gln Gln Ser Glu Glu
                405                 410                 415
Pro Ser Pro Tyr Gln Gln Tyr Pro Gln Gln Gln Pro Ser Gly Ser Asp
                420                 425                 430
Val Ile Ser Ile Ser Gly Leu
                435

<210> SEQ ID NO 22
<211> LENGTH: 1983
```

<212> TYPE: DNA
<213> ORGANISM: Rothia mucilaginosa

<400> SEQUENCE: 22

| | | | | |
|---|---|---|---|---|
| atgactacta | actctggaat | cactaaagaa | tgggtggatg | aaaccgtcaa gccgggcgac | 60 |
| gatttcttcc | gccacgtcaa | cggcaagtgg | cttgctaccc | acgaaatccc ggcggaccgc | 120 |
| cccaaggacg | gcggcctgta | caccctccgc | gataacgcag | agaagcacgt gcgtgagctg | 180 |
| gtggagaaga | tcgcgaagga | gcagccggag | tcccgcatcg | gcgcgctgta caactccttc | 240 |
| atggatgttg | agaagattga | ggcggacggc | ctggaacctc | tgctgaagga aatcgccccg | 300 |
| attctgaact | cggcaacccc | ctcccacctg | gctgtgacct | tggcgctgct gtctcgtgcg | 360 |
| ggtctgccgc | agctgttcgc | ctggtacacc | agcaacgacc | cgaaggaccc gaagaattac | 420 |
| acgttcttcc | tgtaccagtc | gggcctgggt | ctgccggatg | aatcctacta ccgtgaagag | 480 |
| aagcacgagg | ctgcatgcgc | ggcgtatgtt | gagcatattg | cccgcatgtt ccagctgacc | 540 |
| ggtctggctg | agggcttcgg | tctcaccccg | gagcaggcgg | ctcagctggt gttcacccac | 600 |
| gagtctgagc | tggctcgtct | gcactggaac | gtcgtggaga | ccgcgacgc tgaggcgacc | 660 |
| tacaacccgt | accaggcgac | cgagctggac | gagaagttcc | ccggcttccc gttctcgcag | 720 |
| tggctgctgg | ctctgggtgc | tgacccggag | accctgggtc | aggttattgt ggctcagccg | 780 |
| tccttctttg | agggtgcggc | gaagctgttc | acctccatcc | cgctgatgag ctggaagctg | 840 |
| tgggctgtgt | ggactgttct | gcgttcgcgt | gcgccgttca | tgtacgacga gctggttcag | 900 |
| gagagcttca | acttctacgg | caagacccct | tccggtactc | agcagattcg tgagcgttgg | 960 |
| aagcgcggcg | tgggcgctgt | cgagaaggct | ctgggtgagg | agattggcca ggagtacgta | 1020 |
| gctgtgcact | cccgccctc | gcacaaggag | aagatgctgg | ttctggtcgg caacctcctt | 1080 |
| gaggcgtacc | gcgagtctat | tgagtcgctg | gactggatga | ctgaggcaac ccgtcagaag | 1140 |
| gcgctggaga | gctgtcgaa | gttcgtcacc | aagatcggtt | accccgataa gtggcgtgac | 1200 |
| ttctccgcgc | tggagctcgt | tcccggtgac | ctgttcgaga | acctgcgccg caccggtgcg | 1260 |
| ttcgatgctg | actggctgat | tgcccgtaag | ggtcagccgg | tggataaggc ggagtggctg | 1320 |
| atgactccgc | agaccgtgaa | cgcgtactac | atgccgccgg | cgaatgagat tgtgttcccg | 1380 |
| gcagcgattc | tgcagccgcc | gtacttcaac | ccggatgctg | acgatgcggc gaactacggc | 1440 |
| aatatcggca | tgattattgg | ccacgagatt | ggtcacggtt | ttgacgatca gggttcccgc | 1500 |
| tatgacggtg | acggcaagct | ggagagctgg | tggactgagg | aggattacgc gaagttcaag | 1560 |
| gagcgtaccg | cagccctggt | ggagcagtac | aacgcgtacg | ttccggtggg tctggacccg | 1620 |
| aagttccacg | tgaacggtga | gctgactctg | ggcgagaaca | ttggcgacct ggctggcatg | 1680 |
| tcgattgcgt | tgaaggcgta | ccgtctggct | ttgaagaagc | agggcattga gtcgctggct | 1740 |
| gacgcgccgg | tgattgacgg | catgaccggt | attcagcgtt | tcttcttctc gaatgctcgc | 1800 |
| ggctggtgca | cgaagtcccg | cccgcagcat | gctgaggtga | tgatttcggt ggatccgcat | 1860 |
| tcgccggatg | agttccgtgt | gaacggtgtg | gtgcgcaata | ttgatgagtt ctatgaggcg | 1920 |
| tttggcgtct | ctgagggcga | tgcactgtac | ctggctccgg | aggagcgcgt gcgcatctgg | 1980 |
| tag | | | | | 1983 |

<210> SEQ ID NO 23
<211> LENGTH: 660
<212> TYPE: PRT
<213> ORGANISM: Rothia mucilaginosa

<400> SEQUENCE: 23

```
Met Thr Thr Asn Ser Gly Ile Thr Lys Glu Trp Val Asp Glu Thr Val
1               5                   10                  15

Lys Pro Gly Asp Asp Phe Phe Arg His Val Asn Gly Lys Trp Leu Ala
            20                  25                  30

Thr His Glu Ile Pro Ala Asp Arg Pro Lys Asp Gly Leu Tyr Thr
            35                  40                  45

Leu Arg Asp Asn Ala Glu Lys His Val Arg Glu Leu Val Glu Lys Ile
50                      55                  60

Ala Lys Glu Gln Pro Glu Ser Arg Ile Gly Ala Leu Tyr Asn Ser Phe
65              70                  75                  80

Met Asp Val Glu Lys Ile Glu Ala Asp Gly Leu Glu Pro Leu Leu Lys
                85                  90                  95

Glu Ile Ala Pro Ile Leu Asn Ser Ala Thr Pro Ser His Leu Ala Val
                100                 105                 110

Thr Leu Ala Leu Leu Ser Arg Ala Gly Leu Pro Gln Leu Phe Ala Trp
            115                 120                 125

Tyr Thr Ser Asn Asp Pro Lys Asp Pro Lys Asn Tyr Thr Phe Phe Leu
    130                 135                 140

Tyr Gln Ser Gly Leu Gly Leu Pro Asp Glu Ser Tyr Tyr Arg Glu Glu
145                 150                 155                 160

Lys His Glu Ala Ala Cys Ala Ala Tyr Val Glu His Ile Ala Arg Met
                165                 170                 175

Phe Glu Leu Thr Gly Leu Ala Glu Gly Phe Gly Leu Thr Pro Glu Gln
            180                 185                 190

Ala Ala Gln Leu Val Phe Thr His Glu Ser Glu Leu Ala Arg Leu His
        195                 200                 205

Trp Asn Val Val Glu Asn Arg Asp Ala Glu Ala Thr Tyr Asn Pro Tyr
    210                 215                 220

Gln Ala Thr Glu Leu Asp Glu Lys Phe Pro Gly Phe Pro Phe Ser Gln
225             230                 235                 240

Trp Leu Leu Ala Leu Gly Ala Asp Pro Glu Thr Leu Gly Gln Val Ile
            245                 250                 255

Val Ala Gln Pro Ser Phe Phe Glu Gly Ala Ala Lys Leu Phe Thr Ser
            260                 265                 270

Ile Pro Leu Met Ser Trp Lys Leu Trp Ala Val Trp Thr Val Leu Arg
        275                 280                 285

Ser Arg Ala Pro Phe Met Tyr Asp Glu Leu Val Gln Glu Ser Phe Asn
290                 295                 300

Phe Tyr Gly Lys Thr Leu Ser Gly Thr Gln Gln Ile Arg Glu Arg Trp
305             310                 315                 320

Lys Arg Gly Val Gly Ala Val Glu Lys Ala Leu Gly Glu Glu Ile Gly
                325                 330                 335

Gln Glu Tyr Val Ala Val His Phe Pro Pro Ser His Lys Glu Lys Met
            340                 345                 350

Leu Val Leu Val Gly Asn Leu Leu Glu Ala Tyr Arg Glu Ser Ile Glu
            355                 360                 365

Ser Leu Asp Trp Met Thr Glu Ala Thr Arg Gln Lys Ala Leu Glu Lys
    370                 375                 380

Leu Ser Lys Phe Val Thr Lys Ile Gly Tyr Pro Asp Lys Trp Arg Asp
385                 390                 395                 400

Phe Ser Ala Leu Glu Leu Ala Pro Gly Asp Leu Phe Glu Asn Leu Arg
                405                 410                 415

Arg Thr Gly Ala Phe Asp Ala Asp Trp Leu Ile Ala Arg Lys Gly Gln
```

```
                420             425             430
Pro Val Asp Lys Ser Glu Trp Leu Met Thr Pro Gln Thr Val Asn Ala
            435                 440                 445
Tyr Tyr Met Pro Pro Ala Asn Glu Ile Val Phe Pro Ala Ala Ile Leu
450                 455                 460
Gln Pro Pro Tyr Phe Asn Pro Asp Ala Asp Ala Ala Asn Tyr Gly
465                 470                 475                 480
Asn Ile Gly Met Ile Ile Gly His Glu Ile Gly His Gly Phe Asp Asp
                485                 490                 495
Gln Gly Ser Arg Tyr Asp Gly Asp Gly Lys Leu Glu Ser Trp Trp Thr
            500                 505                 510
Glu Glu Asp Tyr Ala Lys Phe Lys Glu Arg Thr Ser Ala Leu Val Glu
            515                 520                 525
Gln Tyr Asn Ala Tyr Val Pro Val Gly Leu Asp Pro Lys Phe His Val
            530                 535                 540
Asn Gly Glu Leu Thr Leu Gly Glu Asn Ile Gly Asp Leu Ala Gly Met
545                 550                 555                 560
Ser Ile Ala Leu Lys Ala Tyr Cys Leu Ala Leu Lys Lys Gln Gly Ile
                565                 570                 575
Glu Ser Leu Ala Asp Ala Pro Val Ile Asp Gly Met Thr Gly Ile Gln
            580                 585                 590
Arg Phe Phe Phe Ser Asn Ala Arg Gly Trp Cys Thr Lys Ser Arg Pro
            595                 600                 605
Gln His Ala Glu Val Met Ile Ser Val Asp Pro His Ser Pro Asp Glu
            610                 615                 620
Phe Arg Val Asn Gly Val Val Arg Asn Ile Asp Glu Phe Tyr Glu Ala
625                 630                 635                 640
Phe Gly Val Ser Glu Gly Asp Ala Leu Tyr Leu Ala Pro Glu Glu Arg
                645                 650                 655
Met Arg Ile Trp
            660

<210> SEQ ID NO 24
<211> LENGTH: 663
<212> TYPE: PRT
<213> ORGANISM: Rothia dentocariosa

<400> SEQUENCE: 24

Met Asp Asn Ala Lys Asn Ser Gly Ile Thr Thr Glu Trp Val Asp Asn
1               5                   10                  15
Ala Val Lys Pro Gly Asp Asp Phe Phe Arg His Val Asn Gly Arg Trp
            20                  25                  30
Leu Asp Thr Tyr Glu Ile Pro Ala Asp Arg Ser Lys Asp Gly Gly Leu
        35                  40                  45
Tyr Thr Leu Arg Asp Asp Ala Glu Lys His Val Arg Glu Ile Val Glu
50                  55                  60
Arg Ile Ala Lys Glu Gln Pro Glu Ser Arg Ile Gly Ala Leu Tyr Asn
65                  70                  75                  80
Ser Phe Met Asp Thr Asp Lys Ile Glu Ser Asp Gly Leu Glu Pro Leu
                85                  90                  95
Met Arg Glu Val Ala Pro Ile Leu Asn Ala Ala Thr Ser Asp Gln Leu
            100                 105                 110
Ala Val Thr Leu Ala Leu Leu Ser Arg Ala Gly Leu Ala Gln Leu Leu
        115                 120                 125
Gly Trp Tyr Thr Ser Ile Asp Gln Lys Asp Pro Glu His Tyr Val Phe
```

```
                130                 135                 140
Tyr Leu Thr Gln Ala Gly Leu Gly Leu Pro Asp Glu Ala Tyr Arg
145                 150                 155                 160

Glu Glu Lys Tyr Glu Gln Val Cys Ala Ala Tyr Ile Glu His Ile Ala
                165                 170                 175

Thr Met Phe Glu Leu Thr Gly Phe Ala Glu Ser Phe Asn Leu Thr Pro
                180                 185                 190

Met Glu Ala Ala Gln Leu Ile Phe Ser His Thr Glu Ile Ala Ala
                195                 200                 205

His His Trp Asp Val Val Lys Asn Arg Asp Ala Glu Ala Lys Tyr Asn
        210                 215                 220

Pro Val Lys Ala Thr Glu Leu Asp Glu Lys Phe Pro Gly Phe Pro Leu
225                 230                 235                 240

Gln Gln Trp Leu Leu Ala Leu Gly Ala Asp Pro Glu Glu Leu Gly Thr
                245                 250                 255

Val Ile Val Ser Gln Pro Ser Phe Leu Glu Gly Val Ala Asn Met Trp
                260                 265                 270

Gln Ser Thr Pro Leu Met Thr Trp Lys Leu Trp Ala Leu Trp Cys Ala
        275                 280                 285

Ile Arg Ser Arg Ala Pro Tyr Leu Pro Asp Ala Phe Val Gln Glu Asn
        290                 295                 300

Phe Asn Phe Tyr Gly Arg Thr Leu Ser Gly Thr Glu Glu Leu Arg Glu
305                 310                 315                 320

Arg Trp Lys Arg Gly Val Ala Ala Val Glu Asn Ala Leu Asp Gln Glu
                325                 330                 335

Leu Gly Lys Glu Tyr Val Ala Val His Phe Pro Glu His Lys Glu
                340                 345                 350

Lys Met Leu Lys Leu Val Asn Asn Leu Leu Glu Ala Tyr Arg Arg Ser
        355                 360                 365

Ile Thr Asn Leu Asp Trp Met Thr Glu Ala Thr Arg Glu Lys Ala Leu
        370                 375                 380

Glu Lys Leu Ser Lys Phe Val Thr Lys Ile Gly Tyr Pro Asp Glu Trp
385                 390                 395                 400

Arg Asp Tyr Ser Lys Leu Thr Leu Val Pro Gly Asp Leu Phe Glu Asn
                405                 410                 415

Leu Arg Arg Thr Ala Ala Phe Asn Ser Asp Phe Met Ile Asp Arg Ala
                420                 425                 430

Gly Asp Pro Val Asp Lys Asn Glu Trp Leu Met Ser Pro Gln Thr Val
        435                 440                 445

Asn Ala Tyr Tyr Met Pro Pro Ala Asn Glu Ile Val Phe Pro Ala Ala
        450                 455                 460

Ile Leu Arg Pro Pro Phe Phe Asp Pro Glu Ala Asp Asp Ala Ala Asn
465                 470                 475                 480

Tyr Gly Gly Ile Gly Met Val Ile Gly His Glu Ile Gly His Gly Phe
                485                 490                 495

Asp Asp Lys Gly Ala Leu Tyr Asp Gly Asp Gly Ala Leu Asn Asn Trp
        500                 505                 510

Trp Thr Glu Glu Asp Phe Ala Glu Phe Thr Lys Arg Thr Ser Ala Leu
        515                 520                 525

Val Gln Gln Tyr Asn Ala Tyr Thr Pro Ala Asn Leu Asp Pro Gln Lys
        530                 535                 540

Phe Gln Val Asn Gly Glu Leu Thr Leu Gly Glu Asn Ile Gly Asp Leu
545                 550                 555                 560
```

```
Ser Gly Leu Ser Ile Ala Leu Arg Ala Tyr Glu Ile Ala Leu Ala Glu
                565                 570                 575

Gln Gly Ile Thr Ser Leu Glu Asp Ala Pro Val Ile Asp Asp Met Thr
            580                 585                 590

Ala Ala Gln Arg Leu Phe Trp Ser Thr Ala Gln Gly Trp Arg Thr Lys
        595                 600                 605

Ser Arg Pro Gln His Ala Glu Met Met Ile Ser Val Asp Pro His Ser
    610                 615                 620

Pro Asp Glu Phe Arg Val Asn Gly Val Val Arg Asn Ile Asp Glu Phe
625                 630                 635                 640

Tyr Asp Ala Phe Asp Val Pro Glu Gly Ser Lys Leu Tyr Leu Ala Pro
                645                 650                 655

Glu Asp Arg Val Arg Ile Trp
                660

<210> SEQ ID NO 25
<211> LENGTH: 663
<212> TYPE: PRT
<213> ORGANISM: Rothia dentocariosa

<400> SEQUENCE: 25

Met Asp Asn Ala Lys Asn Ser Gly Ile Thr Thr Glu Trp Val Asp Asn
1               5                   10                  15

Ala Val Lys Pro Gly Asp Phe Phe Arg His Val Asn Gly Arg Trp
            20                  25                  30

Leu Asp Thr Tyr Glu Ile Pro Ala Asp Arg Ser Lys Asp Gly Gly Leu
        35                  40                  45

Tyr Thr Leu Arg Asp Asp Ala Glu Lys His Val Arg Glu Ile Val Glu
50                  55                  60

Arg Ile Ala Lys Glu Gln Pro Glu Ser Arg Ile Gly Ala Leu Tyr Asn
65                  70                  75                  80

Ser Phe Met Asp Thr Asp Lys Ile Glu Ser Asp Gly Leu Glu Pro Leu
                85                  90                  95

Met Arg Glu Val Ala Pro Ile Leu Asn Ala Ala Thr Ser Glu Gln Leu
            100                 105                 110

Ala Val Thr Leu Ala Leu Leu Ser Arg Ala Gly Leu Ala Gln Leu Leu
        115                 120                 125

Gly Trp Tyr Thr Ser Ile Asp Gln Lys Asp Pro Glu His Tyr Val Phe
130                 135                 140

Tyr Leu Thr Gln Ala Gly Leu Gly Leu Pro Asp Glu Ala Tyr Tyr Arg
145                 150                 155                 160

Glu Glu Lys Tyr Glu Gln Val Cys Ala Ala Tyr Ile Glu His Ile Ala
                165                 170                 175

Thr Met Phe Glu Leu Thr Gly Leu Ala Glu Ser Phe Asn Leu Thr Pro
            180                 185                 190

Met Glu Ala Ala Gln Leu Ile Phe Ser His Glu Thr Glu Ile Ala Ala
        195                 200                 205

His His Trp Asp Val Val Lys Asn Arg Asp Ala Glu Ala Lys Tyr Asn
210                 215                 220

Pro Val Lys Ala Pro Glu Leu Asp Glu Lys Phe Pro Gly Phe Pro Leu
225                 230                 235                 240

Gln Gln Trp Leu Leu Ala Leu Gly Ala Asp Pro Lys Glu Leu Gly Thr
                245                 250                 255

Val Ile Val Ser Gln Pro Ser Phe Leu Glu Gly Val Ala Ser Met Trp
            260                 265                 270
```

```
Gln Ser Thr Pro Leu Met Thr Trp Lys Leu Trp Ala Leu Trp Cys Ala
        275                 280                 285

Ile Arg Ser Arg Ala Pro Tyr Leu Pro Asp Ala Phe Val Gln Glu Asn
290                     295                 300

Phe Asn Phe Tyr Gly Arg Thr Leu Ser Gly Thr Glu Glu Leu Arg Glu
305                 310                 315                 320

Arg Trp Lys Arg Gly Val Ala Ala Val Glu Asn Ala Leu Asp Gln Glu
                325                 330                 335

Leu Gly Lys Glu Tyr Val Ala Val His Phe Pro Glu His Lys Glu
                340                 345                 350

Lys Met Leu Lys Leu Val Asn Asn Leu Leu Glu Ala Tyr Arg Arg Ser
                355                 360                 365

Ile Thr Asn Leu Asp Trp Met Thr Glu Ala Thr Arg Glu Lys Ala Leu
370                     375                 380

Glu Lys Leu Ser Lys Phe Val Thr Lys Ile Gly Tyr Pro Asp Glu Trp
385                     390                 395                 400

Arg Asp Tyr Ser Lys Leu Thr Leu Val Pro Gly Asp Leu Phe Glu Asn
                405                 410                 415

Leu Arg Arg Ala Ala Ala Phe Asn Ser Asp Phe Met Ile Asp Arg Ala
                420                 425                 430

Gly Asp Pro Val Asp Lys Asn Glu Trp Leu Met Ser Pro Gln Thr Val
                435                 440                 445

Asn Ala Tyr Tyr Met Pro Pro Ala Asn Glu Ile Val Phe Pro Ala Ala
450                     455                 460

Ile Leu Arg Pro Pro Phe Phe Asp Pro Glu Ala Asp Ala Ala Asn
465                     470                 475                 480

Tyr Gly Gly Ile Gly Met Val Ile Gly His Glu Ile Gly His Gly Phe
                485                 490                 495

Asp Asp Lys Gly Ala Leu Tyr Asp Gly Asp Gly Ala Leu Asn Asn Trp
                500                 505                 510

Trp Thr Glu Glu Asp Phe Ala Glu Phe Thr Lys Arg Thr Ser Ala Leu
            515                 520                 525

Val Gln Gln Tyr Asn Ala Tyr Thr Pro Ala Asn Leu Asp Pro Gln Lys
                530                 535                 540

Phe Arg Val Asn Gly Glu Leu Thr Leu Gly Glu Asn Ile Gly Asp Leu
545                 550                 555                 560

Ser Gly Leu Ser Ile Ala Leu Arg Ala Tyr Glu Ile Ala Leu Ala Glu
                565                 570                 575

Gln Gly Ile Thr Ser Leu Glu Asp Ala Pro Val Ile Asp Gly Met Thr
                580                 585                 590

Ala Ala Gln Arg Leu Phe Trp Ser Thr Ala Gln Gly Trp Arg Thr Lys
                595                 600                 605

Ser Arg Pro Gln His Ala Glu Met Met Ile Ser Val Asp Pro His Ser
610                     615                 620

Pro Asp Glu Phe Arg Val Asn Gly Val Val Arg Asn Ile Asp Glu Phe
625                     630                 635                 640

Tyr Asp Ala Phe Asp Val Pro Glu Gly Ser Lys Leu Tyr Leu Ala Pro
                645                 650                 655

Glu Asp Arg Val Arg Ile Trp
                660

<210> SEQ ID NO 26
<211> LENGTH: 673
<212> TYPE: PRT
<213> ORGANISM: Sanguibacter keddieii
```

<400> SEQUENCE: 26

```
Met Thr Thr Asn Glu Lys Asn Ala Ala Gln Glu His Asp Leu Arg Pro
1               5                   10                  15

Gly Thr Thr Ser Gly Ile Asp Val Ser Ala Leu Asp His Asp Val Arg
            20                  25                  30

Pro Gln Asp Asp Leu Tyr Arg His Val Asn Gly Arg Trp Ile Ala Ser
        35                  40                  45

His Val Ile Pro Ala Asp Arg Ala Ser Asp Gly Gly Phe Arg Arg Leu
    50                  55                  60

His Asp Glu Ala Glu Ala His Val Arg Gln Ile Ile Glu Glu Leu Gly
65                  70                  75                  80

Gly Arg Asp Asp Leu Ser Gly Glu Glu Ala Gln Ile Gly Ala Leu Tyr
                85                  90                  95

Ala Ser Phe Met Asp Thr Ala Thr Val Glu Ala Ala Gly Val Asp Pro
            100                 105                 110

Leu Ala Gln Asp Leu Ala Leu Val Ser Ser Ala Ser Thr Gln Ala Glu
        115                 120                 125

Leu Thr Gly Ser Leu Gly Ala Leu Gln Arg Thr Gly Gly Ala Gly Ala
    130                 135                 140

Phe Gly Phe Trp Val Asp Asn Asp Ala Lys Asp Pro Glu Lys Tyr Val
145                 150                 155                 160

Val His Leu Tyr Gln Ala Gly Leu Gly Leu Pro Asp Glu Ser Tyr Tyr
                165                 170                 175

Arg Glu Asp Lys Tyr Ala Glu Thr Arg Glu Ala Tyr Val Ala His Val
            180                 185                 190

Ala Arg Met Leu Glu Leu Ser Gly Thr Val Ala Glu Ala Ser Ala
        195                 200                 205

Asp Ala Ala Arg Val Leu Ala Leu Glu Thr Arg Leu Ala Thr His
    210                 215                 220

His Trp Asp Val Val Arg Asp Arg Asp Ser Glu Leu Thr Tyr Asn Pro
225                 230                 235                 240

Thr Thr Leu Ala Ala Leu Ala Glu Thr Ala Pro Gly Phe Asp Trp Arg
                245                 250                 255

Ala Trp Ala Val Ala Leu Gly Ala Pro Glu Gly Ala Leu Asp Asp Val
            260                 265                 270

Val Val Arg Glu Pro Asp Phe Phe Thr Gly Phe Ala Ser Leu Trp Thr
        275                 280                 285

Ser Glu Pro Leu Glu Asp Trp Lys Thr Trp Met Val Tyr His Leu Val
    290                 295                 300

Ser Ala Arg Ala Pro Tyr Leu Thr Asp Glu Leu Val Glu Ala Asn Phe
305                 310                 315                 320

Asp Phe Tyr Gly Arg Thr Leu Ser Gly Thr Gln Glu Val Arg Glu Arg
                325                 330                 335

Trp Lys Arg Gly Val Ser Leu Val Glu Gly Ala Leu Gly Glu Ala Val
            340                 345                 350

Gly Lys Val Tyr Val Asp Arg His Phe Pro Pro Thr His Lys Ser Arg
        355                 360                 365

Met Asp Val Leu Val Ala Asn Leu Ile Glu Ala Tyr Arg Gln Ser Ile
    370                 375                 380

Thr Gln Leu Asp Trp Met Gly Gln Glu Thr Lys Thr Lys Ala Leu Ala
385                 390                 395                 400

Lys Leu Ser Ala Phe Thr Pro Lys Val Gly Tyr Pro Val Arg Trp Arg
                405                 410                 415
```

```
Asp Tyr Ser Ala Leu Val Val Asp Ala Gly Asp Leu Val Gly Asn Val
            420                 425                 430

Arg Arg Ser Asn Ser Val Asp Leu Asp Arg Glu Leu Ala Lys Ile Gly
        435                 440                 445

Gln Pro Ile Asp Arg Asp Glu Trp His Met Thr Pro Gln Thr Val Asn
    450                 455                 460

Ala Tyr Tyr Asn Pro Ser Met Asn Glu Ile Val Phe Pro Ala Ala Ile
465                 470                 475                 480

Leu Arg Pro Pro Phe Phe Asp Pro Glu Ala Glu Asp Ala Ala Asn Tyr
                485                 490                 495

Gly Gly Ile Gly Ala Val Ile Gly His Glu Ile Gly His Gly Phe Asp
            500                 505                 510

Asp Gln Gly Ser Lys Tyr Asp Gly Ala Gly Arg Leu Glu Asp Trp Trp
        515                 520                 525

Thr Gly Ser Asp Arg Ala Glu Phe Glu Lys Arg Thr Ala Ala Leu Ile
    530                 535                 540

Glu Gln Tyr Asp Ala Phe His Pro Ala Gln Leu Asp Ala Asp Arg Thr
545                 550                 555                 560

Val Asn Gly Ala Leu Thr Ile Gly Glu Asn Ile Gly Asp Leu Gly Gly
                565                 570                 575

Leu Ser Ile Ala Leu Lys Ala Tyr Glu Ile Ser Leu Gly Thr Asp Leu
            580                 585                 590

Ser Ala Ala Pro Ser Val Asp Gly Leu Ser Gly Thr Glu Arg Val Phe
        595                 600                 605

Leu Ser Trp Ala Gln Val Trp Gln Thr Thr Met Arg Asp Glu Ala Met
    610                 615                 620

Val Gln Arg Leu Ala Thr Asp Pro His Ser Pro Ala Glu Phe Arg Cys
625                 630                 635                 640

Asn Gly Val Val Ser Asn Leu Asp Glu Phe His Thr Thr Tyr Asn Val
                645                 650                 655

Gln Pro Gly Asp Ala Leu Tyr Leu Ala Pro Glu Asp Arg Val Arg Ile
            660                 665                 670

Trp

<210> SEQ ID NO 27
<211> LENGTH: 671
<212> TYPE: PRT
<213> ORGANISM: Xylanimonas cellulosilytica

<400> SEQUENCE: 27

Met Thr Ile Glu Ala Leu Arg Ser Gly Ile Asp Leu Thr Ala Leu Asp
1               5                   10                  15

Pro Ala Thr Arg Pro Gln Asp Asp Leu Tyr Arg His Val Asn Gly Thr
            20                  25                  30

Trp Ile Ala Thr His Glu Ile Pro Ala Asp Arg Ser Met Asp Gly Ala
        35                  40                  45

Phe Met Lys Leu Arg Asp Leu Ser Glu Glu Arg Val Arg Ala Ile Ile
    50                  55                  60

Thr Asp Leu Ala Gly Ser Ser Asp Thr Glu Pro Gly Thr Thr Ala Gly
65                  70                  75                  80

Lys Ile Gly Asp Leu Tyr Ser Ser Phe Met Asp Thr Ala Arg Ile Ala
                85                  90                  95

Ala Leu Gly Ala Thr Pro Leu Ala Asp Leu Ala Leu Ile Ala Gly
            100                 105                 110
```

```
Ala Thr Ser Gln Ala Glu Leu Thr Gly Val Leu Gly Ala Leu Gln Arg
            115                 120                 125

Thr Gly Gly Gly Ala Val Gly Phe Tyr Val Asp Asn Asp Ala Ala
130                 135                 140

Asp Pro Glu Gln Tyr Arg Val Tyr Leu Cys Gln Ser Gly Leu Gly Leu
145                 150                 155                 160

Pro Asp Glu Ala Tyr Tyr Arg Glu Asp Gln Tyr Ala Pro Ile Arg Glu
                165                 170                 175

Lys Tyr Val Pro His Val Ala Arg Met Leu Arg Leu Gly Gly Ala Ala
                180                 185                 190

Glu Leu Leu Gly Val Asp Ala Asp Ala Ala Ala Arg Val Val Ala
            195                 200                 205

Leu Glu Ser Lys Leu Ala Gly His His Trp Asp Val Val Lys Asp Arg
210                 215                 220

Asp Ala Thr Leu Thr Tyr Asn Pro Thr Thr Ile Ala Glu Leu Ala Val
225                 230                 235                 240

Thr Ala Pro Gly Phe Asp Trp Gln Ala Trp Ala Ile Ala Leu Gly Ala
                245                 250                 255

Pro Thr Gly Ala Leu Asp Ala Leu Val Val Arg Glu Pro Ser Tyr Ala
            260                 265                 270

Glu Gly Leu Ala Ala Leu Trp Gln Ser Glu Pro Leu Glu Asp Trp Gln
            275                 280                 285

Val Trp Ala Ala Tyr Arg Leu Val Thr Ala Arg Ala Pro Tyr Leu Thr
290                 295                 300

Asp Glu Ile Val Glu Ala Asn Phe Asp Phe Tyr Gly Arg Thr Leu Ser
305                 310                 315                 320

Gly Ala Gln Glu Val Arg Glu Arg Trp Lys Arg Gly Val Ala Leu Val
                325                 330                 335

Glu Gly Ala Leu Gly Glu Ala Val Gly Glu Gln Tyr Val Ala Arg His
            340                 345                 350

Phe Pro Pro Ala His Lys Ala Arg Met Asp Glu Leu Val Ala Asn Leu
            355                 360                 365

Val Ala Ala Tyr Arg Glu Ser Ile Glu Gly Leu Asp Trp Met Thr Asp
370                 375                 380

Glu Thr Lys Ala Lys Ala Leu Ala Lys Leu Glu Lys Phe Thr Pro Lys
385                 390                 395                 400

Ile Gly Tyr Pro Val Lys Trp Arg Asp Tyr Ser Ala Leu Val Ile Asp
                405                 410                 415

Ala Asp Asp Leu Val Gly Asn Val Arg Arg Ser Asn Ala Phe Asp Leu
            420                 425                 430

Asp His Glu Leu Gly Lys Val Gly Lys Pro Leu Asp Arg Asp Glu Trp
            435                 440                 445

Phe Met Thr Pro Gln Thr Val Asn Ala Tyr Tyr Asn Pro Gly Met Asn
450                 455                 460

Glu Ile Val Phe Pro Ala Ala Ile Leu Gln Pro Pro Phe Phe Asp Pro
465                 470                 475                 480

Glu Ala Asp Asp Ala Val Asn Tyr Gly Gly Ile Gly Gly Val Ile Gly
                485                 490                 495

His Glu Ile Gly His Gly Phe Asp Asp Gln Gly Ser Lys Tyr Asp Gly
            500                 505                 510

Asp Gly Arg Leu Gln Asp Trp Trp Thr Ala Glu Asp Arg Ala Glu Phe
            515                 520                 525

Glu Lys Arg Thr Gly Ala Leu Ile Ala Gln Tyr Asp Ala Phe Val Pro
530                 535                 540
```

```
Glu Gln Leu Gly Ala Asp Gly His Val Asn Gly Ser Leu Thr Ile
545                 550                 555                 560

Gly Glu Asn Ile Gly Asp Leu Gly Gly Leu Ser Ile Ala Ile Arg Ala
                565                 570                 575

Tyr Arg Ile Ala Leu Ala Ala Ala Arg Glu Gly Ala Thr Leu Asp Asp
            580                 585                 590

Ala Pro Val Ile Asp Gly Leu Thr Gly Leu Glu Arg Val Phe Leu Gly
                595                 600                 605

Trp Ala Gln Val Trp Gln Ser Lys Gly Arg Asp Glu Glu Val Leu Arg
610                 615                 620

Arg Leu Ala Thr Asp Pro His Ser Pro Asn Glu Phe Arg Cys Asn Gly
625                 630                 635                 640

Ile Val Arg Asn Val Asp Glu Phe His Asp Ala Tyr Gly Val Arg Glu
                645                 650                 655

Gly Asp Ala Leu Trp Leu Ala Pro Glu Asp Arg Val Arg Ile Trp
            660                 665                 670

<210> SEQ ID NO 28
<211> LENGTH: 662
<212> TYPE: PRT
<213> ORGANISM: Cellulomonas flavigena

<400> SEQUENCE: 28

Met Thr Arg Ser Gly Val Pro Leu Asp Asp Leu Asp Pro Ser Val Arg
1               5                   10                  15

Pro Gln Asp Asp Leu Asp Leu Phe Val Asn Gly Arg Trp Ala Ala Ser
                20                  25                  30

Tyr Val Ile Pro Pro Asp Arg Ser Met Asp Gly Pro Phe Arg Ala Leu
            35                  40                  45

Tyr Asp Glu Ala Glu Arg Gln Val Leu Asp Ile Ile Thr Asp Ala Ala
        50                  55                  60

Gln Ala Ala Gly Glu Gly Asp Gly Val Glu Ala Lys Ile Gly Ala Leu
65                  70                  75                  80

Tyr Ala Ser Phe Met Asp Thr Asp Ala Val Arg Ala Ala Gly Val Glu
                85                  90                  95

Pro Leu Arg Glu Asp Leu Ala Leu Val Asp Ala Ala Thr Thr Pro Ala
            100                 105                 110

Glu Leu Thr Val Ala Val Gly Arg Leu Gln Arg Thr Gly Ala Leu Ser
        115                 120                 125

Ala Val Asp Leu Tyr Val Asp Asn Asp Ala Lys Asp Pro Asp Ser Tyr
130                 135                 140

Val Val His Leu Val Gln Gly Gly Leu Gly Leu Pro Asp Glu Ala Tyr
145                 150                 155                 160

Tyr Arg Glu Glu Gln His Ala Ala Val Arg Glu Lys Tyr Leu Pro His
                165                 170                 175

Val Ala Arg Met Leu Arg Leu Ala Ala Pro Val Ser Gly Val Val Ala
            180                 185                 190

Ala Gly Asp Ala Asp Asp Leu Ala Ala Arg Val Val Ala Leu Glu Ser
        195                 200                 205

Arg Ile Ala Ala His His Trp Asp Val Val Lys Asp Arg Asp Ala Glu
210                 215                 220

Leu Thr Tyr Asn Ala Leu Thr Leu Ala Glu Leu Ala Ala Arg Ala Pro
225                 230                 235                 240

Gly Phe Asp Trp Arg Ala Trp Ala Glu Ala Leu Gly Ala Pro Ala Gly
                245                 250                 255
```

```
Ala Leu Asp Arg Leu Val Val Arg Glu Pro Ser Phe Ala Glu Gly Leu
            260                 265                 270

Ala Ala Leu Trp Thr Glu Val Pro Val Ala Asp Trp Gln Ala Trp Ala
        275                 280                 285

Thr Tyr His Val Val Ser Ser Arg Ala Pro Tyr Leu Thr Asp Glu Leu
    290                 295                 300

Val Glu Ala Asn Phe Asp Phe Tyr Gly Arg Thr Leu Ser Gly Ala Pro
305                 310                 315                 320

Glu Leu Arg Asp Arg Trp Lys Arg Gly Val Ser Leu Val Gln Gly Ala
                325                 330                 335

Leu Gly Glu Ala Val Gly Lys Val Tyr Val Glu Arg His Phe Pro Pro
            340                 345                 350

Ser His Lys Glu Arg Met Asp Glu Leu Val Ala Asn Leu Val Glu Ala
        355                 360                 365

Tyr Arg Arg Ser Ile Thr Glu Leu Glu Trp Met Gly Glu Glu Thr Arg
    370                 375                 380

Gln Arg Ala Leu Glu Lys Leu Ala Arg Phe Thr Pro Lys Ile Gly Tyr
385                 390                 395                 400

Pro Ala Arg Trp Arg Asp Tyr Ser Ala Leu Glu Val Arg Ala Asp Asp
                405                 410                 415

Leu Val Gly Asn Val Arg Arg Ser Asn Ala Phe Asp Leu Asp Arg Glu
            420                 425                 430

Leu Gly Lys Ile Gly Arg Pro Ile Asp Arg Asp Glu Trp Phe Met Thr
        435                 440                 445

Pro Gln Thr Val Asn Ala Tyr Tyr Asn Pro Gly Met Asn Glu Ile Val
    450                 455                 460

Phe Pro Ala Ala Ile Leu Gln Pro Pro Phe Phe Asp Ala Glu Ala Asp
465                 470                 475                 480

Asp Ala Ala Asn Tyr Gly Gly Ile Gly Ala Val Ile Gly His Glu Ile
                485                 490                 495

Gly His Gly Phe Asp Asp Gln Gly Ser Lys Tyr Asp Gly Asp Gly Arg
            500                 505                 510

Leu Val Asp Trp Trp Thr Ala Glu Asp Arg Ala Glu Phe Glu Arg Arg
        515                 520                 525

Thr Lys Ser Leu Val Asp Gln Tyr Ala Gln Tyr Ser Pro Arg Gln Leu
    530                 535                 540

Gly Gly Ser His Arg Val Asn Gly Glu Leu Thr Ile Gly Glu Asn Ile
545                 550                 555                 560

Gly Asp Leu Gly Gly Leu Ser Ile Ala Val Arg Ala Tyr Glu Ile Ala
                565                 570                 575

Leu Gly His Pro Leu Asp Glu Ala Pro Val Leu Asp Gly Tyr Thr Gly
            580                 585                 590

Leu Gln Arg Leu Phe Met Gly Trp Ala His Ser Trp Arg Thr Lys Gly
        595                 600                 605

Arg Asp Glu Glu Val Ile Arg Arg Leu Ala Thr Asp Pro His Ser Pro
    610                 615                 620

Asp Glu Phe Arg Cys Asn Gly Val Val Arg Asn Ile Asp Glu Phe Tyr
625                 630                 635                 640

Thr Ala Phe Asp Val Gln Pro Asp Asp Ala Leu Trp Leu Asp Pro Glu
                645                 650                 655

Gln Arg Val Arg Ile Trp
            660
```

<210> SEQ ID NO 29
<211> LENGTH: 652
<212> TYPE: PRT
<213> ORGANISM: Rhodococcus equi

<400> SEQUENCE: 29

```
Met Glu Cys Met Thr Arg Ser Gly Ile Asp Leu Thr His Ile Asp Ala
1               5                   10                  15

Gly Thr Arg Pro Gln Asp Asp Leu Phe Val His Val Asn Gly Lys Trp
            20                  25                  30

Leu Asp Glu Tyr Glu Ile Pro Ala Asp Arg Ala Val Asp Gly Ala Phe
        35                  40                  45

Arg Thr Leu Tyr Asp Lys Ala Glu Glu Asp Val Lys Thr Leu Ile Gln
    50                  55                  60

Glu Ala Ser Glu Ser Gly Ala Ala His Gly Thr Asp Ala Gln Lys Ile
65                  70                  75                  80

Gly Asp Leu Tyr Ser Ser Phe Met Asp Ala Asp Ala Val Glu Ala Ala
                85                  90                  95

Gly Leu Ser Pro Ile Ala Glu Glu Leu Ala Ala Val Ala Asn Ala Ala
            100                 105                 110

Asp Leu Ser Glu Leu Ala Gly Ile Val Gly Arg Leu Gln Arg Thr Gly
        115                 120                 125

Val Gly Gly Gly Ile Gly Gln Tyr Val Asp Thr Asp Ala Lys Asp Ser
    130                 135                 140

Ser Arg Tyr Leu Val His Phe Thr Gln Ser Gly Ile Gly Leu Pro Asp
145                 150                 155                 160

Glu Ser Tyr Tyr Arg Glu Asp Asn Tyr Ala Pro Ile Arg Asp Ala Tyr
                165                 170                 175

Val Glu His Ile Arg Lys Met Phe Glu Leu Ala Gly Ile Glu Tyr Asp
            180                 185                 190

Ala Gln Arg Val Phe Asp Leu Glu Thr Ala Ile Ala Gly Gly His Trp
        195                 200                 205

Asp Val Val Lys Arg Arg Asp Ala Glu Leu Gly Tyr Asn Leu Val Thr
    210                 215                 220

Leu Asp Asp Leu Arg Ser Gln Tyr Gly Gly Phe Asp Trp Asp Ala Trp
225                 230                 235                 240

Ile Ser Gly Leu Gln Ala Thr Pro Glu Gln Leu Ala Glu Ile Val Val
                245                 250                 255

Arg Gln Pro Gly Phe Val Glu Ser Phe Thr Glu Leu Trp Thr Ser Arg
            260                 265                 270

Pro Leu Glu Asp Trp Lys Ala Trp Ala Thr Trp Arg Val Leu His Ser
        275                 280                 285

Arg Ala Ala Phe Leu Thr Glu Ala Ile Val Ala Glu Asp Phe Ala Phe
    290                 295                 300

Phe Gly Thr Thr Leu Ser Gly Thr Gln Glu Asn Arg Glu Arg Trp Lys
305                 310                 315                 320

Arg Gly Val Ser Leu Val Gln Asp Leu Leu Gly Glu Ala Val Gly Lys
                325                 330                 335

Leu Tyr Val Glu Arg His Phe Pro Pro Glu Ser Lys Ala Arg Met Gln
            340                 345                 350

Glu Leu Val Ala Asn Leu Gln Glu Ala Tyr Arg Arg Asn Ile Ser Asp
        355                 360                 365

Leu Glu Trp Met Ser Pro Ala Thr Arg Gln Ala Ala Leu Ala Lys Leu
    370                 375                 380

Asp Lys Phe Thr Pro Lys Ile Gly Tyr Pro Asp Lys Trp Arg Asp Tyr
```

```
                385                 390                 395                 400
Ser Ala Val Glu Ile Asp Pro Ala Asp Leu Val Gly Asn Tyr Arg Ser
                    405                 410                 415

Gly Phe Ala Ala Glu His Asp Arg Asp Ile Ala Lys Leu Gly Gly Pro
                420                 425                 430

Val Asp Arg Asp Glu Trp Phe Met Thr Pro Gln Thr Val Asn Ala Tyr
            435                 440                 445

Tyr Asn Pro Gly Met Asn Glu Ile Val Phe Pro Ala Ala Ile Leu Gln
        450                 455                 460

Pro Pro Phe Phe Asp Pro Glu Ala Asp Ala Ala Asn Tyr Gly Gly
465                 470                 475                 480

Ile Gly Ala Val Ile Gly His Glu Ile Gly His Gly Phe Asp Asp Gln
                485                 490                 495

Gly Ala Lys Tyr Asp Gly Asp Gly Asn Met Val Asp Trp Trp Thr Asp
                500                 505                 510

Asp Asp Arg Thr Glu Phe Gly Lys Arg Thr Lys Ala Leu Ile Glu Gln
            515                 520                 525

Tyr Asn Asp Phe Glu Pro Lys Asp Leu Pro Gly His His Val Asn Gly
        530                 535                 540

Glu Phe Thr Ile Gly Glu Asn Ile Gly Asp Leu Gly Gly Leu Ser Ile
545                 550                 555                 560

Ala Leu Glu Ala Tyr Arg Ile Ala Thr Glu Thr Glu Ala Pro Val
                565                 570                 575

Leu Asp Glu Leu Asp Gly Leu Gln Arg Val Phe Phe Gly Trp Ala Gln
            580                 585                 590

Val Trp Arg Thr Lys Ala Arg Lys Glu Glu Ala Leu Arg Arg Leu Ala
        595                 600                 605

Val Asp Pro His Ser Pro Pro Glu Phe Arg Cys Asn Gly Val Ile Arg
610                 615                 620

Asn Leu Asp Ser Phe His Asp Ala Phe Asp Val Gln Pro Gly Asp Ala
625                 630                 635                 640

Leu Tyr Leu Glu Pro Glu Lys Arg Val Lys Ile Trp
                645                 650

<210> SEQ ID NO 30
<211> LENGTH: 726
<212> TYPE: PRT
<213> ORGANISM: Actinomyces viscosus

<400> SEQUENCE: 30

Met Thr Asp Ala Cys Ala Thr Ser Pro Thr Pro Thr Gly Pro Ala Ser
1               5                   10                  15

Asp Ser Pro Ala Gln His Ser Gln Pro Ala Ser Ser Pro Ala Ala
                20                  25                  30

Asp Ala Ile Leu Ala Gly Val Leu Glu Thr Ala His Thr Asp Thr Ser
            35                  40                  45

Val Arg Pro Gln Asp Asp Leu Phe Arg Phe Val Asn Gly Gln Trp Leu
        50                  55                  60

Thr Thr Ala Glu Ile Pro Ala Asp Arg Pro Ser Ser Gly Ala Phe Thr
65                  70                  75                  80

Thr Leu Arg Asp Glu Ser Glu Ala Ala Cys Arg Gln Ile Val Glu Glu
                85                  90                  95

Leu Ala Glu Gln Phe Ser Ser Val Ala Pro Glu Gly Ala Ala Glu Val
                100                 105                 110

Leu Ser Thr Asn Arg Gly Arg Val Gly Ala Leu Tyr Gln Ala Phe Met
```

-continued

```
                115                 120                 125
Asp Glu Ala His Leu Glu Leu Gly Ala Glu Pro Leu Ala Glu Glu
            130                 135                 140
Leu Ala Pro Val Leu Gly Ala Ser Ser Lys Glu Glu Leu Ala Arg Ala
145                 150                 155                 160
Leu Gly Glu Met Thr Pro Val Gly Phe Met Gly Val Val Gly Ala Asp
                165                 170                 175
Val Glu Val Asp Ile Asn Asp Pro Glu Arg Tyr Thr Ser Trp Val Gly
            180                 185                 190
Gln Ser Gly Leu Gly Leu Pro Asp Glu Ser Tyr Tyr Arg Glu Glu Ala
            195                 200                 205
Gln Ala Pro Leu Arg Gln Ala Tyr Val Glu His Val Ala Arg Met Met
            210                 215                 220
Ala Leu Ala Gly Leu Thr Asp Ser Phe Gly Ala Ser Gly Glu Asp Leu
225                 230                 235                 240
Ala Glu Arg Val Met Ala Val Glu Thr Ala Leu Ala Lys Gly His Trp
                245                 250                 255
Asp Arg Val Thr Cys Arg Asp Val Glu Lys Met Asn Asn Pro Met Ser
            260                 265                 270
Trp Gln Gln Ile Val Asp Ser Ala Pro Asp Leu Pro Trp Asp Glu Trp
        275                 280                 285
Arg Glu Gly Ile Arg Ala Ala Arg Ser Ala Gly Ile Glu Gln Thr
        290                 295                 300
Ala Phe Leu Glu Glu Ala Ile Val Thr Gln Pro Asp Tyr Leu Pro His
305                 310                 315                 320
Ala Ala Gly Val Trp Gln Glu Thr Asp Leu Glu Asp Leu Lys Val Trp
                325                 330                 335
Val Ala Trp His Val His Gly Arg Ala Ser Leu Leu Ser Gly Ala
            340                 345                 350
Phe Val Glu Glu Ser Phe Asp Phe Tyr Gly Arg Thr Leu Gln Gly Thr
            355                 360                 365
Asp Glu Leu Arg Pro Arg Trp Lys Arg Gly Val Gly Leu Val Glu Ser
        370                 375                 380
Cys Leu Gly Glu Ala Leu Gly Glu Ile Tyr Val Glu Arg His Phe Pro
385                 390                 395                 400
Pro Ser His Lys Ser Ala Met Glu Ala Leu Val Gly Arg Leu Ile Glu
                405                 410                 415
Ala Tyr His Gln Ser Ile Ser Ser Leu Glu Trp Met Ser Pro Ala Thr
            420                 425                 430
Arg Glu Arg Ala Leu Glu Lys Leu Ala Leu Phe Thr Pro Lys Ile Gly
            435                 440                 445
Tyr Pro Val Arg Trp Arg Asp Tyr Ser Ala Val Glu Val Pro Gly
            450                 455                 460
Asp Val Leu Ala Ser Val Arg Ser Val Glu Arg Ala Asp Met Ala Tyr
465                 470                 475                 480
Ser Leu Asn Lys Leu Thr Lys Pro Val Asp Arg Asp Glu Trp His Met
                485                 490                 495
Thr Pro Gln Thr Val Asn Ala Tyr Tyr Asn Pro Thr Met Asn Glu Ile
            500                 505                 510
Val Phe Pro Ala Ala Ile Leu Gln Pro Phe Phe Asp Pro Gln Ala
        515                 520                 525
Asp Asp Ala Val Asn Tyr Ala Gly Ile Gly Ala Val Ile Gly His Glu
530                 535                 540
```

```
Ile Gly His Gly Phe Asp Asp Gln Gly Ser Thr Phe Asp Gly Thr Gly
545                 550                 555                 560

Lys Val Ser Asp Trp Trp Thr Gln Glu Asp Arg Glu Ala Phe Thr Glu
                565                 570                 575

Arg Thr Ser Ala Leu Ile Ser Gln Tyr Asp Ala Tyr Thr Pro Lys Val
            580                 585                 590

Val Val Ala Lys His Arg Glu Ala Gly Thr Ala Gln Glu Glu Ile Pro
        595                 600                 605

His Val Asn Gly Ala Leu Thr Ile Gly Glu Asn Ile Gly Asp Leu Gly
    610                 615                 620

Gly Leu Gly Ile Ala Leu Lys Ala Tyr Ser Leu Ala Leu Ala Asp Ala
625                 630                 635                 640

Gly Ile Pro Ser Val Asp Glu Ala Pro Val Ile Asp Gly Leu Thr Gly
                645                 650                 655

Leu Gln Arg Phe Phe Tyr Ser Trp Ala Arg Ile Trp Arg Ser Lys Ser
            660                 665                 670

Arg Pro Asp Tyr Ala Glu Leu Leu Thr Val Asp Pro His Ser Pro
        675                 680                 685

Ala Glu Phe Arg Cys Asn Gly Ile Val Arg Asn Val Asp Ala Phe Tyr
    690                 695                 700

Lys Ala Phe Ala Val Asp Ser Asp Asp Ala Leu Trp Leu Pro Pro Asn
705                 710                 715                 720

Glu Arg Val Ser Ile Trp
                725

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Glu Ile Val Phe Pro Ala Ala Ile Leu Gln Pro Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Asp Asp Gln Gly Ser Arg Tyr Asp Gly Asp Gly
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Pro His Ser Pro Asp Glu Phe
1               5

<210> SEQ ID NO 34
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Gly Val Val Arg Asn Ile Asp Glu Phe Tyr
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Val Arg Ile Trp
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Asn Gly Lys Trp Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Ile Pro Ala Asp Arg Pro
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ile Gly Ala Leu Tyr
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ile Ala Pro Ile Leu
```

```
1               5
```

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gln Ser Gly Leu Gly Leu Pro Asp Glu Ser Tyr Tyr Arg Glu Glu
1               5                   10                  15
```

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Phe Tyr Gly Lys Thr Leu Ser Gly Thr Gln Gln Ile Arg Glu
1               5                   10
```

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Arg Trp Lys Arg Gly Val
1               5
```

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Leu Asp Trp Met Thr
1               5
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Trp Arg Asp Phe Ser Ala Leu
1               5
```

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Met Thr Pro Gln Thr Val Asn Ala Tyr Tyr
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Abz
<220> FEATURE:
<221> NAME/KEY: MOD_RES
<222> LOCATION: (7)..(7)
<223> OTHER INFORMATION: Tyr(NO2)

<400> SEQUENCE: 46

Xaa Gln Pro Gln Gln Pro Tyr Asp
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Gly His Glu Ile Gly His Gly Phe
1               5

<210> SEQ ID NO 48
<211> LENGTH: 660
<212> TYPE: PRT
<213> ORGANISM: Rothia mucilaginosa

<400> SEQUENCE: 48

Met Thr Thr Asn Ser Gly Ile Thr Lys Glu Trp Val Asp Glu Thr Val
1               5                   10                  15

Lys Pro Gly Asp Asp Phe Phe Arg His Val Asn Gly Lys Trp Leu Ala
                20                  25                  30

Thr His Glu Ile Pro Ala Asp Arg Pro Lys Asp Gly Gly Leu Tyr Thr
            35                  40                  45

Leu Arg Asp Asn Ala Glu Lys His Val Arg Glu Leu Val Lys Ile
        50                  55                  60

Ala Lys Glu Gln Pro Glu Ser Arg Ile Gly Ala Leu Tyr Asn Ser Phe
65                  70                  75                  80

Met Asp Val Glu Lys Ile Glu Ala Asp Gly Leu Glu Pro Leu Leu Lys
                85                  90                  95

Glu Ile Ala Pro Ile Leu Asn Ser Ala Thr Pro Ser His Leu Ala Val
            100                 105                 110

Thr Leu Ala Leu Leu Ser Arg Ala Gly Leu Pro Gln Leu Phe Ala Trp
        115                 120                 125

Tyr Thr Ser Asn Asp Pro Lys Asp Pro Lys Asn Tyr Thr Phe Phe Leu
    130                 135                 140

Tyr Gln Ser Gly Leu Gly Leu Pro Asp Glu Ser Tyr Tyr Arg Glu Glu
145                 150                 155                 160
```

```
Lys His Glu Ala Ala Cys Ala Ala Tyr Val Glu His Ile Ala Arg Met
                165                 170                 175

Phe Glu Leu Thr Gly Leu Ala Glu Gly Phe Gly Leu Thr Pro Glu Gln
            180                 185                 190

Ala Ala Gln Leu Val Phe Thr His Glu Ser Glu Leu Ala Arg Leu His
        195                 200                 205

Trp Asn Val Val Glu Asn Arg Asp Ala Glu Ala Thr Tyr Asn Pro Tyr
    210                 215                 220

Gln Ala Thr Glu Leu Asp Glu Lys Phe Pro Gly Phe Pro Phe Ser Gln
225                 230                 235                 240

Trp Leu Leu Ala Leu Gly Ala Asp Pro Glu Thr Leu Gly Gln Val Ile
                245                 250                 255

Val Ala Gln Pro Ser Phe Phe Glu Gly Ala Ala Lys Leu Phe Thr Ser
            260                 265                 270

Ile Pro Leu Met Ser Trp Lys Leu Trp Ala Val Trp Thr Val Leu Arg
        275                 280                 285

Ser Arg Ala Pro Phe Met Tyr Asp Glu Leu Val Gln Glu Ser Phe Asn
    290                 295                 300

Phe Tyr Gly Lys Thr Leu Ser Gly Thr Gln Gln Ile Arg Glu Arg Trp
305                 310                 315                 320

Lys Arg Gly Val Gly Ala Val Glu Lys Ala Leu Gly Glu Glu Ile Gly
                325                 330                 335

Gln Glu Tyr Val Ala Val His Phe Pro Pro Ser His Lys Glu Lys Met
            340                 345                 350

Leu Val Leu Val Gly Asn Leu Leu Glu Ala Tyr Arg Glu Ser Ile Glu
        355                 360                 365

Ser Leu Asp Trp Met Thr Glu Ala Thr Arg Gln Lys Ala Leu Glu Lys
    370                 375                 380

Leu Ser Lys Phe Val Thr Lys Ile Gly Tyr Pro Asp Lys Trp Arg Asp
385                 390                 395                 400

Phe Ser Ala Leu Glu Leu Ala Pro Gly Asp Leu Phe Glu Asn Leu Arg
                405                 410                 415

Arg Thr Gly Ala Phe Asp Ala Asp Trp Leu Ile Ala Arg Lys Gly Gln
            420                 425                 430

Pro Val Asp Lys Ser Glu Trp Leu Met Thr Pro Gln Thr Val Asn Ala
        435                 440                 445

Tyr Tyr Met Pro Pro Ala Asn Glu Ile Val Phe Pro Ala Ala Ile Leu
    450                 455                 460

Gln Pro Pro Tyr Phe Asn Pro Asp Ala Asp Ala Ala Asn Tyr Gly
465                 470                 475                 480

Asn Ile Gly Met Ile Ile Gly His Glu Ile Gly His Gly Phe Asp Asp
                485                 490                 495

Gln Gly Ser Arg Tyr Asp Gly Asp Gly Lys Leu Glu Ser Trp Trp Thr
            500                 505                 510

Glu Glu Asp Tyr Ala Lys Phe Lys Glu Arg Thr Ser Ala Leu Val Glu
        515                 520                 525

Gln Tyr Asn Ala Tyr Val Pro Val Gly Leu Asp Pro Lys Phe His Val
    530                 535                 540

Asn Gly Glu Leu Thr Leu Gly Glu Asn Ile Gly Asp Leu Ala Gly Met
545                 550                 555                 560

Ser Ile Ala Leu Lys Ala Tyr Cys Leu Ala Leu Lys Lys Gln Gly Ile
                565                 570                 575

Glu Ser Leu Ala Asp Ala Pro Val Ile Asp Gly Met Thr Gly Ile Gln
            580                 585                 590
```

-continued

```
Arg Phe Phe Phe Ser Asn Ala Arg Gly Trp Cys Thr Lys Ser Arg Pro
            595                 600                 605

Gln His Ala Glu Val Met Ile Ser Val Asp Pro His Ser Pro Asp Glu
    610                 615                 620

Phe Arg Val Asn Gly Val Arg Asn Ile Asp Glu Phe Tyr Glu Ala
625                 630                 635                 640

Phe Gly Val Ser Glu Gly Asp Ala Leu Tyr Leu Ala Pro Glu Arg
            645                 650                 655

Met Arg Ile Trp
            660

<210> SEQ ID NO 49
<211> LENGTH: 671
<212> TYPE: PRT
<213> ORGANISM: Xylanimonas cellulosilytica

<400> SEQUENCE: 49

Met Thr Ile Glu Ala Leu Arg Ser Gly Ile Asp Leu Thr Ala Leu Asp
1               5                   10                  15

Pro Ala Thr Arg Pro Gln Asp Asp Leu Tyr Arg His Val Asn Gly Thr
            20                  25                  30

Trp Ile Ala Thr His Glu Ile Pro Ala Asp Arg Ser Met Asp Gly Ala
        35                  40                  45

Phe Met Lys Leu Arg Asp Leu Ser Glu Glu Arg Val Arg Ala Ile Ile
    50                  55                  60

Thr Asp Leu Ala Gly Ser Ser Asp Thr Glu Pro Gly Thr Thr Ala Gly
65                  70                  75                  80

Lys Ile Gly Asp Leu Tyr Ser Ser Phe Met Asp Thr Ala Arg Ile Ala
                85                  90                  95

Ala Leu Gly Ala Thr Pro Leu Ala Ala Asp Leu Ala Leu Ile Ala Gly
            100                 105                 110

Ala Thr Ser Gln Ala Glu Leu Thr Gly Val Leu Gly Ala Leu Gln Arg
        115                 120                 125

Thr Gly Gly Gly Gly Ala Val Gly Phe Tyr Val Asp Asn Asp Ala Ala
    130                 135                 140

Asp Pro Glu Gln Tyr Arg Val Tyr Leu Cys Gln Ser Gly Leu Gly Leu
145                 150                 155                 160

Pro Asp Glu Ala Tyr Tyr Arg Glu Asp Gln Tyr Ala Pro Ile Arg Glu
                165                 170                 175

Lys Tyr Val Pro His Val Ala Arg Met Leu Arg Leu Gly Ala Ala
            180                 185                 190

Glu Leu Leu Gly Val Asp Ala Asp Ala Ala Arg Val Val Ala
        195                 200                 205

Leu Glu Ser Lys Leu Ala Gly His His Trp Asp Val Val Lys Asp Arg
    210                 215                 220

Asp Ala Thr Leu Thr Tyr Asn Pro Thr Thr Ile Ala Glu Leu Ala Val
225                 230                 235                 240

Thr Ala Pro Gly Phe Asp Trp Gln Ala Trp Ala Ile Ala Leu Gly Ala
                245                 250                 255

Pro Thr Gly Ala Leu Asp Ala Leu Val Val Arg Glu Pro Ser Tyr Ala
            260                 265                 270

Glu Gly Leu Ala Ala Leu Trp Gln Ser Glu Pro Leu Glu Asp Trp Gln
        275                 280                 285

Val Trp Ala Ala Tyr Arg Leu Val Thr Ala Arg Ala Pro Tyr Leu Thr
    290                 295                 300
```

```
Asp Glu Ile Val Glu Ala Asn Phe Asp Phe Tyr Gly Arg Thr Leu Ser
305                 310                 315                 320

Gly Ala Gln Glu Val Arg Glu Arg Trp Lys Arg Gly Val Ala Leu Val
            325                 330                 335

Glu Gly Ala Leu Gly Glu Ala Val Gly Glu Gln Tyr Val Ala Arg His
        340                 345                 350

Phe Pro Pro Ala His Lys Ala Arg Met Asp Glu Leu Val Ala Asn Leu
    355                 360                 365

Val Ala Ala Tyr Arg Glu Ser Ile Glu Gly Leu Asp Trp Met Thr Asp
370                 375                 380

Glu Thr Lys Ala Lys Ala Leu Ala Lys Leu Glu Lys Phe Thr Pro Lys
385                 390                 395                 400

Ile Gly Tyr Pro Val Lys Trp Arg Asp Tyr Ser Ala Leu Val Ile Asp
            405                 410                 415

Ala Asp Asp Leu Val Gly Asn Val Arg Arg Ser Asn Ala Phe Asp Leu
        420                 425                 430

Asp His Glu Leu Gly Lys Val Gly Lys Pro Leu Asp Arg Asp Glu Trp
    435                 440                 445

Phe Met Thr Pro Gln Thr Val Asn Ala Tyr Tyr Asn Pro Gly Met Asn
450                 455                 460

Glu Ile Val Phe Pro Ala Ala Ile Leu Gln Pro Pro Phe Phe Asp Pro
465                 470                 475                 480

Glu Ala Asp Asp Ala Val Asn Tyr Gly Gly Ile Gly Gly Val Ile Gly
            485                 490                 495

His Glu Ile Gly His Gly Phe Asp Asp Gln Gly Ser Lys Tyr Asp Gly
        500                 505                 510

Asp Gly Arg Leu Gln Asp Trp Trp Thr Ala Glu Asp Arg Ala Glu Phe
    515                 520                 525

Glu Lys Arg Thr Gly Ala Leu Ile Ala Gln Tyr Asp Ala Phe Val Pro
530                 535                 540

Glu Gln Leu Gly Ala Asp Gly Ala His Val Asn Gly Ser Leu Thr Ile
545                 550                 555                 560

Gly Glu Asn Ile Gly Asp Leu Gly Gly Leu Ser Ile Ala Ile Arg Ala
            565                 570                 575

Tyr Arg Ile Ala Leu Ala Ala Ala Arg Glu Gly Ala Thr Leu Asp Asp
        580                 585                 590

Ala Pro Val Ile Asp Gly Leu Thr Gly Leu Glu Arg Val Phe Leu Gly
    595                 600                 605

Trp Ala Gln Val Trp Gln Ser Lys Gly Arg Asp Glu Glu Val Leu Arg
610                 615                 620

Arg Leu Ala Thr Asp Pro His Ser Pro Asn Glu Phe Arg Cys Asn Gly
625                 630                 635                 640

Ile Val Arg Asn Val Asp Glu Phe His Asp Ala Tyr Gly Val Arg Glu
            645                 650                 655

Gly Asp Ala Leu Trp Leu Ala Pro Glu Asp Arg Val Arg Ile Trp
        660                 665                 670

<210> SEQ ID NO 50
<211> LENGTH: 662
<212> TYPE: PRT
<213> ORGANISM: Cellulomonas flavigena

<400> SEQUENCE: 50

Met Thr Arg Ser Gly Val Pro Leu Asp Asp Leu Asp Pro Ser Val Arg
1               5                   10                  15
```

Pro Gln Asp Asp Leu Asp Leu Phe Val Asn Gly Arg Trp Ala Ala Ser
                20                  25                  30

Tyr Val Ile Pro Pro Asp Arg Ser Met Asp Gly Pro Phe Arg Ala Leu
            35                  40                  45

Tyr Asp Glu Ala Glu Arg Gln Val Leu Asp Ile Ile Thr Asp Ala Ala
    50                  55                  60

Gln Ala Ala Gly Glu Gly Asp Gly Val Glu Ala Lys Ile Gly Ala Leu
65                  70                  75                  80

Tyr Ala Ser Phe Met Asp Thr Asp Ala Val Arg Ala Ala Gly Val Glu
                85                  90                  95

Pro Leu Arg Glu Asp Leu Ala Leu Val Asp Ala Ala Thr Thr Pro Ala
            100                 105                 110

Glu Leu Thr Val Ala Val Gly Arg Leu Gln Arg Thr Gly Ala Leu Ser
        115                 120                 125

Ala Val Asp Leu Tyr Val Asp Asn Asp Ala Lys Asp Pro Asp Ser Tyr
130                 135                 140

Val Val His Leu Val Gln Gly Gly Leu Gly Leu Pro Asp Glu Ala Tyr
145                 150                 155                 160

Tyr Arg Glu Glu Gln His Ala Ala Val Arg Glu Lys Tyr Leu Pro His
                165                 170                 175

Val Ala Arg Met Leu Arg Leu Ala Ala Pro Val Ser Gly Val Val Ala
            180                 185                 190

Ala Gly Asp Ala Asp Asp Leu Ala Ala Arg Val Ala Leu Glu Ser
        195                 200                 205

Arg Ile Ala Ala His His Trp Asp Val Val Lys Asp Arg Asp Ala Glu
            210                 215                 220

Leu Thr Tyr Asn Ala Leu Thr Leu Ala Glu Leu Ala Arg Ala Pro
225                 230                 235                 240

Gly Phe Asp Trp Arg Ala Trp Ala Glu Ala Leu Gly Ala Pro Ala Gly
            245                 250                 255

Ala Leu Asp Arg Leu Val Val Arg Glu Pro Ser Phe Ala Glu Gly Leu
        260                 265                 270

Ala Ala Leu Trp Thr Glu Val Pro Val Ala Asp Trp Gln Ala Trp Ala
        275                 280                 285

Thr Tyr His Val Val Ser Ser Arg Ala Pro Tyr Leu Thr Asp Glu Leu
        290                 295                 300

Val Glu Ala Asn Phe Asp Phe Tyr Gly Arg Thr Leu Ser Gly Ala Pro
305                 310                 315                 320

Glu Leu Arg Asp Arg Trp Lys Arg Gly Val Ser Leu Val Gln Gly Ala
            325                 330                 335

Leu Gly Glu Ala Val Gly Lys Val Tyr Val Glu Arg His Phe Pro Pro
            340                 345                 350

Ser His Lys Glu Arg Met Asp Glu Leu Val Ala Asn Leu Val Glu Ala
        355                 360                 365

Tyr Arg Arg Ser Ile Thr Glu Leu Glu Trp Met Gly Glu Glu Thr Arg
    370                 375                 380

Gln Arg Ala Leu Glu Lys Leu Ala Arg Phe Thr Pro Lys Ile Gly Tyr
385                 390                 395                 400

Pro Ala Arg Trp Arg Asp Tyr Ser Ala Leu Glu Val Arg Ala Asp Asp
                405                 410                 415

Leu Val Gly Asn Val Arg Arg Ser Asn Ala Phe Asp Leu Asp Arg Glu
            420                 425                 430

Leu Gly Lys Ile Gly Arg Pro Ile Asp Arg Asp Glu Trp Phe Met Thr

```
                        435                 440                 445
        Pro Gln Thr Val Asn Ala Tyr Tyr Asn Pro Gly Met Asn Glu Ile Val
        450                 455                 460

Phe Pro Ala Ala Ile Leu Gln Pro Pro Phe Phe Asp Ala Glu Ala Asp
        465                 470                 475                 480

Asp Ala Ala Asn Tyr Gly Ile Gly Ala Val Ile Gly His Glu Ile
                        485                 490                 495

Gly His Gly Phe Asp Asp Gln Gly Ser Lys Tyr Asp Gly Asp Gly Arg
                        500                 505                 510

Leu Val Asp Trp Trp Thr Ala Glu Asp Arg Ala Glu Phe Glu Arg Arg
                        515                 520                 525

Thr Lys Ser Leu Val Asp Gln Tyr Ala Gln Tyr Ser Pro Arg Gln Leu
        530                 535                 540

Gly Gly Ser His Arg Val Asn Gly Glu Leu Thr Ile Gly Glu Asn Ile
        545                 550                 555                 560

Gly Asp Leu Gly Gly Leu Ser Ile Ala Val Arg Ala Tyr Glu Ile Ala
                        565                 570                 575

Leu Gly His Pro Leu Asp Glu Ala Pro Val Leu Asp Gly Tyr Thr Gly
                        580                 585                 590

Leu Gln Arg Leu Phe Met Gly Trp Ala His Ser Trp Arg Thr Lys Gly
                        595                 600                 605

Arg Asp Glu Glu Val Ile Arg Arg Leu Ala Thr Asp Pro His Ser Pro
                        610                 615                 620

Asp Glu Phe Arg Cys Asn Gly Val Val Arg Asn Ile Asp Glu Phe Tyr
        625                 630                 635                 640

Thr Ala Phe Asp Val Gln Pro Asp Asp Ala Leu Trp Leu Asp Pro Glu
                        645                 650                 655

Gln Arg Val Arg Ile Trp
                        660

<210> SEQ ID NO 51
<211> LENGTH: 726
<212> TYPE: PRT
<213> ORGANISM: Actinomyces viscosus

<400> SEQUENCE: 51

Met Thr Asp Ala Cys Ala Thr Ser Pro Thr Pro Thr Gly Pro Ala Ser
        1               5                   10                  15

Asp Ser Pro Ala Gln His Ser Gln Pro Ala Ser Ser Pro Ala Ala
                        20                  25                  30

Asp Ala Ile Leu Ala Gly Val Leu Glu Thr Ala His Thr Asp Thr Ser
                        35                  40                  45

Val Arg Pro Gln Asp Asp Leu Phe Arg Phe Val Asn Gly Gln Trp Leu
        50                  55                  60

Thr Thr Ala Glu Ile Pro Ala Asp Arg Pro Ser Ser Gly Ala Phe Thr
        65                  70                  75                  80

Thr Leu Arg Asp Glu Ser Glu Ala Ala Cys Arg Gln Ile Val Glu Glu
                        85                  90                  95

Leu Ala Glu Gln Phe Ser Ser Val Ala Pro Glu Gly Ala Ala Glu Val
                        100                 105                 110

Leu Ser Thr Asn Arg Gly Arg Val Gly Ala Leu Tyr Gln Ala Phe Met
                        115                 120                 125

Asp Glu Ala His Leu Glu Glu Leu Gly Ala Glu Pro Leu Ala Glu Glu
                        130                 135                 140

Leu Ala Pro Val Leu Gly Ala Ser Ser Lys Glu Glu Leu Ala Arg Ala
```

```
                145                 150                 155                 160
Leu Gly Glu Met Thr Pro Val Gly Phe Met Gly Val Val Gly Ala Asp
                    165                 170                 175

Val Glu Val Asp Ile Asn Asp Pro Glu Arg Tyr Thr Ser Trp Val Gly
                180                 185                 190

Gln Ser Gly Leu Gly Leu Pro Asp Glu Ser Tyr Tyr Arg Glu Glu Ala
            195                 200                 205

Gln Ala Pro Leu Arg Gln Ala Tyr Val Glu His Val Ala Arg Met Met
        210                 215                 220

Ala Leu Ala Gly Leu Thr Asp Ser Phe Gly Ala Ser Gly Glu Asp Leu
225                 230                 235                 240

Ala Glu Arg Val Met Ala Val Glu Thr Ala Leu Ala Lys Gly His Trp
                245                 250                 255

Asp Arg Val Thr Cys Arg Asp Val Glu Lys Met Asn Asn Pro Met Ser
                260                 265                 270

Trp Gln Gln Ile Val Asp Ser Ala Pro Asp Leu Pro Trp Asp Glu Trp
            275                 280                 285

Arg Glu Gly Ile Arg Ala Ala Arg Ser Ala Gly Ile Glu Gln Thr
        290                 295                 300

Ala Phe Leu Glu Glu Ala Ile Val Thr Gln Pro Asp Tyr Leu Pro His
305                 310                 315                 320

Ala Ala Gly Val Trp Gln Glu Thr Asp Leu Asp Leu Lys Val Trp
                325                 330                 335

Val Ala Trp His Val His Gly Arg Ala Ser Leu Leu Ser Gly Ala
                340                 345                 350

Phe Val Glu Glu Ser Phe Asp Phe Tyr Gly Arg Thr Leu Gln Gly Thr
            355                 360                 365

Asp Glu Leu Arg Pro Arg Trp Lys Arg Gly Val Gly Leu Val Glu Ser
        370                 375                 380

Cys Leu Gly Glu Ala Leu Gly Glu Ile Tyr Val Glu Arg His Phe Pro
385                 390                 395                 400

Pro Ser His Lys Ser Ala Met Glu Ala Leu Val Gly Arg Leu Ile Glu
                405                 410                 415

Ala Tyr His Gln Ser Ile Ser Ser Leu Glu Trp Met Ser Pro Ala Thr
                420                 425                 430

Arg Glu Arg Ala Leu Glu Lys Leu Ala Leu Phe Thr Pro Lys Ile Gly
            435                 440                 445

Tyr Pro Val Arg Trp Arg Asp Tyr Ser Ala Val Glu Val Val Pro Gly
        450                 455                 460

Asp Val Leu Ala Ser Val Arg Ser Val Glu Arg Ala Asp Met Ala Tyr
465                 470                 475                 480

Ser Leu Asn Lys Leu Thr Lys Pro Val Asp Arg Asp Glu Trp His Met
                485                 490                 495

Thr Pro Gln Thr Val Asn Ala Tyr Tyr Asn Pro Thr Met Asn Glu Ile
                500                 505                 510

Val Phe Pro Ala Ala Ile Leu Gln Pro Pro Phe Phe Asp Pro Gln Ala
            515                 520                 525

Asp Asp Ala Val Asn Tyr Ala Gly Ile Gly Ala Val Ile Gly His Glu
        530                 535                 540

Ile Gly His Gly Phe Asp Asp Gln Gly Ser Thr Phe Asp Gly Thr Gly
545                 550                 555                 560

Lys Val Ser Asp Trp Trp Thr Gln Glu Asp Arg Glu Ala Phe Thr Glu
                565                 570                 575
```

```
Arg Thr Ser Ala Leu Ile Ser Gln Tyr Asp Ala Tyr Thr Pro Lys Val
            580                 585                 590

Val Val Ala Lys His Arg Glu Ala Gly Thr Ala Gln Glu Glu Ile Pro
        595                 600                 605

His Val Asn Gly Ala Leu Thr Ile Gly Glu Asn Ile Gly Asp Leu Gly
    610                 615                 620

Gly Leu Gly Ile Ala Leu Lys Ala Tyr Ser Leu Ala Leu Ala Asp Ala
625                 630                 635                 640

Gly Ile Pro Ser Val Asp Glu Ala Pro Val Ile Asp Gly Leu Thr Gly
                645                 650                 655

Leu Gln Arg Phe Phe Tyr Ser Trp Ala Arg Ile Trp Arg Ser Lys Ser
                660                 665                 670

Arg Pro Asp Tyr Ala Glu Leu Leu Leu Thr Val Asp Pro His Ser Pro
            675                 680                 685

Ala Glu Phe Arg Cys Asn Gly Ile Val Arg Asn Val Asp Ala Phe Tyr
        690                 695                 700

Lys Ala Phe Ala Val Asp Ser Asp Ala Leu Trp Leu Pro Pro Asn
705                 710                 715                 720

Glu Arg Val Ser Ile Trp
                725

<210> SEQ ID NO 52
<211> LENGTH: 670
<212> TYPE: PRT
<213> ORGANISM: Gordonia bronchialis

<400> SEQUENCE: 52

Met Thr Ala Ser Asp Thr Thr Leu Asn Ser Ser Arg Asn Ser Gly
1               5                   10                  15

Leu Asp Leu Glu Trp Val Asp Ser Val Arg Val Gln Asp Asp Leu
            20                  25                  30

Phe Ala His Val Asn Gly Lys Trp Leu Glu Arg His Val Ile Pro Glu
        35                  40                  45

Asp Arg Ala Ile Asp Gly Ala Phe His Val Leu Arg Asp Arg Ala Glu
50                  55                  60

Glu Asn Val Arg Asp Ile Ile Thr Glu Cys Ala Glu Ser Ser Pro Pro
65                  70                  75                  80

Ser Gly Ser Asp Ala Leu Lys Ile Gly Asp Leu Phe Ala Ser Phe Met
                85                  90                  95

Asp Thr Asp His Ile Asp Ala Leu Gly Ile Gly Pro Ile Arg Gly Glu
            100                 105                 110

Leu Asp Lys Ile Ala Gly Ile Asp Ser Thr Thr Ala Leu Ala Arg Arg
        115                 120                 125

Met Gly Arg Leu Thr Arg His Gly Val Gly Gly Leu Phe Gly Phe Tyr
130                 135                 140

Val Asp Thr Asp Ala Arg Gln Ser Asp Arg Tyr Leu Val His Ile Val
145                 150                 155                 160

Gln Ser Gly Leu Gly Leu Pro Asp Glu Ser Tyr Tyr His Pro Asp Ala
                165                 170                 175

Asp Gly Asn Asp Ile His Ala Glu Thr Arg Ala Ala Tyr Ala Ala His
            180                 185                 190

Val Glu Arg Met Phe Ala Leu Ala Gly Phe Asp Ala Pro Ala Asp Arg
        195                 200                 205

Ala Ala Thr Val Leu Asp Leu Gly Thr Ala Ile Ala Glu His His Trp
    210                 215                 220
```

-continued

```
Asp Val Val Ala Arg Arg Asp Ala Glu Arg Thr Tyr Asn Leu Met Ser
225                 230                 235                 240

Leu Ala Glu Phe Glu Ser Ala Ala Ala Gly Phe Asp Leu Gly Glu Trp
            245                 250                 255

Phe Gly Gly Leu Gly Thr Val Gly Asp Ala Thr Phe Ala Glu Val Val
        260                 265                 270

Val Gly Gln Pro Ser Phe Val Ser Gly Ala Ala Gly Leu Ile Ala Ser
    275                 280                 285

Arg Pro Leu Asp Asp Trp Lys Thr Trp Leu Ala Trp Arg Leu Leu Arg
290                 295                 300

Ser Ala Ala Pro Tyr Leu Ser Ser Glu Phe Val Glu Glu Asn Phe Asp
305                 310                 315                 320

Phe Tyr Gly Arg Thr Leu Ser Gly Ala Gln Thr Asn Arg Asp Arg Trp
                325                 330                 335

Lys Arg Gly Val Ser Phe Val Glu Gly Ala Met Gly Phe Ala Val Gly
            340                 345                 350

Lys Leu Tyr Val Asp Lys His Phe Pro Pro Glu Ala Lys Ala Arg Met
        355                 360                 365

Asp Glu Leu Ile Ala Asn Leu Val Ala Ala Tyr Arg Arg Asn Ile Thr
370                 375                 380

Asp Leu Glu Trp Met Thr Pro Glu Thr Arg Thr Lys Ala Leu Ala Lys
385                 390                 395                 400

Leu Asp Lys Phe Thr Pro Lys Ile Gly Tyr Pro Ala Thr Trp Arg Asp
                405                 410                 415

Tyr Gly Ala Leu Ile Val Asp Arg Gly Asp Leu Ile Gly Asn Val Ala
            420                 425                 430

Arg Ala Ser Ser Phe Glu Gln Glu Arg Glu Phe Ala Lys Ile Gly Ala
        435                 440                 445

Pro Val Asp Arg Asp Glu Trp Phe Met Thr Pro Gln Thr Val Asn Ala
450                 455                 460

Tyr Tyr Asn Pro Gly Met Asn Glu Ile Val Phe Pro Ala Ala Ile Leu
465                 470                 475                 480

Gln Pro Pro Phe Phe Asp Pro Asp Ala Asp Ala Ala Asn Tyr Gly
                485                 490                 495

Gly Ile Gly Ala Val Ile Gly His Glu Ile Gly His Gly Phe Asp Asp
            500                 505                 510

Gln Gly Ala Lys Tyr Asp Gly Asp Gly Asn Leu Val Asn Trp Trp Ser
        515                 520                 525

Asp Ala Asp Arg Glu Glu Phe Ser Ser Arg Thr Ala Lys Leu Ile Glu
530                 535                 540

Gln Tyr Gly Glu Phe Thr Pro Glu Gly Leu Asp Pro Lys Tyr Lys Val
545                 550                 555                 560

Asn Gly Gly Phe Thr Ile Gly Glu Asn Ile Gly Asp Leu Gly Gly Leu
                565                 570                 575

Ser Ile Ala Leu Val Ala Tyr Gln Leu Ala Thr Glu Gly Thr Thr Pro
            580                 585                 590

Pro Val Ile Asp Gly Leu Thr Gly Val Gln Arg Val Phe Tyr Ser Trp
        595                 600                 605

Ala Glu Ile Trp Arg Thr Lys Thr Arg Glu Ala Glu Ala Ile Lys Arg
610                 615                 620

Leu Ser Ile Asp Pro His Ser Pro Pro Glu Phe Arg Cys Asn Gly Val
625                 630                 635                 640

Val Arg Asn Ile Asp Val Phe Tyr Asp Ala Phe Asp Val Lys Pro Gly
                645                 650                 655
```

Asp Thr Leu Tyr Leu Asp Glu Ala Asp Arg Val Arg Ile Trp
        660                 665                 670

<210> SEQ ID NO 53
<211> LENGTH: 666
<212> TYPE: PRT
<213> ORGANISM: Mycobacterium gilvum

<400> SEQUENCE: 53

Met Thr Val Glu Ala Thr Ser Asp Thr Ser Ala Lys Ser Gly Ile Asp
1               5                   10                  15

Leu Arg Tyr Val Asp Ala Asp Ala Arg Pro Gln Asp Asp Leu Phe Gly
            20                  25                  30

His Val Asn Gly Arg Trp Leu Ala Glu Tyr Gln Ile Pro Gly Asp Arg
        35                  40                  45

Ala Thr Asp Gly Ala Phe Arg Thr Leu Tyr Arg Ala Glu Glu Gln
    50                  55                  60

Ile Arg Asp Leu Ile Thr Glu Ala Ala Ser Ala His Ala Ala Glu Gly
65                  70                  75                  80

Thr Asp Gln Gln Arg Ile Gly Asp Leu Tyr Ala Ser Phe Met Asp Glu
                85                  90                  95

Gln Thr Val Arg Asp Arg Gly Leu Ala Pro Leu Leu Asp Glu Leu Gly
            100                 105                 110

Ala Ile Asp Ala Ala Gly Ser Pro Asp Ala Leu Ala Glu Val Leu Gly
        115                 120                 125

Ser Leu Gln Arg Thr Gly Ile Gly Gly Ala Thr Gly Leu Tyr Val Asp
    130                 135                 140

Thr Asp Ser Lys Asn Ser Thr Arg Tyr Leu Leu His Leu Thr Gln Ser
145                 150                 155                 160

Gly Ile Gly Leu Pro Asp Glu Ser Tyr Phe Arg Glu Glu Gln His Ala
                165                 170                 175

Glu Ile Leu Ala Ala Tyr Pro Gly His Ile Ala Ala Met Phe Gly Leu
            180                 185                 190

Val Leu Gly Gly Asp Pro Gly Glu His Ala Ala Thr Ala Gln Arg Ile
        195                 200                 205

Val Ala Leu Glu Thr Lys Leu Ala Ala Ala His Trp Asp Val Val Lys
    210                 215                 220

Arg Arg Asp Ala Asp Leu Thr Tyr Asn Leu Arg Thr Phe Ala Glu Leu
225                 230                 235                 240

Thr Asp Glu Ser Pro Gly Phe Asp Trp Thr Arg Trp Leu Gly Gly Leu
                245                 250                 255

Gly Ala Asp Arg Asp Lys Ala Ala Asp Val Val Arg Gln Pro Asp
            260                 265                 270

Tyr Leu Thr Ala Phe Ala Ser Leu Trp Ser Gly Ser Ser Leu Glu Asp
    275                 280                 285

Trp Lys Asp Trp Leu Arg Trp Arg Val Ile His Gly Arg Ala Phe Leu
290                 295                 300

Leu Thr Asp Glu Leu Ile Ala Glu Asp Phe Ser Phe Tyr Gly Lys Arg
305                 310                 315                 320

Leu Ser Gly Thr Glu Glu Ile Arg Asp Arg Trp Lys Arg Gly Val Ser
                325                 330                 335

Val Val Glu Ala Leu Met Gly Glu Ala Leu Gly Lys Leu Tyr Val Glu
            340                 345                 350

Arg His Phe Pro Pro Gln Ala Lys Ala Arg Met Asp Glu Leu Val Ala
        355                 360                 365

```
Asn Leu Arg Glu Ala Tyr Arg Val Ser Ile Asn Thr Leu Asp Trp Met
    370                 375                 380

Thr Pro Gln Thr Arg Glu Lys Ala Leu Val Lys Leu Asp Lys Phe Thr
385                 390                 395                 400

Pro Lys Ile Gly Tyr Pro Asn Thr Trp Arg Asp Tyr Ser Ala Leu Val
            405                 410                 415

Ile Glu Arg Asp Asp Leu Tyr Gly Asn Tyr Arg Arg Gly Tyr Ala Leu
        420                 425                 430

Glu Tyr Asp Arg Asp Leu Ala Lys Leu Gly Gly Pro Val Asp Arg Asp
    435                 440                 445

Glu Trp Phe Met Thr Pro Gln Thr Val Asn Ala Tyr Tyr Asn Pro Gly
450                 455                 460

Met Asn Glu Ile Val Phe Pro Ala Ala Ile Leu Gln Pro Pro Phe Phe
465                 470                 475                 480

Asp Ala Asp Ala Asp Ala Ala Asn Tyr Gly Gly Ile Gly Ala Val
            485                 490                 495

Ile Gly His Glu Ile Gly His Gly Phe Asp Asp Gln Gly Ala Lys Tyr
        500                 505                 510

Asp Gly Asp Gly Asn Leu Val Asp Trp Trp Thr Asp Glu Asp Arg Ala
    515                 520                 525

Glu Phe Gly Lys Arg Thr Thr Ala Leu Ile Glu Gln Tyr Glu Gln Phe
530                 535                 540

Thr Pro Arg Gly Leu Glu Pro Ser His His Val Asn Gly Ala Phe Thr
545                 550                 555                 560

Val Gly Glu Asn Ile Gly Asp Leu Gly Leu Ser Ile Ala Leu Leu
            565                 570                 575

Ala Tyr Arg Leu Ser Leu Lys Gly Glu Pro Ala Pro Val Ile Asp Gly
        580                 585                 590

Leu Thr Gly Val Gln Arg Val Phe Tyr Gly Trp Ala Gln Val Trp Arg
    595                 600                 605

Thr Lys Ser Arg Glu Ala Glu Ala Ile Arg Arg Leu Ala Val Asp Pro
610                 615                 620

His Ser Pro Pro Glu Phe Arg Cys Asn Gly Val Ile Arg Asn Met Asp
625                 630                 635                 640

Ala Phe Tyr Asp Ala Phe Asp Val Asp Pro Glu Asp Ala Leu Tyr Leu
            645                 650                 655

Glu Pro Gln Arg Arg Val His Ile Trp Asn
        660                 665

<210> SEQ ID NO 54
<211> LENGTH: 651
<212> TYPE: PRT
<213> ORGANISM: Kribbella flavida

<400> SEQUENCE: 54

Met Thr Ala Gly Ile Asp Ile Thr Gly Leu Ser Thr Thr Val Arg Pro
1               5                   10                  15

Gln Asp Asp Leu Tyr Arg His Ala Asn Gly Arg Trp Leu Asp Glu His
            20                  25                  30

Glu Ile Pro Ala Asp Lys Ala Ile Tyr Gly Ala Phe His Ala Leu Gly
        35                  40                  45

Asp Thr Ala Glu Leu Asn Val Arg Ser Ile Val Glu Arg Thr Leu Asp
    50                  55                  60

Ala Gly His Pro Glu Gly Ser Glu Ala Arg Lys Ile Ala Asp Leu Tyr
65                  70                  75                  80
```

```
Arg Ser Phe Leu Asp Glu Asp Thr Val Glu Arg Leu Gly Ala Asp Pro
            85                  90                  95

Ile Ala Asp Gln Leu Ala Leu Ala Gly Ser Ile Glu Asp Arg Asp Ala
        100                 105                 110

Leu Val Ala Ala Leu Gly Thr Leu Glu Leu Gln Gly Val Gly Gly Ile
        115                 120                 125

Phe His Tyr Trp Val Asp Val Asp Glu Lys Lys Ser Asp Gln Tyr Val
    130                 135                 140

Val Tyr Leu Thr Gln Gly Gly Leu Ser Leu Pro Asp Glu Ser Tyr Tyr
145                 150                 155                 160

Arg Asp Asp Ala Phe Gln Glu Gln Arg Thr Ala Tyr Val Ala His Val
                165                 170                 175

Ala Arg Met Leu Gly Leu Ala Gly Leu Ala Asp Ala Glu Gly Ala Ala
            180                 185                 190

Glu Arg Ile Leu Ala Leu Glu Thr Arg Leu Ala Ala Gly His Trp Asp
        195                 200                 205

Val Val Lys Asn Arg Asp Val Thr Ala Thr Tyr Asn Lys Phe Asp Arg
210                 215                 220

Ala Arg Leu Asp Ala Leu Met Pro Gly Phe Asp Trp Ser Arg Trp Leu
225                 230                 235                 240

Pro Asn Ala Gly Val Pro Glu Ser Ala Phe Glu Gln Val Val Arg
                245                 250                 255

Gln Pro Asp Tyr Phe Thr Ser Ala Ala Glu Ala Leu Gln Glu Leu Glu
                260                 265                 270

Leu Asp His Trp Lys Glu Trp Leu Ser Trp Arg Ile Val His Ser Ala
            275                 280                 285

Ala Pro Leu Leu Ser Ser Ala Phe Val Ala Glu Asn Phe Glu Phe Tyr
        290                 295                 300

Gly Arg Thr Leu Thr Gly Ala Pro Glu Leu Arg Glu Arg Trp Lys Arg
305                 310                 315                 320

Gly Leu Gly Val Val Gly Ser Ala Leu Gly Glu Ala Val Gly Gln Leu
                325                 330                 335

Tyr Val Ala Glu Phe Phe Pro Pro Val Ala Lys Ala Arg Met Val Glu
            340                 345                 350

Leu Val Gly Asn Leu Val Glu Ala Tyr Arg Gln Arg Ile Glu Ala Leu
        355                 360                 365

Asp Trp Met Ser Pro Glu Thr Arg Gln Arg Ala Leu Asp Lys Leu Gly
    370                 375                 380

Arg Phe Thr Pro Lys Ile Gly Tyr Pro Asp Lys Trp Arg Asp Tyr Ser
385                 390                 395                 400

Ala Leu Glu Val Ala Pro Asp Asp Leu Val Gly Asn Val Arg Arg Ser
                405                 410                 415

Val Ala Val Glu Thr Ala Arg Glu Leu Ala Lys Leu Gly Gly Pro Val
            420                 425                 430

Asp Arg Thr Glu Trp Gln Met Thr Pro Gln Thr Val Asn Ala Tyr Tyr
        435                 440                 445

Asn Pro Ala Met Asn Glu Ile Val Phe Pro Ala Ala Ile Leu Gln Pro
    450                 455                 460

Pro Phe Phe Ala Leu Asp Ala Asp Ala Leu Asn Tyr Gly Ala Ile
465                 470                 475                 480

Gly Ala Val Ile Gly His Glu Ile Gly His Gly Phe Asp Asp Gln Gly
                485                 490                 495

Ser Arg Tyr Asp Gly Asp Gly Asn Ile Ser Asp Trp Trp Thr Asp Glu
```

```
                    500                 505                 510
Asp Arg Ala Ala Phe Glu Val Arg Ala Asn Arg Leu Val Glu Gln Tyr
                515                 520                 525

Asp Ala Leu Glu Pro Ala Glu Ala Pro Gly Gln His Val Asn Gly Ala
                530                 535                 540

Leu Thr Leu Gly Glu Asn Ile Gly Asp Leu Gly Gly Leu Ser Ile Ala
545                 550                 555                 560

Tyr Thr Ala Tyr Glu Ile Ser Leu Ala Gly Ala Glu Ala Pro Val Ile
                565                 570                 575

Asp Gly Leu Thr Gly Ala Glu Arg Phe Phe Leu Ala Trp Ala Asn Ala
                580                 585                 590

Trp Ser Thr Lys Thr Arg Pro Ala Glu Val Val Arg Arg Leu Ala Ile
                595                 600                 605

Asp Pro His Ser Pro Glu Phe Arg Cys Asn Ala Val Val Arg Asn
                610                 615                 620

Ile Asp Ala Phe His Glu Ala Phe Gly Val Gly Pro Asp Asp Ala Met
625                 630                 635                 640

Trp Leu Ala Pro Glu Gln Arg Val Arg Ile Trp
                645                 650

<210> SEQ ID NO 55
<211> LENGTH: 673
<212> TYPE: PRT
<213> ORGANISM: Mycobacterium vanbaalenii

<400> SEQUENCE: 55

Met Thr Val Glu Ala Thr Arg Asn Leu Lys Ser Gly Ile Asp Leu Arg
1               5                   10                  15

Tyr Val Asp Thr Asp Ala Arg Pro Gln Asp Asp Leu Phe Gly His Val
                20                  25                  30

Asn Gly Arg Trp Leu Ala Glu Tyr Gln Ile Pro Ala Asp Arg Ala Thr
            35                  40                  45

Asp Gly Ala Phe Arg Thr Leu His Asp Arg Ala Glu Glu Gln Ile Arg
        50                  55                  60

Asp Leu Ile Thr Glu Val Ala Gly Ser Gly Ala Ala Arg Gly Thr Asp
65                  70                  75                  80

Glu Gln Arg Ser Ser Gly Ser Ile Asp Ala Ser Arg Ile Gly Asp Leu
                85                  90                  95

Tyr Ala Ser Phe Met Asp Glu Asp Thr Val Arg Ala Arg Gly Leu Thr
                100                 105                 110

Pro Leu Arg Asp Glu Leu Ala Ala Val Asp Ala Ala Asp Thr Pro Glu
            115                 120                 125

Ala Leu Ala Arg Val Leu Gly Ala Leu Gln Arg Val Gly Val Gly Gly
        130                 135                 140

Gly Thr Gly Leu Tyr Val Asp Thr Asp Ser Lys Asn Ser Ser Arg Tyr
145                 150                 155                 160

Leu Leu His Leu Ser Gln Ser Gly Ile Gly Leu Pro Asp Glu Ser Tyr
                165                 170                 175

Phe Arg Glu Glu Arg His Ala Glu Ile Leu Ala Ala Tyr Pro Gly His
                180                 185                 190

Ile Ala Ala Met Phe Gly Leu Val Tyr Gly Gly Asp Pro Asp His
            195                 200                 205

Ala Ala Thr Ala Asp Arg Ile Val Ala Leu Glu Thr Lys Ile Ala Ala
        210                 215                 220

Ala His Trp Asp Val Val Lys Arg Arg Asp Ala Asp Leu Thr Tyr Asn
```

```
                 225                 230                 235                 240
Leu Arg Thr Phe Ala Glu Val Thr Asp Gln Ala Pro Gly Phe Asp Trp
                245                 250                 255

Pro Gly Trp Leu Ala Gly Leu Gly Thr Ala Glu Gln Ala Ala Glu
            260                 265                 270

Val Val Val Arg Gln Pro Asp Tyr Leu Thr Phe Ala Gly Leu Trp
            275                 280                 285

Ala Asp Glu Ser Leu Glu Asp Trp Lys Asn Trp Leu Arg Trp Arg Val
    290                 295                 300

Ile His Ala Arg Ala Phe Leu Leu Thr Asp Glu Leu Ile Ala Glu Asp
305                 310                 315                 320

Phe Ser Phe Tyr Gly Arg Arg Leu Ser Gly Thr Glu Ile Arg Glu
                325                 330                 335

Arg Trp Lys Arg Gly Val Ser Val Val Glu Ser Leu Met Gly Glu Ala
                340                 345                 350

Leu Gly Arg Leu Tyr Val Glu Arg His Phe Pro Pro His Ala Lys Ala
            355                 360                 365

Arg Met Asp Glu Leu Val Asp Asn Leu Arg Glu Ala Tyr Arg Val Ser
    370                 375                 380

Ile Asn Ser Leu Asp Trp Met Thr Pro Gln Thr Arg Glu Lys Ala Leu
385                 390                 395                 400

Val Lys Leu Asp Lys Phe Thr Pro Lys Ile Gly Tyr Pro Asn Lys Trp
                405                 410                 415

Arg Asp Tyr Ser Ala Leu Val Ile Ala Arg Asp Asp Leu Tyr Gly Asn
            420                 425                 430

Tyr Gln Arg Gly Tyr Ala Leu Glu Tyr Asp Arg Asp Leu Ala Lys Leu
            435                 440                 445

Gly Gly Pro Val Asp Arg Asp Glu Trp Phe Met Thr Pro Gln Thr Val
            450                 455                 460

Asn Ala Tyr Tyr Asn Pro Gly Met Asn Glu Ile Val Phe Pro Ala Ala
465                 470                 475                 480

Ile Leu Gln Pro Pro Phe Phe Asp Ala Asp Ala Asp Ala Ala Asn
                485                 490                 495

Tyr Gly Gly Ile Gly Ala Val Ile Gly His Glu Ile Gly His Gly Phe
            500                 505                 510

Asp Asp Gln Gly Ala Lys Tyr Asp Gly Asp Gly Asn Leu Val Asn Trp
    515                 520                 525

Trp Thr Asp Gln Asp Arg Asp Glu Phe Gly Leu Arg Thr Lys Ala Leu
    530                 535                 540

Ile Glu Gln Tyr Glu Glu Leu Val Pro Arg Gly Leu Glu Pro Ser His
545                 550                 555                 560

His Val Asn Gly Ala Phe Thr Val Gly Glu Asn Ile Gly Asp Leu Gly
            565                 570                 575

Gly Leu Ser Ile Ala Leu Leu Ala Tyr Arg Leu Ser Leu Lys Gly Glu
            580                 585                 590

Pro Ala Pro Val Ile Asp Gly Leu Thr Gly Glu Gln Arg Val Phe Phe
            595                 600                 605

Gly Trp Ala Gln Val Trp Arg Thr Lys Ser Arg Glu Ala Glu Ala Ile
            610                 615                 620

Arg Arg Leu Ala Val Asp Pro His Ser Pro Pro Glu Phe Arg Cys Asn
625                 630                 635                 640

Ala Val Val Arg Asn Met Asp Ala Phe Tyr Asp Ala Phe Glu Val Asp
                645                 650                 655
```

```
Glu Asp Asp Glu Leu Tyr Leu Glu Pro Gln Arg Arg Val His Ile Trp
                660                 665                 670
Asn

<210> SEQ ID NO 56
<211> LENGTH: 661
<212> TYPE: PRT
<213> ORGANISM: Beutenbergia cavernae

<400> SEQUENCE: 56

Met Thr Thr Thr Glu Ala Ala Pro Ser Pro Ala Ala Asp Asp Pro Thr
1               5                   10                  15

Ala Ala Ala Asp Pro Ala Val Arg Pro Gln Asp Asp Leu Tyr Arg His
            20                  25                  30

Val Asn Gly Thr Trp Leu Arg Thr His Glu Ile Pro Ala Asp Arg Ala
        35                  40                  45

Arg Asp Gly Val Val Phe Asp Leu Arg Asp Gln Ala Glu Leu Asp Val
50                  55                  60

Arg Ala Ile Val Glu Glu Ser Gly Ala Gly Thr Leu Asp Ala Pro Asp
65                  70                  75                  80

Ala Asp Glu Ala Arg Lys Ile Ala Ala Leu Tyr Arg Ser Phe Met Asp
                85                  90                  95

Thr Glu Ala Ile Glu Ala Gly Val Ala Pro Leu Ala Pro Asp Leu
            100                 105                 110

Ala Leu Ile Glu Asn Ala Thr Asp Arg Ser Ala Leu Ala Arg Ala Met
        115                 120                 125

Gly Thr Leu Gln Arg Thr Gly Val Gly Gly Ala Leu Gly Met Trp Val
130                 135                 140

Asp Thr Asp Ala Asp Pro Thr Ala Tyr Arg Ala Tyr Leu Tyr Gln
145                 150                 155                 160

Ser Gly Leu Gly Leu Pro Asp Glu Ser Tyr Tyr Arg Ser Glu Gln
                165                 170                 175

Ala Thr Thr Arg Glu Ala Tyr Val Ala His Val Ala Arg Met Leu Arg
            180                 185                 190

Leu Ala Gly Val Ala Ala Asp Ala Glu Asp Ala Val Ala Gly Arg
        195                 200                 205

Ile Met Asp Leu Glu Thr Arg Leu Ala Ala His Trp Asp Arg Val
210                 215                 220

Arg Asp Arg Asp Ala Val Ala Thr His Asn Pro Thr Ala Trp Ala Glu
225                 230                 235                 240

Leu Ala Asp Val Ala Arg Gly Phe Asp Ala Asp Ala Trp Ala Glu Gly
                245                 250                 255

Leu Arg Val Pro Ala Asp Ala Phe Asp Val Val Leu Arg Glu Pro
            260                 265                 270

Ser Phe Phe Ala Ala Leu Gly Glu Ala Trp Thr Asp Val Pro Leu Glu
        275                 280                 285

Gln Trp Arg Glu Trp Leu Thr Trp Arg Val Val Arg Ser Arg Ala Pro
290                 295                 300

Tyr Leu Thr Asp Glu Ile Val Thr Ala Asn Phe Asp Phe Tyr Gly Arg
305                 310                 315                 320

Thr Leu Thr Gly Ala Gln Glu Leu Arg Glu Arg Trp Lys Arg Gly Val
                325                 330                 335

Ala Leu Val Glu Gly Ala Leu Gly Glu Ala Val Gly Arg Ile Tyr Val
            340                 345                 350

Gln Arg His Phe Pro Pro Thr His Lys Ala Arg Met Asp Thr Leu Val
```

```
                355                 360                 365
Ala Asn Leu Val Glu Ala Tyr Arg Arg Ser Ile Thr Ser Leu Asp Trp
370                 375                 380

Met Gly Pro Asp Thr Arg Glu Arg Ala Leu Ala Lys Leu Ala Ala Phe
385                 390                 395                 400

Thr Pro Lys Ile Gly Tyr Pro Val Arg Trp Arg Asp Tyr Ser Ser Leu
                405                 410                 415

Glu Leu Val Pro Gly Asp Val Val Ala Asn Val Arg Ala Ala Ser Thr
            420                 425                 430

Tyr Glu Leu Asp Arg Asp Leu Ala Lys Ile Gly Arg Pro Val Asp Arg
        435                 440                 445

Asp Glu Trp Phe Met Pro Pro Gln Thr Val Asn Ala Tyr Tyr Asn Pro
    450                 455                 460

Gly Met Asn Glu Val Val Phe Pro Ala Ala Ile Leu Gln Pro Pro Phe
465                 470                 475                 480

Phe Asp Pro Asp Ala Ala Asp Ala Ala Asn Tyr Gly Ser Ile Gly Ala
                485                 490                 495

Val Ile Gly His Glu Ile Gly His Gly Phe Asp Asp Gln Gly Ser Arg
            500                 505                 510

Tyr Asp Gly Asp Gly Arg Leu Ala Asp Trp Trp Thr Pro Glu Asp Arg
        515                 520                 525

Ala Glu Phe Glu Thr Arg Thr Ala Ala Leu Val Ala Gln Tyr Asp Ala
    530                 535                 540

Phe Ser Pro Ala Gln Leu Asp Gly Ser Arg His Val Ser Gly Gly Leu
545                 550                 555                 560

Thr Val Gly Glu Asn Ile Gly Asp Leu Gly Gly Leu Ala Ile Ala Val
                565                 570                 575

Asp Ala Tyr Glu Ile Ala Leu Gly Arg Arg Pro Asp Arg Ala Glu Leu
            580                 585                 590

Arg Glu Leu Phe Ala Ser Trp Ala Val Ser Trp Arg Glu Lys Gly His
        595                 600                 605

Asp Ala Glu Val Ile Arg Leu Leu Thr Ile Asp Pro His Ser Pro Pro
    610                 615                 620

Glu Phe Arg Cys Asn Gly Val Val Ala Asn Leu Asp Ala Phe Ala Glu
625                 630                 635                 640

Ala Phe Asp Val Gln Pro Gly Asp Gly Leu Trp Ile Asp Pro Gln Asp
                645                 650                 655

Arg Val Arg Ile Trp
            660

<210> SEQ ID NO 57
<211> LENGTH: 652
<212> TYPE: PRT
<213> ORGANISM: Rhodococcus erythropolis

<400> SEQUENCE: 57

Met Thr Thr Ala His Arg Ser Gly Ile Asp Leu Thr His Leu Asp Gly
1               5                   10                  15

Asp Thr Arg Ala Gln Asp Asp Leu Phe Val His Val Asn Gly Lys Trp
            20                  25                  30

Leu Ala Glu Tyr Glu Ile Pro Ala Asp Arg Ala Val Asp Gly Ala Phe
        35                  40                  45

Arg Thr Leu Tyr Asp Lys Ala Glu Glu Asp Val Gln Thr Ile Ile Thr
    50                  55                  60

Glu Ala Ala Glu Ser Asn Ser Ala Ala Gly Thr Asp Ala Gln Arg Ile
```

-continued

```
             65                  70                  75                  80
Gly Asp Leu Tyr Ser Ser Phe Met Asp Ala Asp Ala Val Glu Ala Ala
                         85                  90                  95

Gly Leu Gly Pro Ile Asp Asp Glu Leu Asp Ala Val Ala Asp Ala Pro
                100                 105                 110

Asp Arg Ser Ser Leu Ala Thr Val Ile Gly Arg His Gln Arg Val Gly
                115                 120                 125

Val Gly Gly Ala Ile Ser His Tyr Val Asp Thr Asp Ala Lys Asn Ser
            130                 135                 140

Glu Arg Tyr Leu Ile His Phe Ser Gln Ser Gly Ile Ser Leu Pro Asp
145                 150                 155                 160

Glu Ser Tyr Tyr Arg Glu Asp Asn Tyr Ala Glu Ile Arg Glu Lys Tyr
                165                 170                 175

Val Ala His Ile Asp Lys Met Phe Thr Leu Ala Gly Val Gly Tyr Asp
                180                 185                 190

Ala Gln Arg Val Phe Glu Leu Glu Lys Lys Ile Ala Ala Gly His Trp
                195                 200                 205

Asp Val Val Lys Arg Arg Asp Ala Asp Leu Ser Tyr Asn Leu Val Gly
            210                 215                 220

Phe Glu Glu Leu Thr Glu Gln Asn Pro Gly Leu Asp Trp Ala Ala Trp
225                 230                 235                 240

Leu Ser Gly Leu Gly Ala Asp Ser Glu Lys Phe Ala Glu Ile Val Val
                245                 250                 255

Arg Gln Pro Asp Phe Leu Arg Thr Phe Thr Ala Leu Trp Ala Ser Glu
                260                 265                 270

Ser Leu Asp Asp Trp Lys Ala Trp Ala Ala Trp Lys Val Leu His Ala
            275                 280                 285

Arg Ser Pro Tyr Leu His Ser Ala Leu Val Asp Glu Thr Phe Ala Phe
            290                 295                 300

Tyr Gly Thr Thr Leu Ser Gly Thr Glu Glu Asn Arg Glu Arg Trp Lys
305                 310                 315                 320

Arg Gly Val Ser Leu Val Gln Asp Leu Leu Gly Glu Ala Val Gly Lys
                325                 330                 335

Leu Tyr Val Asp Arg His Phe Pro Ala Glu Ala Lys Thr Arg Met Leu
                340                 345                 350

Glu Leu Val Ala Asn Leu Gln Glu Ala Tyr Arg Arg Asn Ile Ser Asp
            355                 360                 365

Leu Glu Trp Met Ser Pro Gln Thr Arg Glu Ala Ala Leu Ala Lys Leu
370                 375                 380

Glu Lys Phe Thr Pro Lys Ile Gly Tyr Pro Asp Lys Trp Arg Asp Tyr
385                 390                 395                 400

Ala Gly Leu Glu Ile Ser Ala Thr Asp Leu Val Gly Asn Tyr Arg Arg
                405                 410                 415

Gly Tyr Ala Ala Glu Tyr Asp Arg Asp Leu Ala Lys Leu Gly Gly Pro
                420                 425                 430

Val Asp Arg Asp Glu Trp Phe Met Thr Pro Gln Thr Val Asn Ala Tyr
                435                 440                 445

Tyr Asn Pro Gly Met Asn Glu Ile Val Phe Pro Ala Ala Ile Leu Gln
            450                 455                 460

Pro Pro Phe Phe Asp Ala Ala Asp Ala Ala Asn Tyr Gly Gly
465                 470                 475                 480

Ile Gly Ala Val Ile Gly His Gly Ile Gly His Gly Phe Asp Asp Gln
                485                 490                 495
```

```
Gly Ala Lys Tyr Asp Gly Asp Gly Asn Met Val Asp Trp Trp Thr Asp
                500                 505                 510
Glu Asp Arg Ser Glu Phe Gly Lys Arg Thr Lys Ala Leu Ile Glu Gln
            515                 520                 525
Tyr Asn Glu Phe Glu Pro Lys Glu Leu Pro Gly His His Val Asn Gly
        530                 535                 540
Glu Phe Thr Ile Gly Glu Asn Ile Gly Asp Leu Gly Gly Leu Ser Ile
545                 550                 555                 560
Ala Ile Ala Ala Tyr Lys Ile Ala Thr Glu Gly Thr Glu Pro Pro Val
                565                 570                 575
Ile Asp Gly Leu Thr Gly Leu Gln Arg Val Phe Phe Gly Trp Ala Gln
            580                 585                 590
Val Trp Arg Thr Lys Ala Arg Glu Ala Glu Ala Leu Arg Arg Leu Ala
        595                 600                 605
Val Asp Pro His Ser Pro Glu Phe Arg Cys Asn Gly Val Val Arg
610                 615                 620
Asn Leu Asp Thr Phe His Glu Glu Phe Asp Val Lys Pro Gly Asp Ala
625                 630                 635                 640
Leu Tyr Leu Glu Pro Glu Lys Arg Val Lys Ile Trp
                645                 650

<210> SEQ ID NO 58
<211> LENGTH: 652
<212> TYPE: PRT
<213> ORGANISM: Rhodococcus jostii

<400> SEQUENCE: 58

Met Glu Arg Met Thr Thr Ala Gln Arg Ser Gly Ile Asp Leu Thr His
1                5                  10                  15
Leu Asp Asn Asp Thr Arg Ala Gln Asp Asp Leu Phe Val His Val Asn
                20                  25                  30
Gly Lys Trp Ile Asp Asp Tyr Glu Ile Pro Ala Asp Arg Ala Ile Asp
            35                  40                  45
Gly Ala Phe Arg Thr Leu Tyr Asp Lys Ala Glu Val Asp Val Gln Thr
        50                  55                  60
Ile Ile Glu Glu Ala Ala Asp Ser Gly Ala Ala Pro Gly Thr Asp Ala
65                  70                  75                  80
Gln Arg Ile Gly Asp Leu Tyr Gly Ser Phe Met Asp Ala Asp Val Val
                85                  90                  95
Glu Ala Ala Gly Leu Ala Pro Ile Ala Gly Glu Leu Ala Asp Val Ala
            100                 105                 110
Ser Ala Ala Asp Leu Ser Ala Leu Ala Ala Val Ile Gly Arg Gln Gln
        115                 120                 125
Arg Thr Gly Val Gly Gly Ala Val Gly His Tyr Val Asp Thr Asp Ala
130                 135                 140
Lys Asn Ser Glu Arg Tyr Leu Val His Phe Ser Gln Ser Gly Ile Gly
145                 150                 155                 160
Leu Pro Asp Glu Ser Tyr Tyr Arg Gln Asp Asp His Ala Glu Ile Arg
                165                 170                 175
Ala Ala Tyr Val Lys His Ile Ala Lys Met Phe Ala Leu Ala Gly Val
            180                 185                 190
Asp Tyr Asp Ala Gln Arg Val Phe Asp Leu Glu Thr Lys Ile Ala Ala
        195                 200                 205
Gly His Trp Asp Val Val Lys Arg Arg Asp Ala Glu Leu Ser Tyr Asn
210                 215                 220
```

-continued

```
Leu Leu Thr Leu Asp Gln Leu Pro Ala Gly Leu Asp Trp Ser Ser Trp
225                 230                 235                 240

Ile Gly Ala Leu Gly Gly Thr Ser Glu Gln Phe Ala Glu Ile Val Val
            245                 250                 255

Arg Gln Pro Asp Phe Leu Thr Thr Leu Thr Glu Leu Trp Thr Ser Glu
        260                 265                 270

Asp Ile Asp Asp Trp Lys Ala Trp Ala Thr Trp Asn Val Ile Arg Ser
    275                 280                 285

Arg Ala Pro Tyr Leu Thr Gln Ala Leu Val Asp Glu Asn Phe Ala Phe
290                 295                 300

Tyr Gly Lys Thr Leu Thr Gly Ala Glu Glu Ile Arg Glu Arg Trp Lys
305                 310                 315                 320

Arg Gly Val Ser Leu Val Gln Asp Leu Leu Gly Glu Ala Val Gly Lys
                325                 330                 335

Leu Tyr Val Glu Arg His Phe Pro Ala Asp Ala Lys Ala Arg Met Gln
            340                 345                 350

Glu Leu Val Ala Asn Leu Gln Glu Ala Tyr Arg Arg Asn Ile Ser Asp
        355                 360                 365

Leu Asp Trp Met Ser Pro Glu Thr Arg Gln Ala Ala Leu Arg Lys Leu
    370                 375                 380

Glu Lys Phe Thr Pro Lys Ile Gly Tyr Pro Asp Lys Trp Arg Asp Tyr
385                 390                 395                 400

Ser Ala Val Thr Ile Ser Arg Asp Asp Leu Val Gly Asn Tyr Arg Ser
                405                 410                 415

Gly Tyr Ala Ala Glu Tyr Asp Arg Asp Leu Ala Lys Leu Gly Gly Pro
            420                 425                 430

Val Asp Arg Asp Glu Trp Phe Met Thr Pro Gln Thr Val Asn Ala Tyr
        435                 440                 445

Tyr Asn Pro Gly Met Asn Glu Ile Val Phe Pro Ala Ala Ile Leu Gln
    450                 455                 460

Pro Pro Phe Phe Asp Ala Ala Asp Ala Ala Asn Tyr Gly Gly
465                 470                 475                 480

Ile Gly Ala Val Ile Gly His Glu Ile Gly His Gly Phe Asp Asp Gln
                485                 490                 495

Gly Ala Lys Tyr Asp Gly Asp Gly Asn Met Val Asp Trp Trp Thr Asp
            500                 505                 510

Asp Asp Arg Thr Glu Phe Gly Lys Arg Thr Lys Ala Leu Ile Glu Gln
        515                 520                 525

Tyr Asn Glu Phe Glu Pro Lys Ala Leu Pro Gly His Asn Val Asn Gly
    530                 535                 540

Glu Phe Thr Ile Gly Glu Asn Ile Gly Asp Leu Gly Gly Leu Ser Ile
545                 550                 555                 560

Ala Ile Ala Ala Tyr Arg Ile Ala Thr Glu Gly Ser Glu Pro Glu Val
                565                 570                 575

Leu Asp Gly Leu Thr Gly Ile Gln Arg Val Phe Phe Gly Trp Ala Gln
            580                 585                 590

Val Trp Arg Thr Lys Ala Arg Asp Ala Glu Ala Leu Arg Arg Leu Ala
        595                 600                 605

Val Asp Pro His Ser Pro Pro Glu Phe Arg Cys Asn Gly Val Val Arg
    610                 615                 620

Asn Leu Asp Thr Phe His Asp Ala Phe Asp Val Lys Pro Gly Asp Ala
625                 630                 635                 640

Leu Tyr Leu Asp Gln Glu Glu Arg Val Lys Ile Trp
                645                 650
```

```
<210> SEQ ID NO 59
<211> LENGTH: 651
<212> TYPE: PRT
<213> ORGANISM: Nakamurella multipartita

<400> SEQUENCE: 59

Met Thr Ala Ser Pro Ala Ala Asp Val Ile Val Pro Arg Pro Gln Asp
1               5                   10                  15

Asp Leu Phe Arg His Val Asn Gly Pro Trp Leu Ala Thr Ala Glu Ile
            20                  25                  30

Pro Ala Asp Arg Ser Ala Asp Gly Ala Phe Tyr Gln Leu Arg Asp Glu
        35                  40                  45

Ala Glu Lys Asp Ser Arg Ala Ile Ile Glu Asp Ala Ala Ala Ala
    50                  55                  60

Asp Gly Ala Glu Pro Gly Ser Pro Val Gln Leu Ile Gly Asp Leu Tyr
65                  70                  75                  80

Arg Ser Phe Met Asp Val Ala Val Glu Arg Gln Gly Leu Ala Pro
                85                  90                  95

Ile Ala Ala Arg Leu Thr Glu Val Glu Gly Val Asp Ser Pro Ala Ala
            100                 105                 110

Leu Met Arg Thr Leu Gly Arg Leu Arg Arg Ser Gly Val Gly Gly Ala
        115                 120                 125

Phe Ala Ile Asp Val Asp Thr Asp Pro Gly Asp Pro Asp Arg Tyr Val
130                 135                 140

Leu Asn Leu Tyr Gln Gly Gly Ile Gly Leu Pro Asp Glu Ser Tyr Tyr
145                 150                 155                 160

Ser Asp Ala Ala His Ala Asp Val Leu Ser Ala Tyr Ala Ala Phe Leu
                165                 170                 175

Pro Ser Ile Leu Glu Leu Ala Gly Ile Pro Glu Ser Ala Gly Ala Gly
            180                 185                 190

Ala Ala Val Val Glu Leu Glu Thr Ala Val Ala Ala Gly His Trp Asp
        195                 200                 205

Arg Val Arg Ser Arg Asp Ser Ser Gln Thr Tyr Asn Pro Lys Asp Arg
210                 215                 220

Ala Gly Leu Asp Ala Leu Leu Pro Gly Pro Leu Trp Asp Ala Trp Leu
225                 230                 235                 240

Asp Gly Leu Gly Ala Asp Pro Ser Val Leu Asp Gln Val Val Arg
                245                 250                 255

Gln Pro Asp Tyr Phe Thr Ala Leu Ala Ala Leu Leu Thr Pro Asp His
            260                 265                 270

Leu Pro Ala Trp Arg Ala Trp Leu Ser Trp Gln Ile Val Arg Ser Leu
        275                 280                 285

Ala Pro Leu Gly Pro Ala Glu Leu Val Glu Lys Asn Phe Asp Phe Tyr
290                 295                 300

Gly Arg Thr Leu Ser Gly Thr Pro Glu Leu Arg Glu Arg Trp Lys Arg
305                 310                 315                 320

Gly Val Gly Phe Val Glu Met Ala Ala Asn Glu Ala Val Gly Arg Leu
                325                 330                 335

Tyr Val Glu Arg His Phe Pro Pro Glu Ser Lys Arg Arg Met Asp Glu
            340                 345                 350

Leu Val Ala Asn Leu Leu Ala Ala Tyr Arg Thr Glu Ile Gly Lys Leu
        355                 360                 365

Pro Trp Met Gly Glu Gln Thr Arg Ala Arg Ala Leu Glu Lys Leu Asp
370                 375                 380
```

```
Ala Phe Thr Pro Lys Ile Gly Tyr Pro Ala Arg Trp Arg Asp Tyr Thr
385                 390                 395                 400

Ala Leu Thr Val Ala Ala Asp Asp Leu Ile Gly Asn Ala Ala Arg Ala
            405                 410                 415

Ala Ala Phe Glu Leu Asp Arg Glu Leu Gly Lys Leu Gly Gly Pro Val
        420                 425                 430

Asp Arg Asp Glu Trp Phe Met Ser Pro Gln Thr Val Asn Ala Tyr Tyr
    435                 440                 445

Asn Pro Gly Met Asn Glu Ile Val Phe Pro Ala Ala Ile Leu Gln Pro
    450                 455                 460

Pro Phe Phe Asp Pro Glu Ala Asp Ala Val Asn Tyr Gly Gly Ile
465                 470                 475                 480

Gly Ala Val Ile Gly His Glu Ile Gly His Gly Phe Asp Asp Gln Gly
                485                 490                 495

Ser Lys Tyr Asp Gly Arg Gly Ala Leu Gln Asp Trp Trp Thr Pro Ala
            500                 505                 510

Asp Arg Ala Ala Phe Glu Gln Leu Thr Gly Arg Leu Ile Asp Gln Tyr
        515                 520                 525

Ser Ala Leu Glu Pro Lys Asn Thr Pro Gly His His Val Asn Gly Ala
    530                 535                 540

Leu Thr Ile Gly Glu Asn Ile Gly Asp Val Gly Gly Leu Gly Ile Ala
545                 550                 555                 560

Tyr Gln Ala Trp Arg Ile Ser Leu Gly Asp Gln Ser Ala Pro Val Ile
                565                 570                 575

Asp Gly Leu Thr Gly Ala Gln Arg Phe Phe Arg Ser Trp Ala Thr Val
            580                 585                 590

Trp Arg Leu Lys Met Arg Glu Ala Glu Gln Val Arg Met Leu Ser Ile
        595                 600                 605

Asp Pro His Ser Pro Ala Glu Phe Arg Cys Asn Gln Val Val Arg Asn
    610                 615                 620

Ile Ala Glu Phe His Glu Ala Phe Asp Thr Arg Pro Thr Asp Gly Leu
625                 630                 635                 640

Trp Leu Asp Glu Gln Asp Arg Val Arg Ile Trp
                645                 650

<210> SEQ ID NO 60
<211> LENGTH: 667
<212> TYPE: PRT
<213> ORGANISM: Mobiluncus mulieris

<400> SEQUENCE: 60

Met Thr Lys Asn Pro Leu Leu Gly Ala Leu Asp Pro Asn Glu Phe Asp
1               5                   10                  15

Asn Asn Ile Arg Pro Gln Asp Asp Leu Tyr Arg Phe Val Asn Gly Lys
            20                  25                  30

Trp Ile Glu Ala Cys Gln Ile Pro Ala Asp Lys Ser Ala Asp Gly Ser
        35                  40                  45

Phe Tyr Val Leu Thr Glu Asn Ser Glu Lys Gln Val Arg Ala Ile Ile
    50                  55                  60

Glu Asp Cys Val Glu Gly Lys Ile Ala Gly Leu Ala Gly Lys Val
65                  70                  75                  80

Ala Ala Leu Tyr Gly Ser Phe Met Asp Glu Ala Gln Val Glu Ala Asp
                85                  90                  95

Ser Ala Pro Ser Leu Glu Arg Leu Phe Gly Pro Leu Arg Thr Ala Lys
            100                 105                 110
```

```
Thr Lys Gly Asp Leu Arg Asp Leu Trp Ala Lys Thr Trp Lys Met Gly
        115                 120                 125

Thr Tyr Asp Gly Phe Phe Ser Met Gly Ile Asp Ile Asp Leu Asn Asn
    130                 135                 140

Pro Asp Cys Tyr Ile Asn Tyr Phe Ser Gln Asp Gly Ile Gly Leu Pro
145                 150                 155                 160

Glu Arg Ala Tyr Phe Leu Glu Glu Lys His Arg Glu Val Leu Gln Ala
                165                 170                 175

Tyr Arg Glu His Val Gly Arg Met Phe Ser Leu Ser Gly Phe Met Ser
            180                 185                 190

Ser Glu Ser Gln Ser Gln Ala Ala Gly Asn Thr Val Val Asp Phe Glu
        195                 200                 205

Thr Glu Ile Ala Arg Leu His Trp Asp Asn Val Lys Thr Arg Asp Thr
    210                 215                 220

Asp Ala Thr Asn Asn Pro Met Thr Trp Ala Glu Leu Ala Ala Lys Leu
225                 230                 235                 240

Pro Val Phe Asp Leu Asp Ala Trp Arg Ala Ala Ser Arg Leu Pro Glu
                245                 250                 255

Lys Met Phe Thr Gln Val Asn Val Gly Met Pro Asp Phe Phe Ala Gly
            260                 265                 270

Met Asp Gln Leu Trp Ala Glu Thr Asp Phe Glu Thr Leu Arg Leu Trp
        275                 280                 285

Met Thr Trp Gln Ala Leu Asn Gly Gln Val Ser Leu Leu Ser Asn Ala
    290                 295                 300

Leu Val Gln Ala Asn Phe Glu Phe Tyr Gly Lys Arg Leu Ala Gly Arg
305                 310                 315                 320

Glu Val Ile Arg Asp Arg Trp Lys Arg Gly Val Ser Leu Ala Ser Ser
                325                 330                 335

Val Met Gly Glu Ala Leu Gly Gln Leu Tyr Val Ala Arg His Phe Pro
            340                 345                 350

Pro Asp Ser Lys Glu Lys Met Ser Arg Leu Val Asp Asn Leu Ile Ala
        355                 360                 365

Ala Tyr Arg Glu Ser Ile Ser Ser Leu Glu Trp Met Gly Ser Glu Thr
    370                 375                 380

Arg Ala Lys Ala Leu Glu Lys Leu Ser Leu Phe Thr Pro Lys Ile Gly
385                 390                 395                 400

Tyr Pro Asp Lys Trp Arg Asn Tyr Glu Lys Leu Asp Val Ser Ala Pro
                405                 410                 415

Thr Leu Val Glu Lys Val Ala Ser Ala Ser Gln Phe Gly Thr Asp Phe
            420                 425                 430

Trp Ile Asp Lys Leu Gly Gly Pro Val Asp His Thr Ile Trp His Met
        435                 440                 445

Thr Pro Gln Thr Val Asn Ala Tyr Tyr Asn Pro Thr Asp Asn Glu Ile
    450                 455                 460

Val Phe Pro Ala Gly Ile Leu Gln Pro Phe Phe Asp Pro Gln Ala
465                 470                 475                 480

Asp Asp Ala Val Asn Tyr Gly Ser Ile Gly Ala Val Ile Gly His Glu
                485                 490                 495

Ile Gly His Gly Phe Asp Asp Gln Gly Ala Lys Phe Asp Gly His Gly
            500                 505                 510

Lys Val Glu Asn Trp Trp Thr Glu Thr Asp Leu Lys Glu Phe Glu Lys
        515                 520                 525

Arg Thr Arg Ala Leu Ile Ala Gln Tyr Asp Gln Tyr Val Pro Arg Gly
```

```
                  530                 535                 540
Leu Pro Glu Glu Phe His Val Asn Gly Ala Leu Thr Ile Gly Glu Asn
545                 550                 555                 560

Ile Gly Asp Leu Gly Gly Leu Asp Ile Ala Trp Lys Ala Tyr Leu Leu
                565                 570                 575

Ala Leu Lys Asp Gln Gly Ile Asn Asp Pro Ala Asp Ala Pro Val Ile
            580                 585                 590

Glu Gly Tyr Thr Gly Ala Gln Arg Phe Tyr Ser Trp Ala Leu Ser
                595                 600                 605

Trp Gln Asn Lys Thr Arg Val Glu Ala Ala Lys Gln Leu Ile Ala Ile
            610                 615                 620

Asp Pro His Ser Pro Ala Glu Phe Arg Cys Asn Gly Val Val Ala Asn
625                 630                 635                 640

Leu Asp Leu Phe Ala Lys Thr Phe Gly Leu Lys Pro Gly Asp Asp Leu
                645                 650                 655

Trp Ile Glu Pro Glu Asn Arg Val Arg Ile Trp
                660                 665

<210> SEQ ID NO 61
<211> LENGTH: 676
<212> TYPE: PRT
<213> ORGANISM: Tsukamurella paurometabola

<400> SEQUENCE: 61

Met Thr Ser Glu Pro Ala Leu Asp Leu Ser Phe Val Asp Pro Asp Ile
1               5                   10                  15

Arg Val Gln Asp Asp Leu Phe Gly His Val Asn Gly Lys Trp Leu Asp
                20                  25                  30

Gly His Glu Ile Pro Ala Asp Arg Ser Ser Asp Gly Ala Phe Tyr Ala
            35                  40                  45

Leu Arg Asp Ala Ala Glu Leu His Val Lys Glu Ile Val Glu Glu Ala
        50                  55                  60

Ala Ala Asp Ala Ala Ala Thr Gly Asp Ala Ala Lys Ile Gly Asp Leu
65                  70                  75                  80

Tyr Ser Ser Phe Met Asp Thr Ala Ala Ile Glu Ala Ala Gly Val Ala
                85                  90                  95

Pro Val Ala Asp Glu Ile Ala Glu Ile Arg Trp Ala Asp Ser Ala Thr
            100                 105                 110

Asp Leu Ala Thr Val Leu Gly Arg Leu Gln Arg Thr Gly Val Gly Gly
        115                 120                 125

Leu Leu Gly Tyr Tyr Val Asp Thr Asp Ala Lys Arg Ser Asp Arg Tyr
    130                 135                 140

Leu Val Gln Val Thr Gln Ser Gly Ile Ser Leu Pro Asp Glu Ala Tyr
145                 150                 155                 160

Tyr Arg Asp Glu Gln Tyr Ala Pro Leu Arg Ala Lys Phe Thr Ala His
                165                 170                 175

Val Ala Asp Thr Phe Arg Leu Ala Thr Arg Leu Ala Pro Ala Leu Leu
            180                 185                 190

Glu Gly Ile Val Thr Ala Gly Glu Glu Asp Ala Ala Ala Ala Ser Val
        195                 200                 205

Leu Asp Leu Glu Thr Ala Ile Ala Ala Gly His Trp Asn Val Val Asp
    210                 215                 220

Arg Arg Asp Ala Asp Lys Ser Tyr Asn Leu Arg Thr Phe Ala Asp Leu
225                 230                 235                 240

Gly Thr Glu Ala Pro Ala Leu Gln Leu Arg Ala Trp Thr Ala Ala Leu
```

-continued

```
                245                 250                 255
Thr Ala Ala Glu Ala Phe Ala Glu Val Phe Glu Val Asn Val Arg
            260                 265                 270
Gln Pro Ser Phe Val Thr His Ala Ala Leu Leu Ser Asp Arg Pro
            275                 280                 285
Leu Ala Gln Trp Arg Thr Trp Leu Ala Trp Arg Val Leu Arg Ala Arg
            290                 295                 300
Ser Pro Tyr Leu Ser Asp Glu Leu Val Ala Ala Asn Phe Ala Phe Tyr
305                 310                 315                 320
Gly Thr Ala Leu Thr Gly Ala Thr Glu Asn Arg Glu Arg Trp Lys Arg
                325                 330                 335
Gly Val Gly Leu Val Glu Glu His Leu Gly Phe Ala Val Gly Glu Leu
            340                 345                 350
Tyr Thr Ala Arg His Phe Pro Ala Asp Ser Lys Ala Arg Met Gln Ala
            355                 360                 365
Leu Val Ala Asp Leu Val Glu Ala Tyr Arg Arg Ile Val Glu Leu
370                 375                 380
Pro Trp Met Thr Pro Ala Thr Arg Glu Arg Ala Leu Glu Lys Leu Gly
385                 390                 395                 400
Lys Phe Thr Pro Lys Ile Gly Tyr Pro Asp Ala Ala Arg Asp Tyr Ser
                405                 410                 415
Ser Leu Gln Ile Gln Arg Asp Asp Leu Leu Gly Asn Val Arg Arg Gly
                420                 425                 430
Asn Ala Ala Glu His Asp Arg Glu Phe Ala Lys Ile Gly Ala Pro Val
            435                 440                 445
Asp Arg Asp Glu Trp Phe Met Thr Pro Gln Thr Val Asn Ala Tyr Tyr
450                 455                 460
Asn Pro Gly Met Asn Glu Ile Val Phe Pro Ala Ala Ile Leu Gln Pro
465                 470                 475                 480
Pro Phe Phe Ala Pro Thr Ala Asp Ala Val Asn Phe Gly Gly Ile
                485                 490                 495
Gly Ala Val Ile Gly His Glu Ile Gly His Gly Phe Asp Asp Gln Gly
                500                 505                 510
Ala Lys Tyr Asp Gly Asp Gly Asn Leu Glu Asp Trp Trp Thr Asp Thr
            515                 520                 525
Asp Arg Glu Glu Phe Gly Lys Arg Thr Arg Ala Leu Ile Glu Gln Tyr
            530                 535                 540
Asp Glu Leu Thr Pro Arg Glu Leu Gly Ala Asp Ser Glu His His Val
545                 550                 555                 560
Asn Gly Gly Phe Thr Val Gly Glu Asn Ile Gly Asp Leu Gly Gly Leu
                565                 570                 575
Gly Ile Ala Leu Val Ala Tyr Gly Ile Ala Arg Glu Arg Ala Gly Gly
            580                 585                 590
Thr Val Asp Asp Pro Ser Thr Glu Ala Asp Gly Leu Thr Gly Leu Gln
            595                 600                 605
Arg Val Phe Tyr Ser Trp Gly Gln Ile Trp Arg Gly Lys Ser Arg Pro
610                 615                 620
Glu Glu Ala Ile Arg Arg Leu Ala Ile Asp Pro His Ser Pro Glu
625                 630                 635                 640
Phe Arg Cys Asn Ala Ile Ala Ser Asn Leu Asp Glu Phe Tyr Ser Ala
                645                 650                 655
Phe Gly Val Thr Glu Gly Asp Thr Leu Phe Leu Ala Pro Glu Arg Arg
            660                 665                 670
```

```
Val Ser Ile Trp
        675

<210> SEQ ID NO 62
<211> LENGTH: 677
<212> TYPE: PRT
<213> ORGANISM: Corynebacterium amycolatum

<400> SEQUENCE: 62

Met Thr Asn Ser Thr Asp Thr Glu Thr Gln Ser Ala Thr Ser Gln Phe
1               5                   10                  15

Ser Thr Thr Pro Arg Pro Gln Asp Asp Leu Tyr Leu Ala Ile Asn Gly
            20                  25                  30

Glu Trp Ile Ser Asn His Val Ile Pro Ala Asp Arg Pro Ile Asp Gly
        35                  40                  45

Ala Phe Tyr Lys Leu Arg Asp Glu Ala Glu Glu Asn Val Arg Glu Leu
    50                  55                  60

Ile Thr Thr Ala Ala Asp Ala Asp Pro Asn Ser Arg Val Ala Arg Leu
65                  70                  75                  80

Tyr Asn Ser Phe Met Asp Glu Ala Ala Ile Asn Asp Ala Gly Ala Ala
                85                  90                  95

Pro Leu Ala Gln Asp Leu Glu Met Ile Ala Ser Ala Glu Asn Ala His
            100                 105                 110

Glu Leu Ala Leu Ala Leu Gly Arg Leu Asp Arg Leu Gly Val Gly Gly
        115                 120                 125

Ala Leu Gly Tyr Trp Val Glu Lys Asp Ser Gly Ser Asp Leu Asp Ala
    130                 135                 140

Leu Tyr Leu Leu Gln Ser Gly Leu Gly Leu Pro Asp Glu Ala Tyr Tyr
145                 150                 155                 160

Arg Glu Ser Gly His Ala Asp Thr Leu Ala Ala Tyr Glu Gln His Val
                165                 170                 175

Ala Ala Met Leu Lys Leu Leu Ser Ser His Asp Asp Gly Ala Gly Asp
            180                 185                 190

Leu Ser Thr Ala Leu Ala Ala Phe Glu Leu Val Asp Pro Ala Ala Ala
        195                 200                 205

Ala Ala Arg Ile Val Ala Phe Glu Lys Arg Ile Ala Ala Gly His Trp
    210                 215                 220

Asn Val Val Asp Thr Arg Asp Ala Leu Lys Thr Tyr Asn Lys Thr Ala
225                 230                 235                 240

Ile Ala Asp Leu Pro Thr Gly Phe Pro Val Ala Glu Trp Leu Ala Ala
                245                 250                 255

Thr Gly Val Asn Glu Thr Asn Gln Thr Ala Ile Asp Thr Ile Val Val
            260                 265                 270

Met Met Pro Ser Tyr Phe Glu His Leu Ser Lys Leu Trp Gln Asp Thr
        275                 280                 285

Asp Leu Ala Asp Leu Arg Leu Trp Ala Leu Trp Arg Val Leu His Gln
    290                 295                 300

Arg Ala Ala Tyr Leu Ser Asp Asp Phe Ser Ala Glu Ser Phe Asn Phe
305                 310                 315                 320

Tyr Gly Arg Thr Leu Gln Gly Ser Thr Glu Gln Arg Ala Arg Trp Lys
                325                 330                 335

Arg Gly Val Ala Phe Ala Asp Gly Ala Val Gly His Asp Val Gly Lys
            340                 345                 350

Leu Tyr Val Glu Lys His Phe Pro Pro Glu Tyr Lys Glu Gln Val Leu
        355                 360                 365
```

```
Glu Leu Val Asp Tyr Leu Leu Ala Ala Tyr Arg Glu Arg Ile Ser Gln
    370                 375                 380

Leu Pro Trp Met Thr Lys Ala Thr Gln Glu Arg Ala Leu Glu Lys Leu
385                 390                 395                 400

Ser Leu Phe Lys Ala Lys Ile Gly Tyr Pro Glu Arg Trp Arg Asp Tyr
                405                 410                 415

Ser Ala Met Glu Leu Gly Gly Ser Leu Met Asp Asn Ala Arg Ala Ala
            420                 425                 430

Ser Ala Phe Ala His Asp Tyr Glu Val Ala Lys Leu Gly Thr Pro Ala
        435                 440                 445

Asn Arg Asp Glu Trp His Gly Thr Pro Gln Thr Val Asn Ala Phe Tyr
    450                 455                 460

Asn Pro Val Val Asn Asp Ile Thr Phe Pro Ala Ala Ile Leu Gln Pro
465                 470                 475                 480

Pro Phe Phe Ser Pro Asp Ala Ser Pro Ala Glu Asn Phe Gly Gly Ile
                485                 490                 495

Gly Ala Val Ile Gly His Glu Ile Gly His Gly Phe Asp Asp Gln Gly
            500                 505                 510

Ser Gln Tyr Asp Gly His Gly Asn Leu His Gln Trp Trp Thr Asp Glu
        515                 520                 525

Asp Arg Ala Ala Phe Glu Lys Leu Thr Ser Ala Leu Val Asp Gln Tyr
    530                 535                 540

Glu Gly Leu Val Pro Gln Ala Leu Arg Glu Gln Ala Glu Glu Gly Ala
545                 550                 555                 560

Asp Leu Pro Gly Val Asn Gly Arg Phe Thr Leu Gly Glu Asn Ile Gly
                565                 570                 575

Asp Leu Gly Gly Leu Gly Ile Ala Val Val Ala Phe Arg Arg Phe Leu
            580                 585                 590

Ala Ala Arg Gly Lys Glu Leu Gly Leu Glu Asp Ala Pro Glu Thr Tyr
        595                 600                 605

Arg Asp Leu Phe Lys Gln Trp Ala Leu Val Trp Arg Ser Lys Ile Arg
    610                 615                 620

Pro Glu Phe Ala Arg Gln Leu Leu Ala Ile Asp Pro His Ser Pro Ala
625                 630                 635                 640

Glu Phe Arg Cys Asn Val Ile Ala Ser Asn Ile Asp Glu Phe His Glu
                645                 650                 655

Ala Phe Gly Thr Ser Ala Gly Asp Gly Met Trp Arg Glu Pro Asn Glu
            660                 665                 670

Arg Val Asn Ile Trp
            675

<210> SEQ ID NO 63
<211> LENGTH: 724
<212> TYPE: PRT
<213> ORGANISM: Bifidobacterium longum

<400> SEQUENCE: 63

Met Thr Asn Glu Thr Glu Thr Leu Thr Ser Gly Ile Asp Pro Ala Ser
1               5                   10                  15

Phe Ser Ser Val Ile Lys Pro Thr Asn Asp Leu Phe Arg Tyr Val Asn
                20                  25                  30

Gly Pro Trp Ile Asp Thr Tyr Arg Leu Pro Asp Asp Arg Ser Arg Tyr
            35                  40                  45

Gly Ser Phe Asp Lys Leu Ala Glu Asp Ala Glu Asn Gln Val Arg Asp
        50                  55                  60
```

-continued

```
Ile Leu Asp Ala Asp Asp Cys Pro Ala Thr Lys Ser Gln Ala Leu Tyr
 65                  70                  75                  80

His Ser Phe Leu Asn Thr Asp Ala Ile Glu Ala Ala Gly Leu Asp Pro
                 85                  90                  95

Ile Arg Asp Glu Leu Asp Leu Ile Asp Ser Ala Ile Asp Lys Ala Ala
            100                 105                 110

Leu Thr Arg Val Leu Gly Thr Ile Asn Pro Ala Gly Gly Pro Asp Leu
        115                 120                 125

Phe Gly Leu Ala Val Tyr Gly Asp Pro Gly Asp Pro Asp Arg Asn Ile
    130                 135                 140

Ala His Leu Glu Gln Ala Gly Leu Cys Leu Pro Asp Glu Ala Tyr Tyr
145                 150                 155                 160

Arg Glu Asp His Tyr Val Pro Val Arg Glu Ala Tyr Val Ala Met Val
                165                 170                 175

Ala Thr Gln Leu Val Asn Ala Gly Tyr Ala Pro Ala Ala Glu Ser Asn
            180                 185                 190

Gly Gly Asp Glu Leu Pro Ala Asn Thr Gly Asp Asp Glu Ser Asn Ala
        195                 200                 205

Pro Thr Thr Val Pro Ser Glu Ala Ala Leu Asp Met Ala Arg His Phe
    210                 215                 220

Leu Ala Val Glu Thr Lys Ile Ala Ala Asn His Trp Asp Asn Val Ala
225                 230                 235                 240

Thr Arg Asp Ser Val Lys Thr Tyr Asn Pro Thr Asp Tyr Ala Asp Leu
                245                 250                 255

Ala Ala Thr Leu Lys Asn Phe Asp Leu Ala Ser Trp Ile Asp Ala Trp
            260                 265                 270

Gln Thr Ala Tyr Asp Ala Thr Glu Ala Ala Lys Ala Gln Ser Ile Asp
        275                 280                 285

Phe Lys Ser Val Phe Ala Arg Ile Ile Val His Glu Pro Ser Phe Leu
    290                 295                 300

Thr Gly Leu Asp Ala Phe Trp Ala Glu Ala Asp Leu Ala Asp Leu Lys
305                 310                 315                 320

Leu Trp Ala Arg Val His Met Ile Leu Gly Phe Ala Ser Ser Leu Ser
                325                 330                 335

Arg Asp Phe Asp Thr Thr Asn Phe Asp Phe Tyr Gly Lys Val Leu Ser
            340                 345                 350

Gly Ala Lys Lys Gln Arg Asp Arg Trp Lys Arg Ala Val Ser Leu Val
        355                 360                 365

Asn Gly Val Cys Gly Glu Asp Val Gly Arg Glu Tyr Ala Arg Leu His
    370                 375                 380

Phe Pro Glu Ser Ser Lys Arg Arg Met Glu Glu Leu Val Ala Asn Leu
385                 390                 395                 400

Ile Asp Ala Tyr Arg Val Ser Ile Ala Asn Ser Asp Trp Leu Gly Glu
                405                 410                 415

Asp Thr Lys Ala Lys Ala Leu Glu Lys Ile Ser Lys Phe Thr Pro Lys
            420                 425                 430

Ile Gly Tyr Thr Asn His Trp Arg Asp Tyr Ser Ala Leu Ser Val Ser
        435                 440                 445

Ala Asp Ala Leu Pro Ala Glu Asn Ala Lys Ala Asn Leu Tyr Glu
    450                 455                 460

Thr Gly Tyr Gln Leu Ala Lys Val Gly Lys Ala Val Asp Lys Asp Glu
465                 470                 475                 480

Trp Leu Met Asn Pro Gln Thr Val Asn Ala Tyr Tyr Glu Pro Ser Met
                485                 490                 495
```

-continued

```
Asn Val Ile Val Phe Pro Ala Ala Ile Leu Gln Pro Pro Phe Phe Asp
            500                 505                 510
Pro Lys Ala Glu Asp Ala Ala Asn Tyr Gly Ile Gly Ala Val Ile
        515                 520                 525
Gly His Glu Ile Gly His Gly Phe Asp Asp Gln Gly Ser Gln Tyr Asp
    530                 535                 540
Gly Asp Gly Lys Leu Asn Asn Trp Trp Thr Asp Glu Asp Arg Lys Asn
545                 550                 555                 560
Phe Glu Ala Arg Thr Gly Ala Leu Ile Ala Gln Tyr Asn Ser Phe Val
                565                 570                 575
Pro Leu Gln Leu Ala Glu Lys Tyr Ala Asp Glu Ser Asp Lys Ala Pro
            580                 585                 590
His Val Asn Gly Ala Leu Thr Ile Gly Glu Asn Ile Gly Asp Leu Gly
        595                 600                 605
Gly Val Asn Ile Ala Leu Lys Ala Tyr Ala Phe Ala Leu Gly Lys Ala
    610                 615                 620
Ala Gly Lys Pro Asp Ala Glu Asp Gly Ser Pro Ala Ala Ile Lys
625                 630                 635                 640
Ala Leu Leu Asp Thr Ala Pro Glu Met Asp Gly Phe Thr Gly Leu Gln
                645                 650                 655
Arg Phe Phe Leu Ser Tyr Ala Ser Ile Trp Arg Thr Lys Asn Arg Asp
            660                 665                 670
Glu Leu Ala Glu Gln Tyr Leu Gln Ile Asp Pro His Ser Pro Ala Glu
        675                 680                 685
Phe Arg Thr Asn Gly Ile Ala Ser Asn Val Asp Leu Phe Tyr Asp Ala
    690                 695                 700
Phe Gly Val Thr Glu Gly Asp Ala Met Trp Leu Ala Pro Lys Asp Arg
705                 710                 715                 720
Val Ser Ile Trp

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Pro Tyr Pro Gln Pro Gln
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Pro Tyr Pro Gln Pro Gln
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 66

Leu Pro Tyr Pro Gln Pro Gln
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Gln Pro Gln Pro Phe
1               5

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Gln Pro Gln Leu Pro Tyr Pro Gln Pro Gln
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Gln Pro Gln Leu Pro Tyr Pro Gln Pro Gln
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Gln Pro Gln Leu Pro Tyr Pro Gln Pro Gln
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Gln Pro Gln Leu Pro Tyr
1               5

<210> SEQ ID NO 72
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Gln Pro Gln Leu Pro Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Gln Pro Gln Leu Pro Tyr
1               5

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Pro Tyr Pro Gln Pro Gln Leu Pro Tyr Pro Gln Pro Gln
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Pro Tyr Pro Gln Pro Gln Leu Pro Tyr Pro Gln Pro Gln
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Gln Leu Gln Pro Phe Pro Gln Pro Gln
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Pro Gln Pro Gln Leu Pro Tyr Pro Gln Pro Gln Pro Phe
1               5                   10
```

```
<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Pro Tyr Pro Gln Pro Gln Leu Pro Tyr
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Pro Gln Leu Pro Tyr Pro Gln Pro Gln Leu Pro Tyr Pro Gln Pro
1               5                   10                  15

Gln

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Gln Leu Gln Pro Phe Pro Gln Pro Gln Leu Pro Tyr Pro Gln Pro
1               5                   10                  15

Gln

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Pro Tyr Pro Gln Pro Gln Leu Pro Tyr Pro Gln Pro Gln Pro Phe
1               5                   10                  15

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Gln Leu Gln Pro Phe Pro Gln Pro Gln Leu Pro Tyr
1               5                   10

<210> SEQ ID NO 83
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 83

Pro Gln Gln Pro Gln Gln Pro Tyr Pro Gln
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Gln Gln Pro Gln Gln Pro Tyr Pro Gln Gln Pro Gln
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Gln Gln Pro Gln Gln Pro Tyr
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Pro Gln Gln Pro Tyr Pro Gln
1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Gln Gln Pro Gln Gln Pro Phe Pro Gln
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Pro Gln Gln Pro Phe Pro Gln Gln Pro Gln
1               5                   10
```

```
<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Pro Gln Gln Pro Phe Pro Gln Gln Pro
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Tyr Pro Gln Gln Pro Gln Gln Pro Phe Pro Gln
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Phe Pro Gln Gln Pro Gln Gln Pro Tyr
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Pro Tyr Pro Gln Gln Pro Gln Gln Pro Phe Pro Gln
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Leu Gln Pro Gln Gln Pro Phe Pro Gln Gln Pro Gln
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94
```

Phe Leu Gln Pro Gln Gln Pro Phe Pro Gln
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Leu Gln Pro Gln Gln Pro Phe Pro Gln Gln Pro Gln Gln Pro Tyr
1               5                   10                  15

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Pro Gln Gln Pro Gln Gln Pro Phe Pro
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Phe Leu Gln Pro Gln Gln Pro Phe
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Pro Tyr Pro Gln Pro Gln
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Pro Tyr Pro Gln Pro Gln
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic

```
                                   peptide

<400> SEQUENCE: 100

Leu Pro Tyr Pro Gln Pro Gln
1               5

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Gln Pro Gln Leu Pro Tyr Pro Gln Pro Gln
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Gln Pro Gln Leu Pro Tyr Pro Gln Pro Gln
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Gln Pro Gln Leu Pro Tyr Pro Gln Pro Gln
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Pro Gln Pro Gln Leu Pro Tyr
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Gln Pro Gln Leu Pro Tyr
1               5

<210> SEQ ID NO 106
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Pro Gln Pro Gln Leu Pro Tyr
1               5

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Pro Tyr Pro Gln Pro Gln Leu Pro Tyr Pro Gln Pro Gln
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Pro Tyr Pro Gln Pro Gln Leu Pro Tyr Pro Gln Pro Gln
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu Pro Tyr Pro Gln Pro Gln Leu Pro Tyr Pro Gln
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Pro Tyr Pro Gln Pro Gln Leu Pro Tyr Pro Gln
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Gln Leu Gln Pro Phe Pro Gln Pro Gln
1               5                   10
```

```
<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Pro Tyr Pro Gln Pro Gln Pro Phe
1               5

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Pro Gln Pro Gln Leu Pro Tyr Pro Gln Pro Gln Pro Phe
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Pro Tyr Pro Gln Pro Gln Leu Pro Tyr
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Leu Pro Tyr Pro Gln Pro Gln Leu Pro Tyr
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Pro Gln Leu Pro Tyr Pro Gln Pro Gln Leu Pro Tyr Pro Gln Pro
1               5                   10                  15

Gln

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 117

Leu Gln Leu Gln Pro Phe Pro Gln Pro Gln Leu Pro Tyr Pro Gln Pro
1               5                   10                  15

Gln

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Pro Tyr Pro Gln Pro Gln Leu Pro Tyr Pro Gln Pro Gln Pro Phe
1               5                   10                  15

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Pro Gln Leu Pro Tyr Pro Gln Pro Gln Leu Pro Tyr
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Leu Gln Leu Gln Pro Phe Pro Gln Pro Gln Leu Pro Tyr
1               5                   10

<210> SEQ ID NO 121
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr
                20                  25

<210> SEQ ID NO 122
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Pro Gln Leu Pro Tyr Pro Gln Pro Gln Leu Pro Tyr Pro Gln Pro

```
                1               5                  10                 15
Gln Leu Pro Tyr
            20

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Leu Pro Tyr Pro Gln Pro Gln Leu Pro Tyr Pro Gln Pro Gln Leu
1               5                  10                 15

Pro Tyr Pro Gln Pro Gln
            20

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Gln Gln Pro Gln Gln Pro Tyr Pro Gln
1               5                  10

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Pro Gln Gln Pro Tyr Pro Gln
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Pro Phe Pro Gln Gln Pro Gln
1               5

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Pro Gln Gln Pro Phe Pro Gln Gln Pro
1               5                  10

<210> SEQ ID NO 128
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Gln Gln Pro Gln Gln Pro Phe Pro Gln
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Gln Gln Pro Phe Pro Gln
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Pro Gln Gln Pro Phe Pro Gln
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Pro Gln Gln Pro Phe Pro Gln
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Pro Gln Gln Pro Phe Pro Gln
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Pro Gln Gln Pro Phe Pro Gln Gln Pro
```

-continued

```
<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr Gln Pro Gln Gln Pro Phe Pro
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Gln Pro Gln Gln Pro Phe Pro Gln
1               5

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Phe Leu Gln Pro Gln Gln Pro Phe Pro Gln
1               5                   10
```